US010961319B2

(12) United States Patent
Johnson et al.

(10) Patent No.: US 10,961,319 B2
(45) Date of Patent: *Mar. 30, 2021

(54) ANTI-TRANSGLUTAMINASE 2 ANTIBODIES

(71) Applicant: LIFEARC, London (GB)

(72) Inventors: Tim Johnson, Sheffield (GB); Phil Watson, Sheffield (GB); David Matthews, Sheffield (GB); Alex Brown, London (GB)

(73) Assignee: LIFEARC, London (GB)

( * ) Notice: Subject to any disclaimer, the term of this patent is extended or adjusted under 35 U.S.C. 154(b) by 207 days.

This patent is subject to a terminal disclaimer.

(21) Appl. No.: 15/987,611

(22) Filed: May 23, 2018

(65) Prior Publication Data

US 2018/0355060 A1 Dec. 13, 2018

Related U.S. Application Data

(63) Continuation of application No. 14/402,675, filed as application No. PCT/GB2013/051373 on May 24, 2013, now Pat. No. 10,005,846.

(30) Foreign Application Priority Data

May 24, 2012 (GB) ..................................... 1209096

(51) Int. Cl.
*C07K 16/40* (2006.01)
*A61K 51/10* (2006.01)
*A61K 39/00* (2006.01)

(52) U.S. Cl.
CPC .......... *C07K 16/40* (2013.01); *A61K 51/1075* (2013.01); *A61K 2039/505* (2013.01); *C07K 2317/34* (2013.01); *C07K 2317/40* (2013.01); *C07K 2317/76* (2013.01)

(58) Field of Classification Search
CPC combination set(s) only.
See application file for complete search history.

(56) References Cited

U.S. PATENT DOCUMENTS

| | | | |
|---|---|---|---|
| 4,912,120 | A | 3/1990 | Castelhano et al. |
| 2011/0091386 | A1 | 4/2011 | Kumar et al. |

FOREIGN PATENT DOCUMENTS

| | | | |
|---|---|---|---|
| WO | WO-1992/12238 A1 | | 7/1992 |
| WO | WO-1998/04245 A1 | | 2/1998 |
| WO | WO-2002/068616 A2 | | 9/2002 |
| WO | WO-2004/069175 A2 | | 8/2004 |
| WO | WO-2004/113363 A2 | | 12/2004 |
| WO | WO-2006/100679 A2 | | 9/2006 |
| WO | WO2006100679 | * | 9/2006 |
| WO | WO-2008/063760 A2 | | 5/2008 |
| WO | WO-2009/131256 A1 | | 10/2009 |
| WO | WO-2010/105302 A1 | | 9/2010 |
| WO | WO-2010/113025 A2 | | 10/2010 |
| WO | WO-2010/116196 A2 | | 10/2010 |
| WO | WO-2011/151395 A2 | | 12/2011 |
| WO | WO-2012/146901 A1 | | 11/2012 |

OTHER PUBLICATIONS

Paul, Fundamental Immunology, 3rd Edition, 1993, pp. 292-295, under the heading Fv Structure and Diversity in Three Dimensions (Year: 1993).*

Rudikoff et al, Proc. Natl. Acad. Sci. USA 1982 vol. 79: p. 1979 (Year: 1979).*

Casset et al BBRC 307, 198-205 2003 (Year: 2003).*

Pascalis et al The Journal of Immunology vol. 169, 3076-3084, 2002 (Year: 2002).*

Abcam® Product Sheet, "Anti-Transglutaminase 2 antibody [CUB 7402]" Retrieved from the Internet on Aug. 27, 2013 at: <http://www.abcam.com/transglutaminase-2-antibody-cub-7402-ab2386.html> (2010).

Auld et al., Thrombin upregulates tissue transglutaminase in endothelial cells: a potential role for tissue transglutaminase in stability of atherosclerotic plaque, Arterioscler. Thromb. Vasc. Biol., 21(10):1689-94 (2001).

Birckbichler, et al., "A Monoclonal Antibody to Cellular Transglutaminase," Hybridoma, vol. 4, No. 2, pp. 179-186 (1985).

Caccamo et al., Potential of transglutaminase 2 as a therapeutic target, Expert Opin. Ther. Targets, 14(9):989-1003 (2010).

Casset et al., A peptide mimetic of an anti-CD4 monoclonal antibody by rational design, BBRC, 307:198-205 (2003).

Davies et al., Transglutaminase is essential in receptor-mediated endocytosis of alpha 2-macroglobulin and polypeptide hormones, Nature, 283(5743):162-7 (1980).

De Pascalis et al., Grafting of "abbreviated" complementarity-determining regions containing specificity-determining residues essential for ligand contact to engineer a less immunogenic humanized monoclonal antibody.J. Immunol., 169:3076-84 (2002).

Developmental Studies Hybridoma Bank, 4C1 antibody, dshb.biology.uiowa.edu.

Di Niro et al., Construction of miniantibodies for the in vivo study of human autoimmune diseases in animal models, BMC Biotechnol., 7:46 (2007).

DiNiro et al., Characterizing monoclonal antibody epitopes by filtered gene fragment phage display, Biochem. J., 388:889-94 (2005).

Esposito et al., Anti-tissue transglutaminase antibodies from coeliac patients inhibit transglutaminase activity both in vitro and in situ, Gut, 51(2):177-81 (2002).

(Continued)

*Primary Examiner* — Lei Yao
(74) *Attorney, Agent, or Firm* — Marshall, Gerstein & Borun LLP

(57) ABSTRACT

The invention provides antibodies and antigen-binding fragments thereof that selectively bind to an epitope within the core region of transglutaminase type 2 (TG2). Novel epitopes within the TG2 core are provided. The invention provides human TG2 inhibitory antibodies and uses thereof, particularly in medicine, for example in the treatment and/or diagnosis of conditions including Celiac disease, scarring, fibrosis-related diseases, neurodegenerative/neurological diseases and cancer.

11 Claims, 50 Drawing Sheets

Figure 4:
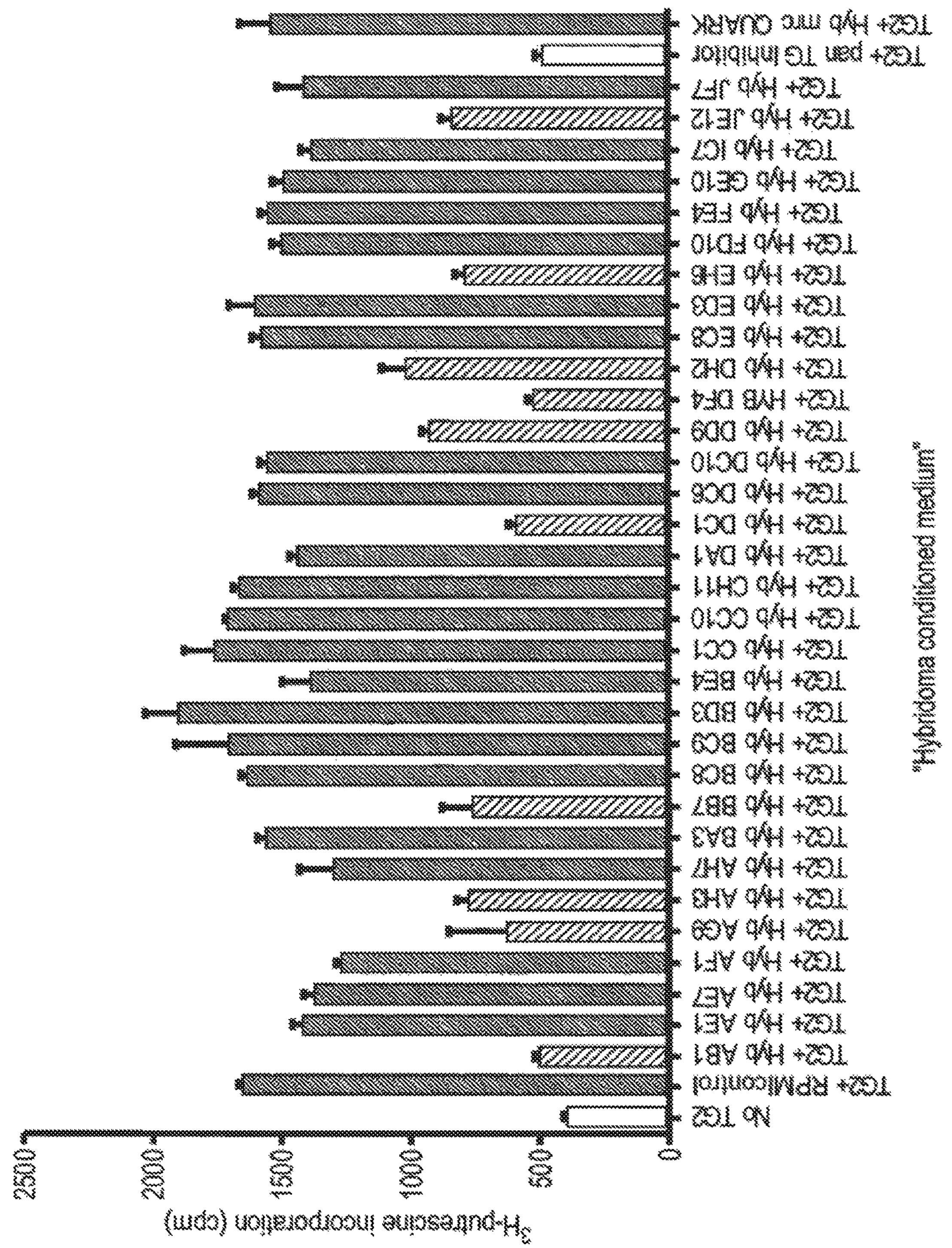

Specification includes a Sequence Listing.

(56) References Cited

OTHER PUBLICATIONS

Fesus et al., Induction and activation of tissue transglutaminase during programmed cell death, FEBS Lett., 224(1):104-8 (1987).
Fesus et al., Searching for the function of tissue transglutaminase: its possible involvement in the biochemical pathway of programmed cell death, Adv. Exp. Med. Biol., 231:119-34 (1988).
Fesus et al., Transglutaminase 2: an enigmatic enzyme with diverse functions, Trends Biochem. Sci., 27(10):534-9 (2002).
Fisher et al., Modulation of tissue transglutaminase in tubular epithelial cells alters extracellular matrix levels: a potential mechanism of tissue scarring, Matrix Biol., 28(1):20-31 (2009).
Grenard et al., Transglutaminase-mediated cross-linking is involved in the stabilization of extracellular matrix in human liver fibrosis, J. Hepatol., 35(3):367-75 (2001).
Griffin et al., Changes in transglutaminase activity in an experimental model of pulmonary fibrosis induced by paraquat, Br. J. Exp. Pathol., 60(6):653-61 (1979).
Huang et al., Do changes in transglutaminase activity alter latent transforming growth factor beta activation in experimental diabetic nephropathy?, Nephrol. Dial. Transplant., 25(12):3897-910 (2010).
Huang et al., Transglutaminase inhibition ameliorates experimental diabetic nephropathy, Kidney Int., 76(4):383-94 (2009).
Iismaa et al., GTP binding and signaling by Gh/transglutaminase II involves distinct residues in a unique GTP-binding pocket, J. Biol. Chem., 275(24):18259-65 (2000).
Iismaa et al., The core domain of the tissue transglutaminase Gh hydrolyzes GTP and ATP, Biochemistry, 36(39):11655-64 (1997).
International Preliminary Report on Patentability, corresponding international application No. PCT/GB2013/051373, dated Nov. 25, 2014.
International Search Report and Written Opinion, International Application No. PCT/GB13/51373, dated Sep. 11, 2013.
Johnson et al., Tissue transglutaminase and the progression of human renal scarring, J. Am. Soc. Nephrol., 14(8):2052-62 (2003).
Johnson et al., Transglutaminase inhibition reduces fibrosis and preserves function in experimental chronic kidney disease, J. Am. Soc. Nephrol., 18(12):3078-88 (2007).
Johnson et al., Transglutaminase transcription and antigen translocation in experimental renal scarring, J. Am. Soc. Nephrol., 10(10):2146-57 (1999).
Kiraly et al., Functional significance of five noncanonical Ca2+-binding sites of human transglutaminase 2 characterized by site-directed mutagenesis, FEBS J., 276(23):7083-96 (2009).
Klock et al., Acylideneoxoindoles: a new class of reversible inhibitors of human transglutaminase 2, Bioorg. Med. Chem. Lett., 21(9):2692-6 (2011).
Korponay-Szabo, et al., "Deamidated Gliadin Peptides Form Epitopes That Transglutaminase Antibodies Recognize," Journal of Pediatric Gastoenterology and Nutrition, 46: 253-261 (2008).
Kuncio et al., TNF-alpha modulates expression of the tissue transglutaminase gene in liver cells, Am. J. Physiol., 274(2 Pt. 1):G240-5 (1998).
Lai et al., Identification of two GTP-independent alternatively spliced forms of tissue transglutaminase in human leukocytes, vascular smooth muscle, and endothelial cells, FASEB J., 21(14):4131-43 (2007).
Lai et al., Identification of two GTP-independent alternatively spliced forms of tissue transglutaminase in human leukocytes, vascular smooth muscle, and endothelial cells, FASEB J., 21:4131-43 (2007).
Lorand et al., Transglutaminases, Mol. Cell Biochem., 58(1-2):9-35 (1984).
Lorand et al., Transglutaminases: crosslinking enzymes with pleiotropic functions, Nat. Rev. Mol. Cell Biol., 4(2):140-56 (2003).
Marzari et al., Molecular dissection of the tissue transglutaminase autoantibody response in Celiac Disease. J. Immunol. 166(6): 4170-6 (2001).
Mosher, Cross-linking of fibronectin to collagenous proteins, Mol. Cell Biochem., 58(1-2):63-8 (1984).
Nakachi et al., Epitopes recognised by tissue transglutaminase antibodies in coeliac disease, J. Autoimmun., 22(1):53-63 (2004).
Nakaoka et al., Gh: a GTP-binding protein with transglutaminase activity and receptor signaling function, Science, 264(5165):1593-6 (1994).
Paul, Immunoglobulins: Structure & Function, Fundamental Immunol., 3:292-5 (1993).
Pinkas et al., Transglutaminase 2 undergoes a large conformational change upon activation, PLoS Biol., 5(12):e327 (2007).
Rudikoff et al., Single amino acid substitution altering antigen-binding specificity. Proc. Natl. Acad. Sci. USA, 79:1979 (1982).
Sblattero et al., the analysis of the fine specificity of celiac disease antibodies using tissue transglutaminase fragments, Eur. J. Biochem., 269(21):5175-81 (2002).
Shweke et al., Tissue transglutaminase contributes to interstitial renal fibrosis by favoring accumulation of fibrillar collagen through TGF-beta activation and cell infiltration, Am. J. Pathol., 173(3):631-42 (2008).
Siegel et al., Structure-based design of alpha-amido aldehyde containing gluten peptide analogues as modulators of HLA-DQ2 and transglutaminase 2, Bioorg. Med. Chem., 15(18):6253-61 (2007).
Siegel et al., Transglutaminase 2 inhibitors and their therapeutic role in disease states, Pharmacol. Ther., 115(2):232-45 (2007).
Simon-Vecsei et al., A single conformational transglutaminase 2 epitope contributed by three domains is critical for celiac antibody binding and effects, Proc. Natl. Acad. Sci. USA, 109(2):431-6 (2012).
Skill et al., Inhibition of transglutaminase activity reduces extracellular matrix accumulation induced by high glucose levels in proximal tubular epithelial cells, J. Biol. Chem., 279(46):47754-62 (2004).
Small et al., Cardiac specific overexpression of transglutaminase II (G(h)) results in a unique hypertrophy phenotype independent of phospholipase C activation, J. Biol. Chem., 274(3):21291-6 (1999).
Sollid et al., Novel therapies for coeliac disease, J. Intern. Med., 269(6):604-13 (2011).
Suto et al., Expression induced by interleukin-6 of tissue-type transglutaminase in human hepatoblastoma HepG2 cells, J. Biol. Chem., 268(10):7469-73 (1993).
Telci et al., Fibronectin-tissue transglutaminase matrix rescues RGD-impaired cell adhesion through syndecan-4 and beta1 integrin co-signaling, J. Biol. Chem., 283(30):20937-47 (2008).
Toth et al., Transglutaminase 2 is needed for the formation of an efficient phagocyte portal in macrophages engulfing apoptotic cells, J. Immunol., 182(4):2084-92 (2009).
Verderio et al., A novel RGD-independent cel adhesion pathway mediated by fibronectin-bound tissue transglutaminase rescues cells from anoikis, J. Biol. Chem., 278(43):42604-14 (2003).
Verderio et al., Regulated expression of tissue transglutaminase in Swiss 3T3 fibroblasts: effects on the processing of fibronectin, cell attachment, and cell death, Exp. Cell Res., 239(1):119-38 (1998).
Verderio et al., Tissue transglutaminase in normal and abnormal wound healing: review article, Amino Acids, 26(4):387-404 (2004).
Xu et al., GPR56, an atypical G protein-coupled receptor, binds tissue transglutaminase, TG2, and inhibits melanoma tumor growth and metastasis, Proc. Natl. Acad. Sci. USA, 103(24):9023-8 (2006).

* cited by examiner

A: PCR product
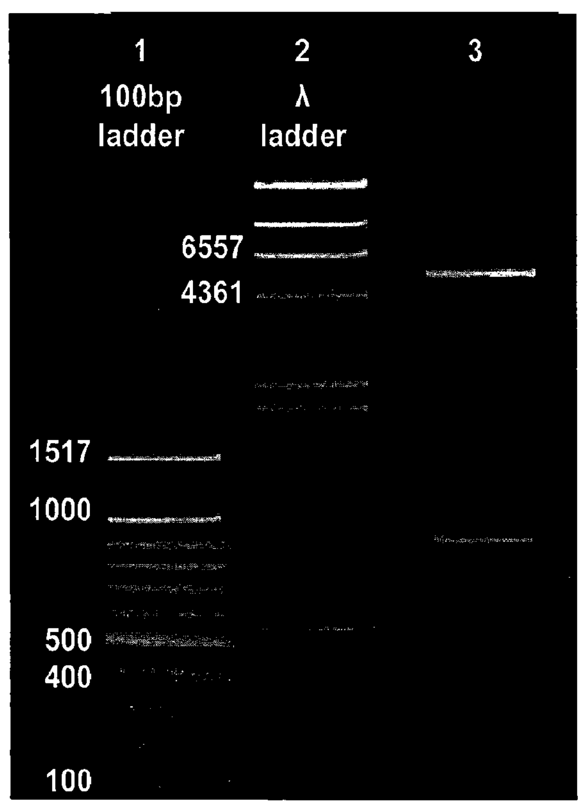
B: Recombinant protein
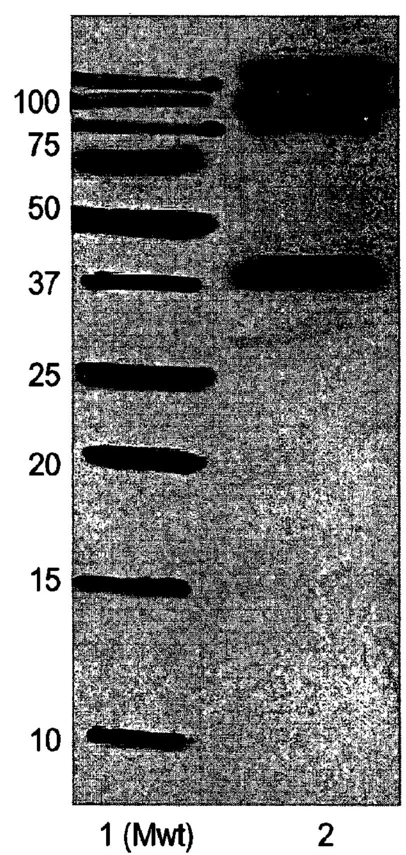
FIG. 1

A: SERUM ELISA
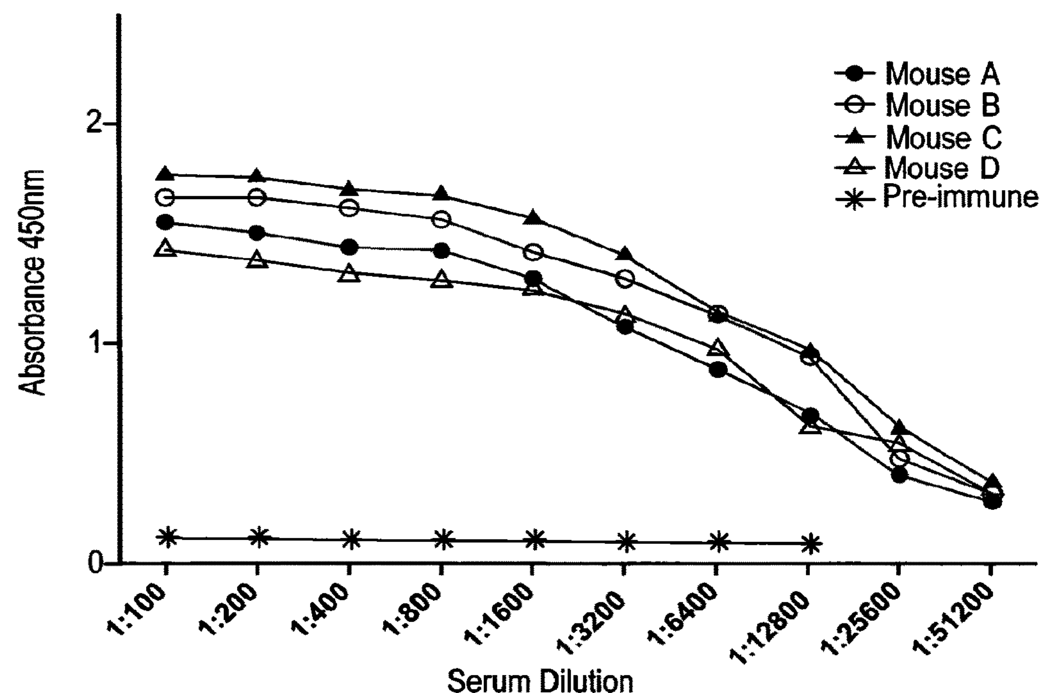
B: SERUM WESTERN BLOT Mouse C
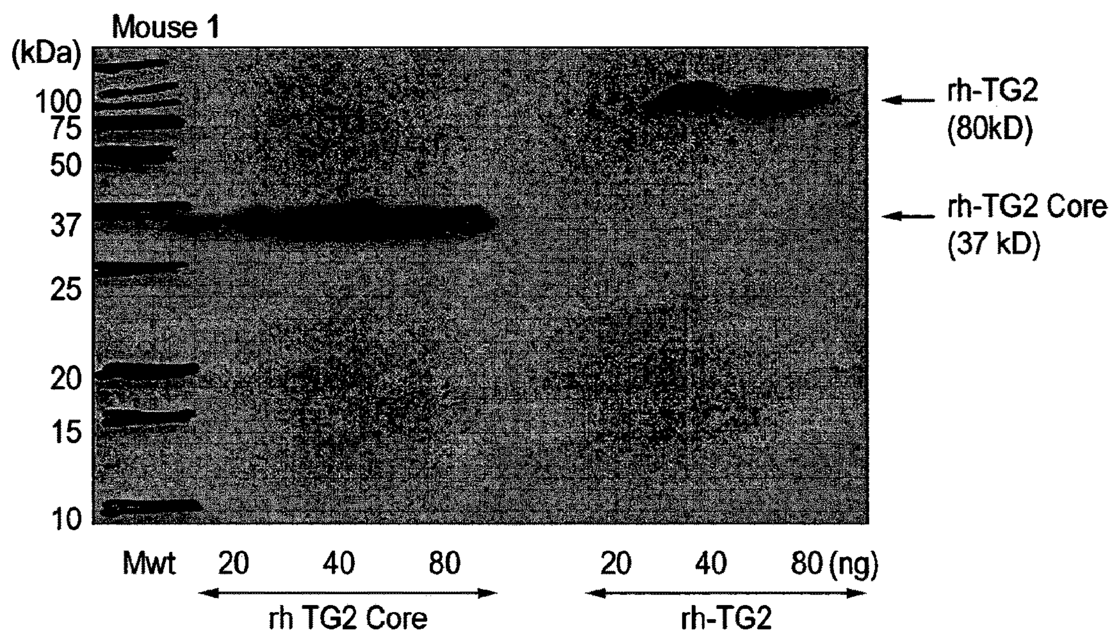
FIG. 2

A: Initial screening of conditioned medium
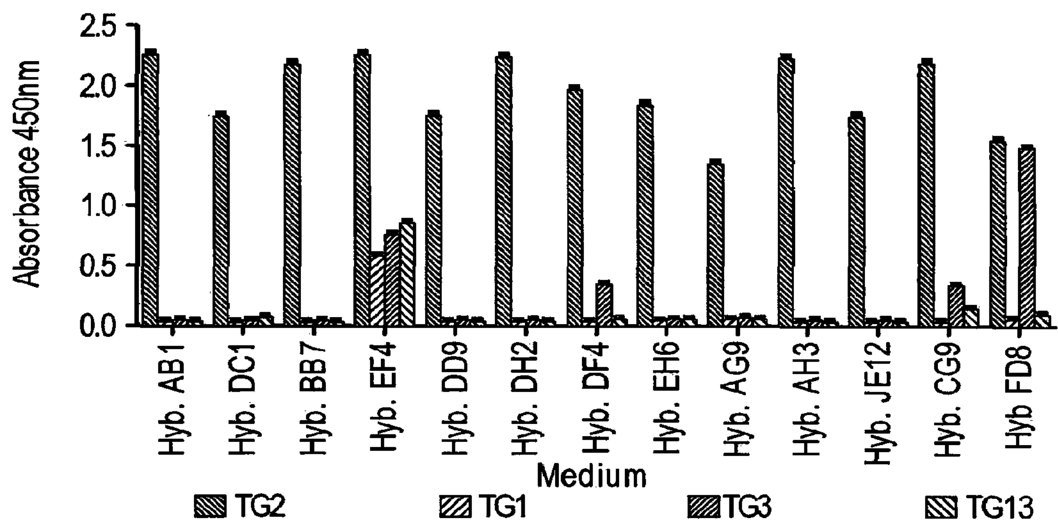
B: Reactivity of clonal purified mAbs
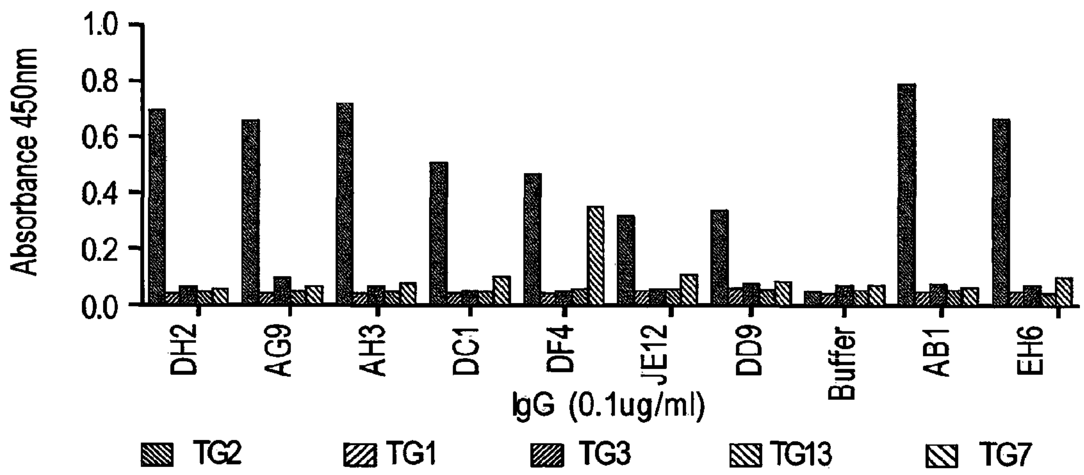
FIG. 3

Group 1: Location - in front of active site - substrate binding pocket

AB-1, AG-1, AH-1, BB-7, DC-1, EH-6, JE-12 mouseTG2 YNSAHDQNSKLLIEYFRNEFGELESNKSEMI
rat YNSAHDQNSKLLIEYFRNEYGELESNKSEMI
human YNSAHDQNSKLLIEYFRNEFGEIQGDKSEMI
*****************:::.:*******

Group 2: Location - on rear of core behind active site

DF-4 mouseTG2 SEMIWNFHCWVESWMTRPDLQPGYEGWQAIDPTPQEKSEGTYCCGPVS
rat SEMIWNFHCWVESWMTRPDLQPGYEGWQAIDPTPQEKSEGTYCCGPVS
human SEMIWNFHCWVESWMTRPDLQPGYEGWQALDPTPQEKSEGTYCCGPVP
**************************:**************.

Group 3: Location - rear of core junction with beta barrel-1
Encompasses Calcium binding site DD-9 and DH-2 mouseTG2 TYKYPEGSPEEREVFTKANHLNKLAEKEETGVAMRIRVG
rat TYKYPEGSPEEREVFTRANHLNKLAEKEETGVAMRIRVG
human TYKYPEGSSEEREAFTRANHLNKLAEKEETGMAMRIRVG
******..:***********:*****

FIG. 5

Antibody AB-1

AB1 VH

GAAGTACAGCTGGAGGAGTCAGGGGGGGGCTTAGTGAAGCCTGGAGGGTCCCTGAAA
CTCTCCTGTGCAGCCTCTGGATTCACTCTCAGTTCCTCTGCCATGTCTTGGGTTCGC
CAGACTCCGGACAGGAGGCTGGAGTGGGTCGCAACCATTAGTGTTGGTGGTGGTAAA
ACCCACTATCCAGACAGTGTGAAGGGTCGCTTCACCATCTCCAGAGACAATGCCAAG
AACACCCTCTATCTGCAAATGAACAGTCTGAGGTCTGAGGACACGGCCATGTATTAC
TGTGCAAAACTAATCAGTCTCTACTGGGGCCAAGGCACCACTCTCACAGTCTCCTCA

AB1 VH

EVQLEESGGGLVKPGGSLKLSCAASGFTLSSSAMSWVRQTPDRRLEWVATISVGGGK
THYPDSVKGRFTISRDNAKNTLYLQMNSLRSEDTAMYYCAKLISLYWGQGTTLTVSS

AB1 VK

GACATCCAGATGACACAGACTCCATCTTCCATGTATGCATCTCTAGGAGAGAGAGTC
ACTATCACTTGCAAGGCGAGTCAGGACATTAATAGCTATTTAACCTGGTTCCAGCAG
AAACCAGGGAAATCTCCTAAGACCCTGATCTATCGTACAAATAGATTGTTTGATGGG
GTCCCATCCAGGTTCAGTGGCAGTGGATCTGGGCAAGATTTTTTTCTCACCATCAGC
AGCCTGGAATATGAAGATATGGGAATTTATTATTGTCTACAGTATGATGACTTTCCG
TACACGTTCGGAGGGGGGACCAAACTGGAAATAAAA

AB1 VK

DIQMTQTPSSMYASLGERVTITCKASQDINSYLTWFQQKPGKSPKTLIYRTNRLFDG
VPSRFSGSGSGQDFFLTISSLEYEDMGIYYCLQYDDFPYTFGGGTKLEIK

FIG. 7

A: TG inhibition
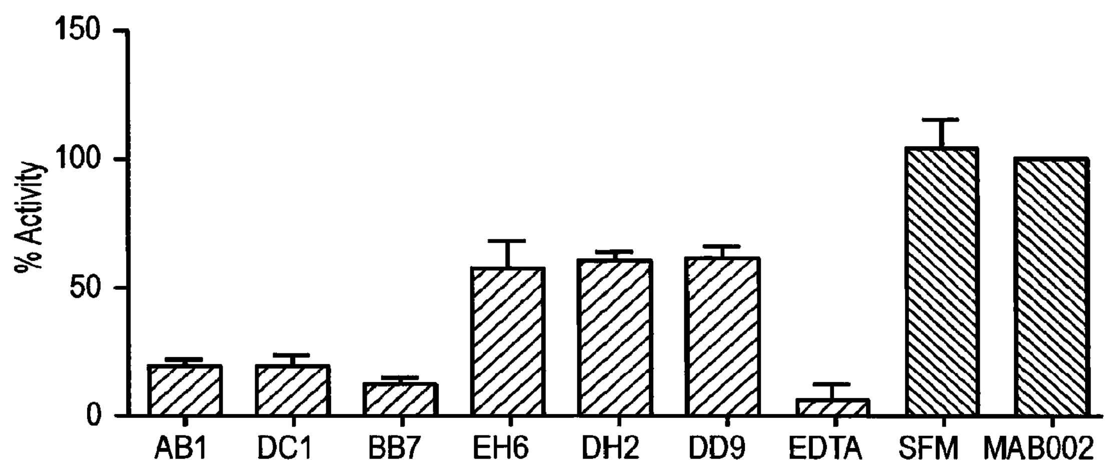
B: Western blot
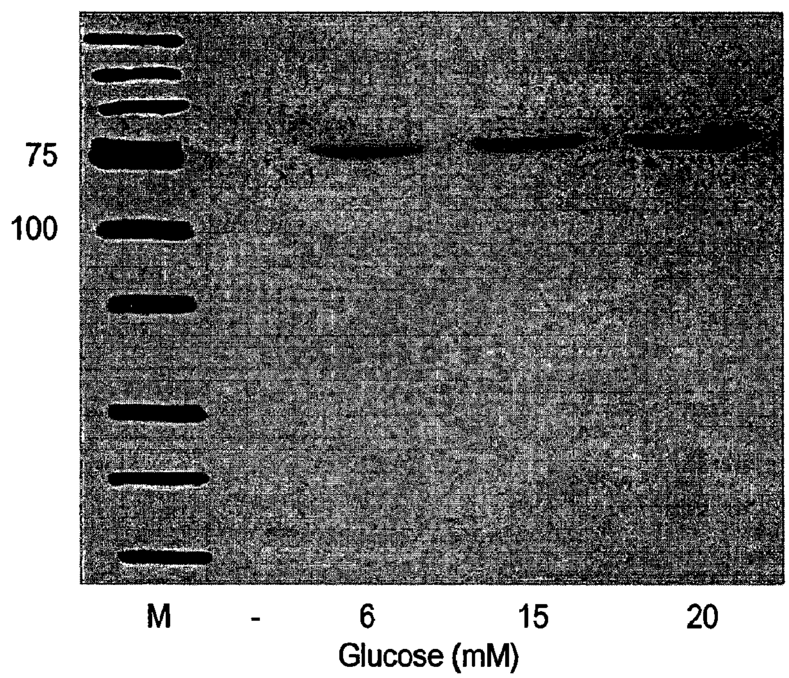
FIG. 8

| | IC50 hTG2 (mg/ml IgG per ng TG2) | IC50 rTG2 (mg/ml IgG per ng TG2) | IC50 mTG2 (mg/ml IgG per ng TG2) | Ratio human/rat | hTG2 IC50 ratio to best human inhibitor | rTG2 IC50 ratio to best human inhibitor |
|---|---|---|---|---|---|---|
| AB1 | $1.09 \times 10^{-5}$ | NI | NI | - | 1 | - |
| DC1 | $1.23 \times 10^{-5}$ | NI | NI | - | 1.1 | - |
| BB7 | $1.59 \times 10^{-5}$ | $3.2 \times 10^{-4}$ | NI | 20 | 1.47 | 29.4 |
| AG9 | $4.87 \times 10^{-5}$ | NI | NI | - | 4.47 | - |
| DD9 | $5.24 \times 10^{-5}$ | $3.03 \times 10^{-4}$ | NI | 6 | 4.87 | 29.22 |
| DH2 | $6.7 \times 10^{-5}$ | $2.23 \times 10^{-4}$ | NI | - | 6.2 | 38.13 |
| EH6 | $6.9 \times 10^{-5}$ | $4.03 \times 10^{-4}$ | NI | 5.8 | 6.33 | 36.714 |
| AH3 | $7.8 \times 10^{-5}$ | NI | NI | - | 7.1 | - |
| JE12 | $12.3 \times 10^{-6}$ | NI | NI | - | 11.3 | - |

FIG. 9

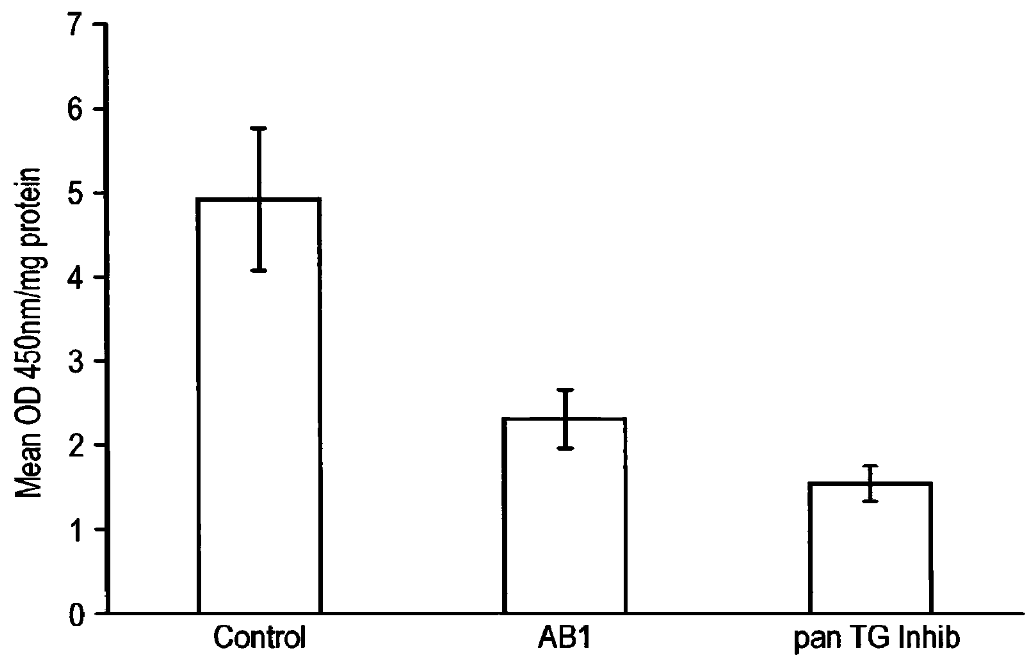
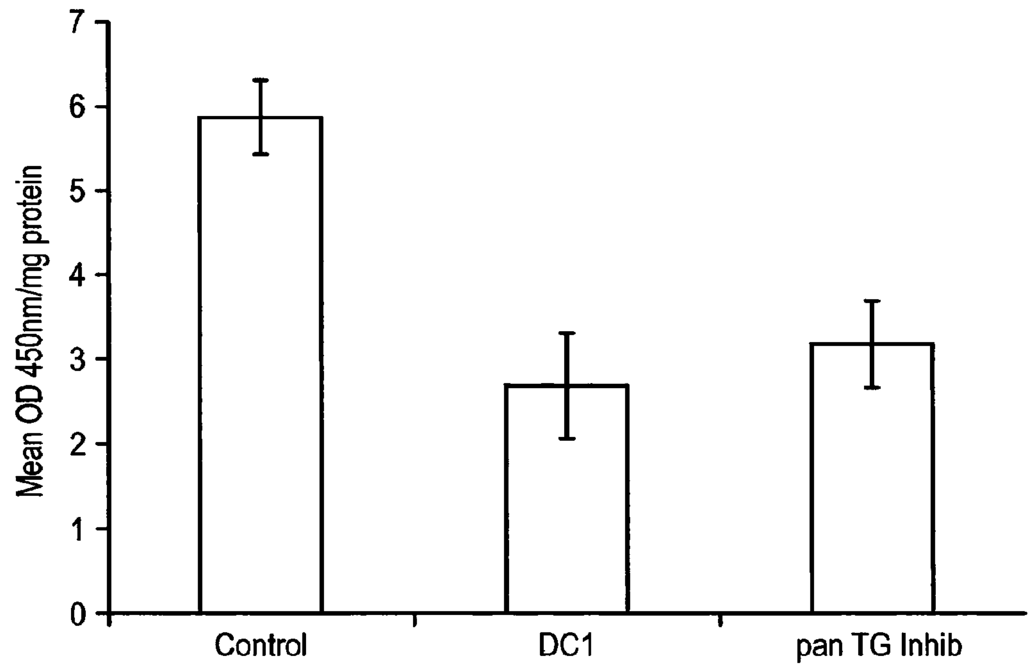
FIG. 10

Antibody AB-1

AB1 VH

GAAGTGCAGCTGGTGGAGTCTGGGGGGGGCTTAGTGAAGCCTGGAGGGTCCCTGAAACTCTC
CTGTGCAGCCTCTGGATTCACTCTCAGTTCCTCTGCCATGTCTTGGGTTCGCCAGACTCCGG
ACAGGAGGCTGGAGTGGGTCGCAACCATTAGTGTTGGTGGTGGTAAAACCTACTATCCAGAC
AGTGTGAAGGGTCGCTTCACCATCTCCAGAGACAATGCCAAGAACACCCTCTATCTGCAAAT
GAACAGTCTGAGGTCTGAGGACACGGCCATGTATTACTGTGCAAAACTAATCAGTCTCTACT
GGGGCCAAGGCACCACTCTCACAGTCTCCTCA

AB1 VH

EVQLVESGGGLVKPGGSLKLSCAASGFTLSSSAMSWVRQTPDRRLEWVATISVGGGKTYYPD
SVKGRFTISRDNAKNTLYLQMNSLRSEDTAMYYCAKLISLYWGQGTTLTVSS

AB1 VK

GACATCAAGATGACCCAGTCTCCATCTTCCATGTATGCATCTCTAGGAGAGAGAGTCACTAT
CACTTGCAAGGCGAGTCAGGACATTAATAGCTATTTAACCTGGTTCCAGCAGAAACCAGGGA
AATCTCCTAAGACCCTGATCTATCGTACAAATAGATTGTTTGATGGGGTCCCATCCAGGTTC
AGTGGCAGTGGATCTGGGCAAGATTTTTTTCTCACCATCAGCAGCCTGGAATATGAAGATAT
GGGAATTTATTATTGTCTACAGTATGATGACTTTCCGTACACGTTCGGAGGGGGGACCAAAC
TGGAAATAAAA

AB1 VK

DIKMTQSPSSMYASLGERVTITCKASQDINSYLTWFQQKPGKSPKTLIYRTNRLFDGVPSRF
SGSGSGQDFFLTISSLEYEDMGIYYCLQYDDFPYTFGGGTKLEIK

FIG. 18

Antibody BB-7

BB7 VH

GCAGTGCAACTGGTAGAGTCTGGGGGAGGCTTGGTGAAGCCTGGAGGGTCCCTGAAACTCTC
CTGTGCAGCCTCTGGAATCATTTTCAGTTCCTCTGCCATGTCTTGGGTTCGCCAGACTCCGG
AAAAGAGACTGGAGTGGGTCGCAACTATTAGTAGTGGTGGTCGTTCCACCTACTATCCAGAC
AGTGTGAAGGGTCGATTCACCGTCTCCAGAGACAGTGCCAAGAACACCCTATACCTGCAAAT
GGACAGTCTGAGGTCTGAGGACACGGCCATTTATTACTGTGCAAAACTAATCAGTCCCTACT
GGGGCCAAGGCACCACTCTCACAGTCTCCTCA

BB7 VH

AVQLVESGGGLVKPGGSLKLSCAASGIIFSSSAMSWVRQTPEKRLEWVATISSGGRSTYYPD
SVKGRFTVSRDSAKNTLYLQMDSLRSEDTAIYYCAKLISPYWGQGTTLTVSS

BB7 VK

GCCATCAAGATGACCCAGTCTCCATCTTCCATGTATGCATCTCTAGGAGAGAGAGTCATCAT
CACTTGCAAGGCGAGTCAGGACATAAATAGTTATTTAACCTGGTTCCAACAGAAACCAGGAA
AGTCTCCTAAGACCCTGATCTATCTTACAAATAGATTGATGGATGGGGTCCCATCAAGGTTC
AGTGGCAGTGGATCTGGGCAAGAATTTTTACTCACCATCAGCGGCCTGGAACATGAAGATAT
GGGCATTTATTATTGTCTCCAGTATGTTGACTTTCCGTACACGTTCGGAGGGGGGACCAAGC
TGGAAATAAAA

BB7 VK

AIKMTQSPSSMYASLGERVIITCKASQDINSYLTWFQQKPGKSPKTLIYLTNRLMDGVPSRF
SGSGSGQEFLLTISGLEHEDMGIYYCLQYVDFPYTFGGGTKLEIK

FIG. 19

Antibody DC-1

DC1 VH
GAAGTGCAGTTGGTGGAGTCTGGGGGAGGCTTAGTGAAGCCTGGAGGGTCCCTGAAACTCTC
CTGTGCAGCCTCTGGATTCACTCTCAGTACCCATGCCATGTCTTGGGTTCGCCAGACTCCGG
AGAAGAGGCTGGAGTGGGTCGCAACCATTAGTAGTGGTGGTCGTTCCACCTACTATCCAGAC
AGTGTGAAGGGTCGATTCACTATCTCCAGAGACAATGTCAAGAACACCCTATATCTGCAACT
GAGCAGTCTGAGGTCTGAGGACACGGCCGTGTATTTCTGTGCAAGACTAATCAGTACCTACT
GGGGCCAAGGCACCACTCTCACAGTCTCCTCA

DC1 VH
EVQLVESGGGLVKPGGSLKLSCAASGFTLSTHAMSWVRQTPEKRLEWVATISSGGRSTYYPD
SVKGRFTISRDNVKNTLYLQLSSLRSEDTAVYFCARLISTYWGQGTTLTVSS

DC1 VK
GACATCACGATGACCCAGTCTCCATCTTCCATATATGCATCTCTGGGAGAGAGAGTCACTAT
CACTTGCAAGGCGAGTCAGGACATTAATAGCTATTTAACCTGGTTCCAGCAGAAACCAGGGA
AATCTCCTAAGATCCTGATCTATCTTGTAAATAGATTGGTAGATGGGGTCCCATCAAGGTTC
AGTGGCAGTGGATCTGGGCAAGATTATGCTCTCACCATCAGCAGTCTGGAATATGAAGATAT
GGGAATTTATTATTGTCTACAATATGATGACTTTCCGTACACGTTCGGAGGGGGGACCAAGC
TGGAAATAAAA

DC1 VK
DITMTQSPSSIYASLGERVTITCKASQDINSYLTWFQQKPGKSPKILIYLVNRLVDGVPSRF
SGSGSGQDYALTISSLEYEDMGIYYCLQYDDFPYTFGGGTKLEIK

FIG. 20

Antibody JE-12

JE12 VH

GAGGTCCAGCTGCAGCAGTCTGGACCTGAGCTGGTAAAGCCTGGGGCTTCAGTGAAGATGTC
CTGCAAGGCTTCTGGATACAGATTCACTAGCTATGTTATGCACTGGGTGAAACAGAAGTCTG
GGCAGGGCCTTGAGTGGATTGGATATATTAATCCTTACAATGATGGTGCTAAGTACAATGAG
AAGTTCAAAGGCAAGGCCACACTGACTTCAGACAAATCCTCCAGCACAGCCTACATGGAGCT
CAGCAGCCTGACCTCTGAGGACTCTGCGGTCTATTACTGTGCAAGACTATCTAGTGACTATT
GGGGCCAAGGCACCACTCTCACAGTCTCCTCA

JE12 VH

EVQLQQSGPELVKPGASVKMSCKASGYRFTSYVMHWVKQKSGQGLEWIGYINPYNDGAKYNE
KFKGKATLTSDKSSSTAYMELSSLTSEDSAVYYCARLSSDYWGQGTTLTVSS

JE12 VK

GATGTTTTGATGACCCAAAATCCACTCTCCCTGCCTGTCAGTCTTGGAGATCAAGCCTCCAT
CTCTTGCAGATCTAGTCAGAGCATTGAACATATTAATGGAAACACCTATTTAGAATGGTACC
TGCAGAAACCAGGCCAGTCTCCAAAGTTCCTGATCTACAAAGTTTCCAACCGATTTTCTGGG
GTCCCAGACAGGTTCAGTGGCAGTGGATCAGGGACAGATTTCACACTCAGGATCAGCAGAGT
GGAGGCTGAAGATCTGGGAATTTATTACTGCTTTCAAGGTTCACATGTTCCGTTCACGTTCG
GAGGGGGGACCAAGCTGGAAATAAAA

JE12 VK

DVLMTQNPLSLPVSLGDQASISCRSSQSIEHINGNTYLEWYLQKPGQSPKFLIYKVSNRFSG
VPDRFSGSGSGTDFTLRISRVEAEDLGIYYCFQGSHVPFTFGGGTKLEIK

FIG. 21

Antibody EH-6

EH6 VH

GAGGTCCAGCTGCAGCAGTCTGGACCTGAGCTGGTAAAGCCTGGGGCTTCAGTGAAGATGTC
CTGCAAGGCTTCTGGATACACATTCACTAGTTATGTTATGCACTGGGTGAAGCAGAAGCCTG
GGCAGGGCCTTGAGTGGATTGGATTTATTAATCCTTACAATGATGGTACTAAGTACAATGAG
AAGTTCAAAGGCAAGGCCACACTGACCTCAGACAAAGCCTCCACCACAGCCTACATGGAGCT
CAGCAGCCTGACCTCTGAGGACTCTGCGGTCTATTACTGTGCAAGATTCTCCTCTGGGTACT
GGGGCCAAGGCACCACTCTCACAGTCTCCTCA

EH6 VH

EVQLQQSGPELVKPGASVKMSCKASGYTFTSYVMHWVKQKPGQGLEWIGFINPYNDGTKYNE
KFKGKATLTSDKASTTAYMELSSLTSEDSAVYYCARFSSGYWGQGTTLTVSS

EH6 VK

GATGTTTTGATGACCCAAACTCCACTCTCCCTGCCTGTCAGTCTTGGAGATCAAGCCTCCAT
CTCTTGCAGATCTAGTCAGAGTATTGTACATAGTAATGGAAACACCTATTTAGAATGGTACC
TGCAGAAACCAGGCCAGTCTCCAAAGCTCCTGATCTACAAAGTTTCCAATCGATTTTCTGGG
GTCCCAGACAGGTTCAGTGGCAGTGGATCAGGGACAGATTTCACACTCAAGATCAGCAGAGT
GGGGGCTGAGGATCTGGGAGTTTATTACTGCCTTCAAGTTTCACATGTTCCTTTCACGTTCG
GCTCGGGGACAAAGTTGGAAATAAAA

EH6 VK

DVLMTQTPLSLPVSLGDQASISCRSSQSIVHSNGNTYLEWYLQKPGQSPKLLIYKVSNRFSG
VPDRFSGSGSGTDFTLKISRVGAEDLGVYYCLQVSHVPFTFGSGTKLEIK

FIG. 22

Antibody AG-9

AG9 VH
GAGGTCCAGCTGCAGCAGTCTGGACCTGAGTTGGTAAAGCCTGGGGCTTCAGTGAAGATGTC
CTGCAGGGCTTCTGGATACACATTCACTACCTATGTTATTCACTGGGTGAAGCAGAAGCCTG
GGCAGGGCCTTGAGTGGATTGGATATATTAATCCTTACAATGATGGTGCTAGGTACAATGAG
AAGTTCAAAGGCAAGGCCACACTGACTTCAGACAAATCCTCCACCACAGCCTACATGGAACT
CAGCAGCCTGACCTCTGAGGACTCTGCGGTCTATTACTGTGCAAGACTTTCTAGTGACTACT
GGGGCCAAGGCACCACTCTCACAGTCTCCTCA

AG9 VH
EVQLQQSGPELVKPGASVKMSCRASGYTFTTYVIHWVKQKPGQGLEWIGYINPYNDGARYNE
KFKGKATLTSDKSSTTAYMELSSLTSEDSAVYYCARLSSDYWGQGTTLTVSS

AG9 VK
GATGTTTTGATGACCCAAAATCCACTCTCCCTGCCTGTCAGTCTTGGCGATCAGGCCTCCAT
CTCTTGCAGATCTAGTCGGAGCATTGAACATAGTAATGGAAACACCTATTTGGAATGGTACC
TGCAGAAACCAGGCCAGTCTCCAAAGTTCCTGATCTACAAAGTTTCCAACCGATTTTCTGGG
GTCCCAGACAGGTTCAGTGGCAGTGGATCAGGGACAGATTTCACACTCAGGATCAGCAGTGT
GGAGGCTGAGGATCTGGGAGTTTATTACTGCTTTCAAGGTTCACATGTTCCGTTCACGTTCG
GAGGGGGGACCAAGCTGGAAATAAAA

AG9 VK
DVLMTQNPLSLPVSLGDQASISCRSSRSIEHSNGNTYLEWYLQKPGQSPKFLIYKVSNRFSG
VPDRFSGSGSGTDFTLRISSVEAEDLGVYYCFQGSHVPFTFGGGTKLEIK

FIG. 23

Antibody AH-3

AH3 VH

GAGGTCCAGCTGCAGCAGTCTGGACCTGAGCTGGTAAAGCCTGGGGCTTCAGTGAAGATGTC
CTGCAGGGCTTCTGGATACACATTCACTACCTATGTTATTCACTGGGTGAAGCAGAAGCCTG
GGCAGGGCCTTGAGTGGATTGGATATATTAATCCTTACAATGATGGTGCTAGGTACAATGAG
AAGTTCAAAGGCAAGGCCACACTGACTTCAGACAAATCCTCCACCACAGCCTACATGGAACT
CAGCAGCCTGACCTCTGAGGACTCTGCGGTCTATTACTGTGCAAGACTATCTAGTGACTACT
GGGGCCAAGGCACCACTCTCACAGTCTCCTCA

AH3 VH

EVQLQQSGPELVKPGASVKMSCRASGYTFTTYVIHWVKQKPGQGLEWIGYINPYNDGARYNE
KFKGKATLTSDKSSTTAYMELSSLTSEDSAVYYCARLSSDYWGQGTTLTVSS

AH3 VK

GATGTTTTGATGACCCAAAATCCACTCTCCCTGCCTGTCAGTCTTGGAGATCAGGCCTCCAT
CTCTTGCAGATCTAGTCGGAGCATTGAACATAGTAATGGAAACACCTATTTGGAATGGTACC
TGCAGAAACCAGGCCAGTCTCCAAAGTTCCTGATCTACAAAGTTTCCAACCGATTTTCTGGG
GTCCCAGACAGGTTCAGTGGCAGTGGATCAGGGACAGATTTCACACTCAGGATCAGCAGTGT
GGAGGCTGAGGATCTGGGAGTTTATTACTGCTTTCAAGGTTCACATGTTCCGTTCACGTTCG
GAGGGGGGACCAAGCTGGAAATAAAA

AH3 VK

DVLMTQNPLSLPVSLGDQASISCRSSRSIEHSNGNTYLEWYLQKPGQSPKFLIYKVSNRFSG
VPDRFSGSGSGTDFTLRISSVEAEDLGVYYCFQGSHVPFTFGGGTKLEIK

FIG. 24

Antibody DD-9

DD9 VH
CAGGTTACTCTGAAAGAGTCTGGCCCTGGGATATTGCAGCCCTCCCAGACCCTCAGTCTGAC
TTGTTCTTTTTCTGGGTTTTCACTGAGCACTTCGGGTATGGGTGTGAGTTGGATTCGTCAGT
CCTCAGGAAAGGGTCTGGAGTGGCTGGCACACATTTACTGGGATGATGACAAGCGCTATAAC
CCATCCCTGAAGAGCCGGATCACAATCTCCAAGGATTCCTCAAGCAACCAGGTATTCCTCAA
GATCACCAGTGTGGACACTGCAGATACTGCCACATATTACTGTGCTCGAAGTTGGACTACGG
CCCCGTTTGCTTTCTGGGGCCAAGGGACTCTGGTCACTGTCTCTGCA

DD9 VH
QVTLKESGPGILQPSQTLSLTCSFSGFSLSTSGMGVSWIRQSSGKGLEWLAHIYWDDDKRYN
PSLKSRITISKDSSSNQVFLKITSVDTADTATYYCARSWTTAPFAFWGQGTLVTVSA

DD9 VK
CAAATTGTTCTCACCCAGTCTCCAGCAATCATGTCTGCATCTCCAGGGGAGAAGGTCACCAT
GACCTGCAGTGCCAGCTCAAGTGTAGATTACATGTACTGGTACCAGCAGAAGCCAGGATCCT
CCCCCAGACTCCTGATTTATGACACATCCAACCTGGCTTCTGGAGTCCCTGTTCGCTTCAGT
GGCAGTGGGTCTGGGACCTCTTACTCTCTCACAATCAGCCGAATGGGGGCTGAAGATGCTGC
CACTTATTACTGCCAACAGTGGAATAGTTCCCCGCTCACGTTCGGTGCTGGGACCAAGCTGG
AGCTGAAA

DD9 VK
QIVLTQSPAIMSASPGEKVTMTCSASSSVDYMYWYQQKPGSSPRLLIYDTSNLASGVPVRFS
GSGSGTSYSLTISRMGAEDAATYYCQQWNSSPLTFGAGTKLELK

FIG. 25

Antibody DH-2

DH2 VH

CAGGTTACTCTGAAAGAGTCTGGCCCTGGGATATTGCAGCCCTCCCAGACCCTCAGTCTGAC
TTGTTCTTTCTCTGGGTTTTCACTGAGCACTTCTGGTATGGGTGTGAGCTGGATTCGTCAGC
CTTCAGGAAAGGGTCTGGAGTGGCTGGCACACATTTACTGGGATGATGACAAGCGCTATAAC
CCATCCCTGAAGAGCCGGCTCACAATCTCCAAGGATACCTCCAGCAACCAGGTATTCCTCAA
GATCACCAGTGTGGACACTGCAGATACTGCCACATACTACTGTGCTCGAAGTGGGACTACGG
CCCCGTTTGCTTACTGGGGCCAAGGGACTCTGGTCACTGTCTCTGCA

DH2 VH

QVTLKESGPGILQPSQTLSLTCSFSGFSLSTSGMGVSWIRQPSGKGLEWLAHIYWDDDKRYN
PSLKSRLTISKDTSSNQVFLKITSVDTADTATYYCARSGTTAPFAYWGQGTLVTVSA

DH2 VK

CAAATTGTTCTCACTCAGTCTCCAGCAATCATGTCTGCATCTCCAGGGGAGAAGGTCACCAT
GACCTGCAGTGCCAGCTCAAGTGTAAGTTACATGTACTGGTACCAGCAGAAGCCAGGATCCT
CCCCCAGACTCCTGATTTATGACACATCCAACCTGGCTTCTGGAGTCCCTGTTCGCTTCAGT
GGCAGTGGGTCTGGGACCTCTTACTCTCTCACAATCAGCCGAATGGAGGCTGAAGATGCTGC
CACTTTTTACTGCCAGCAGTGGAGTAGTTCCCCGCTCACGTTCGGTGCTGGGACCAAGCTGG
AGCTGAAA

DH2 VK

QIVLTQSPAIMSASPGEKVTMTCSASSSVSYMYWYQQKPGSSPRLLIYDTSNLASGVPVRFS
GSGSGTSYSLTISRMEAEDAATFYCQQWSSSPLTFGAGTKLELK

FIG. 26

Antibody DD-6

DD6 VH

GAGGTCCAGCTGCAACAGTCTGGGCCTGAACTGGTGAAGCCTGGGGCTTCAGTGAAGATGTC
CTGCAAGGCTTCTGGATACAGATTCACTGACTACAACATGCACTGGGTGAAGCAGAACCTTG
GAAAGAGCCTTGAGTGGATTGGATATATTAACCCTAAAAATGGTGTTATTTACTACAACCAG
AAGTTCAAGGGCAAGGCCACATTGACAGTGAACAGGTCCTCCAACACAGCCTACATGGAGAT
CCGCAGCCTGACATCGGAAGATTCTGCAGTCTATTACTGTGCAACAGCTCTGACTTACTGGG
GACAAGGGACTCTGGTCACTGTCTCTGCA

DD6 VH

EVQLQQSGPELVKPGASVKMSCKASGYRFTDYNMHWVKQNLGKSLEWIGYINPKNGVIYYNQ
KFKGKATLTVNRSSNTAYMEIRSLTSEDSAVYYCATALTYWGQGTLVTVSA

DD6 VL

CAGGCTGTTGTGACTCAGGAATCTGCACTCACCACATCACCTGGTGAAACAGTCACACTCAC
TTGTCGCTCAAGTACTGGGGCTGTTGCAGCTAATAACTATGCCAACTGGATCCAAGAAAAAC
CAGATCATTTATTCACTGGTCTGATAGCTGGTACCAACAAGCGAGCTCCAGGTGTTCCTGCC
AGATTCTCAGGCTCCCTGATAGGAGACAAGGCTGCCCTCACCATCACAGGGGCACAGACTGA
GGATGAGGCAATATATTTCTGTGCTCTATGGTACAGCAACTATTGGGTGTTCGGTGGAGGAA
CCAAAGTGACTGTCCTAGGC

DD6 VL

QAVVTQESALTTSPGETVTLTCRSSTGAVAANNYANWIQEKPDHLFTGLIAGTNKRAPGVPA
RFSGSLIGDKAALTITGAQTEDEAIYFCALWYSNYWVFGGGTKVTVLG

FIG. 27

Antibody IA-12

IA12 VH

CAGATCCAGTTGGTACAGTCTGGACCTGAGCTGAAGAAGCCTGGAGAGACAGTCAAGATCTC
CTGCAAGGCTTCTGGGTATACCTTCACAACCTATGGAATGACCTGGGTGAAACAGGCTCCAG
GAAAGGGTTTAAAGTGGATGGGCTGGATAAACACCTCCTCTGGAGTGCCAACATATGCTGAT
GACTTCAAGGGACGGTTTGCCTTCTCTTTGGAAACCTCTGCCAGCACTGCCTATTTGCAGAT
CAACAACCTCAAAAGTGAGGACACGGCTACATATTTCTGTGCAAGACCGGAAGTTGCTTACT
GGGGCCAAGGGACTCTGGTCACTGTCTCTGCA

IA12 VH

QIQLVQSGPELKKPGETVKISCKASGYTFTTYGMTWVKQAPGKGLKWMGWINTSSGVPTYAD
DFKGRFAFSLETSASTAYLQINNLKSEDTATYFCARPEVAYWGQGTLVTVSA

IA12 VK

GATGTTGTGATGACCCAGACTCCACTCACTTTGTCGGTTACCTTTGGACAACCAGCCTCTAT
CTCTTGCAAGTCAAGTCAGAGCCTCTTATATGATAATGGAAAGACTTATTTGCATTGGTTAT
TTCAGAGGCCAGGCCAGTCTCCAAGGCGCCTAATCTATCTGGTGTCTAAACTGGACTCTGGA
GTCCCTGACAGGTTCACTGGCAGTGGATCAGGAACAGATTTTACACTGAAAATCAGCAGAGT
GGAGGCTGAGGATTTGGGAGTTTATTACTGCGTGCAAGGTACACATTTTCCGTACACGTTCG
GAGGGGGGACCAAACTGGAAATAAAA

IA12 VK

DVVMTQTPLTLSVTFGQPASISCKSSQSLLYDNGKTYLHWLFQRPGQSPRRLIYLVSKLDSG
VPDRFTGSGSGTDFTLKISRVEAEDLGVYYCVQGTHFPYTFGGGTKLEIK

FIG. 28

A
| | IC50 nM (SD) |
|---|---|
| cAB003 | 1.172 (0.297) |
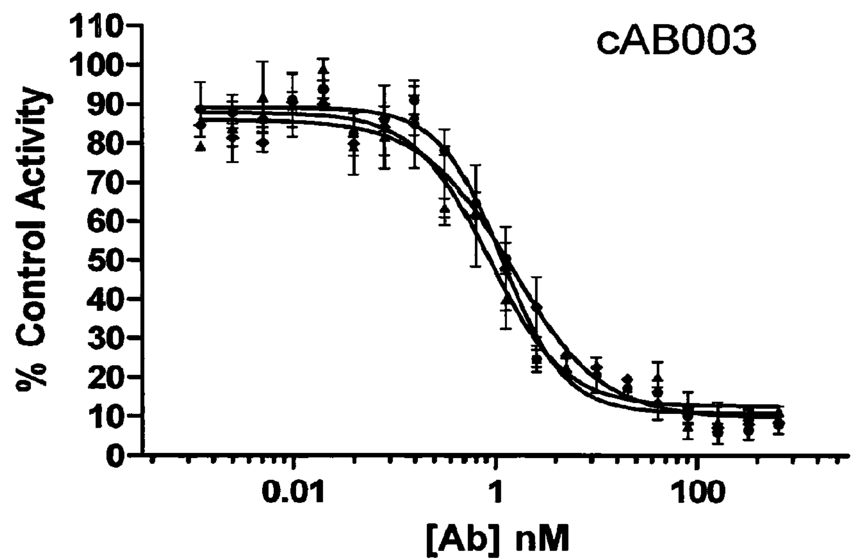
B
| | IC50 nM (SD) |
|---|---|
| cBB001 | 0.925 (0.228) |
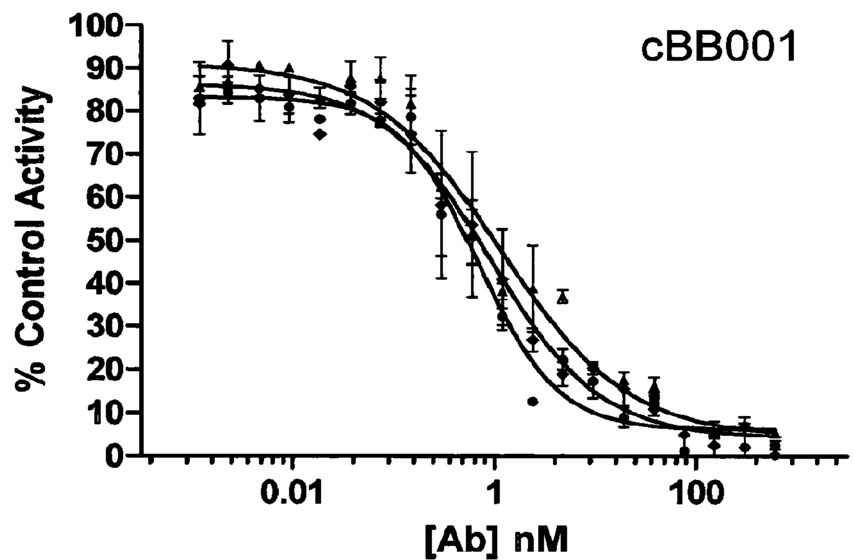
FIG. 29

C
| | IC50 nM (SD) |
|---|---|
| cDC001 | 0.851 (0.177) |
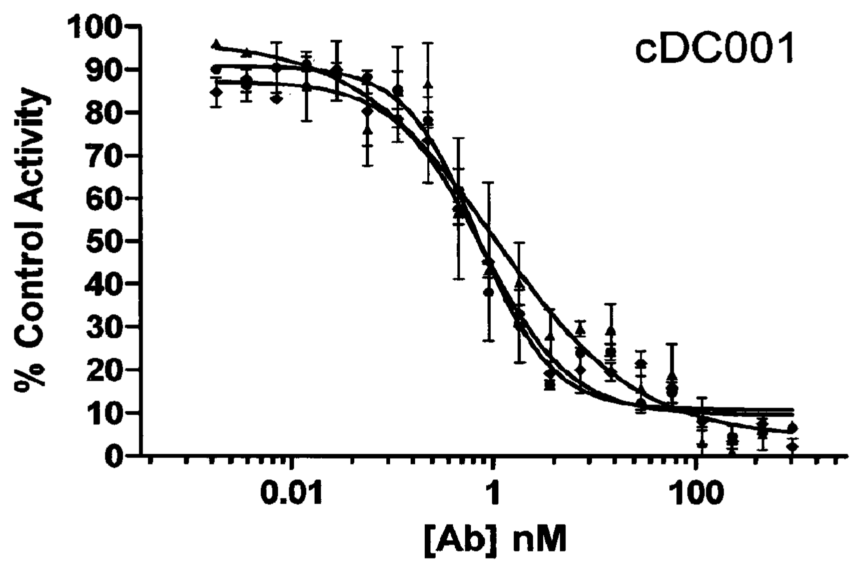
D
| | IC50 nM (SD) |
|---|---|
| cDD9001 | 172.033 (23.353) |
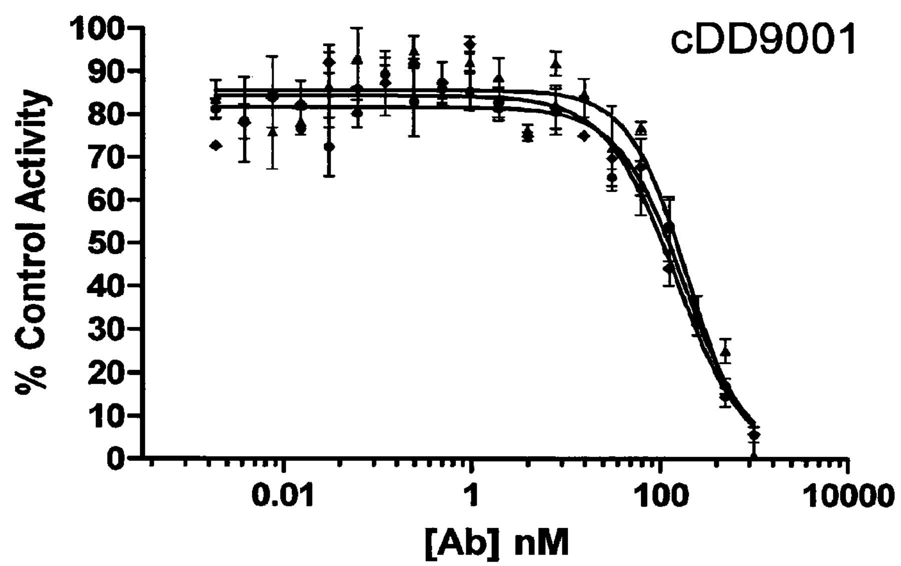
FIG. 29 (continued)

E
| | IC50 nM (SD) |
|---|---|
| cDH001 | 829.233 (59.923) |
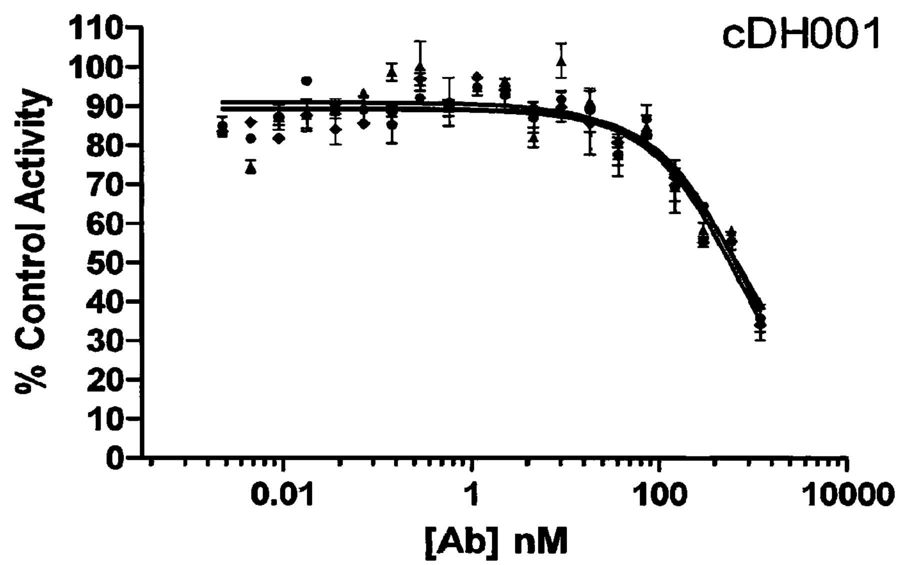
F
| | IC50 nM |
|---|---|
| CUB7402 | >100 |
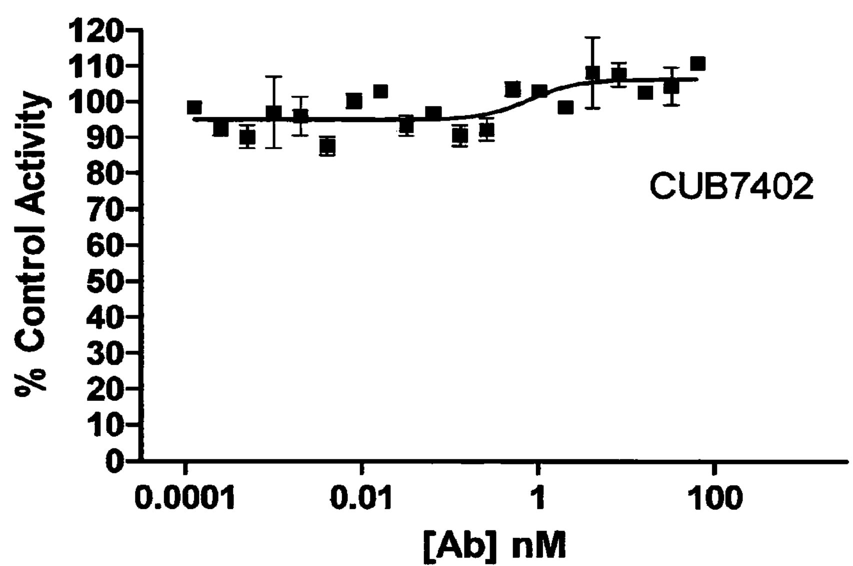
FIG. 29 (continued)

A
| | IC50 nM |
|---|---|
| cDC001 | 5.862 |
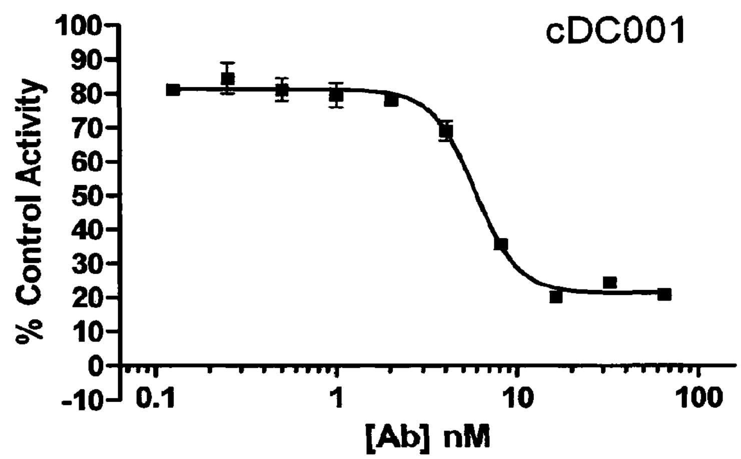
B
| | IC50 nM |
|---|---|
| CUB7402 | >100 |
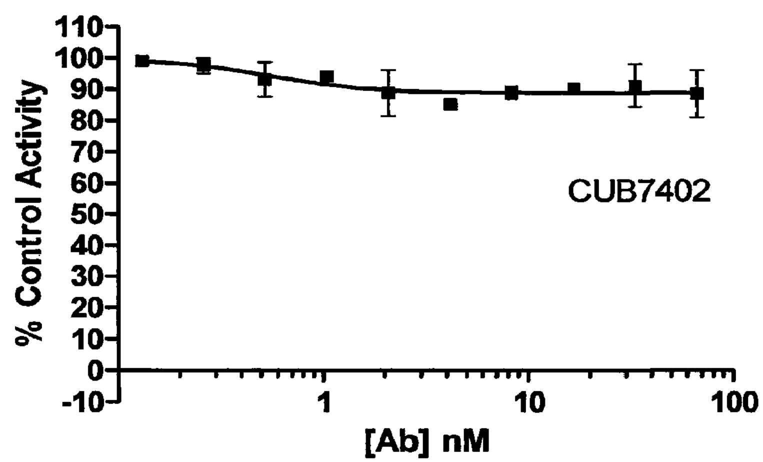
FIG. 30

A
| | IC50 nM (SD) |
|---|---|
| hBB001AA | 5.987 (2.643) |
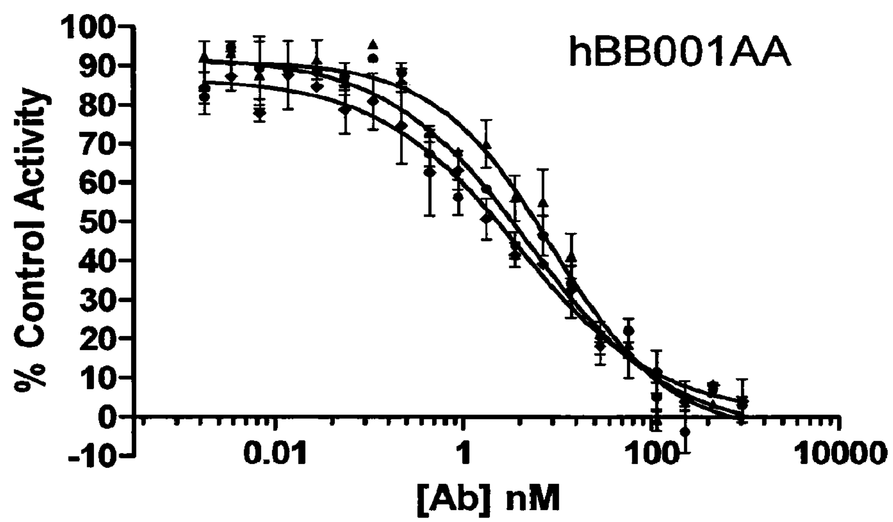
B
| | IC50 nM (SD) |
|---|---|
| hBB001BB | 0.985 (0.140) |
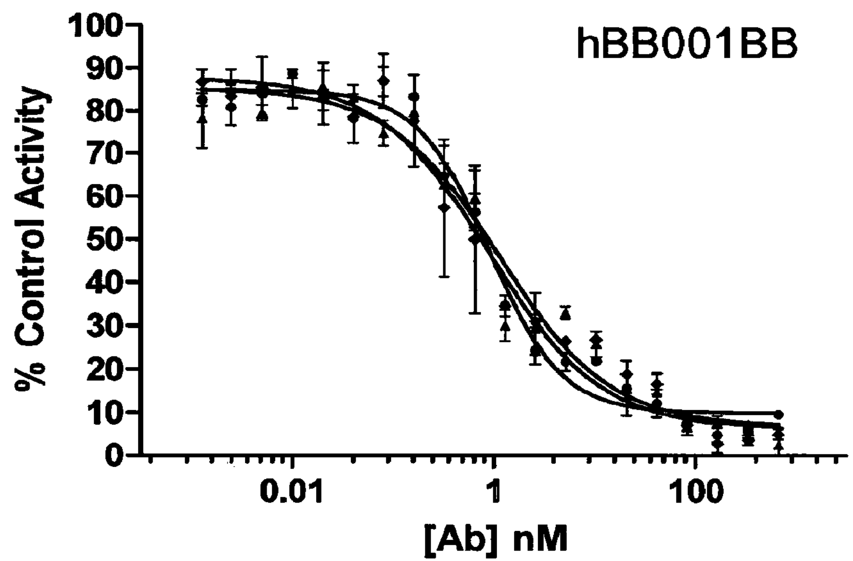
FIG. 31

C
| | IC50 nM (SD) |
|---|---|
| hAB005 | 6.868 (4.895) |
2 batches shown
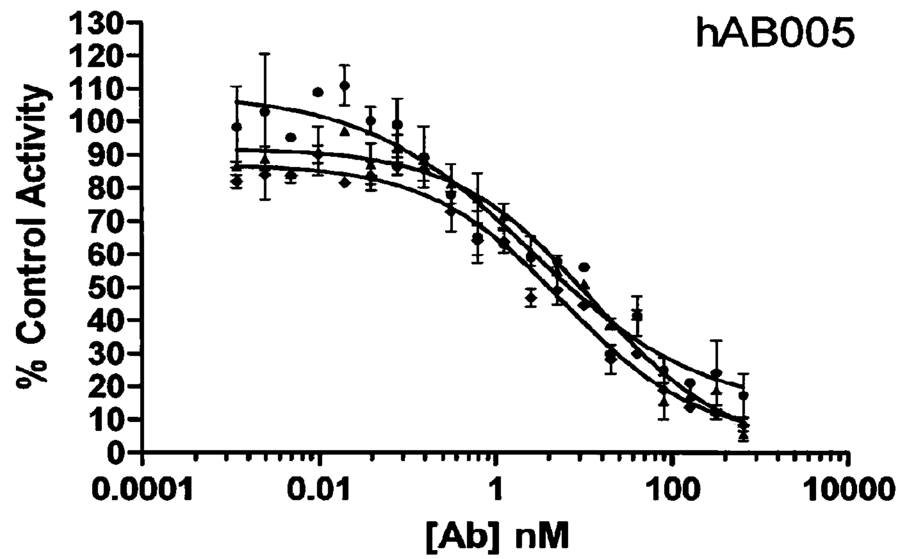
D
| | IC50 nM (SD) |
|---|---|
| hAB004 | 3.854 (0.886) |
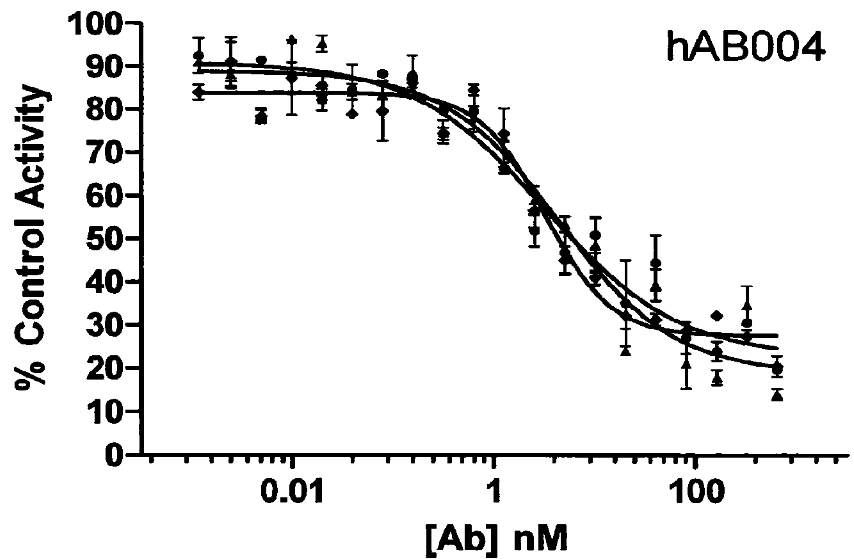
FIG. 31 (continued)

A
| | EC50 nM |
|---|---|
| mAB003 | 9.501 |
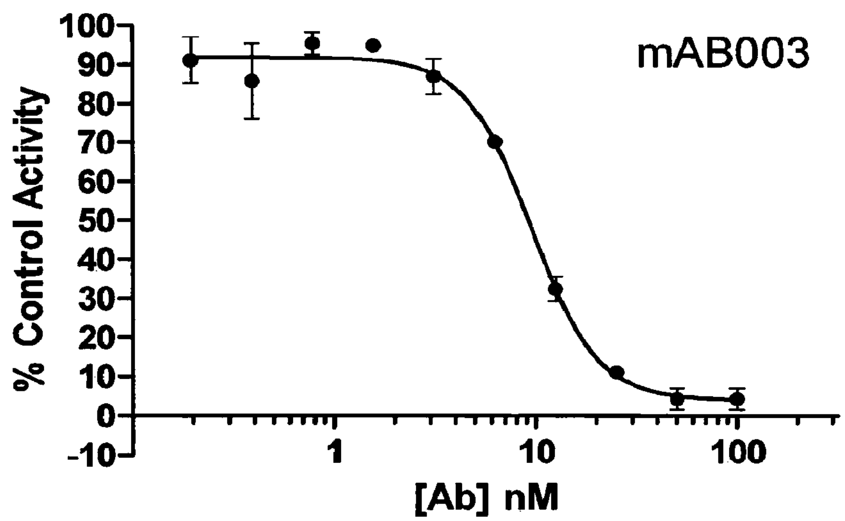
B
| | EC50 nM |
|---|---|
| mBB001 | 0.752 |
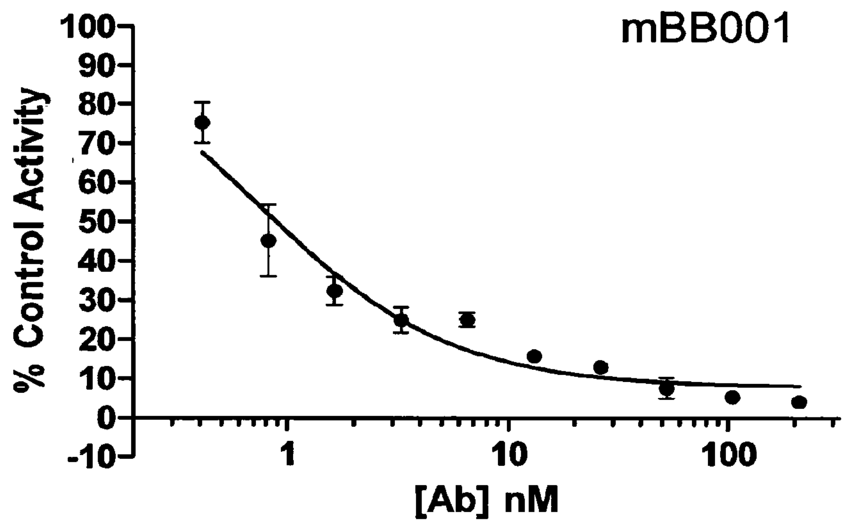
FIG. 33

C
| | EC50 nM (SD) |
|---|---|
| mDC001 | 0.5712 (0.2409) |
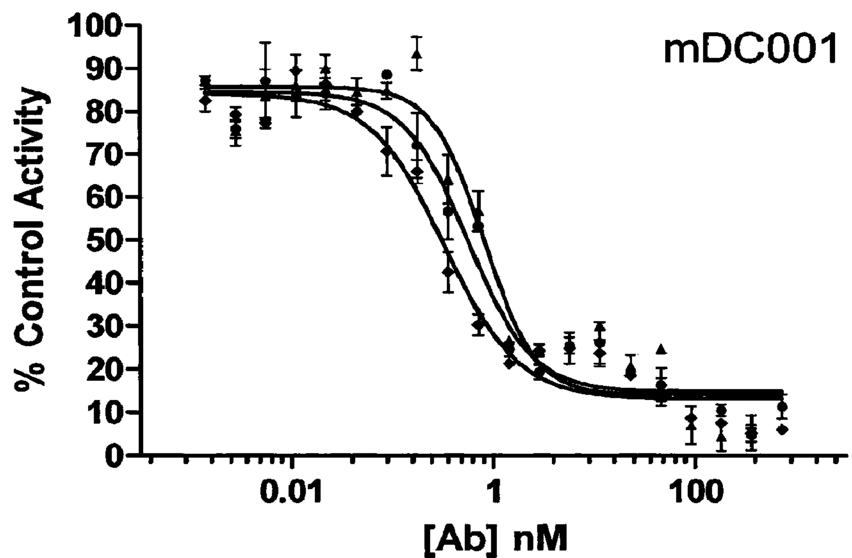
D
| | EC50 nM (SD) |
|---|---|
| mDD9001 | 564.233 (83.996) |
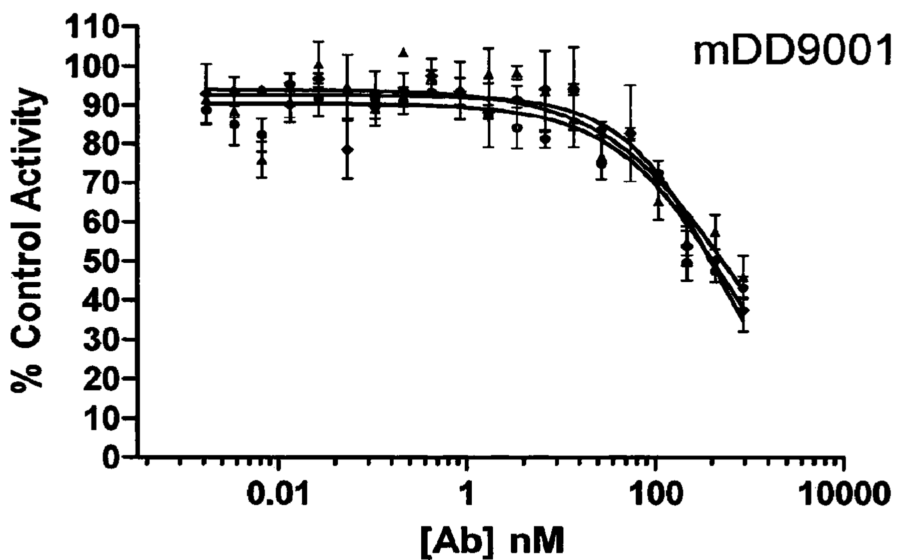
FIG. 33 (continued)

E
| | EC50 nM (SD) |
|---|---|
| mDH001 | ~7000 |
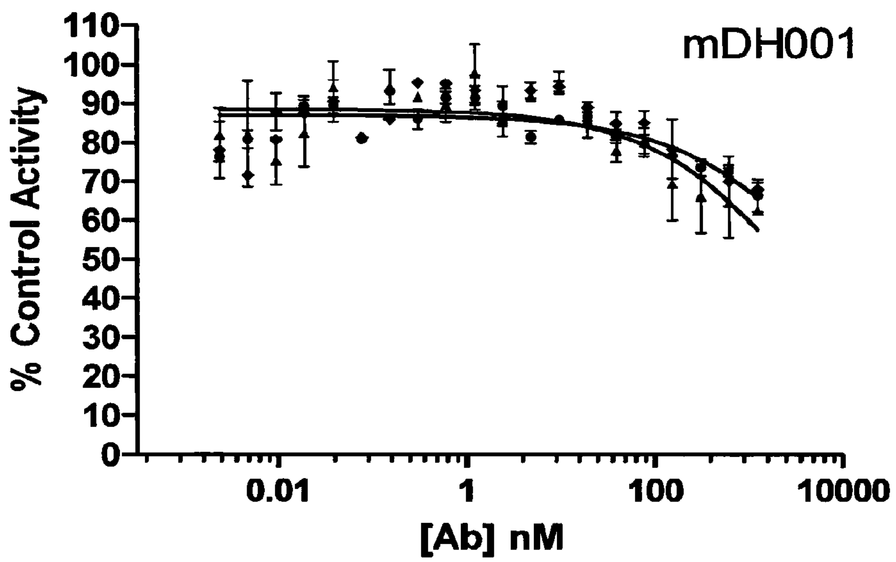
F
| | EC50 nM (SD) |
|---|---|
| mDD6001 | 43.196 (10.948) |
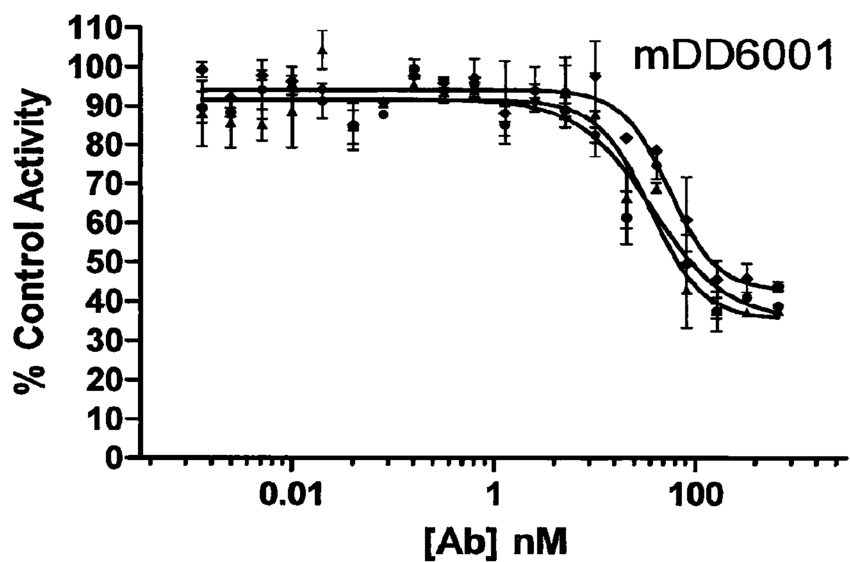
FIG. 33 (continued)

A

| | CUB7402 | CDD9001 | CDH001 | CDC001 |
|---|---|---|---|---|
| EC50 (nM) | 0.3804 | 0.2099 | 0.3401 | 0.4418 |
| r2 | 0.9991 | 0.998 | 0.9968 | 0.9985 |
| EC50 (95% confidence range) | 0.3291 to 0.4396 | 0.1860 to 0.2368 | 0.2890 to 0.4002 | 0.3927 to 0.4971 |

Figure 35:
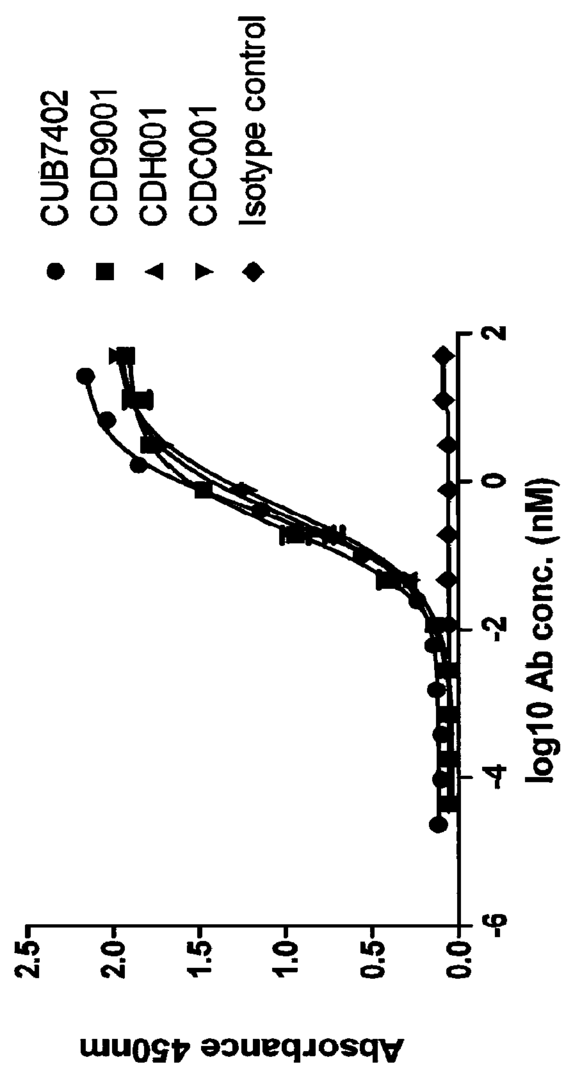

B
| | CBB001 |
|---|---|
| EC50 (nM) | 0.04811 |
| r2 | 0.9682 |
| EC50 (95% confidence range) | 0.03611 to 0.06410 |
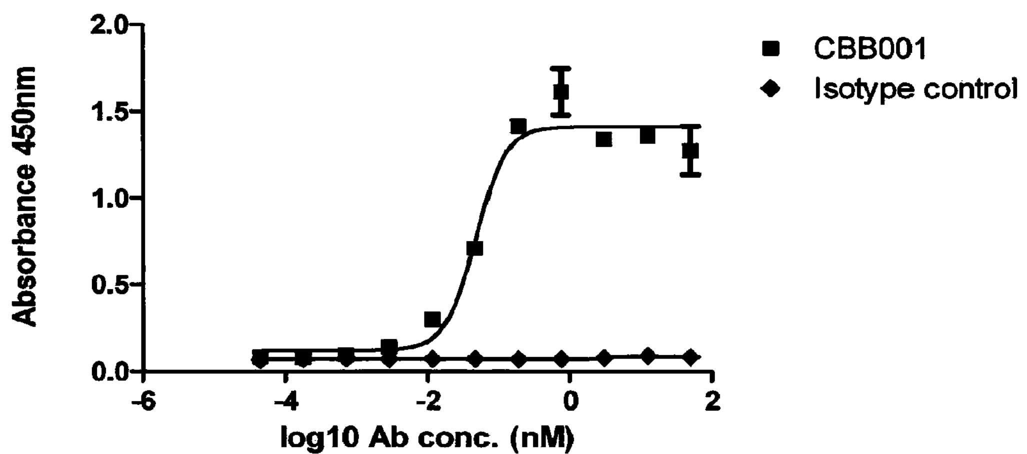
C
| | CAB003 |
|---|---|
| EC50 (nM) | 0.06141 |
| r2 | 0.9568 |
| EC50 (95% confidence range) | 0.03066 to 0.1230 |
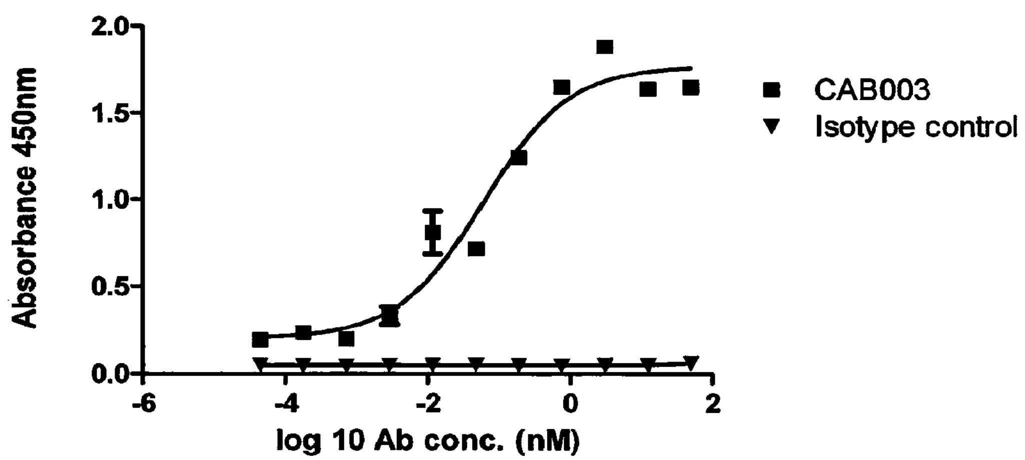
FIG. 35 (continued)

Figure 36:
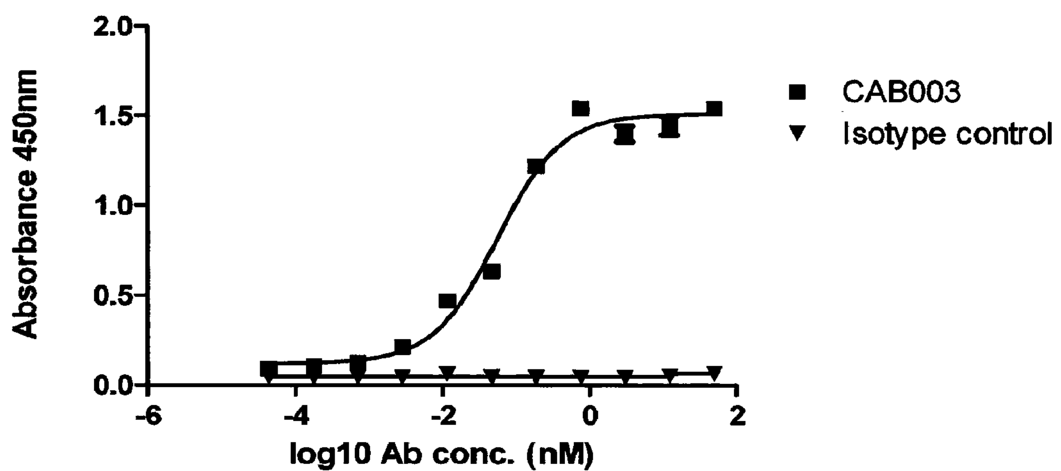

A
| | CUB7402 | CDD9001 | CDH001 | CDC001 |
|---|---|---|---|---|
| EC50 (nM) | 0.4161 | 0.3279 | 0.7385 | 0.4177 |
| r2 | 0.9994 | 0.9992 | 0.9986 | 0.9993 |
| EC50 (95% confidence range) | 0.3762 to 0.4603 | 0.3040 to 0.3536 | 0.6682 to 0.8162 | 0.3887 to 0.4489 |
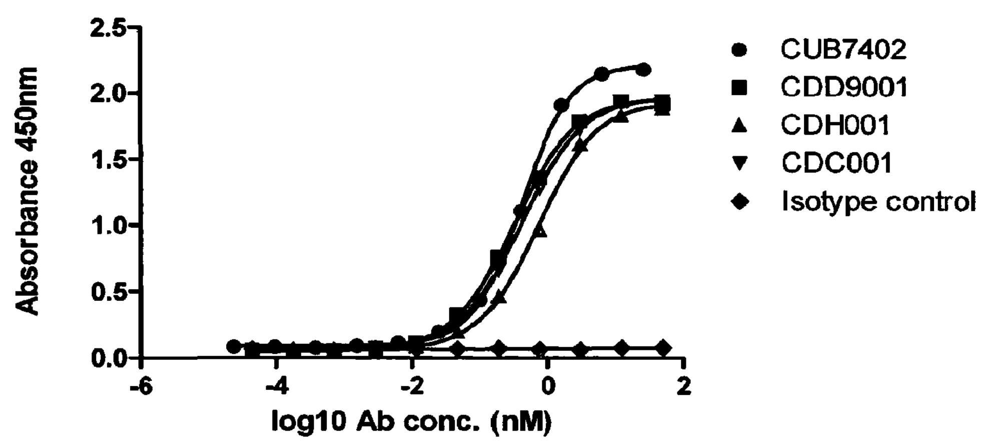
B
| | CBB001 |
|---|---|
| EC50 (nM) | 0.05166 |
| r2 | 0.9383 |
| EC50 (95% confidence range) | 0.03303 to 0.08079 |
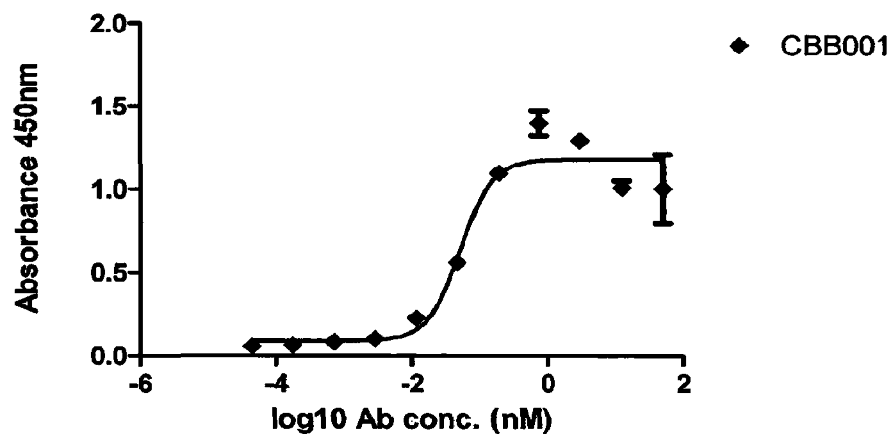
FIG. 36

C

| | CAB003 |
|---|---|
| EC50 (nM) | 0.05682 |
| r2 | 0.9837 |
| EC50 (95% confidence range) | 0.04054 to 0.07966 |

A
| | CUB7402 | HBB001AA | HBB001BB |
|---|---|---|---|
| EC50 (nM) | 0.1277 | ~ 0.04739 | 0.06274 |
| r2 | 0.9588 | 0.9792 | 0.9771 |
| EC50 (95% confidence range) | 0.06801 to 0.2396 | ND | 0.04636 to 0.08491 |
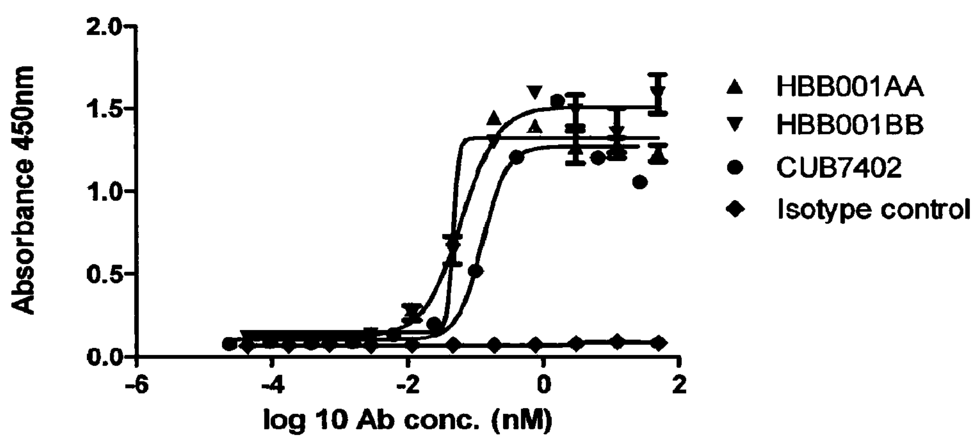
B
| | HAB004 |
|---|---|
| EC50 (nM) | 0.02001 |
| r2 | 0.9794 |
| EC50 (95% confidence range) | 0.01199 to 0.03342 |
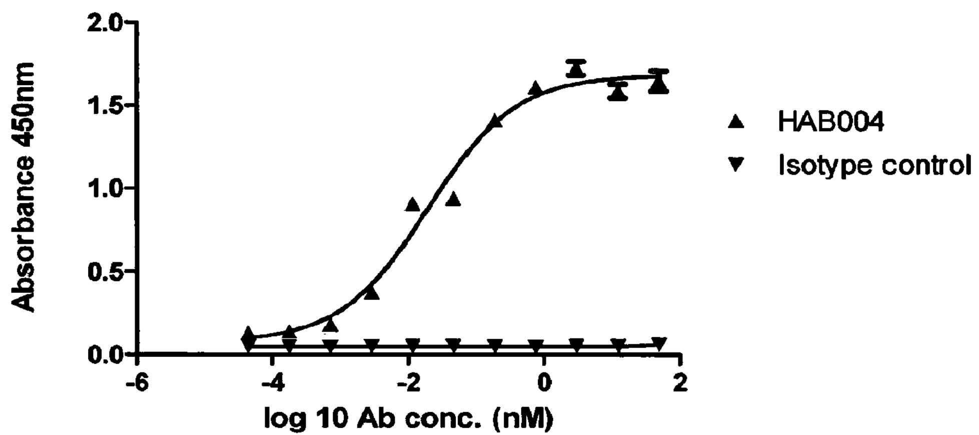
FIG. 37

A
| | CUB7402 | HBB001AA | HBB001BB |
|---|---|---|---|
| EC50 (nM) | 0.1982 | 0.0561 | 0.07377 |
| r2 | 0.9586 | 0.9329 | 0.9361 |
| EC50 (95% confidence range) | 0.09303 to 0.4223 | 0.03522 to 0.08934 | 0.04198 to 0.1296 |
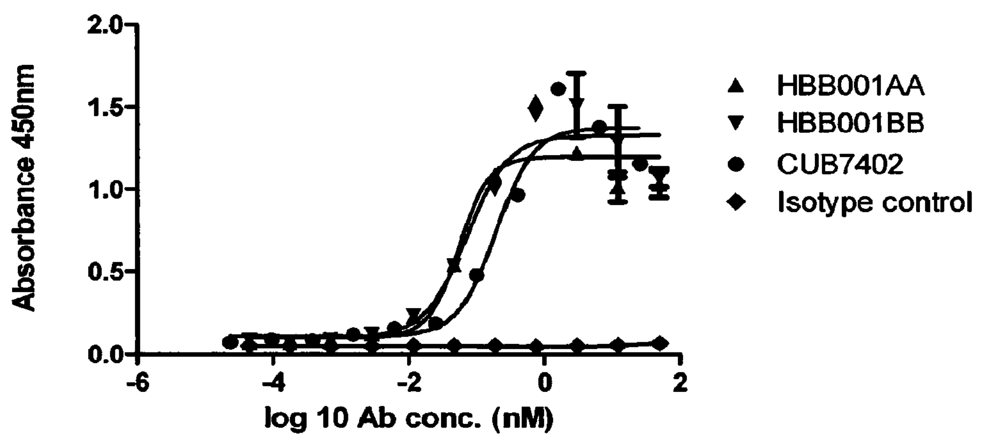
B
| | HAB004 |
|---|---|
| EC50 (nM) | 0.06117 |
| r2 | 0.9766 |
| EC50 (95% confidence range) | 0.04047 to 0.09246 |
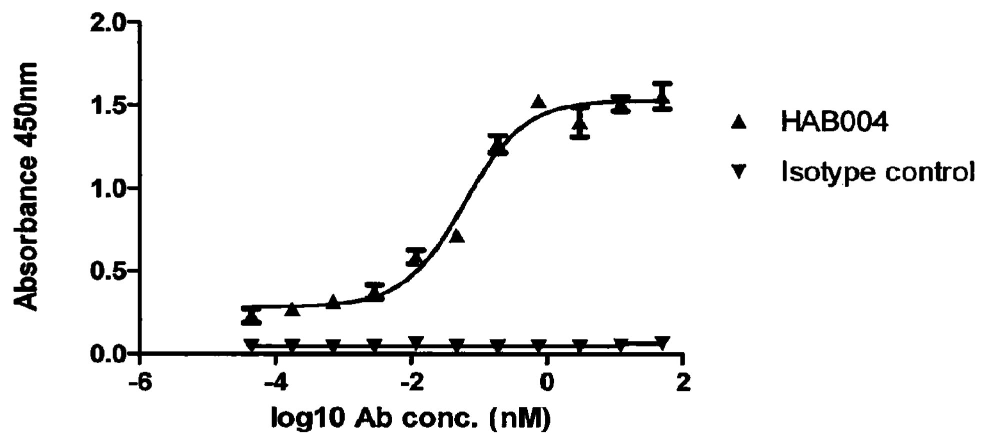
FIG. 38

IC50 = 71.85nM

ANTI-TRANSGLUTAMINASE 2 ANTIBODIES

This application is a continuation application of U.S. patent application Ser. No. 14/402,675, filed Nov. 20, 2014, which is a National Stage Application of International Patent Application No. PCT/GB2013/051373, filed May 24, 2013, which claims the priority from Great Britain Patent Application No. 1209096.5, filed May 24, 2012.

The present invention relates to inhibitors of TG2 and methods for providing and using such inhibitors.

Transglutaminase type 2 (TG2; also known as tissue transglutaminase, tTg) is part of the wider 9 member transglutaminase family that includes Factor XIIIa, which is critical for blood clotting, as well as Keratinocyte Transglutaminase (TG1) and Epidermal Transglutaminase (TG3) that are involved in terminal differentiation of the keratinocyte. In addition, there are other TG family members such as TG types 4 to 7 where no definitive role has been identified to date.

TG2 functions primarily as a protein cross-linking enzyme by catalysing the formation of ε(γ-glutamyl) lysine iso-dipeptide bonds. Elevated expression of TG2 leads to aberrant protein cross-linking which has been associated with several pathologies including various types of tissue scarring, the formation of neurofibrillary tangles in several brain disorders and resistance to chemotherapy in some cancers. TG2 is also able to deamidate proteins. TG2 deamidates gliadin and the TG2/Gliadin complex is the primary autoantigen in celiac disease. In addition, TG2 has a GTP binding function and can act as a GTPase, although this has not been linked to a pathological role.

Elevated TG2 activity is primarily associated with abnormal wound healing [1] leading to liver [2], pulmonary [3], heart [4] and kidney fibrosis, [5] as well as atherosclerosis [6]. The process of scarring and fibrosis is linked to the increased synthesis and, most importantly, raised export of TG2 to the interstitial space. Once outside the cell, TG2 is able to crosslink extracellular matrix (ECM) proteins such as fibronectin and collagen [7] by the incorporation of an ε(γ-glutamyl) lysine di-peptide bond [8]. Studies have shown that this can accelerate the deposition of available ECM components, while at the same time conferring resistance to proteolytic clearance by the matrix metalloproteinase (MMP) system [9, 10]. Taken together, this causes an accumulation of ECM proteins and thus scar tissue [9]. Further, TG2 has an emerging role in the activation of latent TGF-β1 in the scarring process [11] and has also been associated with interleukin-6 [12] and tumour necrosis factor-α activation pathways [13].

Inhibition of TG2 in vitro decreases extracellular matrix levels [14] while cells derived from TG2 knockout mice have lower levels of mature ECM [9]. In vivo application of pan TG inhibitors in models of chronic kidney disease reduce the development of glomerulosclerosis and tubulointerstitial fibrosis preserving renal function [15, 16]. Similar benefits are seen in the TG2 knockout mouse subjected to unilateral ureteric obstruction [17].

There are several neurodegenerative diseases characterised by the presence of protein aggregates in the degenerative region of the brain that TG2 has been implicated in forming. The best characterised is in Huntington's chorea. Huntington protein (htt) contains expanded polyglutamine repeats in its N-terminal domain. Wild-type htt contains less than 35 consecutive glutamines while disease-related htt typically has over consecutive glutamines which makes it an excellent TG2 substrate. Subsequently, insoluble aggregates are formed in the striatum and cortex of Huntington's disease patients. The frequency of aggregates correlates well with the severity of the disease. Alzheimer's disease is typified by the presence of extracellular senile plaques composed of aggregated amyloid β-protein and intracellular neurofibrillary tangles consisting of a highly phosphorylated form of the protein tau. These plaques contain large amounts of ε(γ-glutamyl) lysine iso-dipeptide bonds.

Finally, a hallmark of Parkinson's disease is the presence of alpha-synuclein aggregates called Lewy bodies in the cytoplasm of affected neurons which again contain ε(γ-glutamyl) lysine iso-dipeptide bonds. All of the aforementioned proteins are good substrates of TG2 in vitro. Furthermore, the affected region of the brain contains higher levels of TG2 protein than non-affected regions of the brain in the same patients. The correlation between the TG2 substrate specificity for disease-relevant aggregated proteins and increased TG2 expression levels suggest a role for enzymatically active TG2 in each disease.

TG inhibitors have been shown to exert therapeutic effects in multiple biological models of neurodegenerative diseases. In a cell culture model of Parkinson's disease transfecting COS-7 cells with alpha-synuclein and TG2 simultaneously, covalent—synuclein aggregates, reminiscent of Lewy bodies in Parkinson's disease, form and are dependent upon enzymatically active TG2 since the C277S inactive TG2 mutant failed to induce aggregate formation. Treatment of these cotransfected cells with cystamine significantly reduced the quantity of alpha-synuclein aggregates as well as the percentage of cells containing the aggregates. There have been two other reports in which proteins with normal length and expanded polyglutamine repeat proteins, representative of expanded CAG diseases, such as Huntington's disease, have been transfected into cell lines and shown to form aggregates. Treatment of these cell lines with the TG competitive inhibitor monodansylcadaverine led to a decrease in nuclear fragmentation, while treatment with cystamine lead to both a decrease in nuclear fragmentation, and a decrease in protein aggregate formation. An example of a pan TG inhibitor is 1,3-Dimethyl-2-[(2-oxo-propyl) thio]imidazolium chloride which is available from Zedira GmbH and referred to in several publications as NTU283 or r283.

Cystamine has a beneficial therapeutic effect in vivo when dosed in mouse models of Huntington's disease. Huntington R6/2 mice dosed with cystamine showed improved motor function, less severe weight loss, and increased survival compared to non-treated controls. Importantly, ex vivo TG2 activity in brain homogenates was lower after dosing with cystamine at least 60 min after injection. In a different mouse model of Huntington's disease, the YAC128 strain, cystamine was able to decrease the level of striatal atrophy but unable to improve animal weight or motor function, indicating a beneficial effect of cystamine at the cellular and tissue level but not in disease symptoms.

Probably the most convincing evidence that the beneficial therapeutic effect of cystamine on Huntington mice is independent of TG2 inhibition has come from crossing the R6/2 Huntington mouse with the TG2 knockout mouse to create a strain susceptible to neurodegeneration in the absence of TG2. When the R6/2 $TG2^{-/-}$ mice were treated with cystamine, the improved motor function and increased lifespan were not statistically different from the improvement seen in R6/2 $TG2^{+/+}$ mice treated with cystamine. Additionally, R6/1 and R6/2 $TG2^{-/-}$ mice had increased levels of neuronal protein aggregates compared to R6/1 and R6/2 $TG2^{+/+}$ mice suggesting a mechanism of protein aggregation independent of TG2 transamidation activity in these models. However, it is noteworthy that R6/2 $TG2^{-/-}$ mice showed a delay in the onset of motor dysfunction and improved survival compared to R6/2 $TG2^{+/+}$ mice implying a role for TG2 in the pathogenesis of neurodegeneration in the R6/2 model.

TG2 is also heavily implicated in celiac disease which affects 1 in 100 people in Western Europe. Celiac sprue is a T cell-mediated inflammatory disorder of the small intestine caused by a class of proteins called prolamins found in wheat, barley, and rye. The high proline and glutamine content of these proteins makes them resistant to natural gastric, pancreatic, and intestinal proteases, and peptidases during digestion. The resulting peptide fragments remain undigested well into the small intestine and gain access to the intestinal lamina propria where, after modification by TG2, they can stimulate a T cell-mediated immune response leading to inflammation and destruction of intestinal architecture. Intestinal TG2 deamidates specific glutamine residues in the prolamin peptides to glutamate residues. In HLA-DQ2/8 individuals these modified peptides are presented to corresponding autoreactive T cells by class II MHC molecules. Although prolamins have a high glutamine content (around 30-35%), only a few of these glutamine residues are targeted by human TG2. An excellent correlation between TG2 substrate specificity, DQ2 binding affinity, and T cell stimulatory potential of TG2-treated prolamins strongly suggests that peptide deamidation is mediated by TG2 and plays a significant role in determining the severity of disease. Further, celiac patients generate an autoantibody response to TG2-gliadin complexes. These anti-TG2 antibodies are found in both the small intestine, where they have been shown to co-localize with extracellular TG2, and in the blood, where they are exploited as a diagnostic disease marker.

Despite the lack of animal models of celiac disease, ex vivo experiments indicate that TG2 inhibition has the potential to benefit patients with celiac sprue. Culturing celiac patient small intestinal biopsies with either TG2 treated (deamidated) or non-TG2 treated (non-deamidated) gluten digests both resulted in the generation of patient T-cell lines that preferentially recognised deamidated gluten peptides rather than non-deamidated gluten peptides. Also by blocking the activity of endogenous TG2 in the celiac biopsies with cystamine more than half of the resultant T-cell lines had reduced proliferative responses compared to non-cystamine-treated controls. Cell lines did not respond well to the non-deamidated digests. These results imply that the gluten responsive T-cell populations in celiac intestinal biopsies are naturally biased towards recognizing deamidated gluten peptides as opposed to non-deamidated peptides, that endogenous TG2 activity in these biopsies can result in gluten peptide deamidation in situ and that treatment of celiac biopsies with TG2 inhibitors can reduce the proliferative response of gluten-reactive T cells.

Another study showed that the pan-TG inhibitor 2-[(2-oxopropyl)thio]imidazolium inhibitor was able to prevent the in situ crosslinking of gluten peptides to endogenous proteins in thin tissue sections taken from both celiac sprue patients and controls. More importantly, the authors showed that incubation of intact celiac small intestinal biopsies with 2-[(2-oxopropyl)thio]imidazolium prevented T-cell activation induced by the non-deamidated form of an immunodominant gluten peptide. In contrast, TG inhibition was ineffective at controlling T-cell activation when the biopsies were incubated with the deamidated version of the same peptide. These results suggest that inhibition of endogenous TG2 in celiac patient biopsies can prevent gluten peptide deamidation and, therefore, reduce T-cell activation.

Several observations support the hypothesis that TG2 plays a role in the development of certain types of cancer. Multiple studies have shown that TG2 protein is up-regulated in cancerous tissue relative to healthy tissue in cancers such as glioblastomas, malignant melanomas, and pancreatic ductal adenocarcinomas to name a few. A positive correlation between the chemotherapeutic resistance and metastatic potential of certain cancers with TG2 expression levels has been demonstrated, while in certain cell types TG2 has been shown to exert anti-apoptotic effects on cells while siRNA down-regulation of TG2 protein expression levels or treatment with TG2 inhibitors sensitizes these cells to apoptosis. On the other hand, there are also reports of the down-regulation of TG2 expression in certain types of cancer [18]. Recently, it has been shown that TG2 is a binding partner for GPR56, a protein down-regulated in highly metastatic cancer cells, suggesting that TG2 can act as a tumor suppressing protein through its interaction with GPR56 [18].

Current transglutaminase inhibitors fall into 3 main classes: 1) Competitive amine inhibitors (e.g. cystamine and spermine) that compete with natural amine substrates; 2) Reversible allosteric inhibitors such as GTP and a newly discovered class of compound with a thieno[2,3-d] pyrimidin-4-one acylhydrazide backbone; and 3) Irreversible inhibitors including 2-[(2-oxopropyl)thio]imidazolium derivatives (acetylate active site cysteine), 3-halo-4,5-dihydroisoxazoles (form a stable iminothioether in the active site) and carbobenzyloxy-L-glutaminyl glycine analogues with a variety of reactive moieties inserted.

Most have been used in the experimental systems above and shown beneficial outcomes. However, none of these inhibitors show TG isoform specificity as they all target the conserved catalytic triad within the transglutaminase family catalytic core. Consequently, all potentially have the disadvantage of co-inhibition of Factor XIIIa, TG1 and TG3, which effectively prevents their application in human disease due to the side effects that can be expected.

WO 2006/100679 describes a specific anti-TG2 antibody produced by recombinant technology from samples collected from three adult celiac patients with high anti-TG2 antibody titres.

Given the association of TG2 with numerous disease states and compelling data from non specific inhibitors, there is a need for highly selective and high efficacy TG2 inhibitors with minimal off target effects.

The listing or discussion of an apparently prior-published document in this specification should not necessarily be taken as an acknowledgement that the document is part of the state of the art or is common general knowledge.

In a first aspect the present invention provides an antibody or an antigen-binding fragment thereof that selectively binds to an epitope within the core region of transglutaminase type 2 (TG2).

In certain embodiments it is envisaged that the antibody or antigen-binding fragment thereof will selectively bind to an epitope within the core region of human TG2, rat TG2, and/or mouse TG2. In a particularly preferred embodiment, the TG2 is human TG2.

The full amino acid sequences of human, rat and mouse TG2 can be found under the Genbank Accession numbers NM_004613, NM_019386.2 and NM_009373.3. The coding part of these sequences are as follows:

Human TG2 nucleotide sequence (SEQ ID NO: 1):
atggccgaggagctggtcttagagaggtgtgatctggagctggagaccaa tggccgagaccaccacacggccgacctgtgccgggagaagctggtggtgc gacggggccagcccttctggctgaccctgcactttgagggccgcaactac gaggccagtgtagacagtctcaccttcagtgtcgtgaccggcccagcccc tagccaggaggccgggaccaaggcccgttttccactaagagatgctgtgg aggagggtgactggacagccaccgtggtggaccagcaagactgcaccctc tcgctgcagctcaccaccccggccaacgcccccatcggcctgtatcgcct cagcctggaggcctccactggctaccagggatccagctttgtgctgggcc acttcattttgctcttcaacgcctggtgcccagcggatgctgtgtacctg gactcggaagaggagcggcaggagtatgtcctcacccagcagggctttat ctaccagggctcggccaagttcatcaagaacataccttggaattttgggc agtttgaagatgggatcctagacatctgcctgatccttctagatgtcaac cccaagttcctgaagaacgccggccgtgactgctcccgccgcagcagccc cgtctacgtgggccgggtggtgagtggcatggtcaactgcaacgatgacc agggtgtgctgctgggacgctgggacaacaactacggggacggcgtcagc cccatgtcctggatcggcagcgtggacatcctgcggcgctggaagaacca cggctgccagcgcgtcaagtatggccagtgctgggtcttcgccgccgtgg cctgcacagtgctgaggtgcctgggcatccctacccgcgtcgtgaccaac tacaactcggcccatgaccagaacagcaaccttctcatcgagtacttccg caatgagtttggggagatccagggtgacaagagcgagatgatctggaact tccactgctgggtggagtcgtggatgaccaggccggacctgcagccgggg tacgagggctggcaggccctggacccaacgccccaggagaagagcgaagg gacgtactgctgtggcccagttccagttcgtgccatcaaggagggcgacc tgagcaccaagtacgatgcgccctttgtctttgcggaggtcaatgccgac gtggtagactggatccagcaggacgatgggtctgtgcacaaatccatcaa ccgttccctgatcgttgggctgaagatcagcactaagagcgtgggccgag acgagcgggaggatatcacccacacctacaaatacccagaggggtcctca gaggagagggaggccttcacaagggcgaaccacctgaacaaactggccga gaaggaggagacagggatggccatgcggatccgtgtgggccagagcatga acatgggcagtgactttgacgtctttgcccacatcaccaacaacaccgct gaggagtacgtctgccgcctcctgctctgtgcccgcaccgtcagctacaa tgggatcttggggcccgagtgtggcaccaagtacctgctcaacctcaacc tggagcctttctctgagaagagcgttcctctttgcatcctctatgagaaa taccgtgactgccttacggagtccaacctcatcaaggtgcgggccctcct cgtggagccagttatcaacagctacctgctggctgagagggacctctacc tggagaatccagaaatcaagatccggatccttggggagcccaagcagaaa cgcaagctggtggctgaggtgtccctgcagaacccgctccctgtggccct ggaaggctgcaccttcactgtggagggggccggcctgactgaggagcaga agacggtggagatcccagaccccgtggaggcaggggaggaagttaaggtg agaatggacctgctgccgctccacatgggcctccacaagctggtggtgaa -continued cttcgagagcgacaagctgaaggctgtgaagggcttccggaatgtcatca ttggccccgcctaa Human TG2 Amino Acid sequence (SEQ ID NO: 2):
MAEELVLERCDLELETNGRDHHTADLCREKLVVRRGQPFWLTLHFEGRNY

EASVDSLTFSVVTGPAPSQEAGTKARFPLRDAVEEGDWTATVVDQQDCTL

SLQLTTPANAPIGLYRLSLEASTGYQGSSFVLGHFILLFNAWCPADAVYL

DSEEERQEYVLTQQGFIYQGSAKFIKNIPWNFGQFEDGILDICLILLDVN

PKFLKNAGRDCSRRSSPVYVGRVVSGMVNCNDDQGVLLGRWDNNYGDGVS

PMSWIGSVDILRRWKNHGCQRVKYGQCWVFAAVACTVLRCLGIPTRVVTN

YNSAHDQNSNLLIEYFRNEFGEIQGDKSEMIWNFHCWVESWMTRPDLQPG

YEGWQALDPTPQEKSEGTYCCGPVPVRAIKEGDLSTKYDAPFVFAEVNAD

VVDWIQQDDGSVHKSINRSLIVGLKISTKSVGRDEREDITHTYKYPEGSS

EEREAFTRANHLNKLAEKEETGMAMRIRVGQSMNMGSDFDVFAHITNNTA

EEYVCRLLLCARTVSYNGILGPECGTKYLLNLNLEPFSEKSVPLCILYEK

YRDCLTESNLIKVRALLVEPVINSYLLAERDLYLENPEIKIRILGEPKQK

RKLVAEVSLQNPLPVALEGCTFTVEGAGLTEEQKTVEIPDPVEAGEEVKV

RMDLLPLHMGLHKLVVNFESDKLKAVKGFRNVIIGPA*

Rat TG2 Nucleotide sequence (SEQ ID NO: 3):
Atggccgaggagctgaacctggagaggtgcgatttggagatacaggccaa tggccgtgatcaccacacggccgacctgtgccaagagaaactggtgctgc ggcgaggccagcgcttccggctgacactgtacttcgagggccgtggctat gaggccagcgtggacagacttacatttggtgccgtgaccggcccagatcc cagtgaagaggcagggaccaaggcccgcttctcactgtctgacgatgtgg aggagggatcctggtcagcctctgtgctggaccaacaggacaatgtcctc tcgctgcagctctgcaccccagccaatgctcctgttggccagtaccgcct cagcctggagacttctactggctaccaaggctccagcttcatgctgggtc acttcatcctgctcttcaatgcctggtgcccagcggatgacgtgtaccta gattcagaggcggagcgccgggaatacgtcctcacacagcagggcttcat ctaccagggctctgtcaagttcatcaagagtgtgccttggaactttgggc agtttgaggatgggatcctggatgcctgcctgatgcttttggatgtgaac cccaagttcctgaaggaccgtagccgggactgctcacgacgcagcagtcc catctatgtgggccgcgtggtgagcggcatggtcaactgcaatgatgacc agggtgtgcttctgggtcgctgggacaacaattatggggacggtatcagt cccatggcctggattggcagcgtggacattctgcggcgctggaaggaaca cggctgtcagcaagtgaagtatggccagtgctgggtgtttgcggcggtag cctgcacagtgctgcggtgccttggcatccctaccagagtggtgaccaac tacaactccgcccacgaccagaacagcaacctgctcatcgagtacttccg aaacgagtacggggagctggagagcaacaagagcgagatgatctggaatt tccactgctgggtggagtcctggatgaccaggccagacctacagccaggc tatgaggggtggcaggccattgaccccacaccgcaggagaagagcgaagg aacatactgttgtggcccagtctcagtgcgggccatcaaggagggtgacc tgagcaccaagtatgatgcgtccttcgtgtttgccgaggtcaacgctgat -continued gtggtggactggatccggcagtcagatgggtctgtgctcaaatccatcaa caattccctggtcgtggggcagaagatcagcactaagagcgtgggccgtg atgaccgggaggacatcacctatacctacaagtacccagaggggtcccca gaggagagggaagtcttcaccagagccaaccacctgaacaaactggcaga gaaagaggagacaggggtggccatgcggatccgagtgggggatggtatga gcttgggcaatgactttgacgtgtttgcccacatcggcaacgacacctcg gagagccgtgagtgccgcctcctgctctgtgcccgcactgtcagctacaa cggcgtgctggggcccgagtgtggcactgaggacatcaacctgaccctgg atccctactctgagaacagcatccccttcgcatcctctacgagaagtac agcggttgcctgaccgagtcaaacctcatcaaggtgcggggtctcctcgt cgagccagccgctaacagctacctgctggctgagagagatctctacctgg agaatcctgaaatcaagatccggatcctggggagcccaagcagaaccgc aaactggtggctgaggtgtccctgaagaacccactttctgattccctgta tgactgtgtcttcactgtggagggggctggcctgaccaaggaacagaagt ctgtggaggtctcagaccctgtgccagcaggagatgcggtcaaggtgcgg gttgacctgttcccgactgatattggcctccacaagttggtggtgaactt ccagtgtgacaagctgaagtcggtcaagggttaccggaatatcatcatcg gcccggcctaag Rat TG2 Amino Acid sequence (SEQ ID NO: 4):
MAEELNLERCDLEIQANGRDHHTADLCQEKLVLRRGQRFRLTLYFEGRGY

EASVDRLTFGAVTGPDPSEEAGTKARFSLSDDVEEGSWSASVLDQQDNVL

SLQLCTPANAPVGQYRLSLETSTGYQGSSFMLGHFILLFNAWCPADDVYL

DSEAERREYVLTQQGFIYQGSVKFIKSVPWNFGQFEDGILDACLMLLDVN

PKFLKDRSRDCSRRSSPIYVGRVVSGMVNCNDDQGVLLGRWDNNYGDGIS

PMAWIGSVDILRRWKEHGCQQVKYGQCWVFAAVACTVLRCLGIPTRVVTN

YNSAHDQNSNLLIEYFRNEYGELESNKSEMIWNFHCWVESWMTRPDLQPG

YEGWQAIDPTPQEKSEGTYCCGPVSVRAIKEGDLSTKYDASFVFAEVNAD

VVDWIRQSDGSVLKSINNSLVVGQKISTKSVGRDDREDITYTYKYPEGSP

EEREVFTRANHLNKLAEKEETGVAMRIRVGDGMSLGNDFDVFAHIGNDTS

ESRECRLLLCARTVSYNGVLGPECGTEDINLTLDPYSENSIPLRILYEKY

SGCLTESNLIKVRGLLVEPAANSYLLAERDLYLENPEIKIRILGEPKQNR

KLVAEVSLKNPLSDSLYDCVFTVEGAGLTKEQKSVEVSDPVPAGDAVKVR

VDLFPTDIGLHKLVVNFQCDKLKSVKGYRNIIIGPA*X

Mouse TG2 Nucleotide sequence (SEQ ID NO: 5):
atggcagaggagctgctcctggagaggtgtgatttggagattcaggccaa tggccgtgaccaccacacggccgacctatgccaagagaaactggtgctgc gtcgtggtcagcgcttccggctgactctgtacttcgagggccgtggctac gaggccagcgtggacagcctcacgttcggtgctgtgaccggcccagatcc cagtgaagaggcagggaccaaggcccgcttctcactgtctgacaatgtgg aggagggatcttggtcagcctcagtgctggaccaacaggacaatgtcctc tcgctacagctctgcaccccagccaatgctcctattggcctgtaccgtct -continued cagcctagaggcttctactggctaccagggctccagctttgtgctgggcc acttcatcctgctctacaatgcctggtgcccagccgatgatgtgtaccta gactcagaggaggagcgacgggaatatgtccttacgcaacagggcttcat ctaccaaggctctgtcaagttcatcaagagtgtgccttggaactttgggc agttcgaggatggaatcctggatacctgcctgatgctcttggatatgaac cccaagttcctgaagaaccgtagtcgggactgctcacgccgcagcagtcc catctatgtgggccgcgtggtgagcgccatggtcaactgcaatgatgacc agggtgtgcttctgggccgctgggacaacaactatggggatggtatcagt cccatggcctggattggcagtgtggacattctgcggcgctggaaggaaca cggctgtcagcaagtgaagtacgggcagtgctgggtgtttgcagcggtgg cctgcacagtgctgcggtgcctcggcatccctaccagagtggtgaccaac tacaactccgcccacgaccagaacagcaacctgctcatcgagtacttccg aaatgagttcggggagctggagagcaacaagagcgagatgatctggaact tccactgctgggtggagtcctggatgaccaggccagacctacagccgggc tatgaggggtggcaggccattgaccccacaccacaggagaagagcgaagg gacatactgttgtggcccagtctcagtgcgagccatcaaggagggagacc tgagtaccaagtatgatgcacccttcgtgtttgccgaggtcaacgctgat gtggtggactggatccggcaggaagatgggtctgtgctcaaatccatcaa ccgttccttggtcgtggggcagaagatcagcactaagagtgtgggccgtg atgaccgggaggacatcacccatacctacaagtacccagaggggtcaccc gaggagagggaagtcttcaccaaggccaaccacctgaacaaactggcaga gaaagaggagacaggggtggccatgcgcatccgagtgggggacagtatga gcatgggcaacgacttcgacgtgtttgcccacatcggcaacgacacctcg gagactcgagagtgtcgtctcctgctctgtgcccgcactgtcagctacaa cggggtgctggggcccgagtgtggcactgaggacatcaacctgaccctgg atccctactctgagaacagcatcccacttcgaatcctctacgagaagtac agcgggtgcctgacagagtcaaacctcatcaaggtgcggggccttctcat cgaaccagctgccaacagctacctgctggctgagagagatctctacctgg agaatcccgaaatcaagatccgggtcctgggagaacccaagcaaaaccgc aaactggtggctgaggtgtccctgaagaacccactttccgatcccctgta tgactgcatcttcactgtggagggggctggcctgaccaaggagcagaagt ctgtggaagtctcagacccggtgccagcgggcgatttggtcaaggcacgg gtcgacctgttcccgactgatattggcctccacaagctggtggtgaactt ccagtgtgacaagctgaagtcggtgaagggttaccggaatgttatcatcg gcccggcctaa Mouse TG2 Amino Acid sequence (SEQ ID NO: 6):
MAEELLLERCDLEIQANGRDHHTADLCQEKLVLRRGQRFRLTLYFEGRGY

EASVDSLTFGAVTGPDPSEEAGTKARFSLSDNVEEGSWSASVLDQQDNVL

SLQLCTPANAPIGLYRLSLEASTGYQGSSFVLGHFILLYNAWCPADDVYL

DSEEERREYVLTQQGFIYQGSVKFIKSVPWNFGQFEDGILDTCLMLLDMN

PKFLKNRSRDCSRRSSPIYVGRVVSAMVNCNDDQGVLLGRWDNNYGDGIS

-continued

```
PMAWIGSVDILRRWKEHGCQQVKYGQCWVFAAVACTVLRCLGIPTRVVTN

YNSAHDQNSNLLIEYFRNEFGELESNKSEMIWNFHCWVESWMTRPDLQPG

YEGWQAIDPTPQEKSEGTYCCGPVSVRAIKEGDLSTKYDAPFVFAEVNAD

VVDWIRQEDGSVLKSINRSLVVGQKISTKSVGRDDREDITHTYKYPEGSP

EEREVFTKANHLNKLAEKEETGVAMRIRVGDSMSMGNDFDVFAHIGNDTS

ETRECRLLLCARTVSYNGVLGPECGTEDINLTLDPYSENSIPLRILYEKY

SGCLTESNLIKVRGLLIEPAANSYLLAERDLYLENPEIKIRVLGEPKQNR

KLVAEVSLKNPLSDPLYDCIFTVEGAGLTKEQKSVEVSDPVPAGDLVKAR

VDLFPTDIGLHKLVVNFQCDKLKSVKGYRNVIIGPA
```

The present inventors have raised antibodies to TG2 by immunising mice with a recombinant protein encompassing amino acids 143 to 473 of the human TG2 core. Hybridoma were screened for TG2 specificity and inhibition with any suitable candidates cloned. IgG was purified from these to calculate efficacy and the target epitope mapped by screening of a human TG2 library by phage display.

The present approach to producing antibodies against TG2 by using a recombinant TG2 core protein has not been tried before and it surprisingly led to the isolation and characterisation of antibodies to TG2 that were highly selective for TG2 and showed strong inhibitory characteristics. Prior attempts to raise antibodies to TG2 have led to the isolation of relatively unselective antibodies that cross-react with other members of the transglutaminase family and thus would not represent promising antibodies for clinical use. The antibodies of the present invention on the other hand are promising candidates for clinical trials for diseases exacerbated by or mediated by TG2 activity.

It is surprising that the approach in the present application has led to the production of much more effective antibodies than those previously produced. There was no guarantee that it would have been possible to raise antibodies that are effective inhibitors of TG2 by immunising with the core region. As indicated above, antibodies that are effective inhibitors may not be specific enough for TG2 to be used effectively in medicine. It is surprising that antibodies to the divergent regions (in particular, regions of the core that diverge slightly between different transglutaminase family members of TG2) are effective and selective inhibitors of TG2.

Without being bound by any theory we think that by raising antibodies to a smaller protein covering just the central core, we not only eliminate some of the favoured immunological epitopes present on the full length protein, but we also force core targeting. This appears to increase the variety of antibodies available for selection and provides wider coverage of the core.

Immunising with just the TG2 core removed much of the tertiary structure of the enzyme (in particular the two carboxy terminal beta barrel domains). It is possible that some of the epitopes that perhaps may be less available or immunogenic within a native full length TG2 molecule may be more attractive epitopes with the core in the format described herein. The antibodies described herein recognised linear epitopes (i.e. bound to TG2 on a reducing SDS PAGE gel), whereas 80% of the antibodies we previously isolated using full length TG2 as an immunogen were conformation dependent. We were able to show that the recombinant core domain retained enzyme activity, and so the isolation of inhibitory antibodies was probably aided by the exposure of previously less favourable epitopes located in or near the active site. It is interesting and surprising that inhibitory antibodies to human TG2 were raised by immunising with the core given that the recombinant core protein may not have demonstrated the same folding characteristics as the full length protein.

The TG catalytic core is highly conserved between members of the TG family and across species. This suggests that development of not only specific small molecule inhibitors but also of antibody-based inhibitors may be technically challenging. Nevertheless, the present disclosure provides antibodies that are highly selective. That this is possible may reflect the fact that there are some regions within the TG2 catalytic domain where there is some heterogeneity. The present antibodies may therefore exploit these small differences. The surprising selectivity of the present antibodies may enable the development of therapeutics that can interfere efficiently with TG2 activity and thus provide potentially effective therapies for conditions exacerbated by or caused by TG2 activity where there is currently no satisfactory therapeutic option.

By way of comparison, the antibodies described in WO 2006/100679, which were produced by recombinant technology from samples from three adult celiac patients with high anti-TG2 antibody titres, proved to be of low efficacy when tested by the present inventors (Example 2). The antibodies of the present invention were far superior to those of WO 2006/100679 in terms of selectivity for TG2 and in terms of inhibitory activity. For example, the present inventors generated a Fab fragment of the antibody of WO 2006/100679, which was applied at the same concentration in TG2 inhibition assays as the antibodies of the present invention. The Fab fragment amount in the tests was twice molar wise that of the antibodies of the present invention, but they still failed to show any inhibition of TG2 activity. When the full length WO 2006/100679 antibody was tested for inhibition in our standard putrescine incorporation assay no inhibition of TG2 activity was found. Thus, the methods of the present invention and the antibodies produced by those methods are superior to those previously described.

By "antibody" we include substantially intact antibody molecules, as well as chimeric antibodies, humanised antibodies, human antibodies (wherein at least one amino acid is mutated relative to the naturally occurring human antibodies), single chain antibodies, bi-specific antibodies, antibody heavy chains, antibody light chains, homodimers and heterodimers of antibody heavy and/or light chains, and antigen binding fragments and derivatives of the same. We also include variants, fusions and derivatives of the antibodies and antigen-binding fragments thereof within the meaning of the terms "antibody" and "antigen-binding fragments thereof".

The term "antibody" also includes all classes of antibodies, including IgG, IgA, IgM, IgD and IgE. Thus, the antibody may be an IgG molecule, such as an IgG1, IgG2, IgG3, or IgG4 molecule. Preferably, the antibody of the invention is an IgG molecule, or an antigen-binding fragment, or variant, fusion or derivative thereof. More preferably the antibody is an IgG2 molecule.

The antibodies, compositions, uses and methods of the invention encompass variants, fusions and derivatives of the defined antibodies and antigen-binding fragments thereof, as well as fusions of a said variants or derivatives, provided such variants, fusions and derivatives have binding specificity for TG2.

As antibodies and antigen-binding fragments thereof comprise one or more polypeptide component, variants, fusions and derivatives of the antibody and antigen-binding fragment thereof as defined herein may be made using the methods of protein engineering and site-directed mutagenesis well known in the art using the recombinant polynucleotides (see example, see Molecular Cloning: a Laboratory Manual, 3rd edition, Sambrook & Russell, 2001, Cold Spring Harbor Laboratory Press, which is incorporated herein by reference).

Thus, variants, fusions and derivatives of the antibody or antigen-binding fragment thereof as defined herein, may be made based on the polypeptide component of the antibody or antigen-binding fragment thereof.

By "fusion" we include said polypeptide fused to any other polypeptide. For example, the said polypeptide may be fused to a polypeptide such as glutathione-S-transferase (GST) or protein A in order to facilitate purification of said polypeptide. Examples of such fusions are well known to those skilled in the art. Similarly, the said polypeptide may be fused to an oligo-histidine tag such as His6 or to an epitope recognised by an antibody such as the well-known Myc-tag epitope. Fusions to any variant or derivative of said polypeptide are also included in the scope of the invention. It will be appreciated that fusions (or variants or derivatives thereof) which retain desirable properties, such as have binding specificity for TG2, are preferred.

The fusion may comprise or consist of a further portion which confers a desirable feature on the said polypeptide; for example, the portion may be useful in detecting or isolating the polypeptide, or promoting cellular uptake of the polypeptide. The portion may be, for example, a biotin moiety, a radioactive moiety, a fluorescent moiety, for example a small fluorophore or a green fluorescent protein (GFP) fluorophore, as well known to those skilled in the art. The moiety may be an immunogenic tag, for example a Myc-tag, as known to those skilled in the art or may be a lipophilic molecule or polypeptide domain that is capable of promoting cellular uptake of the polypeptide, as known to those skilled in the art.

By "variants" of said polypeptide we refer to a polypeptide wherein at one or more positions there have been amino acid insertions, deletions, and/or substitutions, either conservative or non-conservative, provided that such changes result in a protein whose basic properties, for example binding properties, thermostability, activity in a certain pH-range (pH-stability) have not significantly been changed. "Significantly" in this context means that one skilled in the art would say that the properties of the variant may still be different but would not be unobvious over the ones of the original protein. Thus, we include variants of the polypeptide where such changes do not substantially alter the activity of the said polypeptide. In particular, we include variants of the polypeptide where such changes do not substantially alter the binding specificity for TG2.

By "conservative substitutions" is intended combinations such as Gly, Ala; Val, le, Leu; Asp, Glu; Asn, Gln; Ser, Thr; Lys, Arg; and Phe, Tyr.

Such variants may be made using the methods of protein engineering and site-directed mutagenesis.

The polypeptide variant may have an amino acid sequence which has at least 75% identity with one or more of the amino acid sequences given herein, for example at least 80%, at least 90%, at least 95%, at least 96%, at least 97%, at least 98%, or at least 99% identity with one or more of the amino acid sequences specified herein.

The percent sequence identity between two polypeptides may be determined using suitable computer programs, for example the GAP program of the University of Wisconsin Genetic Computing Group and it will be appreciated that percent identity is calculated in relation to polypeptides whose sequences have been aligned optimally.

The alignment may alternatively be carried out using the Clustal W program (as described in Thompson et al., 1994, *Nucl. Acid Res.* 22:4673-4680, which is incorporated herein by reference).

The parameters used may be as follows:

Fast pair-wise alignment parameters: K-tuple(word) size; 1, window size; 5, gap penalty; 3, number of top diagonals; 5. Scoring method: x percent.

Multiple alignment parameters: gap open penalty; 10, gap extension penalty; 0.05.

Scoring matrix: BLOSUM.

Alternatively, the BESTFIT program may be used to determine local sequence alignments.

The antibody, antigen-binding fragment, variant, fusion or derivative used in the methods or uses of the invention may comprise or consist of one or more amino acids which have been modified or derivatised.

Chemical derivatives of one or more amino acids may be achieved by reaction with a functional side group. Such derivatised molecules include, for example, those molecules in which free amino groups have been derivatised to form amine hydrochlorides, p-toluene sulphonyl groups, carboxybenzoxy groups, t-butyloxycarbonyl groups, chloroacetyl groups or formyl groups. Free carboxyl groups may be derivatised to form salts, methyl and ethyl esters or other types of esters and hydrazides. Free hydroxyl groups may be derivatised to form O-acyl or O-alkyl derivatives. Also included as chemical derivatives are those peptides which contain naturally occurring amino acid derivatives of the twenty standard amino acids. For example: 4-hydroxyproline may be substituted for proline; 5-hydroxylysine may be substituted for lysine; 3-methylhistidine may be substituted for histidine; homoserine may be substituted for serine and ornithine for lysine. Derivatives also include peptides containing one or more additions or deletions as long as the requisite activity is maintained. Other included modifications are amidation, amino terminal acylation (e.g. acetylation or thioglycolic acid amidation), terminal carboxylamidation (e.g. with ammonia or methylamine), and the like terminal modifications.

It will be further appreciated by persons skilled in the art that peptidomimetic compounds may also be useful. Thus, by 'polypeptide' we include peptidomimetic compounds which are capable of binding to an epitope within the TG2 core region. The term 'peptidomimetic' refers to a compound that mimics the conformation and desirable features of a particular peptide as a therapeutic agent.

For example, the said polypeptide includes not only molecules in which amino acid residues are joined by peptide (—CO—NH—) linkages but also molecules in which the peptide bond is reversed. Such retro-inverso peptidomimetics may be made using methods known in the art, for example such as those described in Meziere et al. (1997) *J. Immunol.* 159, 3230-3237, which is incorporated herein by reference. This approach involves making pseudopeptides containing changes involving the backbone, and not the orientation of side chains. Retro-inverse peptides, which contain NH—CO bonds instead of CO—NH peptide bonds, are much more resistant to proteolysis. Alternatively, the said polypeptide may be a peptidomimetic compound wherein one or more of the amino acid residues are linked by a -y($CH_2NH$)— bond in place of the conventional amide linkage.

In a further alternative, the peptide bond may be dispensed with altogether provided that an appropriate linker moiety which retains the spacing between the carbon atoms of the amino acid residues is used; it may be advantageous for the linker moiety to have substantially the same charge distribution and substantially the same planarity as a peptide bond.

It will be appreciated that the said polypeptide may conveniently be blocked at its N- or C-terminus so as to help reduce susceptibility to exo-proteolytic digestion.

A variety of un-coded or modified amino acids such as D-amino acids and N-methyl amino acids have also been used to modify mammalian peptides. In addition, a presumed bioactive conformation may be stabilised by a covalent modification, such as cyclisation or by incorporation of lactam or other types of bridges, for example see Veber et al., 1978, *Proc. Natl. Acad. Sci. USA* 75:2636 and Thursell et al., 1983, *Biochem. Biophys. Res. Comm.* 111:166, which are incorporated herein by reference.

A common theme among many of the synthetic strategies has been the introduction of some cyclic moiety into a peptide-based framework. The cyclic moiety restricts the conformational space of the peptide structure and this frequently results in an increased specificity of the peptide for a particular biological receptor. An added advantage of this strategy is that the introduction of a cyclic moiety into a peptide may also result in the peptide having a diminished sensitivity to cellular peptidases.

Thus, exemplary polypeptides useful in the methods and uses of the invention comprise or consist of terminal cysteine amino acids. Such a polypeptide may exist in a heterodetic cyclic form by disulphide bond formation of the mercaptide groups in the terminal cysteine amino acids or in a homodetic form by amide peptide bond formation between the terminal amino acids. As indicated above, cyclising small peptides through disulphide or amide bonds between the N- and C-terminus cysteines may circumvent problems of specificity and half-life sometime observed with linear peptides, by decreasing proteolysis and also increasing the rigidity of the structure, which may yield higher specificity compounds. Polypeptides cyclised by disulphide bonds have free amino and carboxy-termini which still may be susceptible to proteolytic degradation, while peptides cyclised by formation of an amide bond between the N-terminal amine and C-terminal carboxyl and hence no longer contain free amino or carboxy termini. Thus, the peptides can be linked either by a C—N linkage or a disulphide linkage.

The present invention is not limited in any way by the method of cyclisation of peptides, but encompasses peptides whose cyclic structure may be achieved by any suitable method of synthesis. Thus, heterodetic linkages may include, but are not limited to formation via disulphide, alkylene or sulphide bridges. Methods of synthesis of cyclic homodetic peptides and cyclic heterodetic peptides, including disulphide, sulphide and alkylene bridges, are disclosed in U.S. Pat. No. 5,643,872, which is incorporated herein by reference. Other examples of cyclisation methods are discussed and disclosed in U.S. Pat. No. 6,008,058, which is incorporated herein by reference.

A further approach to the synthesis of cyclic stabilised peptidomimetic compounds is ring-closing metathesis (RCM). This method involves steps of synthesising a peptide precursor and contacting it with an RCM catalyst to yield a conformationally restricted peptide. Suitable peptide precursors may contain two or more unsaturated C—C bonds. The method may be carried out using solid-phase-peptide-synthesis techniques. In this embodiment, the precursor, which is anchored to a solid support, is contacted with a RCM catalyst and the product is then cleaved from the solid support to yield a conformationally restricted peptide.

Another approach, disclosed by D. H. Rich in *Protease Inhibitors*, Barrett and Selveson, eds., Elsevier (1986), which is incorporated herein by reference, has been to design peptide mimics through the application of the transition state analogue concept in enzyme inhibitor design. For example, it is known that the secondary alcohol of staline mimics the tetrahedral transition state of the scissile amide bond of the pepsin substrate.

In summary, terminal modifications are useful, as is well known, to reduce susceptibility by proteinase digestion and therefore to prolong the half-life of the peptides in solutions, particularly in biological fluids where proteases may be present. Polypeptide cyclisation is also a useful modification because of the stable structures formed by cyclisation and in view of the biological activities observed for cyclic peptides.

Thus, in one embodiment the said polypeptide is cyclic. However, in an alternative embodiment, the said polypeptide is linear.

By "selectively binds to an epitope within the core region of TG2" we mean an antibody or antigen-binding fragment thereof that is capable of binding to an epitope in the TG2 core region selectively. By "capable of binding selectively" we include such antibody-derived binding moieties which bind at least 10-fold more strongly to the TG2 core than to other proteins; for example at least 50-fold more strongly, or at least 100-fold more strongly. The binding moiety may be capable of binding selectively to an epitope in the TG2 core under physiological conditions, e.g. in vivo.

Such binding specificity may be determined by methods well known in the art, such as enzyme-linked immunosorbent assay (ELISA), immunohistochemistry, immunoprecipitation, western blot and flow cytometry using transfected cells expressing TG2 or the TG2 core, or a fragment thereof. Suitable methods for measuring relative binding strengths include immunoassays, for example where the binding moiety is an antibody (see Harlow & Lane, "Antibodies: A Laboratory Manual", Cold Spring Habor Laboratory Press, New York, which is incorporated herein by reference). Alternatively, binding may be assessed using competitive assays or using Biacore analysis (Biacore International AB, Sweden).

It is preferred that the antibody or antigen-binding fragment of the invention binds exclusively to TG2.

It will be appreciated by persons skilled in the art that the binding specificity of an antibody or antigen binding fragment thereof is conferred by the presence of complementarity determining regions (CDRs) within the variable regions of the constituent heavy and light chains. As discussed below, in a particularly preferred embodiment of the antibodies and antigen-binding fragments thereof defined herein, binding specificity for TG2 is conferred by the presence of one or more of the CDRs identified. For example, sequences that may comprise or consist of the CDR sequences of AB-1 VL and VH include KASQDINSYLT (SEQ ID NO: 7), RTNRLFD(SEQ ID NO: 8), LQYDDFPYT(SEQ ID NO: 9), SSAMS(SEQ ID NO: 10), TISVGGGKTYYPDSVKG(SEQ ID NO: 11), and LISLY (SEQ ID NO: 12). In a further example, sequences that may comprise or consist of the CDR sequences of BB-7 VL and VH include KASQDINSYLT(SEQ ID NO: 7), LTNRLMD (SEQ ID NO: 13), LQYVDFPYT(SEQ ID NO: 14), SSAMS (SEQ ID NO: 10), TISSGGRSTYYPDSVKG(SEQ ID NO: 15), and LISPY(SEQ ID NO: 16). Sequences that may comprise or consist of the CDR sequences of DC-1 VL and VH include KASQDINSYLT(SEQ ID NO: 7), LVNRLVD (SEQ ID NO: 17), LQYDDFPYT (SEQ ID NO: 9), THAMS (SEQ ID NO: 18), TISSGGRSTYYPDSVKG(SEQ ID NO: 15), and LISTY(SEQ ID NO: 19). It is preferred that the antibodies and antigen-binding fragments thereof defined herein comprise or consist of CDR sequences, or CDR and flanking sequences, as defined in Table 24A. It is most preferred that the antibodies and antigen-binding fragments thereof defined herein comprise or consist of the CDR sequences, or CDR and flanking sequences, of the exemplary antibody AB-1, or BB-7, or DC-1 (as defined, for example, in Table 24A).

It is preferred that the antibody or antigen-binding fragment thereof retains the binding specificity for TG2 of the original antibody. By "retains the binding specificity" we mean that the antibody or antigen-binding fragment thereof is capable of competing for binding to TG2 with the exemplary antibodies of the invention, for example AB-1, AG-1, AG-9, AH-1, AH-3, BB-7, DC-1, EH-6, JE-12, IA-12, DF-4, DH-2, DD-6 and/or DD-9 (see accompanying Examples). For example, the antibody or antigen-binding fragment thereof may bind to the same epitope on TG2 as an antibody comprising the following sequences: KASQDINSYLT(SEQ ID NO: 7), RTNRLFD(SEQ ID NO: 8), LQYDDFPYT(SEQ ID NO: 9), SSAMS(SEQ ID NO: 10), TISVGGGKTYYPDSVKG(SEQ ID NO: 11), and LISLY (SEQ ID NO: 12).

By "epitope" it is herein intended to mean a site of a molecule to which an antibody binds, i.e. a molecular region of an antigen. An epitope may be a linear epitope, which is determined by e.g. the amino acid sequence, i.e. the primary structure, or a three-dimensional epitope, defined by the secondary structure, e.g. folding of a peptide chain into beta sheet or alpha helical, or by the tertiary structure, e.g. way which helices or sheets are folded or arranged to give a three-dimensional structure, of an antigen.

Methods for determining whether a test antibody is capable of competing for binding with second antibody are well known in the art (such as, for example sandwich-ELISA or reverse-sandwich-ELISA techniques) and described, for example, in *Antibodies: A Laboratory Manual*, Harlow & Lane (1988, CSHL, NY, ISBN 0-87969-314-2), which is incorporated herein by reference.

The antibody or antigen-binding fragment thereof, with binding specificity for an epitope in the TG2 core region may also retain one or more of the same biological properties as the original antibody (such as the exemplary antibodies provided in the Examples).

As explained above, TG2 is a calcium-dependent multifunctional protein that catalyzes the formation of Nε-(γ-glutamyl)lysine isopeptide bonds between lysine and glutamine residues. TG2 comprises an N terminal beta sandwich domain that contains binding sites (e.g. fibronectin) and sequences required for enzyme export. This links to the catalytic core domain. Central to the domain is a catalytic triad consisting of Cys 277, Asp 358, and His 355, plus several putative calcium binding sites. This links to the third domain, beta barrel 1 where a GTP binding site resides conveying the enzyme with GTPase activity. Beta barrel 1 also contains an integrin binding site used in cell adhesion. Beta Barrel 1 along with the fourth TG2 domain, Beta barrel 2, are involved in the conformational change in TG2 required for its activation. In a high calcium, low GTP environment Barrel 1 and 2 swing down from the closed and folded inactive form to convey TG2 with a linear structure opening up the catalytic core allowing activation (Pinkas et al (2007) *PLoS Biol*. Transglutaminase 2 undergoes a large conformational change upon activation. 5(12): e327).

By "the core region of transglutaminase type 2 (TG2)" we include a region of TG2 comprising the catalytic triad described above, excluding the beta sandwich domain and beta barrels 1 and 2. Preferably the core region comprises or consists of amino acids 143 to 473 of human TG2, or a fragment thereof.

Amino acids 143 to 473 of human TG2 consist of the following sequence (SEQ ID NO: 20):

```
CPADAVYLDSEEERQEYVLTQQGFIYQGSAKFIKNIPWNFGQFEDGILDI

CLILLDVNPKFLKNAGRDCSRRSSPVYVGRVVSGMVNCNDDQGVLLGRWD

NNYGDGVSPMSWIGSVDILRRWKNHGCQRVKYGQCWVFAAVACTVLRCLG

IPTRVVTNYNSAHDQNSNLLIEYFRNEFGEIQGDKSEMIWNFHCWVESWM

TRPDLQPGYEGWQALDPTPQEKSEGTYCCGPVPVRAIKEGDLSTKYDAPF

VFAEVNADVVDWIQQDDGSVHKSINRSLIVGLKISTKSVGRDEREDITHT

YKYPEGSSEEREAFTRANHLNKLAEKEETGM
```

Thus, in an embodiment of the invention, the core region may consist of amino acids 143 to 473 of human TG2. In this embodiment, the epitope of the antibody of the invention could thus be any epitope within the region defined by amino acids 143 to 473 of human TG2. Thus, the epitope may be a fragment of this sequence or it could be made up of various amino acid residues within this fragment that may not be adjacent one another in the primary amino acid structure but localise with one another in the secondary, tertiary or even quaternary structure of the protein, as would be understood by a person of skill in the art.

In an embodiment of the invention the antibody or antigen-binding fragment thereof may selectively bind in whole or in part to a region comprising amino acids 304 to 326 of human TG2. This region (amino acids 304 to 326 of human TG2) is referred to as Group 1 in FIG. 5 and comprises the amino acid sequence AHDQNSNLLIEYFRNEFGEIQGD (SEQ ID NO: 21).

In a further embodiment, the antibody or antigen-binding fragment thereof may selectively bind in whole or in part to a region comprising amino acids 351 to 365 of human TG2. This region (amino acids 351 to 365 of human TG2) is referred to as Group 2 in FIG. 5 and comprises the amino acid sequence YEGWQALDPTPQEKS(SEQ ID NO: 22).

In a yet further embodiment of the invention, the antibody or antigen-binding fragment thereof may selectively bind in whole or in part to a region comprising amino acids 450 to 467 of human TG2. This region (amino acids 450 to 467 of human TG2) is referred to as Group 3 in FIG. 5 and comprises the amino acid sequence SEEREAFTRA-NHLNKLAE (SEQ ID NO: 23).

In a preferred embodiment of any aspect of the invention, the antibody or antigen-binding fragment thereof inhibits TG2 activity, for example human TG2 activity.

In an embodiment of the invention the antibody or antigen-binding fragment thereof may comprise one or more of the following amino acid sequences:

```
                    (SEQ ID NO: 7)
KASQDINSYLT;
and/or

                    (SEQ ID NO: 8)
RTNRLFD;
and/or

                    (SEQ ID NO: 9)
LQYDDFPYT;
and/or

                    (SEQ ID NO: 10)
SSAMS;
and/or

                    (SEQ ID NO: 11)
TISVGGGKTYYPDSVKG;
and/or

                    (SEQ ID NO: 12)
LISLY.
```

The antibody or antigen-binding fragment thereof of the invention may comprise one or more of the following amino acid sequences:

```
                    (SEQ ID NO: 24)
TCKASQDINSYLTWF;
and/or

                    (SEQ ID NO: 25)
TLIYRTNRLFDGVP or

                    (SEQ ID NO: 26)
TLIYRTNRLFDGVPXXFSGSGSGQDFF;
and/or

                    (SEQ ID NO: 27)
YCLQYDDFPYTFG;
and/or

                    (SEQ ID NO: 28)
FTLSSSAMSWVR or

                    (SEQ ID NO: 29)
CXAXXFTLSSSAMSWVR;
and/or

                    (SEQ ID NO: 30)
WVATISVGGGKTYYPDSVKGRFTISR or

                    (SEQ ID NO: 31)
WVATISVGGGKTYYPDSVKGRFTISRXNXXXXL;
and/or

                    (SEQ ID NO: 32)
YCAKLISLYWG, wherein X is any amino acid.
```

The sequences of the immediately preceding embodiments are considered to comprise the complementarity determining regions of the light and heavy variable regions of the exemplary antibody AB-1 (see Example 1) and certain specified humanised variants of the AB-1 antibody. In a further embodiment, the antibody may comprise the amino acid sequence KASQDINSYLTXXXXXXXXXXXXXXXRTNRLFDXXXXXXXXXXXXXXXFXXXXXXXXXX XXXXXXLQYDDFPYT(SEQ ID NO: 33); or KASQDINSYLTXXXXXXXXXXXXXXXXXXXXXXXXXXXXXXXXXXXXXXXF(SEQ ID NO: 34); or RTNRLFDXXXXXXXXXXXXXXXXF(SEQ ID NO: 35); or FXXXXXXXXXXXXXXXXLQYDDFPYT(SEQ ID NO: 36), wherein X is any amino acid.

In a further embodiment, the antibody or antigen-binding fragment thereof may comprise the amino acid sequence

```
                    (SEQ ID NO: 24)
TCKASQDINSYLTWF
or

                    (SEQ ID NO: 37)
TCKASQDINSYLTWY;
and/or

                    (SEQ ID NO: 38)
LLIYRTNRLFDGVP
or

                    (SEQ ID NO: 39)
SLIYRTNRLFDGVP
or

                    (SEQ ID NO: 40)
LLIYRTNRLFDGVPXXFSGSGSGQDFF
or

                    (SEQ ID NO: 41)
SLIYRTNRLFDGVPXXFSGSGSGQDFF;
and/or

                    (SEQ ID NO: 27)
YCLQYDDFPYTFG;
and/or

                    (SEQ ID NO: 42)
FTFSSSAMSWVR
or

                    (SEQ ID NO: 43)
CXAXXFTFSSSAMSWVR;
and/or

                    (SEQ ID NO: 44)
WVSTISVGGGKTYYPDSVKGRFTISR
or

                    (SEQ ID NO: 45)
WVSTISVGGGKTYYPDSVKGRFTISRXNXXXXL;
and/or

                    (SEQ ID NO: 32)
YCAKLISLYWG,
wherein X is any amino acid.
```

Thus, in an embodiment, the antibody or antigen-binding fragment thereof may have at least one light chain variable region comprising the following sequences: KASQDINSYLT(SEQ ID NO: 7); and RTNRLFD(SEQ ID NO: 8); and LQYDDFPYT(SEQ ID NO: 9).

In a further embodiment, the antibody or antigen-binding fragment thereof may have at least one heavy chain variable region comprising the following sequences: SSAMS(SEQ ID NO: 10); and TISVGGGKTYYPDSVKG(SEQ ID NO: 11); and LISLY(SEQ ID NO: 12).

In an embodiment of the invention the antibody or antigen-binding fragment thereof may have at least one light chain variable region comprising the amino acid sequence

```
                    (SEQ ID NO: 46)
DIQMTQTPSSMYASLGERVTITCKASQDINSYLTWFQQKPGKS

PKTLIYRTNRLFDGVPSRFSGSGSGQDFFLTISSLEYEDMGIY

YCLQYDDFPYTFGGGTKLEIK
or

                    (SEQ ID NO: 47)
DIKMTQSPSSMYASLGERVTITCKASQDINSYLTWFQQKPGKS

PKTLIYRTNRLFDGVPSRFSGSGSGQDFFLTISSLEYEDMGIY

YCLQYDDFPYTFGGGTKLEIK.
```

These light chain variable regions correspond with that found in exemplary antibody AB-1 (FIGS. 7 and 18).

Alternatively, the antibody or antigen-binding fragment thereof may have at least one light chain variable region comprising the amino acid sequence:

```
                                      (SEQ ID NO: 48)
EIVLTQSPSSMYASLGERVTITCKASQDINSYLTWFQQKPGKSPKTLIYR

TNRLFDGVPSRFSGSGSGQDFFLTISSLEYEDMGIYYCLQYDDFPYTFGG

GTKLEIK (AB-1_VK)
or

                                      (SEQ ID NO: 49)
DIQMTQSPSSMYASLGERVTITCKASQDINSYLTWFQQKPGKSPKTLIYR

TNRLFDGVPSRFSGSGSGQDFFLTISSLEYEDMGIYYCLQYDDFPYTFGG

GTKLEIK (AB-1_VK1).
```

In a particularly preferred embodiment the antibody or antigen-binding fragment thereof may have at least one light chain variable region comprising the amino acid sequence:

```
                                      (SEQ ID NO: 50)
EIVLTQSPSSLSASVGDRVTITCKASQDINSYLTWYQQKPGKAPKLLIYR

TNRLFDGVPSRFSGSGSGTDFFFTISSLQPEDFGTYYCLQYDDFPYTFGG

GTKLEIK (hAB-1_RKE);
or

                                      (SEQ ID NO: 51)
DIQMTQSPSSLSASVGDRVTITCKASQDINSYLTWFQQKPGKAPKSLIYR

TNRLFDGVPSRFSGSGSGTDFFLTISSLQPEDFATYYCLQYDDFPYTFGQ

GTKVEIK (hAB-1_RKJ).
```

These sequences are humanised variants of the AB-1 light chain sequences provided above.

In an embodiment of the invention, the antibody or antigen-binding fragment thereof may have at least one heavy chain variable region comprising the amino acid sequence

```
                                      (SEQ ID NO: 52)
EVQLEESGGGLVKPGGSLKLSCAASGFTLSSSAMSWVRQTPD

RRLEWVATISVGGGKTYYPDSVKGRFTISRDNAKNTLYLQMN

SLRSEDTAMYYCAKLISLYWGQGTTLTVSS
or

                                      (SEQ ID NO: 53)
EVQLVESGGGLVKPGGSLKLSCAASGFTLSSSAMSWVRQTPD

RRLEWVATISVGGGKTYYPDSVKGRFTISRDNAKNTLYLQMN

SLRSEDTAMYYCAKLISLYWGQGTTLTVSS.
```

These heavy chain variable regions correspond with that found in exemplary antibody AB-1 (FIGS. 7 and 18).

Alternatively, the antibody or antigen-binding fragment thereof may have at least one heavy chain variable region comprising the amino acid sequence:

```
                                      (SEQ ID NO: 54)
EVQLQESGGGLVKPGGSLKLSCAASGFTLSSSAMSWVRQTPDRRLEWVAT

ISVGGGKTYYPDSVKGRFTISRDNAKNTLYLQMNSLRSEDTAMYYCAKLI

SLYWGQGTTLTVSS (AB-1_VH).
```

In a particularly preferred embodiment, the antibody or antigen-binding fragment thereof may have at least one heavy chain variable region comprising the amino acid sequence:

```
                              (SEQ ID NO: 55) (hAB-1_RHA)
EVQLLESGGGLVQPGGSLRLSCAASGFTFSSSAMSWVRQAPGKG

LEWVSTISVGGGKTYYPDSVKGRFTISRDNSKNTLYLQMNSLRA

EDTAVYYCAKLISLYWGQGTLVTVSS.
```

This sequence is a humanised variant of the AB-1 heavy chain sequence provided above.

Thus, it is envisaged that in an embodiment, the antibody or antigen-binding fragment thereof may have:

```
i) at least one light chain variable region
comprising the amino acid sequence
                                      (SEQ ID NO: 46)
DIQMTQTPSSMYASLGERVTITCKASQDINSYLTWFQQKPGKSPKTLIYR

TNRLFDGVPSRFSGSGSGQDFFLTISSLEYEDMGIYYCLQYDDFPYTFGG

GTKLEIK
or

                                      (SEQ ID NO: 47)
DIKMTQSPSSMYASLGERVTITCKASQDINSYLTWFQQKPGKSPKTLIYR

TNRLFDGVPSRFSGSGSGQDFFLTISSLEYEDMGIYYCLQYDDFPYTFGG

GTKLEIK,
or

                                      (SEQ ID NO: 48)
EIVLTQSPSSMYASLGERVTITCKASQDINSYLTWFQQKPGKSPKTLIYR

TNRLFDGVPSRFSGSGSGQDFFLTISSLEYEDMGIYYCLQYDDFPYTFGG

GTKLEIK (AB-1_VK),
or

                                      (SEQ ID NO: 49)
DIQMTQSPSSMYASLGERVTITCKASQDINSYLTWFQQKPGKSPKTLIYR

TNRLFDGVPSRFSGSGSGQDFFLTISSLEYEDMGIYYCLQYDDFPYTFGG

GTKLEIK (AB-1_VK1),
or

                                      (SEQ ID NO: 50)
EIVLTQSPSSLSASVGDRVTITCKASQDINSYLTWYQQKPGKAPKLLIYR

TNRLFDGVPSRFSGSGSGTDFFFTISSLQPEDFGTYYCLQYDDFPYTFGG

GTKLEIK (hAB-1_RKE),
or

                                      (SEQ ID NO: 51)
DIQMTQSPSSLSASVGDRVTITCKASQDINSYLTWFQQKPGKAPKSLIYR

TNRLFDGVPSRFSGSGSGTDFFLTISSLQPEDFATYYCLQYDDFPYTFGQ

GTKVEIK (hAB-1_RKJ);
and

ii) at least one heavy chain variable region
comprising the amino acid sequence
```

-continued (SEQ ID NO: 52)
EVQLEESGGGLVKPGGSLKLSCAASGFTLSSSAMSWVRQTPDRRLEWVAT

ISVGGGKTYYPDSVKGRFTISRDNAKNTLYLQMNSLRSEDTAMYYCAKLI

SLYWGQGTTLTVSS
or (SEQ ID NO: 53)
EVQLVESGGGLVKPGGSLKLSCAASGFTLSSSAMSWVRQTPDRRLEWVAT

ISVGGGKTYYPDSVKGRFTISRDNAKNTLYLQMNSLRSEDTAMYYCAKLI

SLYWGQGTTLTVSS,
or (SEQ ID NO: 54)
EVQLQESGGGLVKPGGSLKLSCAASGFTLSSSAMSWVRQTPDRRLEWVAT

ISVGGGKTYYPDSVKGRFTISRDNAKNTLYLQMNSLRSEDTAMYYCAKLI

SLYWGQGTTLTVSS (AB-1_VH),
or (SEQ ID NO: 55)
EVQLLESGGGLVQPGGSLRLSCAASGFTFSSSAMSWVRQAPGKGLEWVST

ISVGGGKTYYPDSVKGRFTISRDNSKNTLYLQMNSLRAEDTAVYYCAKLI

SLYWGQGTLVTVSS (hAB-1_RHA).

In an embodiment of any aspect of the present invention the antibody or antigen-binding fragment thereof may comprise one or more of the following amino acid sequences:

(SEQ ID NO: 7)
KASQDINSYLT;
and/or (SEQ ID NO: 13)
LTNRLMD;
and/or (SEQ ID NO: 14)
LQYVDFPYT;
and/or (SEQ ID NO: 10)
SSAMS;
and/or (SEQ ID NO: 15)
TISSGGRSTYYPDSVKG;
and/or (SEQ ID NO: 16)
LISPY.

The sequences of the immediately preceding embodiment are considered to comprise the complementarity determining regions of the light and heavy variable regions of the exemplary antibody BB-7 (see FIG. 19). In a further embodiment, the antibody may comprise the amino acid sequence KASQDINSYLTXXXXXXXXXXXXXXXLTNRLMDXXXXXXX XXXXXXXFXXXXXXXXXXX XXXXXXLQYVDFPYT(SEQ ID NO: 56); or KASQDINSYLTXXXXXXXXXXXXXXXXXXXXXXXXXXXXXX XXXXXXXF(SEQ ID NO: 57); or LTNRLMDXXXXXXXXXXXXXXF(SEQ ID NO: 58); or FXXXXXXXXXXXXXXXXLQYVDFPYT(SEQ ID NO: 59), wherein X is any amino acid.

Thus, in an embodiment of any aspect of the present invention, the antibody or antigen-binding fragment thereof may have at least one light chain variable region comprising the following sequences: KASQDINSYLT(SEQ ID NO: 7); and LTNRLMD(SEQ ID NO: 13); and LQYVDFPYT(SEQ ID NO: 14).

In a further embodiment of any aspect of the present invention, the antibody or antigen-binding fragment thereof may have at least one heavy chain variable region comprising the following sequences: SSAMS(SEQ ID NO: 10); and TISSGGRSTYYPDSVKG(SEQ ID NO: 15); and LISPY (SEQ ID NO: 16).

In an embodiment of any aspect of the present invention the antibody or antigen-binding fragment thereof may have at least one light chain variable region comprising the amino acid sequence (SEQ ID NO: 60)
AIKMTQSPSSMYASLGERVIITCKASQDINSYLTWFQQKPGKSP

KTLIYLTNRLMDGVPSRFSGSGSGQEFLLTISGLEHEDMGIYYC

LQYVDFPYTFGGGTKLEIK.

This light chain variable region corresponds with that found in exemplary antibody BB-7 (FIG. 19).

In an embodiment of any aspect of the present invention, the antibody or antigen-binding fragment thereof may have at least one heavy chain variable region comprising the amino acid sequence (SEQ ID NO: 61)
AVQLVESGGGLVKPGGSLKLSCAASGIIFSSSAMSWVRQTPEKR

LEWVATISSGGRSTYYPDSVKGRFTVSRDSAKNTLYLQMDSLRS

EDTAIYYCAKLISPYWGQGTTLTVSS.

This heavy chain variable region corresponds with that found in exemplary antibody BB-7 (FIG. 19).

Thus, it is envisaged that in an embodiment of any aspect of the present invention, the antibody or antigen-binding fragment thereof may have:

i) at least one light chain variable region comprising the amino acid sequence (SEQ ID NO: 60)
AIKMTQSPSSMYASLGERVIITCKASQDINSYLTWFQQKPGKSPKTLIYL

TNRLMDGVPSRFSGSGSGQEFLLTISGLEHEDMGIYYCLQYVDFPYTFGG

GTKLEIK;
and ii) at least one heavy chain variable region comprising the amino acid sequence (SEQ ID NO: 61)
AVQLVESGGGLVKPGGSLKLSCAASGIIFSSSAMSWVRQTPEKRLEWVAT

ISSGGRSTYYPDSVKGRFTVSRDSAKNTLYLQMDSLRSEDTAIYYCAKLI

SPYWGQGTTLTVSS.

It is further envisaged that in an embodiment of any aspect of the present invention, the antibody or antigen-binding fragment thereof may have:

i) at least one light chain variable region comprising the amino acid sequence
DIQMTQSPSSLSASVGDRVTITCKASQDINSYLTWFQQKPGKAPKSLIYL

TNRLMDGVPSRFSGSGSGTDFFLTISSLQPEDFATYYCLQYVDFPYTFGQ

-continued

GTKVEIK (SEQ ID NO: 62) or DIKMTQSPSSLSASVGDRVTITC

KASQDINSYLTWFQQKPGKAPKTLIYLTNRLMDGVPSRFSGSGSGQEFLL

STISLQPEDFATYYCLQYVDFPYTFGQGTKVEIK (SEQ ID NO: 63); and/or ii) at least one heavy chain variable region comprising the amino acid sequence EVQLLESGGGLVQPGGSLRLSCAASGFTFSSSAMSWVRQAPGKGLEWVST

ISSGGRSTYYPDSVKGRFTISRDNSKNTLYLQMNSLRAEDTAVYYCAKLI

SPYWGQGTLVTVSS (SEQ ID NO: 64) or

EVQLLESGGGLVQPGGSLRLSCAASGIIFSSSAMSWVRQAPGKGLEWVAT

ISSGGRSTYYPDSVKGRFTVSRDSSKNTLYLQMNSLRAEDTAVYYCAKLI

SPYWGQGTLVTVSS (SEQ ID NO: 65).

These sequences correspond to humanised variants of antibody BB-7 (see Tables 23, 24 and 24A).

In an embodiment of any aspect of the present invention the antibody or antigen-binding fragment thereof may comprise one or more of the following amino acid sequences:

KASQDINSYLT; (SEQ ID NO: 7) and/or

LVNRLVD; (SEQ ID NO: 17) and/or

LQYDDFPYT (SEQ ID NO: 9) and/or

THAMS; (SEQ ID NO: 18) and/or

TISSGGRSTYYPDSVKG; (SEQ ID NO: 15) and/or

LISTY. (SEQ ID NO: 19)

The sequences of the immediately preceding embodiment are considered to comprise the complementarity determining regions of the light and heavy variable regions of the exemplary antibody DC-1 (see FIG. 20). In a further embodiment, the antibody may comprise the amino acid sequence KASQDINSYLTXXXXXXXXXXXXXXXLVNRLVDXXXXXXXXXXXXXXXAXXXXXXXXXXX XXXXXXLQYDDFPYT(SEQ ID NO: 66) or KASQDINSYLTXXXXXXXXXXXXXXXXXXXXXXXXXXXXXXXXXXXXXA(SEQ ID NO: 67); or LVNRLVDXXXXXXXXXXXXXXXA(SEQ ID NO: 68); or AXXXXXXXXXXXXXXXLQYDDFPYT(SEQ ID NO: 69), wherein X is any amino acid.

Thus, in an embodiment of any aspect of the present invention, the antibody or antigen-binding fragment thereof may have at least one light chain variable region comprising the following sequences: KASQDINSYLT(SEQ ID NO: 7); and LVNRLVD(SEQ ID NO: 17); and LQYDDFPYT(SEQ ID NO: 9)

In a further embodiment of any aspect of the present invention, the antibody or antigen-binding fragment thereof may have at least one heavy chain variable region comprising the following sequences: THAMS(SEQ ID NO: 18); and TISSGGRSTYYPDSVKG(SEQ ID NO: 15); and LISTY (SEQ ID NO: 19).

In an embodiment of any aspect of the present invention the antibody or antigen-binding fragment thereof may have at least one light chain variable region comprising the amino acid sequence (SEQ ID NO: 70)
DITMTQSPSSIYASLGERVTITCKASQDINSYLTWFQQKPGKSP

KILIYLVNRLVDGVPSRFSGSGSGQDYALTISSLEYEDMGIYYC

LQYDDFPYTFGGGTKLEIK.

This light chain variable region corresponds with that found in exemplary antibody DC-1 (FIG. 20). In an embodiment of any aspect of the present invention, the antibody or antigen-binding fragment thereof may have at least one heavy chain variable region comprising the amino acid sequence (SEQ ID NO: 71)
EVQLVESGGGLVKPGGSLKLSCAASGFTLSTHAMSWVRQTPEKR

LEWVATISSGGRSTYYPDSVKGRFTISRDNVKNTLYLQLSSLRS

EDTAVYFCARLISTYWGQGTTLTVSS.

This heavy chain variable region corresponds with that found in exemplary antibody DC-1 (FIG. 20).

Thus, it is envisaged that in an embodiment of any aspect of the present invention, the antibody or antigen-binding fragment thereof may have:

i) at least one light chain variable region comprising the amino acid sequence DITMTQSPSSIYASLGERVTITCKASQDINSYLTWFQQKPGKSPKILIYL

VNRLVDGVPSRFSGSGSGQDYALTISSLEYEDMGIYYCLQYDDFPYTFGG

GTKLEIK (SEQ ID NO: 70); and ii) at least one heavy chain variable region comprising the amino acid sequence EVQLVESGGGLVKPGGSLKLSCAASGFTLSTHAMSWVRQTPEKRLEWVAT

ISSGGRSTYYPDSVKGRFTISRDNVKNTLYLQLSSLRSEDTAVYFCARLI

STYWGQGTTLTVS (SEQ ID NO: 71).

It is further envisaged that in an embodiment of any aspect of the present invention, the antibody or antigen-binding fragment thereof may have:

i) at least one light chain variable region comprising the amino acid sequence DIQMTQSPSSLSASVGDRVTITCKASQDINSYLTWFQQKPGKAPKSLIYL

VNRLVDGVPSRFSGSGSGTDFFLTISSLQPEDFATYYCLQYDDFPYTFGQ

GTKVEIK (SEQ ID NO: 72) or

DITMTQSPSSLSASVGDRVTITCKASQDINSYLTWFQQKPGKAPKILIYL

VNRLVDGVPSRFSGSGSGQDYALTISSLQPEDFATYYCLQYDDFPYTFGQ

GTKVEIK (SEQ ID NO: 73); and/or

-continued

```
ii) at least one heavy chain variable region
comprising the amino acid sequence
EVQLLESGGGLVQPGGSLRLSCAASGFTFSTHAMSWVRQAPGKGLEWVST

ISSGGRSTYYPDSVKGRFTISRDNSKNTLYLQMNSLRAEDTAVYYCAKLI

STYWGQGTLVTVSS (SEQ ID NO: 74)
or

EVQLLESGGGLVQPGGSLRLSCAASGFTLSTHAMSWVRQAPGKGLEWVAT

ISSGGRSTYYPDSVKGRFTISRDNSKNTLYLQMNSLRAEDTAVYFCARLI

STYWGQGTLVTVSS (SEQ ID NO: 75).
```

These sequences correspond with the humanised variants of DC-1 provided in Tables 23, 24 and 24A.

In an embodiment of any aspect of the present invention the antibody or antigen-binding fragment thereof may comprise one or more of the following amino acid sequences:

```
                              (SEQ ID NO: 7)
KASQDINSYLT;
and/or

                              (SEQ ID NO: 76)
XXNRLXD;
and/or

                              (SEQ ID NO: 77)
LQYXDFPYT;
and/or

                              (SEQ ID NO: 78)
XXAMS;
and/or

                              (SEQ ID NO: 79)
TISXGGXXTYYPDSVKG;
and/or

                              (SEQ ID NO: 80)
LISXY, wherein X is any amino acid.
```

In an embodiment of any aspect of the present invention the antibody or antigen-binding fragment thereof may comprise one or more of the following amino acid sequences:

```
                                        (SEQ ID NO: 81)
(K/Q/R)ASQ(D/G)I(N/S/R)(S/N)YL(T/N/A);
and/or

                                        (SEQ ID NO: 82)
(R/L/V/D/A)(T/V/A)(N/S)(R/N)L(F/M/V/E/Q)(D/T/S);
and/or

                                        (SEQ ID NO: 83)
(L/Q)Q(Y/H)(D/V/N)(D/T)(F/Y)P(Y/L/W)T;
and/or

                                        (SEQ ID NO: 84)
(S/T)(S/H/Y)AMS;
and/or

                                        (SEQ ID NO: 85)
(T/A)IS(V/S/G)(G/S)G(G/R)(K/S)TYY(P/A)DSVKG;
and/or

(L/D)(I/G)(S/G)(L/P/T/V)Y.
```

In a further embodiment of any aspect of the present invention the antibody or antigen-binding fragment thereof may have at least one light chain variable region comprising the amino acid sequence

```
                                        (SEQ ID NO: 87)
QIVLTQSPAIMSASPGEKVTMTCSASSSVDYMYWYQQKPGSSPR

LLIYDTSNLASGVPVRFSGSGSGTSYSLTISRMGAEDAATYYCQ

QWNSSPLTFGAGTKLELK.
```

This light chain variable region corresponds with that found in exemplary antibody DD-9 (FIG. 25).

In an embodiment of any aspect of the present invention, the antibody or antigen-binding fragment thereof may have at least one heavy chain variable region comprising the amino acid sequence

```
                                        (SEQ ID NO: 88)
QVTLKESGPGILQPSQTLSLTCSFSGFSLSTSGMGVSWIRQSSGKGLEWL

AHIYWDDDKRYNPSLKSRITISKDSSSNQVFLKITSVDTADTATYYCARS

WITAPFAFWGQGTLVTVSA.
```

This heavy chain variable region corresponds with that found in exemplary antibody DD-9 (FIG. 25).

Thus, it is envisaged that in an embodiment of any aspect of the present invention, the antibody or antigen-binding fragment thereof may have:

```
i) at least one light chain variable region
comprising the amino acid sequence
QIVLTQSPAIMSASPGEKVTMTCSASSSVDYMYWYQQKPGSSPRLLIYDT

SNLASGVPVRFSGSGSGTSYSLTISRMGAEDAATYYCQQWNSSPLTFGAG

TKLELK (SEQ ID NO: 87);
and

ii) at least one heavy chain variable region
comprising the amino acid sequence
QVTLKESGPGILQPSQTLSLTCSFSGFSLSTSGMGVSWIRQSSGKGLEWL

AHIYWDDDKRYNPSLKSRITISKDSSSNQVFLKITSVDTADTATYYCARS

WTTAPFAFWGQGTLVTVSA (SEQ ID NO: 88).
```

In a further embodiment of any aspect of the present invention the antibody or antigen-binding fragment thereof may have at least one light chain variable region comprising the amino acid sequence

```
                                        (SEQ ID NO: 89)
QIVLTQSPAIMSASPGEKVTMTCSASSSVSYMYWYQQKPGSSPRLLIYDT

SNLASGVPVRFSGSGSGTSYSLTISRMEAEDAATFYCQQWSSSPLTFGAG

TKLELK.
```

This light chain variable region corresponds with that found in exemplary antibody DH-2 (FIG. 26).

In an embodiment of any aspect of the present invention, the antibody or antigen-binding fragment thereof may have at least one heavy chain variable region comprising the amino acid sequence

```
                                        (SEQ ID NO: 90)
QVTLKESGPGILQPSQTLSLTCSFSGFSLSTSGMGVSWIRQPSGKGLEWL

AHIYWDDDKRYNPSLKSRLTISKDTSSNQVFLKITSVDTADTATYYCARS

GTTAPFAYWGQGTLVTVSA.
```

This heavy chain variable region corresponds with that found in exemplary antibody DH-2 (FIG. 26).

Thus, it is envisaged that in an embodiment of any aspect of the present invention, the antibody or antigen-binding fragment thereof may have:

```
i) at least one light chain variable region
comprising the amino acid sequence
QIVLTQSPAIMSASPGEKVTMTCSASSSVSYMYWYQQKPGSSPRLLIYDT

SNLASGVPVRFSGSGSGTSYSLTISRMEAEDAATFYCQQWSSSPLTFGAG

TKLELK (SEQ ID NO: 89);
and

ii) at least one heavy chain variable region
comprising the amino acid sequence
QVTLKESGPGILQPSQTLSLTCSFSGFSLSTSGMGVSWIRQPSGKGLEWL

AHIYWDDDKRYNPSLKSRLTISKDTSSNQVFLKITSVDTADTATYYCARS

GTTAPFAYWGQGTLVTVSA (SEQ ID NO: 90).
```

In an embodiment of any aspect of the invention, it is envisaged that, the antibody or antigen-binding fragment thereof may have:

i) at least one light chain variable region comprising an amino acid sequence corresponding with any of the VK sequences provided in any of FIGS. 18 to 28; and/or
ii) at least one heavy chain variable region comprising an amino acid sequence corresponding with any of the VH sequences provided in any of FIGS. 18 to 28 or a fragment, variant or derivative thereof.

As indicated above, it is envisaged that the antibody or antigen-binding fragment of the preceding embodiments may comprise an amino acid sequence having at least 75% identity with one or more of the amino acid sequences given above, for example at least 80%, at least 90%, at least 95%, at least 96%, at least 97%, at least 98%, or at least 99% identity with one or more of the amino acid sequences specified above. It is also envisaged that the antibody or antigen-binding fragment may comprise up to 1, 2, 3, 4, 5, 6, 7, 8, 9, 10 or more insertions, deletions, conservative substitutions and/or non-conservative substitutions.

In a second aspect, the invention provides an antibody or antigen-binding fragment thereof comprising one or more of the following amino acid sequences:

```
                                (SEQ ID NO: 7)
KASQDINSYLT;
and/or

                                (SEQ ID NO: 76)
XXNRLXD;
and/or

                                (SEQ ID NO: 77)
LQYXDFPYT;
and/or

                                (SEQ ID NO: 78)
XXAMS;
and/or

                                (SEQ ID NO: 79)
TISXGGXXTYYPDSVKG;
and/or

                                (SEQ ID NO: 80)
LISXY, wherein X is any amino acid.
```

In an embodiment, the invention provides an antibody or antigen-binding fragment thereof comprising one or more of the following amino acid sequences:

```
                                (SEQ ID NO: 81)
(K/Q/R)ASQ(D/G)I(N/S/R)(S/N)YL(T/N/A);
and/or

                                (SEQ ID NO: 82)
(R/L/V/D/A)(T/V/A)(N/S)(R/N)L(F/M/V/E/Q)(D/T/S);
and/or

                                (SEQ ID NO: 83)
(L/Q)Q(Y/H)(D/V/N)(D/T)(F/Y)P(Y/L/W)T;
and/or

                                (SEQ ID NO: 84)
(S/T)(S/H/Y)AMS;
and/or

                                (SEQ ID NO: 85)
(T/A)IS(V/S/G)(G/S)G(G/R)(K/S)TYY(P/A)DSVKG;
and/or

                                (SEQ ID NO: 86)
(L/D)(I/G)(S/G)(L/P/T/V)Y.
```

In an embodiment, the invention provides an antibody or antigen-binding fragment thereof comprising one or more of the following amino acid sequences:

```
                                (SEQ ID NO: 7)
KASQDINSYLT;
and/or

                                (SEQ ID NO: 8)
RTNRLFD;
and/or

                                (SEQ ID NO: 9)
LQYDDFPYT;
and/or

                                (SEQ ID NO: 10)
SSAMS;
and/or

                                (SEQ ID NO: 11)
TISVGGGKTYYPDSVKG;
and/or

                                (SEQ ID NO: 12)
LISLY.
```

In an embodiment, the antibody or antigen-binding fragment thereof of the second aspect may comprise one or more of the following amino acid sequences:

```
                                (SEQ ID NO: 24)
TCKASQDINSYLTWF;
and/or

                                (SEQ ID NO: 25)
TLIYRTNRLFDGVP
or

                                (SEQ ID NO: 26)
TLIYRTNRLFDGVPXXFSGSGSGQDFF;
and/or

                                (SEQ ID NO: 27)
YCLQYDDFPYTFG;
and/or

                                (SEQ ID NO: 28)
FTLSSSAMSWVR
or

                                (SEQ ID NO: 29)
CXAXXFTLSSSAMSWVR;
and/or
```

-continued

```
                                        (SEQ ID NO: 30)
WVATISVGGGKTYYPDSVKGRFTISR
or

                                        (SEQ ID NO: 31)
WVATISVGGGKTYYPDSVKGRFTISRXNXXXXL;
and/or

                                        (SEQ ID NO: 32)
YCAKLISLYVVG, wherein X is any amino acid.
```

The sequences of the preceding embodiment are considered to comprise the complementarity determining regions of the light and heavy variable regions of the exemplified antibody AB-1.

In a further embodiment, the antibody or antigen-binding fragment thereof may comprise the amino acid sequence KASQDINSYLTXXXXXXXXXXXXXXXRTNRLFDXXXXXXXXXXXXXXXFXXXXXXXXXX XXXXXXLQYDDFPYT(SEQ ID NO: 33); or KASQDINSYLTXXXXXXXXXXXXXXXXXXXXXXXXXXXXXXXXXXXXXF(SEQ ID NO: 34); or RTNRLFDXXXXXXXXXXXXXXXXF(SEQ ID NO: 35); or FXXXXXXXXXXXXXXXXLQYDDFPYT(SEQ ID NO: 36), wherein X is any amino acid.

In a further embodiment, the antibody or antigen-binding fragment thereof may comprise the amino acid sequence

```
                                        (SEQ ID NO: 37)
TCKASQDINSYLTWY;
and/or

                                        (SEQ ID NO: 38)
LLIYRTNRLFDGVP
or

                                        (SEQ ID NO: 39)
SLIYRTNRLFDGVP
or

                                        (SEQ ID NO: 40)
LLIYRTNRLFDGVPXXFSGSGSGQDFF
or

                                        (SEQ ID NO: 41)
SLIYRTNRLFDGVPXXFSGSGSGQDFF;
and/or

                                        (SEQ ID NO: 27)
YCLQYDDFPYTFG;
and/or

                                        (SEQ ID NO: 42)
FTFSSSAMSWVR
or

                                        (SEQ ID NO: 43)
CXAXXFTFSSSAMSWVR;
and/or

                                        (SEQ ID NO: 44)
WVSTISVGGGKTYYPDSVKGRFTISR
or

                                        (SEQ ID NO: 45)
WVSTISVGGGKTYYPDSVKGRFTISRXNXXXXL;
and/or

                                        (SEQ ID NO: 32)
YCAKLISLYWG,
wherein X is any amino acid.
```

Thus, in an embodiment, the antibody or antigen-binding fragment thereof may have at least one light chain variable region comprising the following CDRs: KASQDINSYLT (SEQ ID NO: 7); and RTNRLFD(SEQ ID NO: 8); and LQYDDFPYT(SEQ ID NO: 9).

In a further embodiment, the antibody or antigen-binding fragment thereof may have at least one heavy chain variable region comprising the following CDRs: SSAMS(SEQ ID NO: 10); and TISVGGGKTYYPDSVKG(SEQ ID NO: 11); and LISLY(SEQ ID NO: 12).

In a further embodiment, the antibody or antigen-binding fragment thereof of the second aspect may have at least one light chain variable region comprising the amino acid sequence

```
                                        (SEQ ID NO: 46)
DIQMTQTPSSMYASLGERVTITCKASQDINSYLTWFQQKPGKSPKTLIYR

TNRLFDGVPSRFSGSGSGQDFFLTISSLEYEDMGIYYCLQYDDFPYTFGG

GTKLEIK
or

                                        (SEQ ID NO: 47)
DIKMTQSPSSMYASLGERVTITCKASQDINSYLTWFQQKPGKSPKTLIYR

TNRLFDGVPSRFSGSGSGQDFFLTISSLEYEDMGIYYCLQYDDFPYTFGG

GTKLEIK,
or

                                        (SEQ ID NO: 48)
EIVLTQSPSSMYASLGERVTITCKASQDINSYLTWFQQKPGKSPKTLIYR

TNRLFDGVPSRFSGSGSGQDFFLTISSLEYEDMGIYYCLQYDDFPYTFGG

GTKLEIK (AB-1_VK),
or

                                        (SEQ ID NO: 49)
DIQMTQSPSSMYASLGERVTITCKASQDINSYLTWFQQKPGKSPKTLIYR

TNRLFDGVPSRFSGSGSGQDFFLTISSLEYEDMGIYYCLQYDDFPYTFGG

GTKLEIK (AB-1_VK1),
or

                                        (SEQ ID NO: 50)
EIVLTQSPSSLSASVGDRVTITCKASQDINSYLTWYQQKPGKAPKLLIYR

TNRLFDGVPSRFSGSGSGTDFFFTISSLQPEDFGTYYCLQYDDFPYTFGG

GTKLEIK (hAB-1_RKE),
or

                                        (SEQ ID NO: 51)
DIQMTQSPSSLSASVGDRVTITCKASQDINSYLTWFQQKPGKAPKSLIYR

TNRLFDGVPSRFSGSGSGTDFFLTISSLQPEDFATYYCLQYDDFPYTFGQ

GTKVEIK (hAB-1_RKJ).
```

In a yet further embodiment of the second aspect, the antibody or antigen-binding fragment thereof may have at least one heavy chain variable region comprising the amino acid sequence

```
                                        (SEQ ID NO: 52)
EVQLEESGGGLVKPGGSLKLSCAASGFTLSSSAMSWVRQTPDRRLEWVAT

ISVGGGKTYYPDSVKGRFTISRDNAKNTLYLQMNSLRSEDTAMYYCAKLI

SLYWGQGTTLTVSS
or

                                        (SEQ ID NO: 53)
EVQLVESGGGLVKPGGSLKLSCAASGFTLSSSAMSWVRQTPDRRLEWVAT

ISVGGGKTYYPDSVKGRFTISRDNAKNTLYLQMNSLRSEDTAMYYCAKLI
```

-continued

```
SLYWGQGTTLTVSS,
or

                                    (SEQ ID NO: 54)
EVQLQESGGGLVKPGGSLKLSCAASGFTLSSSAMSWVRQTPDRRLEWVAT

ISVGGGKTYYPDSVKGRFTISRDNAKNTLYLQMNSLRSEDTAMYYCAKLI

SLYWGQGTTLTVSS (AB-1_VH),
or

                                    (SEQ ID NO: 55)
EVQLLESGGGLVQPGGSLRLSCAASGFTFSSSAMSWVRQAPGKGLEWVST

ISVGGGKTYYPDSVKGRFTISRDNSKNTLYLQMNSLRAEDTAVYYCAKLI

SLYWGQGTLVTVSS (hAB-1_RHA).
```

The invention also provides an antibody or antigen-binding fragment thereof having at least one light chain variable region as embodied in the second aspect and at least one heavy chain variable region as embodied in the second aspect.

For the avoidance of doubt, the antibody or antigen-binding fragment thereof of the second aspect may comprise any amino acid sequence provided in relation to the first aspect. Thus, the antibody or antigen-binding fragment thereof of the second aspect may include any VK and/or VK region as exemplified in any of FIGS. 18 to 28 or Tables 14 to 24 and 24A, or any variant, fragment or derivative thereof.

Further, the antibody or antigen-binding fragment thereof of any aspect of the invention may be or comprise any humanised or chimeric antibody described herein, in particular, antibody or antigen-binding fragment thereof may comprise or consist of any of the sequences provided in Tables 14 to 24 and 24A.

It is envisaged that the antibody or antigen-binding fragment of the second aspect and related embodiments may comprise an amino acid sequence having at least 75% identity with one or more of the amino acid sequences given above, for example at least 80%, at least 90%, at least 95%, at least 96%, at least 97%, at least 98%, or at least 99% identity with one or more of the amino acid sequences specified above. It is also envisaged that the antibody or antigen-binding fragment may comprise up to 1, 2, 3, 4, 5, 6, 7, 8, 9, 10 or more insertions, deletions, conservative substitutions and/or non-conservative substitutions.

In a preferred embodiment of any aspect of the invention, the antibody or antigen-binding fragment thereof may comprise or consist of an intact antibody. Alternatively, the antibody or antigen-binding fragment thereof may consist essentially of an intact antibody. By "consist essentially of" we mean that the antibody or antigen-binding fragment thereof consists of a portion of an intact antibody sufficient to display binding specificity for TG2.

The antibody or antigen-binding fragment of the invention may be a non-naturally occurring antibody. Of course, where the antibody is a naturally occurring antibody, it is provided in an isolated form (i.e. distinct from that in which it is found in nature).

In an embodiment of any aspect of the invention, the antibody or antigen-binding fragment thereof may comprise or consist of an antigen-binding fragment selected from the group consisting of: an Fv fragment; an Fab fragment; and an Fab-like fragment. In a further embodiment, the Fv fragment may be a single chain Fv fragment or a disulphide-bonded Fv fragment. In a yet further embodiment, the Fab-like fragment may be an Fab' fragment or an $F(ab)_2$ fragment.

The variable heavy ($V_H$) and variable light ($V_L$) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent-parented antibody (Morrison et al (1984) *Proc. Natl. Acad. Sci. USA* 81, 6851-6855).

Antigenic specificity is conferred by variable domains and is independent of the constant domains, as known from experiments involving the bacterial expression of antibody fragments, all containing one or more variable domains. These molecules include Fab-like molecules (Better et al (1988) Science 240, 1041); Fv molecules (Skerra et al (1988) Science 240, 1038); single-chain Fv (ScFv) molecules where the $V_H$ and $V_L$ partner domains are linked via a flexible oligopeptide (Bird et al(1988) Science 242, 423; Huston et al (1988) *Proc. Natl. Acad. Sci. USA* 85, 5879) and single domain antibodies (dAbs) comprising or consisting of isolated V domains (Ward et al (1989) *Nature* 341, 544). A general review of the techniques involved in the synthesis of antibody fragments which retain their specific binding sites is to be found in Winter & Milstein (1991) *Nature* 349, 293-299.

Thus, by "antigen-binding fragment" we include a functional fragment of an antibody that is capable of binding to TG2.

Exemplary antigen-binding fragments may be selected from the group consisting of Fv fragments (e.g. single chain Fv and disulphide-bonded Fv), and Fab-like fragments (e.g. Fab fragments, Fab' fragments and $F(ab)_2$ fragments).

In one embodiment of the invention, the antigen-binding fragment is an scFv.

The advantages of using antibody fragments, rather than whole antibodies, are several-fold. The smaller size of the fragments may lead to improved pharmacological properties, such as better penetration of solid tissue. Moreover, antigen-binding fragments such as Fab, Fv, ScFv and dAb antibody fragments can be expressed in and secreted from *E. coli*, thus allowing the facile production of large amounts of the said fragments.

Also included within the scope of the invention are modified versions of antibodies and an antigen-binding fragments thereof, e.g. modified by the covalent attachment of polyethylene glycol or other suitable polymer.

It is particularly preferred that the antibody or antigen-binding fragment thereof is a recombinant molecule.

Methods of generating antibodies and antibody fragments are well known in the art. For example, antibodies may be generated via any one of several methods which employ induction of in vivo production of antibody molecules, screening of immunoglobulin libraries (Orlandi. et al, 1989. *Proc. Natl. Acad. Sci. U.S.A.* 86:3833-3837; Winter et al., 1991, *Nature* 349:293-299) or generation of monoclonal antibody molecules by cell lines in culture. These include, but are not limited to, the hybridoma technique, the human B-cell hybridoma technique, and the Epstein-Barr virus (EBV)-hybridoma technique (Kohler et al., 1975. *Nature* 256:4950497; Kozbor et al., 1985. *J. Immunol. Methods* 81:31-42; Cote et al., 1983. *Proc. Natl. Acad. Sci. USA* 80:2026-2030; Cole et al., 1984. *Mol. Cell. Biol.* 62:109-120).

Conveniently, the invention provides an antibody or antigen-binding fragment thereof wherein the antibody is a recombinant antibody (i.e. wherein it is produced by recombinant means).

In a particularly preferred embodiment of any aspect of the invention, the antibody may be a monoclonal antibody.

Suitable monoclonal antibodies to selected antigens may be prepared by known techniques, for example those disclosed in "*Monoclonal Antibodies: A manual of techniques*", H Zola (CRC Press, 1988) and in "*Monoclonal Hybridoma Antibodies: Techniques and Applications*", J G R Hurrell (CRC Press, 1982), which are incorporated herein by reference. Exemplary monoclonal antibodies of the invention and suitable methods for their manufacture are provided in the Examples below.

Antibody fragments can also be obtained using methods well known in the art (see, for example, Harlow & Lane, 1988, *"Antibodies: A Laboratory Manuaul*", Cold Spring Harbor Laboratory, New York, which is incorporated herein by reference). For example, antibody fragments of the present invention can be prepared by proteolytic hydrolysis of the antibody or by expression in *E. coli* or mammalian cells (e.g. Chinese hamster ovary cell culture or other protein expression systems) of DNA encoding the fragment. Alternatively, antibody fragments can be obtained by pepsin or papain digestion of whole antibodies by conventional methods.

In an embodiment of any aspect of the invention, the antibody or antigen-binding fragment thereof may be a human antibody or a humanised antibody.

It will be appreciated by persons skilled in the art that for human therapy or diagnostics, humanised antibodies may be used. Humanised forms of non-human (e.g. murine) antibodies are genetically engineered chimeric antibodies or antibody fragments having minimal-portions derived from non-human antibodies. Humanised antibodies include antibodies in which complementary determining regions of a human antibody (recipient antibody) are replaced by residues from a complementary determining region of a non human species (donor antibody) such as mouse, rat or rabbit having the desired functionality. In some instances, Fv framework residues of the human antibody are replaced by corresponding non-human residues. Humanised antibodies may also comprise residues which are found neither in the recipient antibody nor in the imported complementarity determining region or framework sequences. In general, the humanised antibody will comprise substantially all of at least one, and typically two, variable domains, in which all or substantially all of the complementarity determining regions correspond to those of a non-human antibody and all, or substantially all, of the framework regions correspond to those of a relevant human consensus sequence. Humanised antibodies optimally also include at least a portion of an antibody constant region, such as an Fc region, typically derived from a human antibody (see, for example, Jones et al., 1986. *Nature* 321:522-525; Riechmann et al., 1988, *Nature* 332:323-329; Presta, 1992, *Curr. Op. Struct. Biol.* 2:593-596, which are incorporated herein by reference).

Methods for humanising non-human antibodies are well known in the art. Generally, the humanised antibody has one or more amino acid residues introduced into it from a source which is non-human. These non-human amino acid residues, often referred to as imported residues, are typically taken from an imported variable domain. Humanisation can be essentially performed as described (see, for example, Jones et al., 1986, *Nature* 321:522-525; Reichmann et al., 1988. *Nature* 332:323-327; Verhoeyen et al., 1988, *Science* 239: 1534-15361; U.S. Pat. No. 4,816,567, which are incorporated herein by reference) by substituting human complementarity determining regions with corresponding rodent complementarity determining regions. Accordingly, such humanised antibodies are chimeric antibodies, wherein substantially less than an intact human variable domain has been substituted by the corresponding sequence from a non-human species. In practice, humanised antibodies may be typically human antibodies in which some complementarity determining region residues and possibly some framework residues are substituted by residues from analogous sites in rodent antibodies.

Human antibodies can also be identified using various techniques known in the art, including phage display libraries (see, for example, Hoogenboom & Winter, 1991, *J. Mol. Biol.* 227:381; Marks et al., 1991, *J. Mol. Biol.* 222:581; Cole et al., 1985, In: Monoclonal antibodies and Cancer Therapy, Alan R. Liss, pp. 77; Boerner et al., 1991. *J. Immunol.* 147:86-95, Soderlind et al., 2000, *Nat Biotechnol* 18:852-6 and WO 98/32845 which are incorporated herein by reference).

The term "amino acid" as used herein includes the standard twenty genetically-encoded amino acids and their corresponding stereoisomers in the 'D' form (as compared to the natural 'L' form), omega-amino acids other naturally-occurring amino acids, unconventional amino acids (e.g. $\alpha,\alpha$-disubstituted amino acids, N-alkyl amino acids, etc.) and chemically derivatised amino acids.

When an amino acid is being specifically enumerated, such as "alanine" or "Ala" or "A", the term refers to both L-alanine and D-alanine unless explicitly stated otherwise. Other unconventional amino acids may also be suitable components for polypeptides of the present invention, as long as the desired functional property is retained by the polypeptide. For the peptides shown, each encoded amino acid residue, where appropriate, is represented by a single letter designation, corresponding to the trivial name of the conventional amino acid.

In one embodiment, the polypeptides as defined herein comprise or consist of L-amino acids.

Once suitable antibodies are obtained, they may be tested for activity, such as binding specificity or a biological activity of the antibody, for example by ELISA, immunohistochemistry, flow cytometry, immunoprecipitation, Western blots, etc. The biological activity may be tested in different assays with readouts for that particular feature.

In a further aspect, the present invention provides a polynucleotide encoding an antibody or an antigen-binding fragment thereof according to the second aspect and the related embodiments of the second aspect.

Accordingly, in an embodiment, the invention provides an isolated polynucleotide comprising or consisting of the nucleotide sequences:

```
i)
                                         (SEQ ID NO: 91)
GACATCCAGATGACACAGACTCCATCTTCCATGTATGCATCTCTAGGAGA

GAGAGTCACTATCACTTGCAAGGCGAGTCAGGACATTAATAGCTATTTAA

CCTGGTTCCAGCAGAAACCAGGGAAATCTCCTAAGACCCTGATCTATCGT

ACAAATAGATTGTTTGATGGGGTCCCATCCAGGTTCAGTGGCAGTGGATC

TGGGCAAGATTTTTTTCTCACCATCAGCAGCCTGGAATATGAAGATATGG
```

-continued

GAATTTATTATTGTCTACAGTATGATGACTTTCCGTACACGTTCGGAGGG

GGGACCAAACTGGAAATAAAA;
and/or ii)

(SEQ ID NO: 92)
GAAGTACAGCTGGAGGAGTCAGGGGGGGGCTTAGTGAAGCCTGGAGGGTC

CCTGAAACTCTCCTGTGCAGCCTCTGGATTCACTCTCAGTTCCTCTGCCA

TGTCTTGGGTTCGCCAGACTCCGGACAGGAGGCTGGAGTGGGTCGCAACC

ATTAGTGTTGGTGGTGGTAAAACCTACTATCCAGACAGTGTGAAGGGTCG

CTTCACCATCTCCAGAGACAATGCCAAGAACACCCTCTATCTGCAAATGA

ACAGTCTGAGGTCTGAGGACACGGCCATGTATTACTGTGCAAAACTAATC

AGTCTCTACTGGGGCCAAGGCACCACTCTCACAGTCTCCTCA.

In a further embodiment, the invention provides an isolated polynucleotide comprising or consisting of any of the nucleic acid sequences listed in any of FIGS. 18 to 28.

Thus, in an embodiment, the invention provides an isolated polynucleotide comprising or consisting of the nucleotide sequences:

i)

(SEQ ID NO: 93)
GCCATCAAGATGACCCAGTCTCCATCTTCCATGTATGCATCTCTAGGAGA

GAGAGTCATCATCACTTGCAAGGCGAGTCAGGACATAAATAGTTATTTAA

CCTGGTTCCAACAGAAACCAGGAAAGTCTCCTAAGACCCTGATCTATCTT

ACAAATAGATTGATGGATGGGGTCCCATCAAGGTTCAGTGGCAGTGGATC

TGGGCAAGAATTTTTACTCACCATCAGCGGCCTGGAACATGAAGATATGG

GCATTTATTATTGTCTCCAGTATGTTGACTTTCCGTACACGTTCGGAGGG

GGGACCAAGCTGGAAATAAAA;
and/or ii)

(SEQ ID NO: 94)
GCAGTGCAACTGGTAGAGTCTGGGGGAGGCTTGGTGAAGCCTGGAGGGTC

CCTGAAACTCTCCTGTGCAGCCTCTGGAATCATTTTCAGTTCCTCTGCCA

TGTCTTGGGTTCGCCAGACTCCGGAAAAGAGACTGGAGTGGGTCGCAACT

ATTAGTAGTGGTGGTCGTTCCACCTACTATCCAGACAGTGTGAAGGGTCG

ATTCACCGTCTCCAGAGACAGTGCCAAGAACACCCTATACCTGCAAATGG

ACAGTCTGAGGTCTGAGGACACGGCCATTTATTACTGTGCAAAACTAATC

AGTCCCTACTGGGGCCAAGGCACCACTCTCACAGTCTCCTCA.

In a further embodiment, the invention provides an isolated polynucleotide comprising or consisting of the nucleotide sequences:

i)

(SEQ ID NO: 95)
GACATCACGATGACCCAGTCTCCATCTTCCATATATGCATCTCTGGGAGA

GAGAGTCACTATCACTTGCAAGGCGAGTCAGGACATTAATAGCTATTTAA

CCTGGTTCCAGCAGAAACCAGGGAAATCTCCTAAGATCCTGATCTATCTT

GTAAATAGATTGGTAGATGGGGTCCCATCAAGGTTCAGTGGCAGTGGATC

-continued

TGGGCAAGATTATGCTCTCACCATCAGCAGTCTGGAATATGAAGATATGG

GAATTTATTATTGTCTACAATATGATGACTTTCCGTACACGTTCGGAGGG

GGGACCAAGCTGGAAATAAAA;
and/or ii)

(SEQ ID NO: 96)
GAAGTGCAGTTGGTGGAGTCTGGGGGAGGCTTAGTGAAGCCTGGAGGGTC

CCTGAAACTCTCCTGTGCAGCCTCTGGATTCACTCTCAGTACCCATGCCA

TGTCTTGGGTTCGCCAGACTCCGGAGAAGAGGCTGGAGTGGGTCGCAACC

ATTAGTAGTGGTGGTCGTTCCACCTACTATCCAGACAGTGTGAAGGGTCG

ATTCACTATCTCCAGAGACAATGTCAAGAACACCCTATATCTGCAACTGA

GCAGTCTGAGGTCTGAGGACACGGCCGTGTATTTCTGTGCAAGACTAATC

AGTACCTACTGGGGCCAAGGCACCACTCTCACAGTCTCCTCA.

It is preferred that the antibody or antigen-binding fragment thereof of the invention inhibits TG2 activity. Thus, it is preferred that the antibody of the invention inhibits TG2 enzymatic activity and thus prevents it from functioning to cross-link lysine and glutamine residues with Nε-(γ-glutamyl)lysine isopeptide bonds. It is preferred that the enzymatic activity of TG2 is completely abrogated, but it is envisaged that the inhibition may be partial inhibition in instances where this partial inhibition is sufficient to provide a useful therapeutic or non-therapeutic outcome. The skilled person would be able to determine whether the extent of inhibition is effective to achieve the desired outcome.

It is preferred that the antibody or antigen-binding fragment thereof is specific for TG2 inhibition. Thus, it is preferred that the antibody or antigen-binding fragment thereof does not inhibit TG1, TG3, TG13 and/or TG7 activity. It is envisaged that an antibody that effectively inhibits TG2 activity but is sufficiently selective so that it does not significantly inhibit TG1, TG3, TG13 and/or TG7 activity may be particularly useful in medicine. Thus, it is preferred that the antibody exclusively inhibits TG2 activity.

In a further aspect, the invention provides an antibody or antigen-binding fragment thereof whose binding to TG2 (for example, human TG2) is inhibited or reduced when an antibody according to any preceding aspect is bound to TG2 (for example, human TG2).

Thus, the invention includes any antibody that selectively binds to an epitope within the region of TG2 such that it may compete with and disrupt binding of any antibody of the preceding aspects.

In a further aspect, the present invention provides a compound comprising an antibody or antigen-binding fragment thereof according to any preceding aspect and a further moiety.

In an embodiment, the further moiety may be a directly or indirectly cytotoxic moiety.

By "directly cytotoxic" we include the meaning that the moiety is one which on its own is cytotoxic. By "indirectly cytotoxic" we include the meaning that the moiety is one which, although is not itself cytotoxic, can induce cytotoxicity, for example by its action on a further molecule or by further action on it.

The cytotoxic moiety may be selected from, but is not limited to, the group comprising a directly cytotoxic chemotherapeutic agent, a directly cytotoxic polypeptide, a moiety which is able to convert a relatively non-toxic prodrug into a cytotoxic drug, a radiosensitizer, a directly cytotoxic nucleic acid, a nucleic acid molecule that encodes a directly or indirectly cytotoxic polypeptide, a nucleic acid molecule that encodes a therapeutic polypeptide, or a radioactive atom. It is envisaged that the radioactive atom may be any one of phosphorus-32, iodine-125, iodine-131, indium-111, rhenium-186, rhenium-188 or yttrium-90.

Cytotoxic chemotherapeutic agents, such as anticancer agents, include: alkylating agents including nitrogen mustards such as mechlorethamine ($HN_2$), cyclophosphamide, ifosfamide, melphalan (L-sarcolysin) and chlorambucil; ethylenimines and methylmelamines such as hexamethylmelamine, thiotepa; alkyl sulphonates such as busulfan; nitrosoureas such as carmustine (BCNU), lomustine (CCNU), semustine (methyl-CCNU) and streptozocin (streptozotocin); and triazenes such as decarbazine (DTIC; dimethyltriazenoimidazole-carboxamide); Antimetabolites including folic acid analogues such as methotrexate (amethopterin); pyrimidine analogues such as fluorouracil (5-fluorouracil; 5-FU), floxuridine (fluorodeoxyuridine; FUdR) and cytarabine (cytosine arabinoside); and purine analogues and related inhibitors such as mercaptopurine (6-mercaptopurine; 6-MP), thioguanine (6-thioguanine; TG) and pentostatin (2'-deoxycoformycin). Natural Products including vinca alkaloids such as vinblastine (VLB) and vincristine; epipodophyllotoxins such as etoposide and teniposide; antibiotics such as dactinomycin (actinomycin D), daunorubicin (daunomycin; rubidomycin), doxorubicin, bleomycin, plicamycin (mithramycin) and mitomycin (mitomycin C); enzymes such as L-asparaginase; and biological response modifiers such as interferon alphenomes. Miscellaneous agents including platinum coordination complexes such as cisplatin (cis-DDP) and carboplatin; anthracenedione such as mitoxantrone and anthracycline; substituted urea such as hydroxyurea; methyl hydrazine derivative such as procarbazine (N-methylhydrazine, MIH); and adrenocortical suppressant such as mitotane (o,p'-DDD) and aminoglutethimide; taxol and analogues/derivatives; and hormone agonists/antagonists such as flutamide and tamoxifen.

Various of these agents have previously been attached to antibodies and other target site-delivery agents, and so compounds of the invention comprising these agents may readily be made by the person skilled in the art. For example, carbodiimide conjugation (Bauminger & Wilchek (1980) *Methods Enzymol.* 70, 151-159; incorporated herein by reference) may be used to conjugate a variety of agents, including doxorubicin, to antibodies.

Cytotoxic peptides or polypeptide moieties include any moiety which leads to cell death. Cytotoxic peptide and polypeptide moieties are well known in the art and include, for example, ricin, abrin, *Pseudomonas* exotoxin, tissue factor and the like. Methods for linking them to targeting moieties such as antibodies are also known in the art. The use of ricin as a cytotoxic agent is described in Burrows & Thorpe (1993) *Proc. Natl. Acad. Sci. USA* 90, 8996-9000, incorporated herein by reference, and the use of tissue factor, which leads to localised blood clotting and infarction of a tumour, has been described by Ran et al (1998) *Cancer Res.* 58, 4646-4653 and Huang et al (1997) *Science* 275, 547-550. Tsai et al (1995) *Dis. Colon Rectum* 38, 1067-1074 describes the abrin A chain conjugated to a monoclonal antibody and is incorporated herein by reference. Other ribosome inactivating proteins are described as cytotoxic agents in WO 96/06641. *Pseudomonas* exotoxin may also be used as the cytotoxic polypeptide moiety (see, for example, Aiello et al (1995) *Proc. Natl. Acad. Sci. USA* 92, 10457-10461; incorporated herein by reference).

Certain cytokines, such as TNFα and IL-2, may also be useful as cytotoxic agents.

Certain radioactive atoms may also be cytotoxic if delivered in sufficient doses. Thus, the cytotoxic moiety may comprise a radioactive atom which, in use, delivers a sufficient quantity of radioactivity to the target site so as to be cytotoxic. Suitable radioactive atoms include phosphorus-32, iodine-125, iodine-131, indium-111, rhenium-186, rhenium-188 or yttrium-90, or any other isotope which emits enough energy to destroy neighbouring cells, organelles or nucleic acid. Preferably, the isotopes and density of radioactive atoms in the compound of the invention are such that a dose of more than 4000 cGy (preferably at least 6000, 8000 or 10000 cGy) is delivered to the target site and, preferably, to the cells at the target site and their organelles, particularly the nucleus. The radioactive atom may be attached to the antibody in known ways. For example EDTA or another chelating agent may be attached to the antibody and used to attach $^{111}$In or $^{90}$Y. Tyrosine residues may be labelled with $^{125}$I or $^{131}$I.

The cytotoxic moiety may be a suitable indirectly cytotoxic polypeptide. In a particularly preferred embodiment, the indirectly cytotoxic polypeptide is a polypeptide which has enzymatic activity and can convert a relatively non-toxic prodrug into a cytotoxic drug. When the targeting moiety is an antibody this type of system is often referred to as ADEPT (Antibody-Directed Enzyme Prodrug Therapy). The system requires that the targeting moiety locates the enzymatic portion to the desired site in the body of the patient (ie the site expressing MR, such as new vascular tissue associated with a tumour) and after allowing time for the enzyme to localise at the site, administering a prodrug which is a substrate for the enzyme, the end product of the catalysis being a cytotoxic compound. The object of the approach is to maximise the concentration of drug at the desired site and to minimise the concentration of drug in normal tissues (see Senter, P. D. et al (1988) "Anti-tumor effects of antibody-alkaline phosphatase conjugates in combination with etoposide phosphate" *Proc. Natl. Acad. Sci. USA* 85, 4842-4846; Bagshawe (1987) *Br. J. Cancer* 56, 531-2; and Bagshawe, K. D. et al (1988) "A cytotoxic agent can be generated selectively at cancer sites" *Br. J. Cancer.* 58, 700-703.)

The cytotoxic substance may be any existing anti-cancer drug such as an alkylating agent; an agent which intercalates in DNA; an agent which inhibits any key enzymes such as dihydrofolate reductase, thymidine synthetase, ribonucleotide reductase, nucleoside kinases or topoisomerase; or an agent which effects cell death by interacting with any other cellular constituent. Etoposide is an example of a topoisomerase inhibitor.

Reported prodrug systems include: a phenol mustard prodrug activated by an *E. coli* β-glucuronidase (Wang et al, 1992 and Roffler et al, 1991); a doxorubicin prodrug activated by a human β-glucuronidase (Bosslet et al, 1994); further doxorubicin prodrugs activated by coffee bean α-galactosidase (Azoulay et al, 1995); daunorubicin prodrugs, activated by coffee bean α-D-galactosidase (Gesson et al, 1994); a 5-fluorouridine prodrug activated by an *E. coli* β-D-galactosidase (Abraham et al, 1994); and methotrexate prodrugs (eg methotrexate-alanine) activated by carboxypeptidase A (Kuefner et al, 1990, Vitols et al, 1992 and Vitols et al, 1995). These and others are included in Table 1.

TABLE 1

| Enzyme | Prodrug |
|---|---|
| Carboxypeptidase G2 | Derivatives of L-glutamic acid and benzoic acid mustards, aniline mustards, phenol mustards and phenylenediamine mustards; fluorinated derivatives of these |
| Alkaline phosphatase | Etoposide phosphate<br>Mitomycin phosphate |
| Beta-glucuronidase | p-Hydroxyaniline mustard-glucuronide<br>Epirubicin-glucuronide |
| Penicillin-V-amidase | Adriamycin-N phenoxyacetyl |
| Penicillin-G-amidase | N-(4'-hydroxyphenyl acetyl) palytoxin<br>Doxorubicin and melphalan |
| Beta-lactamase | Nitrogen mustard-cephalosporin p-phenylenediamine; doxorubicin derivatives; vinblastine derivative-cephalosporin, cephalosporin mustard; a taxol derivative |
| Beta-glucosidase | Cyanophenylmethyl-beta-D-gluco-pyranosiduronic acid |
| Nitroreductase | 5-(Azaridin-1-yl-)-2,4-dinitrobenzamide |
| Cytosine deaminase | 5-Fluorocytosine |
| Carboxypeptidase A | Methotrexate-alanine |

(This table is adapted from Bagshawe (1995) *Drug Dev. Res.* 34, 220-230, from which full references for these various systems may be obtained; the taxol derivative is described in Rodrigues, M. L. et al (1995) *Chemistry & Biology* 2, 223).

Suitable enzymes for forming part of the enzymatic portion of the invention include: exopeptidases, such as carboxypeptidases G, G1 and G2 (for glutamylated mustard prodrugs), carboxypeptidases A and B (for MTX-based prodrugs) and aminopeptidases (for 2-α-aminocyl MTC prodrugs); endopeptidases, such as eg thrombolysin (for thrombin prodrugs); hydrolases, such as phosphatases (eg alkaline phosphatase) or sulphatases (eg aryl sulphatases) (for phosphylated or sulphated prodrugs); amidases, such as penicillin amidases and arylacyl amidase; lactamases, such as β-lactamases; glycosidases, such as β-glucuronidase (for β-glucuronomide anthracyclines), α-galactosidase (for amygdalin) and β-galactosidase (for β-galactose anthracycline); deaminases, such as cytosine deaminase (for 5FC); kinases, such as urokinase and thymidine kinase (for gancyclovir); reductases, such as nitroreductase (for CB1954 and analogues), azoreductase (for azobenzene mustards) and DT-diaphorase (for CB1954); oxidases, such as glucose oxidase (for glucose), xanthine oxidase (for xanthine) and lactoperoxidase; DL-racemases, catalytic antibodies and cyclodextrins.

The prodrug is relatively non-toxic compared to the cytotoxic drug. Typically, it has less than 10% of the toxicity, preferably less than 1% of the toxicity as measured in a suitable in vitro cytotoxicity test. It is likely that the moiety which is able to convert a prodrug to a cytotoxic drug will be active in isolation from the rest of the compound but it is necessary only for it to be active when (a) it is in combination with the rest of the compound and (b) the compound is attached to, adjacent to or internalised in target cells.

When each moiety of the compound is a polypeptide, the two portions may be linked together by any of the conventional ways of cross-linking polypeptides, such as those generally described in O'Sullivan et al (1979) *Anal. Biochem.* 100, 100-108. Alternatively, the compound may be produced as a fusion compound by recombinant DNA techniques whereby a length of DNA comprises respective regions encoding the two moieties of the compound of the invention either adjacent one another or separated by a region encoding a linker peptide which does not destroy the desired properties of the compound. Conceivably, the two portions of the compound may overlap wholly or partly.

The cytotoxic moiety may be a radiosensitizer. Radiosensitizers include fluoropyrimidines, thymidine analogues, hydroxyurea, gemcitabine, fludarabine, nicotinamide, halogenated pyrimidines, 3-aminobenzamide, 3-aminobenzodiamide, etanixadole, pimonidazole and misonidazole (see, for example, McGinn et al (1996) *J. Natl. Cancer Inst.* 88, 1193-11203; Shewach & Lawrence (1996) *Invest. New Drugs* 14, 257-263; Horsman (1995) *Acta Oncol.* 34, 571-587; Shenoy & Singh (1992) *Clin. Invest.* 10, 533-551; Mitchell et al (1989) *Int. J. Radiat. Biol.* 56, 827-836; Iliakis & Kurtzman (1989) *Int. J. Radiat. Oncol. Biol. Phys.* 16, 1235-1241; Brown (1989) *Int. J. Radiat. Oncol. Biol. Phys.* 16, 987-993; Brown (1985) *Cancer* 55, 2222-2228).

Also, delivery of genes into cells can radiosensitise them, for example delivery of the p53 gene or cyclin D (Lang et al (1998) *J. Neurosurg.* 89, 125-132; Coco Martin et al (1999) *Cancer Res.* 59, 1134-1140).

The further moiety may be one which becomes cytotoxic, or releases a cytotoxic moiety, upon irradiation. For example, the boron-10 isotope, when appropriately irradiated, releases a particles which are cytotoxic (see for example, U.S. Pat. No. 4,348,376 to Goldenberg; Primus et al (1996) *Bioconjug. Chem.* 7, 532-535).

Similarly, the cytotoxic moiety may be one which is useful in photodynamic therapy such as photofrin (see, for example, Dougherty et al(1998) *J. Natl. Cancer Inst.* 90, 889-905).

The cytotoxic moiety may be a nucleic acid molecule which is directly or indirectly cytotoxic. For example, the nucleic acid molecule may be an antisense oligonucleotide which, upon localisation at the target site is able to enter cells and lead to their death. The oligonucleotide, therefore, may be one which prevents expression of an essential gene, or one which leads to a change in gene expression which causes apoptosis.

Examples of suitable oligonucleotides include those directed at bcl-2 (Ziegler et al(1997) *J. Natl. Cancer Inst.* 89, 1027-1036), and DNA polymerase a and topoisomerase IIα (Lee et al (1996) *Anticancer Res.* 16, 1805-1811.

Peptide nucleic acids may be useful in place of conventional nucleic acids (see Knudsen & Nielsen (1997) *Anticancer Drugs* 8, 113-118).

In an embodiment of the compound of the invention, the antibody or antigen-binding fragment thereof and the cytotoxic moiety may be polypeptides which are fused. Thus, the invention further provides a polynucleotide encoding such a compound.

In a further embodiment, the further moiety may be a readily detectable moiety. It is envisaged that readily detectable moiety may comprise a suitable amount of any one of iodine-123, iodine-131, indium-111, fluorine-19, carbon-13, nitrogen-15, oxygen-17, technitium-99m, gadolinium, manganese or iron.

By a "readily detectable moiety" we include the meaning that the moiety is one which, when located at the target site following administration of the compound of the invention into a patient, may be detected, typically non-invasively from outside the body and the site of the target located. Thus, the compounds of this embodiment of the invention are useful in imaging and diagnosis.

Typically, the readily detectable moiety is or comprises a radioactive atom which is useful in imaging. Suitable radioactive atoms include technetium-99m or iodine-123 for scintigraphic studies. Other readily detectable moieties include, for example, spin labels for magnetic resonance imaging (MRI) such as iodine-123 again, iodine-131, indium-111, fluorine-19, carbon-13, nitrogen-15, oxygen-17, gadolinium, manganese or iron. Clearly, the compound of the invention must have sufficient of the appropriate atomic isotopes in order for the molecule to be readily detectable.

The radio- or other labels may be incorporated in the compound of the invention in known ways. For example, if the antibody is a polypeptide it may be biosynthesised or may be synthesised by chemical amino acid synthesis using suitable amino acid precursors involving, for example, fluorine-19 in place of hydrogen. Labels such as $^{99m}$Tc, $^{123}$I, $^{186}$Rh, $^{188}$Rh and $^{111}$In can, for example, be attached via cysteine residues in the antibody. Yttrium-90 can be attached via a lysine residue. The IODOGEN method (Fraker er al (1978) *Biochem. Biophys. Res. Comm.* 80, 49-57) can be used to incorporate iodine-123. Reference ("Monoclonal Antibodies in Immunoscintigraphy", J-F Chatal, CRC Press, 1989) describes other methods in detail.

In a further aspect, the present invention provides a vector comprising any polynucleotide of the invention.

Typical prokaryotic vector plasmids are: pUC18, pUC19, pBR322 and pBR329 available from Biorad Laboratories (Richmond, Calif., USA); pTrc99A, pKK223-3, pKK233-3, pDR540 and pRIT5 available from Pharmacia (Piscataway, N.J., USA); pBS vectors, Phagescript vectors, Bluescript vectors, pNH8A, pNH16A, pNH18A, pNH46A available from Stratagene Cloning Systems (La Jolla, Calif. 92037, USA).

A typical mammalian cell vector plasmid is pSVL available from Pharmacia (Piscataway, N.J., USA). An example of an inducible mammalian expression vector is pMSG, also available from Pharmacia (Piscataway, N.J., USA).

Useful yeast plasmid vectors are pRS403-406 and pRS413-416 and are generally available from Stratagene Cloning Systems (La Jolla, Calif. 92037, USA). Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (YCps).

Methods well known to those skilled in the art can be used to construct expression vectors containing the coding sequence and, for example appropriate transcriptional or translational controls.

Yet further, the invention provides a host cell comprising any polynucleotide or vector of the invention.

Many expression systems are known, including systems employing: bacteria (eg. *E. coli and Bacillus subtilis*) transformed with, for example, recombinant bacteriophage, plasmid or cosmid DNA expression vectors; yeasts (eg. *Saccharomyces cerevisiae*) transformed with, for example, yeast expression vectors; insect cell systems transformed with, for example, viral expression vectors (eg. baculovirus); plant cell systems transfected with, for example viral or bacterial expression vectors; animal cell systems transfected with, for example, adenovirus expression vectors.

The vectors can include a prokaryotic replicon, such as the Col E1 ori, for propagation in a prokaryote, even if the vector is to be used for expression in other, non-prokaryotic cell types. The vectors can also include an appropriate promoter such as a prokaryotic promoter capable of directing the expression (transcription and translation) of the genes in a bacterial host cell, such as *E. coli*, transformed therewith.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention.

The polynucleotide in a suitable host cell may be expressed to produce the antibody or compound of the invention. Thus, the polynucleotide may be used in accordance with known techniques, appropriately modified in view of the teachings contained herein, to construct an expression vector, which is then used to transform an appropriate host cell for the expression and production of the antibody or compound of the invention. Such techniques include those disclosed in U.S. Pat. Nos. 4,440,859; 4,530,901; 4,582,800; 4,677,063; 4,678,751; 4,704,362; 4,710,463; 4,757,006; 4,766,075; and 4,810,648, all of which are incorporated herein by reference.

The polynucleotide may be joined to a wide variety of other DNA sequences for introduction into an appropriate host. The companion DNA will depend upon the nature of the host, the manner of the introduction of the DNA into the host, and whether episomal maintenance or integration is desired.

Generally, the polynucleotide is inserted into an expression vector, such as a plasmid, in proper orientation and correct reading frame for expression. If necessary, the DNA may be linked to the appropriate transcriptional and translational regulatory control nucleotide sequences recognised by the desired host, although such controls are generally available in the expression vector. Thus, the DNA insert may be operatively linked to an appropriate promoter. Bacterial promoters include the *E. coli* lacI and lacZ promoters, the T3 and T7 promoters, the gpt promoter, the phage λ PR and PL promoters, the phoA promoter and the trp promoter. Eukaryotic promoters include the CMV immediate early promoter, the HSV thymidine kinase promoter, the early and late SV40 promoters and the promoters of retroviral LTRs. Other suitable promoters will be known to the skilled artisan. The expression constructs will desirably also contain sites for transcription initiation and termination, and in the transcribed region, a ribosome binding site for translation. (Hastings et al, International Patent No. WO 98/16643, published 23 Apr. 1998)

The vector is then introduced into the host through standard techniques. Generally, not all of the hosts will be transformed by the vector and it will therefore be necessary to select for transformed host cells. One selection technique involves incorporating into the expression vector a DNA sequence marker, with any necessary control elements, that codes for a selectable trait in the transformed cell. These markers include dihydrofolate reductase, G418 or neomycin resistance for eukaryotic cell culture, and tetracyclin, kanamycin or ampicillin resistance genes for culturing in *E. coli* and other bacteria. Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

The antibody or compound can be recovered and purified from recombinant cell cultures by well-known methods including ammonium sulphate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Yet further, the invention provides a stable host cell line producing an antibody or antigen-binding fragment thereof according to any preceding aspect or a compound of the invention resulting from incorporation in the cell line an exogenous polynucleotide or vector of the invention.

The host cell can be either prokaryotic or eukaryotic. Bacterial cells are preferred prokaryotic host cells and typically are a strain of *Escherichia coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast and mammalian cells, preferably vertebrate cells such as those from a mouse, rat, monkey or human fibroblastic cell line. Yeast host cells include YPH499, YPH500 and YPH501 which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, and monkey kidney-derived COS-1 cells available from the ATCC as CRL 1650.

In addition to the transformed host cells themselves, the present invention also contemplates a culture of those cells, preferably a monoclonal (clonally homogeneous) culture, or a culture derived from a monoclonal culture, in a nutrient medium.

In a further aspect, the present invention provides a pharmaceutical composition/formulation comprising an antibody or antigen-binding fragment thereof according to any aspect of the invention, or a polynucleotide according to the invention, or a compound according to the invention, in admixture with a pharmaceutically acceptable excipient, adjuvant, diluent or carrier.

By "pharmaceutically acceptable" is included that the formulation is sterile and pyrogen free. Suitable pharmaceutical carriers are well known in the art of pharmacy. The carrier(s) must be "acceptable" in the sense of being compatible with the compound of the invention and not deleterious to the recipients thereof. Typically, the carriers will be water or saline which will be sterile and pyrogen free; however, other acceptable carriers may be used.

In an embodiment, the pharmaceutical composition/formulation of the invention may further comprise a further active ingredient, i.e. a therapeutically active agent other than the antibody or antigen-binding fragment thereof of the invention. It is envisaged that one or more additional active agents may increase the efficacy of the pharmaceutical composition/formulation against the targeted disease as appropriate. In an embodiment, the further active ingredient may be a therapeutic agent selected from an agent involved in reducing tissue scarring, reducing neurofibrilliary tangles, and/or reducing resistance to chemotherapy.

In a preferred embodiment, pharmaceutical composition/formulation may be formulated for intravenous, intramuscular, or subcutaneous delivery to a patient.

It is preferred that the pharmaceutical composition/formulation comprises an amount of the antibody or antigen-binding fragment of the invention effective to treat the various conditions described above and further below.

A further aspect of the invention provides a kit of parts comprising an antibody or antigen-binding fragment thereof according to any aspect of the invention, or a polynucleotide according of the invention, or a compound of the invention; and one or more further agents. It is envisaged that the further agents may be any one of the further active ingredients described above, or any other suitable agent.

In a yet further aspect, the invention provides a therapeutically effective amount of an antibody or antigen-binding fragment thereof according to any aspect of the invention, or a polynucleotide of the invention, or a compound, pharmaceutical composition/formulation, or kit of parts of the invention, for use in medicine.

TG2 clearly is a multifunction enzyme and has been linked to a range of cellular functions including nuclear stabilisation and transport [28, 29], endocytosis [30, 31], GTPase signalling [32-34], Apoptosis [35, 36], cell adhesion [37-39], cytoskeletal integrity [28, 29] and ECM stabilisation [9]. A small molecule inhibitor may impede on all of these functions as in general they have free access to the extracellular space and cell interior. An antibody cannot enter the cell and as such the intracellular roles of TG2 would not be affected by a TG2 specific antibody administered in vivo.

Importantly most of the pathological roles of TG2 appear to be extracellular such as its role in tissue scarring and fibrosis, celiac disease and cancer. Thus using an antibody which selectively binds TG2 in medicine would bring an additional degree of selectivity preventing undesired intracellular effects that could translate into undesired side effects of therapy.

Therefore the antibodies and antigen-binding fragments thereof of the invention would offer clinical advantages over previously available drugs, for example in blocking TG2 in fibrotic and scarring diseases where TG2 crosslinks ECM proteins, in celiac disease where gliadin is deamidated in the extracellular space and in chemo-resistance in cancer where cell adhesion appears to be the protective factor. Further, the small antibody fragments of the invention, for example the Fab fragments could cross the blood brain barrier and inhibit TG2 in the brain and potentially offer effective therapies for neurological pathologies with TG2 involvement.

Thus, a further aspect of the invention provides an antibody or antigen-binding fragment thereof according to any aspect of the invention, or a polynucleotide of the invention, or a compound, pharmaceutical composition/formulation, or kit of parts of the invention, for use in reducing or inhibiting TG2 enzyme activity in an individual in need thereof.

The invention further provides for the use of an antibody or antigen-binding fragment thereof according to any aspect of the invention, or a polynucleotide of the invention, or a compound, pharmaceutical composition/formulation, or kit of parts of the invention, in the manufacture of a medicament for reducing or inhibiting TG2 enzyme activity in an individual in need thereof.

The invention also provides a method of reducing or inhibiting TG2 enzyme activity in an individual in need thereof, the method comprising the step of administering an antibody or antigen-binding fragment thereof, or a variant, fusion or derivative thereof according to any aspect of the invention, or a polynucleotide of the invention, or a compound, pharmaceutical composition/formulation, or kit of parts of the invention, to the individual.

A further aspect of the invention provides a therapeutically effective amount of an antibody or antigen-binding fragment thereof according to any aspect of the invention, or a polynucleotide of the invention, or a compound, pharmaceutical composition/formulation, or kit of parts of the invention, for use in the treatment and/or diagnosis of Celiac disease, abnormal wound healing, scarring, scleroderma, keloids and hypertrophic scars, ocular scarring, inflammatory bowel disease, macular degeneration, Grave's opthalmopathy, drug-induced ergotism, psoriasis, fibrosis-related diseases (e.g. liver fibrosis, pulmonary fibrosis such as interstitial lung disease and fibrotic lung disease, cardiac fibrosis, skin fibrosis, myelofibrosis, kidney fibrosis such as glomerulosclerosis and tubulointerstitial fibrosis), atherosclerosis, restenosis, inflammatory diseases, autoimmune diseases, neurodegenerative/neurological diseases (e.g. Huntington's Disease, Alzheimer's disease, Parkinson's disease, polyglutamine disease, spinobulbar muscular atrophy, dentatorubral-pallidoluysian atrophy, spinocerebellar ataxias 1, 2, 3, 6, 7 and 12, rubropallidal atrophy, spinocerebellar palsy), and/or cancer (e.g. glioblastomas such as glioblastoma in Li-Fraumeni syndrome and sporadic glioblastoma, malignant melanomas, pancreatic ductal adenocarcinomas, myeloid leukemia, acute myelogenous leukemia, myelodysplastic syndrome, myeloproliferative syndrome, gynaecological cancer, Kaposi's sarcoma, Hansen's disease, collagenous colitis).

The invention also provides for the use of a therapeutically effective amount of an antibody or antigen-binding fragment thereof according to any aspect of the invention, or a polynucleotide of the invention, or a compound, pharmaceutical composition/formulation, or kit of parts of the invention, in the manufacture of a medicament for treating and/or diagnosing Celiac disease, abnormal wound healing, scarring, scleroderma, keloids and hypertrophic scars, ocular scarring, inflammatory bowel disease, macular degeneration, Grave's opthalmopathy, drug-induced ergotism, psoriasis, fibrosis-related diseases (e.g. liver fibrosis, pulmonary fibrosis such as interstitial lung disease and fibrotic lung disease, cardiac fibrosis, skin fibrosis, myelofibrosis, kidney fibrosis such as glomerulosclerosis and tubulointerstitial fibrosis), atherosclerosis, restenosis, inflammatory diseases, autoimmune diseases, neurodegenerative/neurological diseases (e.g. Huntington's Disease, Alzheimer's disease, Parkinson's disease, polyglutamine disease, spinobulbar muscular atrophy, dentatorubral-pallidoluysian atrophy, spinocerebellar ataxias 1, 2, 3, 6, 7 and 12, rubropallidal atrophy, spinocerebellar palsy), and/or cancer (e.g. glioblastomas such as glioblastoma in Li-Fraumeni syndrome and sporadic glioblastoma, malignant melanomas, pancreatic ductal adenocarcinomas, myeloid leukemia, acute myelogenous leukemia, myelodysplastic syndrome, myeloproliferative syndrome, gynaecological cancer, Kaposi's sarcoma, Hansen's disease, collagenous colitis).

The invention also provides a method of treating and/or diagnosing Celiac disease, abnormal wound healing, scarring, scleroderma, keloids and hypertrophic scars, ocular scarring, inflammatory bowel disease, macular degeneration, Grave's opthalmopathy, drug-induced ergotism, psoriasis, fibrosis-related diseases (e.g. liver fibrosis, pulmonary fibrosis such as interstitial lung disease and fibrotic lung disease, cardiac fibrosis, skin fibrosis, myelofibrosis, kidney fibrosis such as glomerulosclerosis and tubulointerstitial fibrosis), atherosclerosis, restenosis, inflammatory diseases, autoimmune diseases, neurodegenerative/neurological diseases (e.g. Huntington's Disease, Alzheimer's disease, Parkinson's disease, polyglutamine disease, spinobulbar muscular atrophy, dentatorubral-pallidoluysian atrophy, spinocerebellar ataxias 1, 2, 3, 6, 7 and 12, rubropallidal atrophy, spinocerebellar palsy), and/or cancer (e.g. glioblastomas such as glioblastoma in Li-Fraumeni syndrome and sporadic glioblastoma, malignant melanomas, pancreatic ductal adenocarcinomas, myeloid leukemia, acute myelogenous leukemia, myelodysplastic syndrome, myeloproliferative syndrome, gynaecological cancer, Kaposi's sarcoma, Hansen's disease, collagenous colitis) in a patient, the method comprising administering a therapeutically effective amount of an antibody or antigen-binding fragment thereof according to any aspect of the invention, or a polynucleotide of the invention, or a compound, pharmaceutical composition/formulation, or kit of parts of the invention, to the patient.

By "treatment" we include both therapeutic and prophylactic treatment of a subject/patient. The term "prophylactic" is used to encompass the use of an antibody, medicament, compound, composition, or kit described herein which either prevents or reduces the likelihood of the occurrence or development of a condition or disorder (such as a fibrosis-related disorder) in an individual.

It is preferred that the patient is a human but the patient may be any other mammal that may benefit from the treatment. For example, the patient may be a mouse, a rat, a hamster, a rabbit, a cat, a dog, a goat, a sheep, a monkey or an ape.

A "therapeutically effective amount", or "effective amount", or "therapeutically effective", as used herein, refers to that amount which provides a therapeutic effect for a given condition and administration regimen. This is a predetermined quantity of active material calculated to produce a desired therapeutic effect in association with the required additive and diluent, i.e. a carrier or administration vehicle. Further, it is intended to mean an amount sufficient to reduce or prevent a clinically significant deficit in the activity, function and response of the host. Alternatively, a therapeutically effective amount is sufficient to cause an improvement in a clinically significant condition in a host, for example a mammal.

The agents (i.e. antibody, antigen-binding fragment, variant, fusion or derivative thereof), medicaments, compounds, pharmaceutical compositions/formulations and kits of the invention may be delivered using an injectable sustained-release drug delivery system. These are designed specifically to reduce the frequency of injections. An example of such a system is Nutropin Depot which encapsulates recombinant human growth hormone (rhGH) in biodegradable microspheres that, once injected, release rhGH slowly over a sustained period. Preferably, delivery is performed intramuscularly (i.m.) and/or sub-cutaneously (s.c.) and/or intravenously (i.v.).

The agents, medicaments, compounds, pharmaceutical compositions/formulations and kits of the invention can be administered by a surgically implanted device that releases the drug directly to the required site. For example, Vitrasert releases ganciclovir directly into the eye to treat CMV retinitis. The direct application of this toxic agent to the site of disease achieves effective therapy without the drug's significant systemic side-effects.

Preferably, the medicaments and/or pharmaceutical compositions/formulations of the present invention is a unit dosage containing a daily dose or unit, daily sub-dose or an appropriate fraction thereof, of the active ingredient(s).

The agents, medicaments, compounds, pharmaceutical compositions and kits of the invention will normally be administered by any parenteral route, in the form of a pharmaceutical composition comprising the active ingredient(s), optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

In human therapy, the agents, medicaments, compounds, pharmaceutical compositions/formulations, and kits of the invention can be administered alone but will generally be administered in admixture with a suitable pharmaceutical excipient, diluent or carrier selected with regard to the intended route of administration and standard pharmaceutical practice.

The agents, medicaments, compounds, pharmaceutical compositions/formulations and kits of the invention can be administered parenterally, for example, intravenously, intra-arterially, intraperitoneally, intra-thecally, intra-muscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Medicaments and pharmaceutical compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The medicaments and pharmaceutical compositions may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

For parenteral administration to human patients, the daily dosage level of the agents, medicaments and pharmaceutical compositions of the invention will usually be from 1 μg to 10 mg per adult per day administered in single or divided doses. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

Typically, the medicaments, pharmaceutical compositions/formulations and kits of the invention will contain the agent of the invention at a concentration of between approximately 2 mg/ml and 150 mg/ml or between approximately 2 mg/ml and 200 mg/ml. In a preferred embodiment, the medicaments, pharmaceutical compositions/formulations and kits of the invention will contain the agent of the invention at a concentration of 10 mg/ml.

Generally, in humans, parenteral administration of the agents, medicaments, compounds, pharmaceutical compositions/formulations and kits of the invention is the preferred route, being the most convenient.

For veterinary use, the agents, medicaments, compounds, pharmaceutical compositions/formulations, and kits of the invention are administered as a suitably acceptable formulation in accordance with normal veterinary practice and the veterinary surgeon will determine the dosing regimen and route of administration which will be most appropriate for a particular animal.

The present invention also includes pharmaceutical compositions/formulations comprising pharmaceutically acceptable acid or base addition salts of the polypeptide binding moieties of the present invention. The acids which are used to prepare the pharmaceutically acceptable acid addition salts of the aforementioned base compounds useful in this invention are those which form non-toxic acid addition salts, i.e. salts containing pharmacologically acceptable anions, such as the hydrochloride, hydrobromide, hydroiodide, nitrate, sulphate, bisulphate, phosphate, acid phosphate, acetate, lactate, citrate, acid citrate, tartrate, bitartrate, succinate, maleate, fumarate, gluconate, saccharate, benzoate, methanesulphonate, ethanesulphonate, benzenesulphonate, p-toluenesulphonate and pamoate [i.e. 1,1'-methylene-bis-(2-hydroxy-3 naphthoate)] salts, among others.

Pharmaceutically acceptable base addition salts may also be used to produce pharmaceutically acceptable salt forms of the agents (i.e. antibody or antigen-binding fragment thereof) according to the present invention.

The chemical bases that may be used as reagents to prepare pharmaceutically acceptable base salts of the present agents that are acidic in nature are those that form non-toxic base salts with such compounds. Such non-toxic base salts include, but are not limited to those derived from such pharmacologically acceptable cations such as alkali metal cations (e.g. potassium and sodium) and alkaline earth metal cations (e.g. calcium and magnesium), ammonium or water-soluble amine addition salts such as N-methylglucamine-(meglumine), and the lower alkanolammonium and other base salts of pharmaceutically acceptable organic amines, among others.

The agents and/or polypeptide binding moieties of the invention may be lyophilised for storage and reconstituted in a suitable carrier prior to use. Any suitable lyophilisation method (e.g. spray drying, cake drying) and/or reconstitution techniques can be employed. It will be appreciated by those skilled in the art that lyophilisation and reconstitution can lead to varying degrees of antibody activity loss (e.g. with conventional immunoglobulins, IgM antibodies tend to have greater activity loss than IgG antibodies) and that use levels may have to be adjusted upward to compensate. In one embodiment, the lyophilised (freeze dried) polypeptide binding moiety loses no more than about 20%, or no more than about 25%, or no more than about 30%, or no more than about 35%, or no more than about 40%, or no more than about 45%, or no more than about 50% of its activity (prior to lyophilisation) when re-hydrated.

Preferably, the invention provides an antibody, compound, pharmaceutical composition/formulation, kit, use or method wherein the effective amount of the antibody or antigen-binding fragment thereof is between about 0.0001 mg/kg to 50 mg/kg of the antibody or antigen-binding fragment thereof.

As is appreciated by those skilled in the art, the precise amount of a compound may vary depending on its specific activity. Suitable dosage amounts may contain a predetermined quantity of active composition calculated to produce the desired therapeutic effect in association with the required diluent. In the methods and use for manufacture of compositions of the invention, a therapeutically effective amount of the active component is provided. A therapeutically effective amount can be determined by the ordinary skilled medical or veterinary worker based on patient characteristics, such as age, weight, sex, condition, complications, other diseases, etc., as is well known in the art.

A further aspect of the invention provides an in vitro method of reducing or inhibiting TG2 enzyme activity, the method comprising administering an antibody or antigen-binding fragment thereof according to any aspect of the invention, or a polynucleotide according to the invention, or a compound or kit of the invention, to a sample comprising TG2.

The "sample" may be any sample obtained from an appropriate source, for example a mammalian source. For example, the sample may be a tissue or cell sample comprising TG2. Exemplary tissues include tissue obtained from a patient's brain, gastro-intestinal tract, lung, pancreas, liver, skin, kidney, eye, heart, blood vessels, lymph nodes, spine, and skeletal or smooth muscle.

The invention also provides a method of reducing or inhibiting TG2 enzyme activity in an individual in need thereof, the method comprising administering an effective amount of a polynucleotide encoding an antibody or antigen-binding fragment thereof according to any aspect of the invention, to the individual.

A further aspect provides the use of a polynucleotide encoding an antibody or antigen-binding fragment thereof according to any aspect of the invention, in the manufacture of a medicament for reducing or inhibiting TG2 enzyme activity in an individual in need thereof.

The invention also provides an in vitro method of reducing or inhibiting TG2 enzyme activity, the method comprising administering a polynucleotide encoding an antibody or antigen-binding fragment thereof according to any aspect of the invention, to a sample comprising TG2, for example a tissue or cell sample comprising TG2.

In a yet further aspect, the invention provides a method of producing an antibody or antigen-binding fragment according to the second aspect of the invention, or a compound of the invention comprising an antibody or antigen-binding fragment according to the second aspect of the invention, the method comprising expressing a polynucleotide of the invention, or culturing a stable host cell line of the invention.

In a further aspect, the invention provides a method of selecting an antibody or antigen-binding fragment thereof that selectively binds a transglutaminase protein, the method comprising the step of selecting an antibody or antigen-binding fragment thereof that selectively binds a polypeptide comprising a transglutaminase core region/catalytic domain but not comprising a transglutaminase barrel or sandwich domain.

In a further aspect, the invention provides a method of selecting an antibody or antigen-binding fragment thereof according to the first or second aspects of the invention, or a compound of the invention comprising an antibody or antigen-binding fragment according to the first or second aspect of the invention, the method comprising the step of selecting an antibody or antigen-binding fragment thereof that selectively binds a polypeptide sequence consisting of the polypeptide sequence of amino acids 143 to 473 of human TG2 or a fragment thereof.

In an embodiment, the method may be carried out using antibody phage display. It is preferred that the antibody or antigen-binding fragment thereof is an inhibitory antibody that inhibits catalytic activity of the transglutaminase protein.

In a further aspect, the invention provides a method of producing an antibody or antigen-binding fragment thereof that selectively binds a transglutaminase protein, the method comprising administering to a non-human animal a compound comprising:

i) a polypeptide comprising a transglutaminase core region/catalytic domain but not comprising a transglutaminase barrel or sandwich domain, or a fragment thereof; and, optionally, ii) an adjuvant.

It is envisaged that the polypeptide comprising a transglutaminase core region/catalytic domain but not comprising a transglutaminase barrel or sandwich domain will comprise the catalytic triad described above, and optionally, also the GTP binding site of the transglutaminase protein.

In an embodiment, the method may further comprise the step of selecting an antibody or antigen-binding fragment thereof on the basis of its selective binding to a transglutaminase protein.

In a further aspect, the invention provides a method of selecting an antibody or antigen-binding fragment thereof that selectively binds a transglutaminase protein, the method comprising the step of selecting an antibody or antigen-binding fragment thereof that selectively binds a polypeptide sequence consisting of the polypeptide sequence of amino acids 143 to 473 of human TG2 or a fragment thereof.

In a yet further aspect, the invention provides a method of producing an antibody or antigen-binding fragment according to any aspect of the invention comprising administering to a non-human animal a compound comprising:

i) a polypeptide sequence consisting of the polypeptide sequence of amino acids 143 to 473 of human TG2 or a fragment thereof; and optionally, ii) an adjuvant.

In an embodiment, the method may further comprise the step of selecting an antibody or antigen-binding fragment thereof on the basis of its selective binding to TG2, for example human TG2.

In a further aspect, the invention provides an antibody or antigen-binding fragment thereof obtainable by any of the preceding methods of producing or selecting an antibody or antigen-binding fragment thereof.

By "adjuvant" we include any a pharmacological or immunological agent that enhances the recipient's immune response to the polypeptide of the invention. Immunologic adjuvants are added to vaccines to stimulate the immune system's response to the target antigen, but do not in themselves confer immunity. Examples of adjuvants include oil emulsions, inorganic compounds such as aluminium salts, for example aluminum hydroxide or aluminium phosphate, organic compounds such as Squalene, virosomes, or any other suitable compound or compounds as would be understood by a person of skill in the art.

In a further aspect, the invention provides an isolated polypeptide consisting of:

i) the polypeptide sequence of amino acids 143 to 473 of human TG2;

ii) the polypeptide sequence of amino acids 304 to 326 of human TG2;

iii) the polypeptide sequence of amino acids 351 to 365 of human TG2;

iv) the polypeptide sequence of amino acids 450 to 467 of human TG2; or a fragment, derivative or polypeptide mimic thereof.

The invention also provides an isolated polynucleotide encoding the polypeptide of the immediately preceding aspect.

The invention provides an antibody or antigen-binding fragment thereof for use in treating a condition associated with TG2 activity substantially as described herein with reference to the description and figures.

The invention also provides the use of an antibody or antigen-binding fragment thereof substantially as described herein with reference to the description and figures.

As used herein, the singular forms "a", "and", and "the" include plural referents unless the context clearly dictates otherwise. Thus, for example, reference to "an antibody"

includes a plurality of such antibodies and reference to "the dosage" includes reference to one or more dosages and equivalents thereof known to those skilled in the art, and so forth.

All documents referred to herein are hereby incorporated by reference.

The invention is now described in more detail by reference to the following, non-limiting, Figures and Examples.

FIG. 1: Generation of a human TG2 recombinant protein

A: The TG2 catalytic core cDNA was generated by PCR from the pClineo-hTG2 vector and inserted into the pET 21a plasmid. Following amplification in *E. coli* this was digested with Nhe I and Hind III to release the TG2 core cDNA and run on a 1% Agarose gel (lane 3). Bands were sized by reference to a 100 bp ladder (lane 1) and A DNA molecular weight marker (Lane 2).

B: The pET21a TG2 core vector was used to transform *E. coli* strain BL21-CodonPlus(DE3)-RIPL. Expression was induced using IPTG for 4 hours. TG2 core protein formed insoluble bodies that were recovered from lysates by centrifugation. These were re solubilised, and the 37 kDa His tagged TG2 core purified on a nickel column. 10 ng was separated by SDS-PAGE, western blotted and probed with CUB7402 anti TG2 antibody (lane 2) with reference to a precision plus molecular weight marker (lane 1).

FIG. 2: Immunological Response in mice to rhTG2 core protein

A: Test bleeds were taken from 4 catalytic core immunised mice at day 45 after the first immunisation and 10 days after the second boost. Serum was serially diluted and reactivity checked by ELISA against immobilised TG2 core protein.

B Reactivity was further checked by screened against human rh TG2 and rh TG2 catalytic core domain. 20, 40, 80 ng of protein was fractionated by SDS PAGE and western blotted onto a PVDF membrane. This was immunoprobed with a 1:1000 dilution of serum. Antibody binding was revealed using anti-mouse γ-chain specific HRP. For size reference to a precision plus molecular weight marker was used.

FIG. 3: Hybridoma Reactivity Against TG family Members

A: ELISA were carried out using plates coated with recombinant TGs (100 ng/well) to determine TG type specificity in 109 hybridoma supernatants that showed good reactivity to TG2. Antibody binding was revealed using anti-mouse γ-chain specific HRP. A random selection of those screened is shown including EF4, CG9 & FD8 that showed cross reactivity.

B: Nine selected hybridomas were double cloned. IgG was purified and tested for reactivity at 0.1 ug/ml against recombinant human TG1, TG2, TG3, TG7 and Factor XIIIa using ELISA with plates coated with 100 ng of each TG. Data represents mean OD value from 3 separate ELISA±SEM.

Factor XIIIa is denoted on graphs as TG13.

FIG. 4: Identification of Hybridoma with inhibitory activity against TG2 Conditioned media from 32 hybridoma wells with specificity to TG2 were screened for their effects on 100 ng of rhTG2 activity using the $^3$H putrescine incorporation assay. The chemical pan TG2 inhibitor 1,3-Dimethyl-2-[(2-oxo-propyl)thio]imidazolium chloride was used as a positive control for inhibition. RPMI (unconditioned medium) was used a negative control. 500 ng of a TG2 inhibitory antibody piloted by Quark biotechnology was included for comparison. Data represents mean CPM incorporated in 30 mins from at least three experiments done in duplicate±SEM. Bars shown in grey show significant TG2 inhibition ($p<0.05$).

FIG. 5: Mapping of Inhibitory Antibody Epitopes.

Each inhibitory monoclonal antibody was bound to an ELISA plate and panned against a human TG2 phage library. Phage binding to the antibody were rescued, amplified and subjected to 4 further rounds of panning. TG2 library fragments in the phage were then sequenced and overlapping sequences used to determine the epitope for each antibody. Common sequences between antibodies were then used to determine a consensus sequence for a particular inhibitory epitope and antibodies grouped accordingly. 3 inhibitory epitopes were identified.

Figure 6:
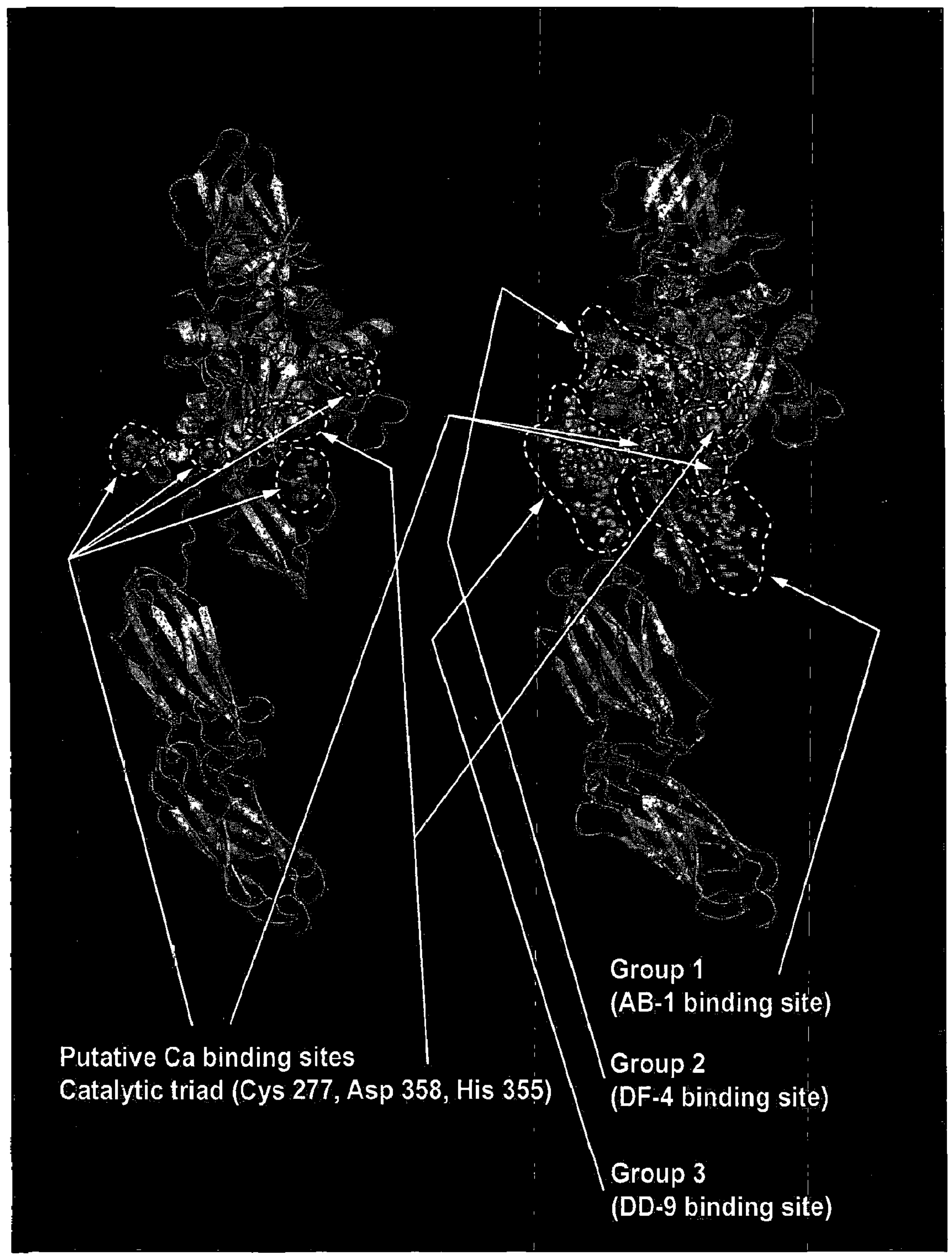

FIG. 6: Structural location of Inhibitory Epitopes with the TG2 catalytic Core The TG2 amino acid sequence was entered into Pymol and a 3D graphical representation of the structure generated in its open, $Ca^{2+}$ activated state with putative calcium binding sites (turquoise) and the catalytic triad (grey) shown for reference (left panel). The consensus inhibitory epitopes were then added in blue (Antibody group 1—AB1 site), red (antibody group 2—DF4 site) and yellow (antibody group 3, DD9 site).

FIG. 7: VL Sequence of Inhibitory antibodies

RNA from each inhibitory hybridoma was extracted, reverse transcribed and amplified by PCR using a degenerate FR1 primers, MH1 and MH2 primers and 3 constant region primers to amplify VH genes. The resulting VH and VK sequences are shown for AB1.

FIG. 8. Efficacy of AB1 to inhibit TG2 activity in a cell homogenate

A: Hep2G cells were lysed and 45 ug of protein mixed with 750 ng of IgG from AB1, DH2, DD9, BB7, DC1 and EH6 for 20 minutes. This was subsequently assayed using the $^3$H Putrescine incorporation TG activity assay with sampling over 1 hour. The rate of reaction was calculated and expressed as a percentage of the same lysate incubated with a random antibody (MAB002). Data represents the mean percentage inhibition±SEM from 2 separate experiments done in duplicate. * $p<0.05$ B: HepG2 cells were exposed to increasing glucose concentrations for 96 hours to up regulate TG2 expression. Cells were harvested, lysed and 25 ug of lysate fractionated by SDS-PAGE, western blotted and then immunoprobed with a 1 ng/ml solution of AB1 IgG using a chemiluminesant end point.

FIG. 9. (Table 1): Comparative IC50 values for TG2 inhibitory antibodies

To determine an IC50 value for each antibody against human, rat and mouse the $^3$H Putrescine assay was used. 100 ng of human TG2 or 25 ng of mouse and rat TG2 was used to generate a reaction where approximately 3000 cpm of Putrescine were incorporated per hour in 10 ul of the reaction mixture. Serial dilutions of each antibody were then applied starting from adding 500 ng (5 ug/ml final concentration) to the reaction mixture and incubated with the TG2 for 20 minutes prior to activating the reaction. IC50 values were calculated by determining the concentration at which the enzymatic rate of reaction was reduced by 50% using an appropriate curve fit in graphpad prism. Values are expressed as the amount of IgG in mg/ml in the reaction that would inhibit 1 ng of TG2.

FIG. 10. Extracellular TG activity in HK2 cells in response to TG2 inhibition.

HK2 cells were plated onto fibronectin and incubated for 2 hours in the presence of 0.1M biotin cadaverine with either 4 ng/μl of human anti-TG2 antibody (AB1) (part A), 4 ng/μl of human anti-TG2 antibody (DC1) (part B) or 400 μM of the site-specific pan TG inhibitor 1,3-Dimethyl-2-[(2-oxo-propyl)thio]imidazolium chloride. Extracellular TG activity was measured by the incorporation of biotin cadaverine into fibronectin with incorporation revealed using extravadin-HRP and a TMB substrate. Changes in optical density were measured at 450 nm in a 96 well plate reader. Data represents mean OD at 450 nm corrected to 1 mg of cell protein. n=6 wells per experimental group.

Figure 11:
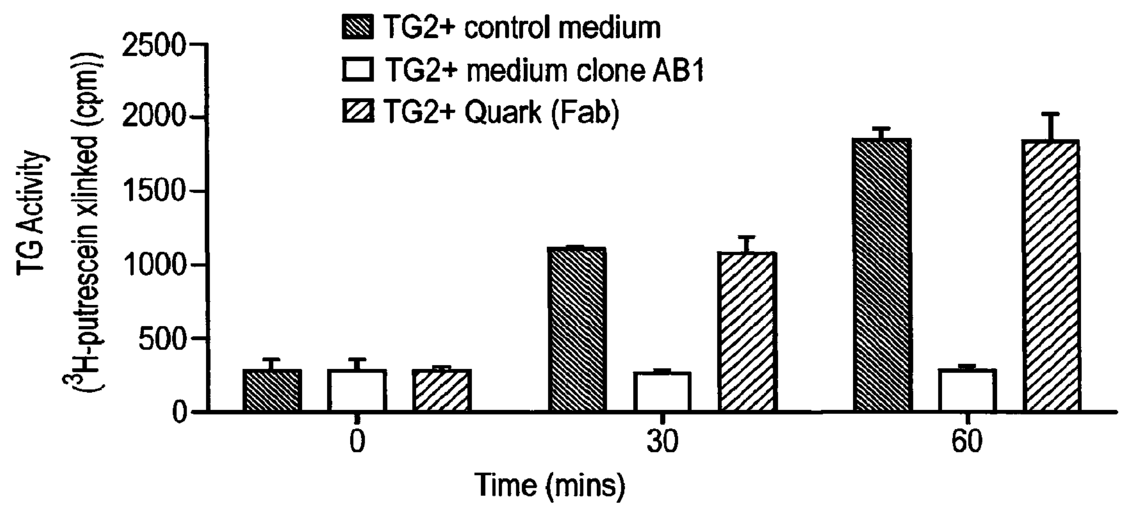

FIG. 11. Comparison of TG2 inhibition by antibody AB1 to a fab fragment of Quark's TG2 inhibitory antibody using a $^{3}$H putrescine incorporation assay 100 ng of hTG2 was assayed for TG2 activity based on the incorporation of $^{3}$H Putrescine into dimethylcasein over a 60 minute period with the addition of either 1 μg of a fab fragment of an antibody described by Quark in WO2006/100679 and synthesised at Sheffield University or 500 ng of AB1. Data represents mean TG activity as incorporation of $^{3}$H putrescine (CPM)±SEM from 3 independent experiments done in duplicate.

Figure 12:
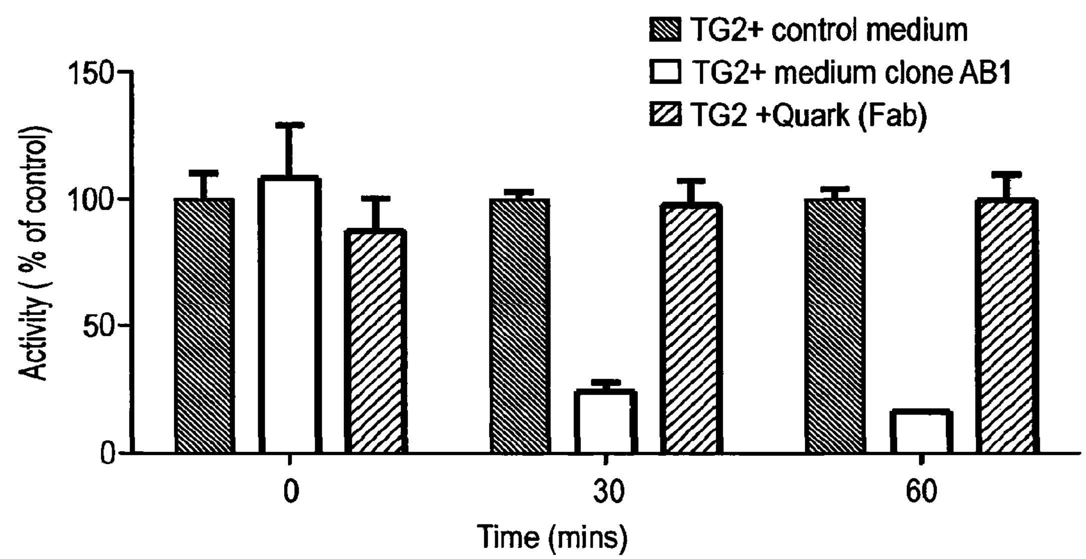

FIG. 12. Percentage comparison of TG2 inhibition by antibody AB1 with a fab fragment of Quark's TG2 inhibitory antibody using a $^{3}$H putrescine incorporation assay Data from FIG. 11 is alternatively expressed as a percentage of TG activity at each time point to display the relative comparative knockdown of TG2 activity by application of AB1 and the Quark antibody fab fragment.

Figure 13:
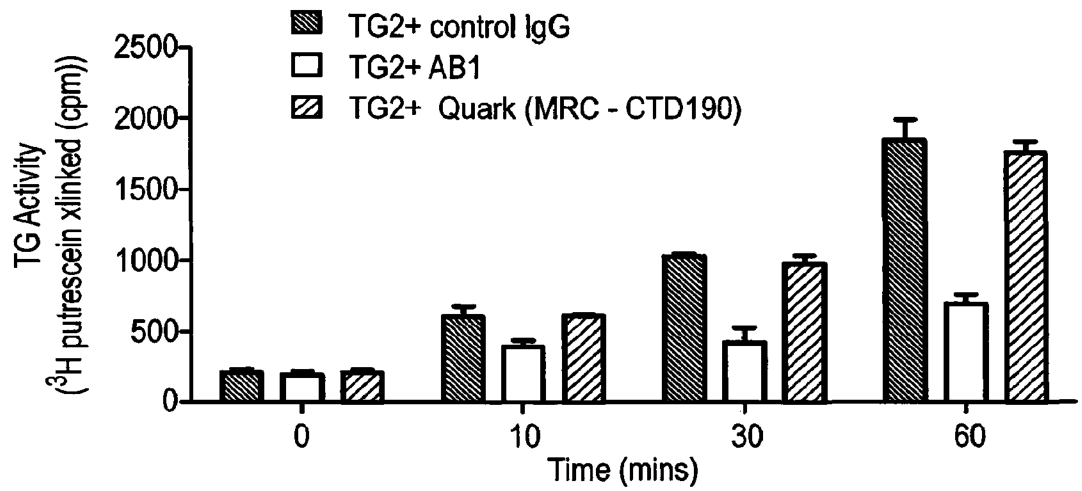

FIG. 13. Comparison of TG2 inhibition by antibody AB1 to a recombinant rat IgG of Quark's TG2 inhibitory antibody using a $^{3}$H putrescine incorporation assay 100 ng of hTG2 was assayed for TG2 activity based on the incorporation of $^{3}$H Putrescine into dimethylcasein over a 60 minute period with the addition of either 500 ng of a recombinant rat version of a TG2 inhibitory antibody described by Quark in WO2006/100679 and synthesised at Medical Research Council Technology or 500 ng of AB1. Data represents mean TG activity as incorporation of $^{3}$H putrescine (CPM)±SEM from 3 independent experiments done in duplicate.

Figure 14:
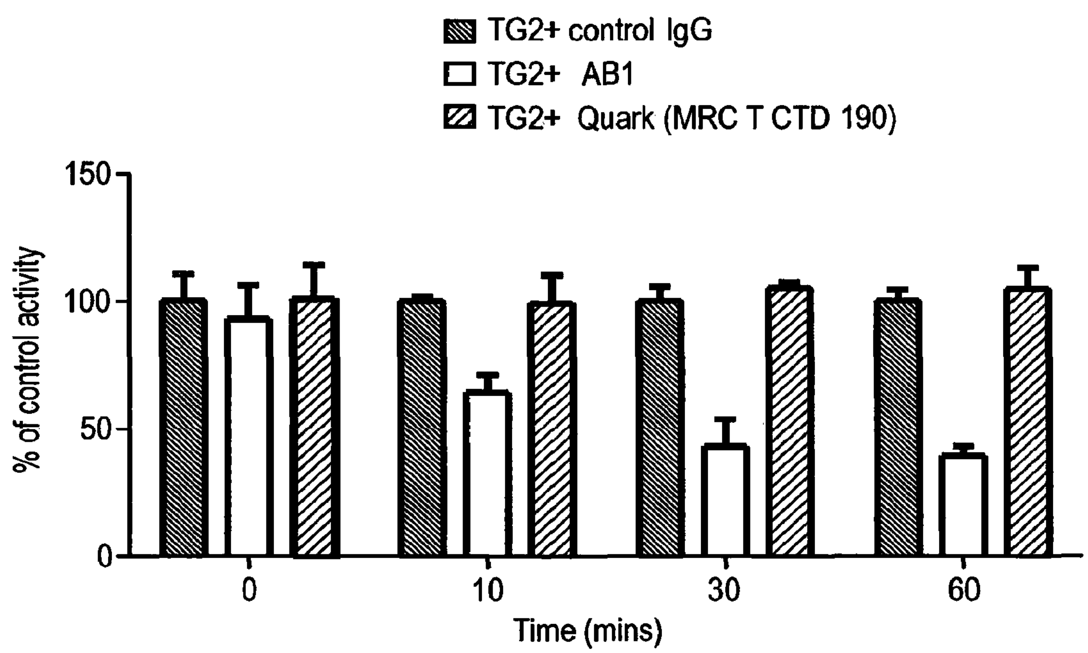

FIG. 14. Percentage comparison of TG2 inhibition by antibody AB1 to a recombinant rat IgG of Quark's TG2 inhibitory antibody using a $^{3}$H putrescine incorporation assay Data from FIG. 13 is alternatively expressed as a percentage of TG activity at each time point to display the relative comparative knockdown of TG2 activity by application of AB1 and the Quark recombinant rat IgG.

Figure 15:
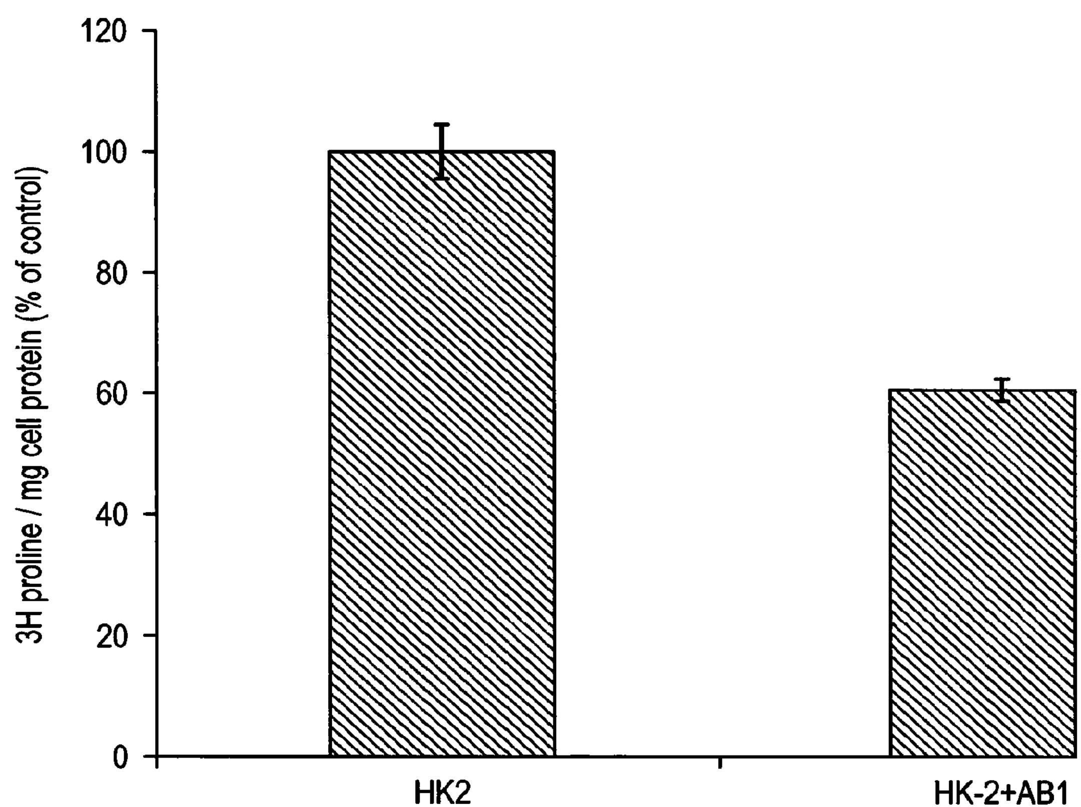

FIG. 15. Effect of AB1 on ECM levels in HK2 cells

Mature collagen levels in HK-2 cells were measured by the incorporation of $^{3}$H proline into the ECM over a 76 hour period either with or without the addition of TG2 inhibitory antibody AB1. Data represents the incorporation of $^{3}$H proline per mg of cellular protein expressed as a percentage of the mean level in untreated cells±SEM. n=2.

Figure 16:
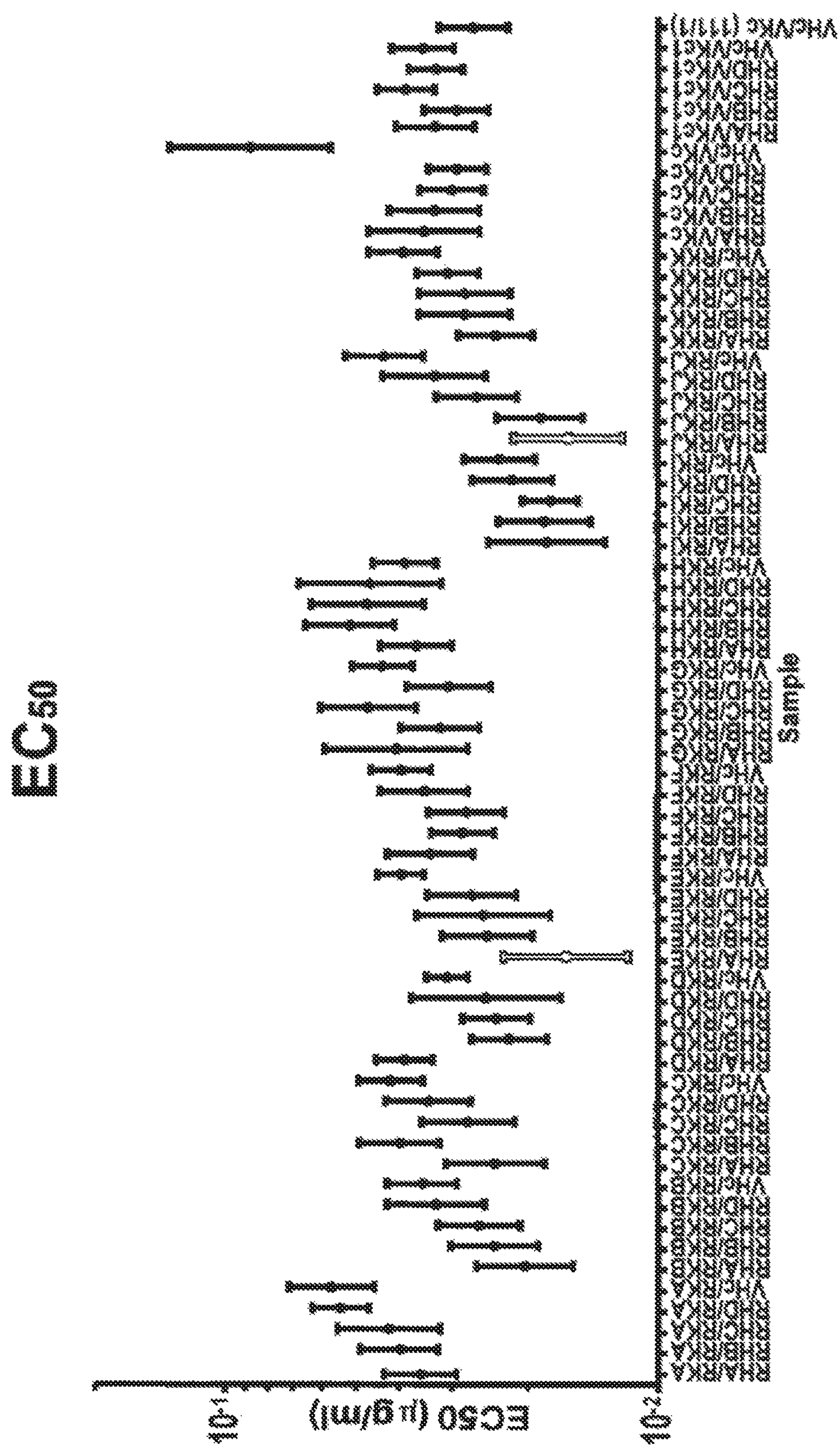

FIG. 16. Binding ELISA of humanised versions of antibodies.

Supernatants from HEK293F cells co-transfected with different combinations of humanised light chains and heavy chain vectors were assayed in an anti-human IgG ELISA to determine concentration and in an anti huTG2 ELISA. Each supernatant was assayed in triplicate and $IC_{50}$'s determined. The most potent combination was selected for further studies and as the candidate humanised antibody.

Figure 17:
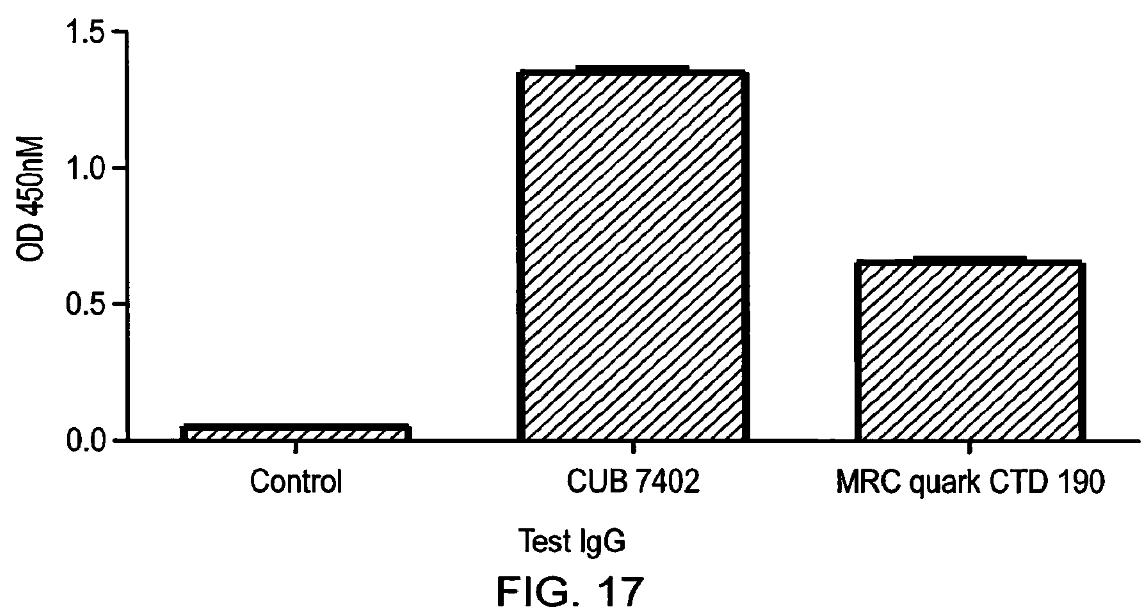

FIG. 17. Testing MRC Quark CTD190 on human Tg2 by ELISA.

96 well plates were plated with hTG2 (1 μg/ml) in carbonate buffer overnight and ELISA detection performed using 100 ng/ml primary antibody. Detection was performed using anti-mouse IgG (SIGMA 3673) for CUB and anti-rat IgG (SIGMA A5795) for the Quark (both 1:5000). The Quark antibody made by MRC T reacts with human TG2.

FIG. 18: RNA from the AB1 hybridoma was extracted, reverse transcribed and amplified by PCR using the degenerate signal sequence primer MHV4 with heavy chain constant region primer MHCG1, or using the degenerate signal sequence primer MKV4 with a kappa light chain constant region primer MKC. The resulting VH and VK sequences are shown.

FIG. 19: RNA from the BB7 hybridoma was extracted, reverse transcribed and amplified by PCR using the degenerate signal sequence primer MHV4 with heavy chain constant region primer MHCG1, or using the degenerate signal sequence primer MKV4 with a kappa light chain constant region primer MKC. The resulting VH and VK sequences are shown.

FIG. 20: RNA from the DC1 hybridoma was extracted, reverse transcribed and amplified by PCR using the degenerate signal sequence primer MHV4 with heavy chain constant region primer MHCG1, or using the degenerate signal sequence primer MKV4 with a kappa light chain constant region primer MKC. The resulting VH and VK sequences are shown.

FIG. 21: RNA from the JE12 hybridoma was extracted, reverse transcribed and amplified by PCR using a 5' RACE PCR with heavy chain constant region primer MHCG1, or using the signal sequence primer MKV1 with a kappa light chain constant region primer MKC. The resulting VH and VK sequences are shown.

FIG. 22: RNA from the EH6 hybridoma was extracted, reverse transcribed and amplified by PCR using a 5' RACE PCR with heavy chain constant region primer MHCG2B, or using the signal sequence primer MKV with a kappa light chain constant region primer MKC. The resulting VH and VK sequences are shown.

FIG. 23: RNA from the AG9 hybridoma was extracted, reverse transcribed and amplified by PCR using the degenerate signal sequence primer MHV7 with heavy chain constant region primer MHCG1, or using a mix of degenerate signal sequence primers MKV1—11 with a kappa light chain constant region primer MKC. The resulting VH and VK sequences are shown.

FIG. 24: RNA from the AH3 hybridoma was extracted, reverse transcribed and amplified by PCR using the degenerate signal sequence primer MHV7 with heavy chain constant region primer MHCG2B, or using the signal sequence primer MKV1 with a kappa light chain constant region primer MKC. The resulting VH and VK sequences are shown.

FIG. 25: RNA from the DD9 hybridoma was extracted, reverse transcribed and amplified by PCR using a 5' RACE PCR with heavy chain constant region primer MHCG2A, or using the degenerate signal sequence primer MKV5 with a kappa light chain constant region primer MKC. The resulting VH and VK sequences are shown.

FIG. 26: RNA from the DH2 hybridoma was extracted, reverse transcribed and amplified by PCR using a 5' RACE PCR with heavy chain constant region primer MHCG2B, or using the degenerate signal sequence primer MKV45 with a kappa light chain constant region primer MKC. The resulting VH and VK sequences are shown.

FIG. 27: RNA from the DD6 hybridoma was extracted, reverse transcribed and amplified by PCR using a 5' RACE PCR with heavy chain constant region primer MHCG2B, or using a 5' RACE PCR with a lambda light chain constant region primer MLC. The resulting VH and VL sequences are shown.

FIG. 28: RNA from the IA12 hybridoma was extracted, reverse transcribed and amplified by PCR using the degenerate signal sequence primer MHV9 with heavy chain constant region primer MHCG1, or using the degenerate signal sequence primer CL14 with a kappa light chain constant region primer MKC. The resulting VH and VK sequences are shown.

FIG. 29. Dose response curves and IC50 values for enzymatic inhibition of recombinant human TG2 by chimeric anti-TG2 antibodies, (a) cAB003, (b) cBB001, (c) cDOC001, (d) cDD9001, (e) cDH001 and (f) the commercial TG2 antibody CUB7402. IC50 values are mean of 3 independent experiments.

FIG. 30. Dose response curves and IC50 values for enzymatic inhibition of recombinant cynomogulus monkey TG2 by chimeric anti-TG2 antibodies (a) cDC001 and (b) the commercial TG2 antibody CUB7402.

FIG. 31. Dose response curves and IC50 values for enzymatic inhibition of recombinant human TG2 by humanized anti-TG2 antibodies, (a) hBB001AA, (b) hBB001BB, (c) hAB005 and (d) hAB004.

Figure 32:
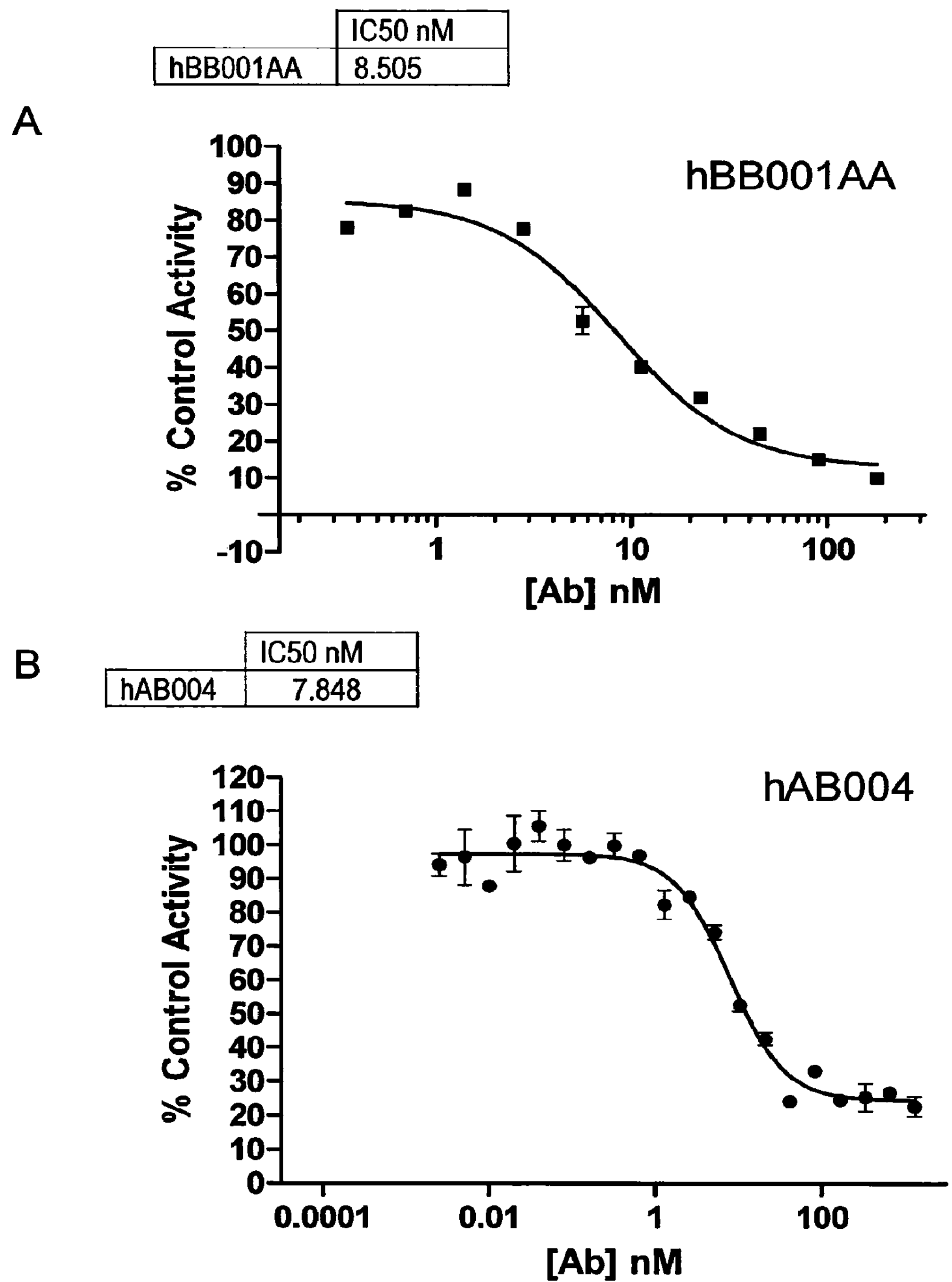

FIG. 32. Dose response curves and IC50 values for enzymatic inhibition of recombinant cynomogulus monkey TG2 by humanized anti-TG2 antibodies (a) hBB01AA and (b) hAB004.

FIG. 33. Dose response curves and IC50 values for enzymatic inhibition of recombinant human TG2 by murine monoclonal anti-TG2 antibodies, (a) mAB003, (b) mBB001, (c) mDC001, (d) mDD9001, (e) mDH001 and (f) mDD6001.

Figure 34:
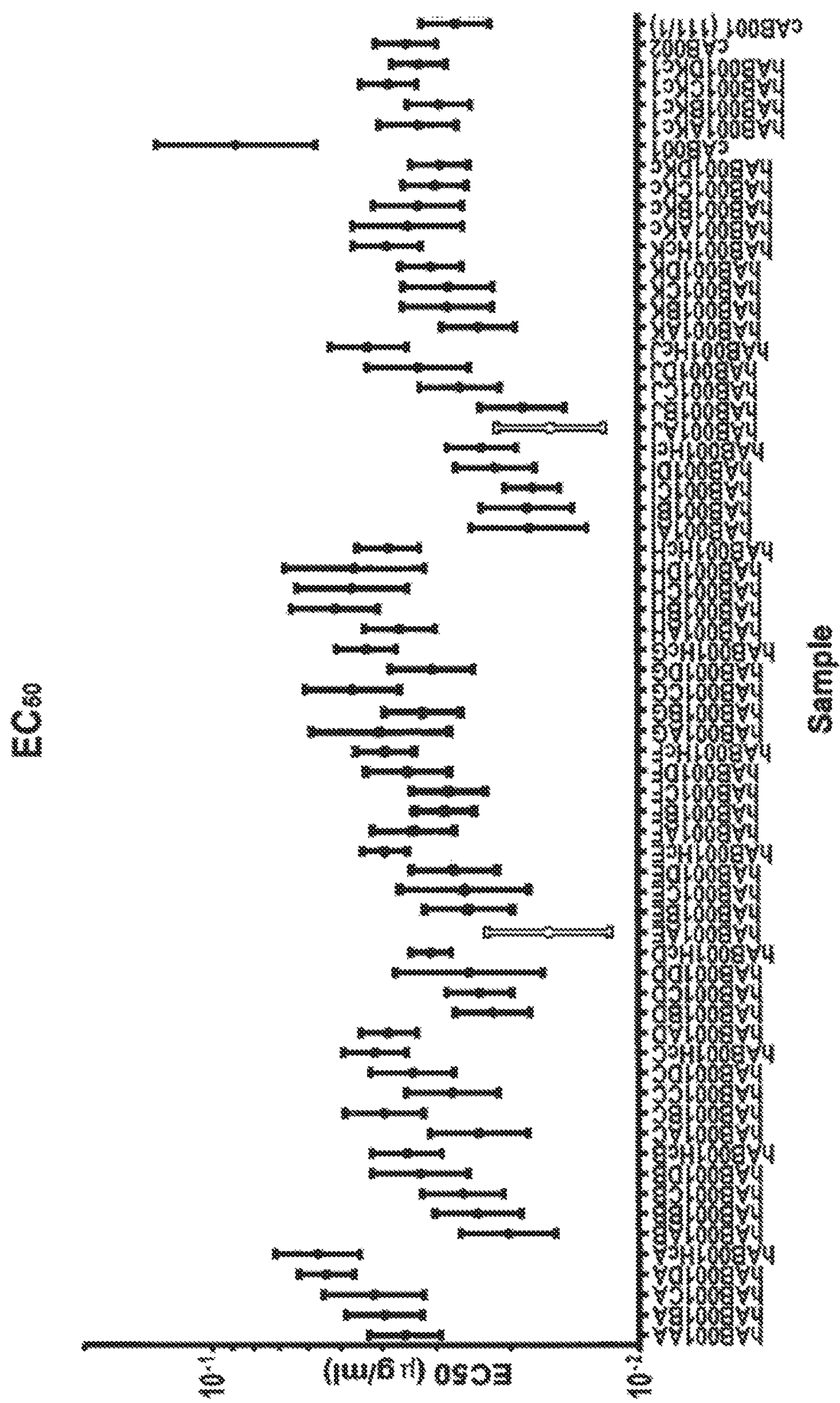

FIG. 34—Binding ELISA of humanised versions of AB1 antibodies.

Supernatants from HEK293F cells co-transfected with different combinations of humanised AB1 light chains and AB1 heavy chain vectors were assayed in an anti-human IgG ELISA to determine concentration and in an anti huTG2 ELISA. Each supernatant was assayed in triplicate and $IC_{50}$'s determined. The most potent combination was selected for further studies and as the candidate humanised antibody.

FIG. 35. Dose response ELISA binding curves and EC50 data for antibodies binding to human TG2 (a) chimeric antibodies cDD9001, cDH001, cDC001, commercial TG2 antibody CUB7402 and isotype-matched control, (b) chimeric antibody cBB001 and isotype-matched control and (c) chimeric antibody cAB003 and isotope-matched control.

FIG. 36. Dose response ELISA binding curves and EC50 data for antibodies binding to cynomogulus monkey TG2 (a) chimeric antibodies cDD9001, cDH001, cD0001, commercial TG2 antibody CUB7402 and isotype-matched control, (b) chimeric antibody cBB001 and isotype-matched control and (c) chimeric antibody cAB003 and isotope-matched control.

FIG. 37. Dose response ELISA binding curves and EC50 data for antibodies binding to human TG2 (a) humanized antibodies hBB001AA, HBB001BB, commercial TG2 antibody CUB7402 and isotype-matched control and (b) humanized antibody hAB004.

FIG. 38. Dose response ELISA binding curves and EC50 data for antibodies binding to cynomogulus monkey TG2 (a) humanized antibodies hBB001AA, HBB001BB, commercial TG2 antibody CUB7402 and isotype-matched control and (b) humanized antibody hAB004 and isotope-matched control.

Figure 39:
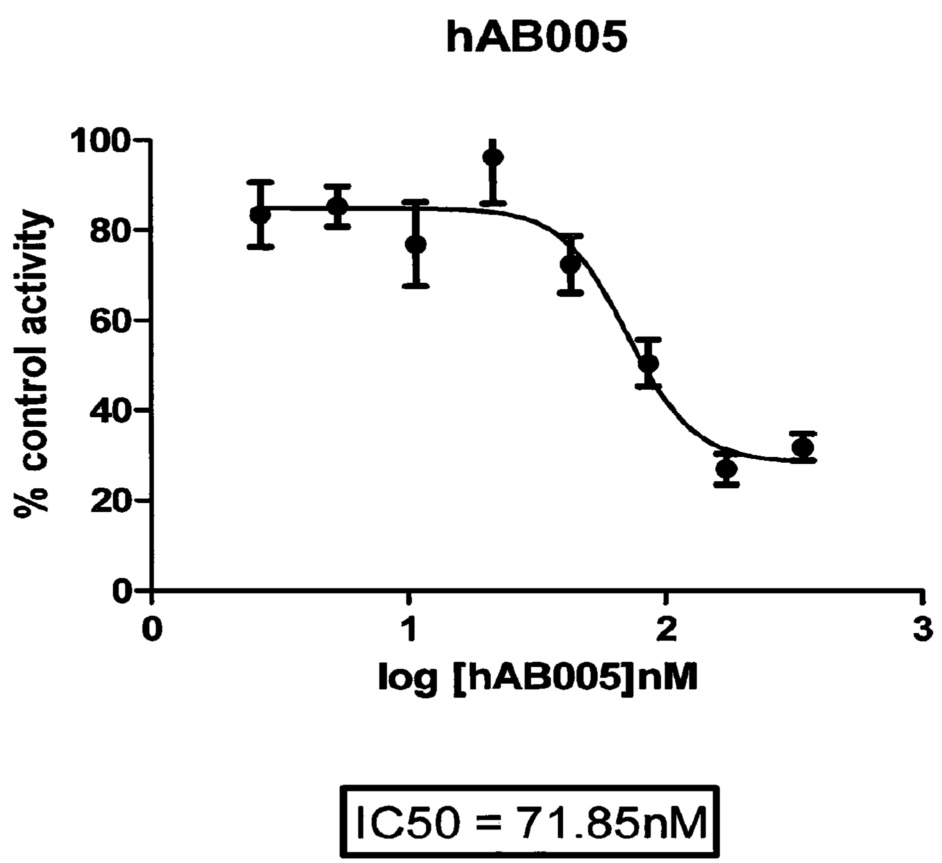

FIG. 39: Humanised AB1 binding activity with extracellular TG2 Inhibition of Extracellular TG2 activity produced by HK2 cells was assayed using an ELISA measuring the incorporation of biotin cadaverine into fibronectin. An exemplar curve showing the inhibition of TG2 activity by humanised AB1 (hAB005) and the IC obtained is shown.

Figure 40:
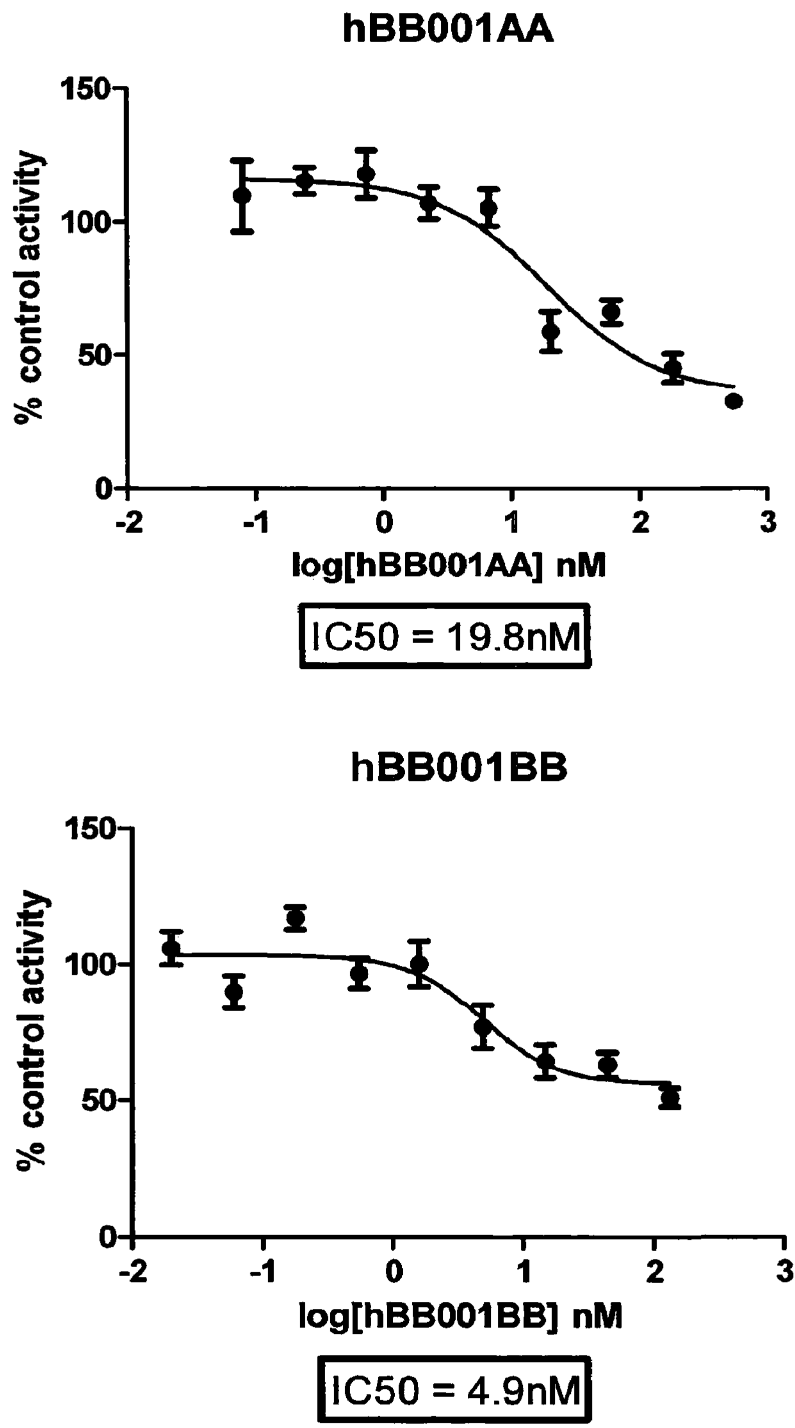

FIG. 40: Humanised BB7 binding activity with extracellular TG2.

Inhibition of Extracellular TG2 activity produced by HK2 cells was assayed using an ELISA measuring the incorporation of biotin cadaverine into fibronectin. An exemplar curve showing the inhibition of TG2 activity by versions of humanised BB7 (hBB001AA and hBB001BB) and the ICs obtained is shown.

Figure 41:
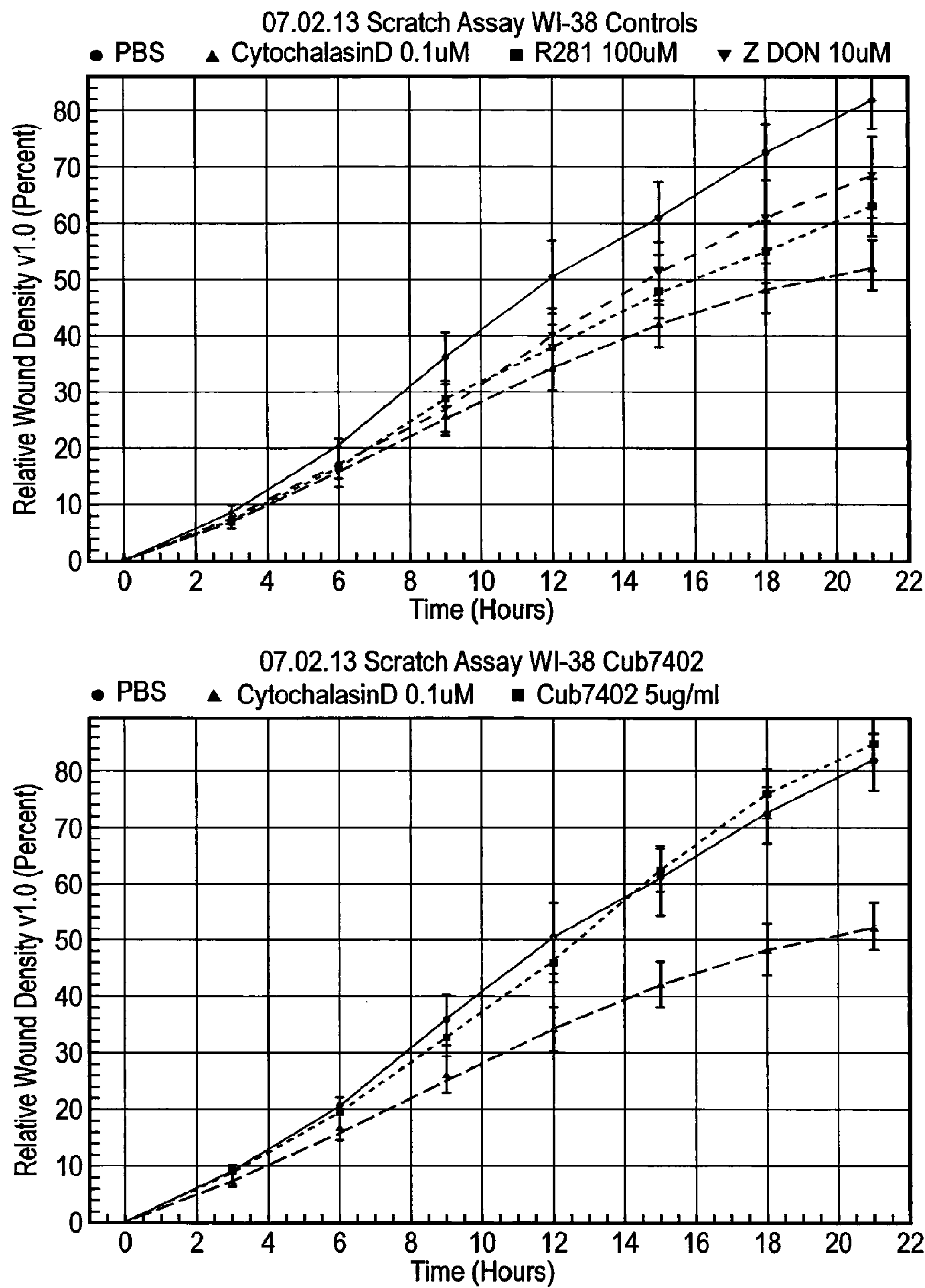

FIG. 41: Cytochalasin D, R281 and ZDON control scratch assay results and commercial antibody CUB7402 scratch assay results.

Scratch wound assays were performed using WI-38 cell, after plating and overnight growth, cells were washed in media without serum and a scratch wound generated using an Essen Wound Maker. Media was removed and replaces with 95 ul/well serum free media containing controls and test antibodies. The plate was placed in an Essen Incycte and the closure of the wound analysed using Incucyte software. Relative wound density was plotted against time for the controls cytochalasin D, R281 and Z-Don (panel A) and the commercial antibody CUB7402 and cytochalasin (panel B).

Figure 42:
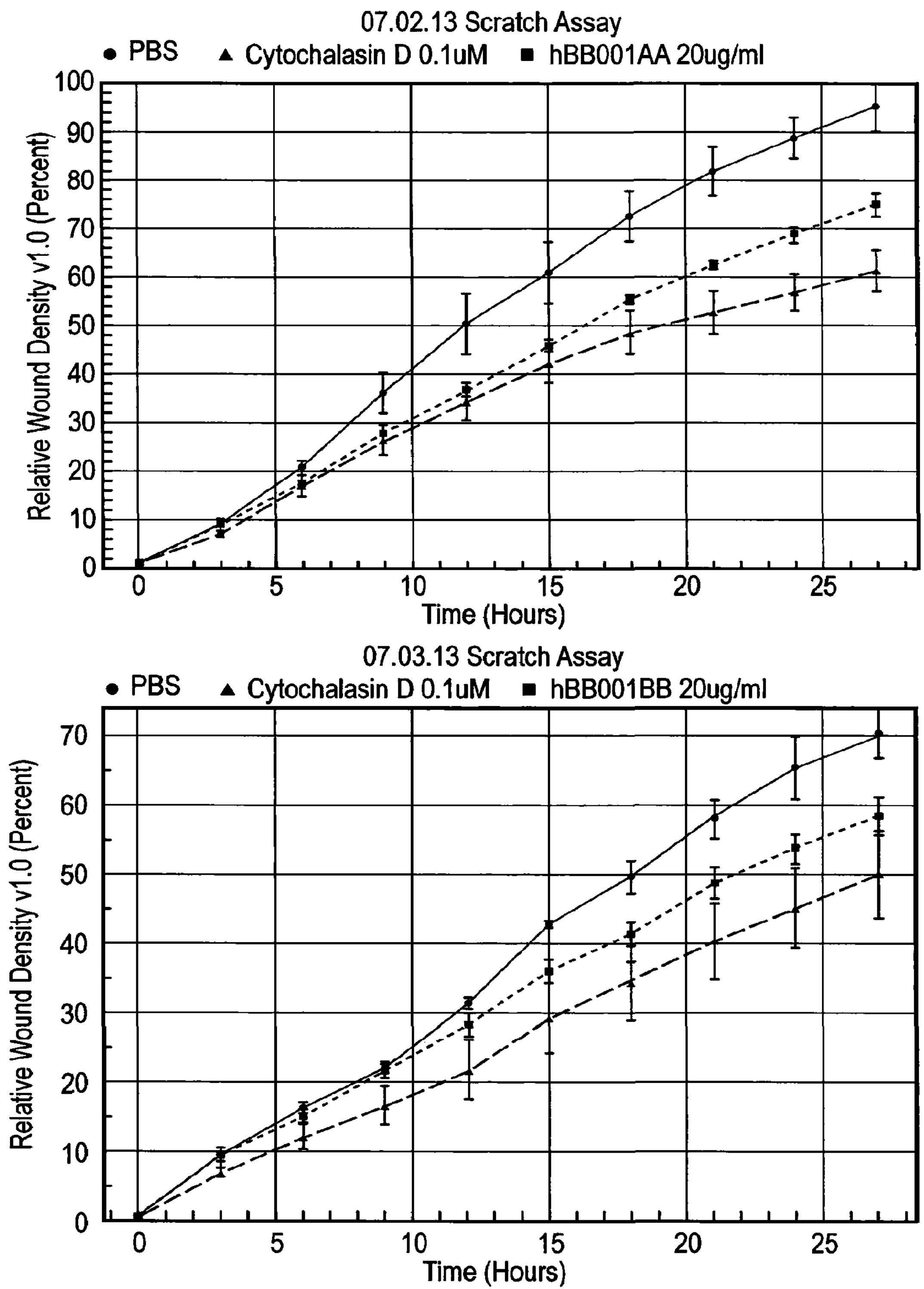

FIG. 42: Humanised BB7 scratch assay results.

Scratch wound assays were performed using WI-38 cell, after plating and overnight growth, cells were washed in media without serum and a scratch wound generated using an Essen Wound Maker. Media was removed and replaces with 95 ul/well serum free media containing controls and test antibodies. The plate was placed in an Essen Incycte and the closure of the wound analysed using Incucyte software. Relative wound density was plotted against time for the humanised hBB001 AA and the control cytochalasin D (panel A) and hBB001BB and the control cytochalasin D (panel B).

Figure 43:
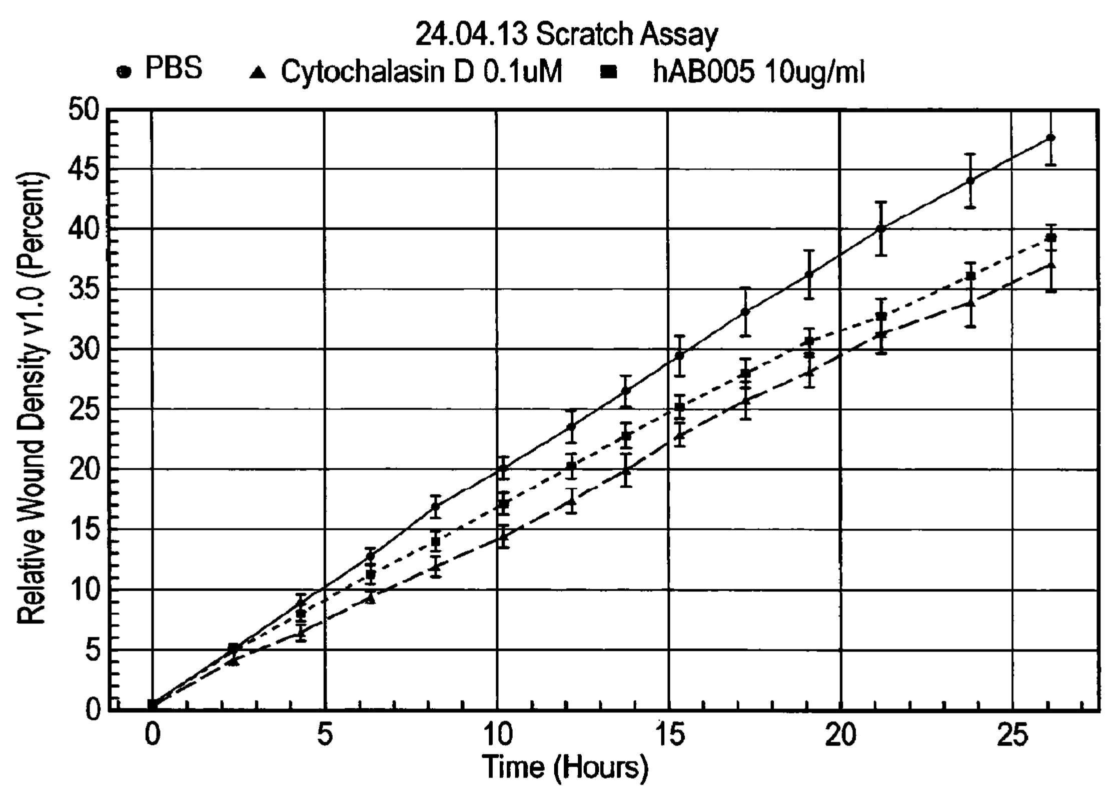

FIG. 43: Humanised AB1 scratch assay results.

Figure 44:
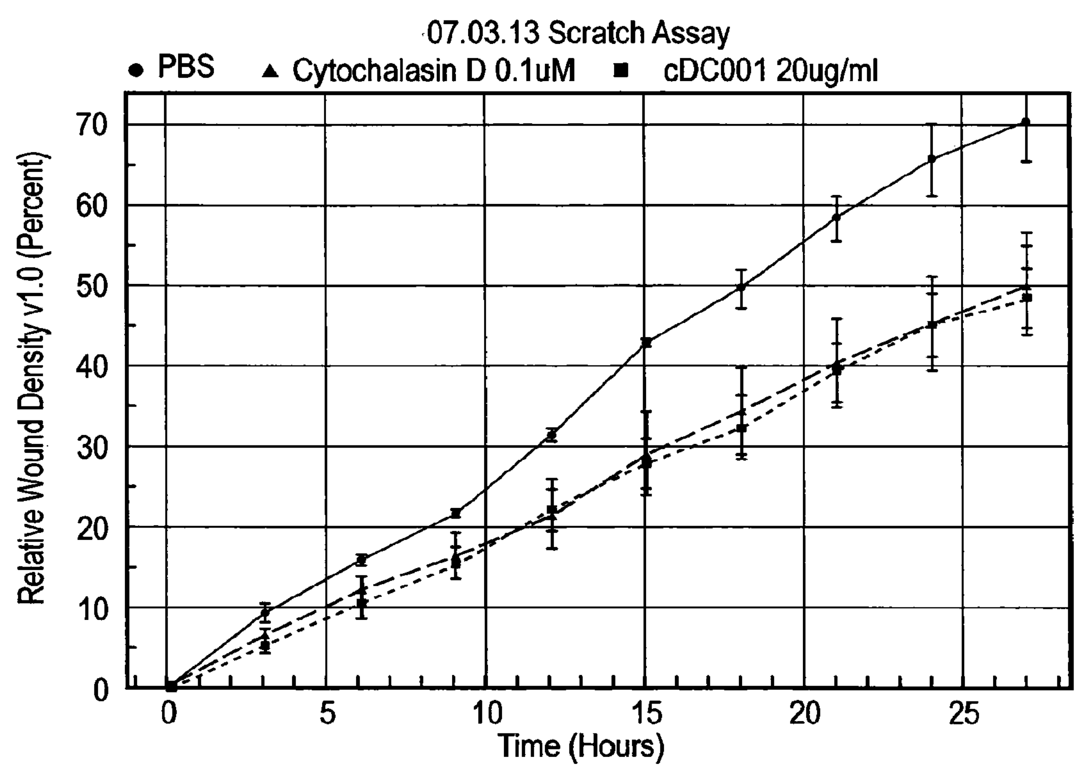

Scratch wound assays were performed using WI-38 cell, after plating and overnight growth, cells were washed in media without serum and a scratch wound generated using an Essen Wound Maker. Media was removed and replaces with 95 ul/well serum free media containing controls and test antibodies. The plate was placed in an Essen Incycte and the closure of the wound analysed using Incucyte software. Relative wound density was plotted against time for the humanised hAB005 and the control cytochalasin D FIG. 44: Chimeric DC1 scratch assay results.

Scratch wound assays were performed using WI-38 cell, after plating and overnight growth, cells were washed in media without serum and a scratch wound generated using an Essen Wound Maker. Media was removed and replaces with 95 ul/well serum free media containing controls and test antibodies. The plate was placed in an Essen Incycte and the closure of the wound analysed using Incucyte software. Relative wound density was plotted against time for the chimeric antibody cDC001 and the control cytochalasin D FIG. 45: Human TG2 binding to cAB003 immobilised antibody by Biacore. The association phases of human TG2 injections over the cAB003-coated biosensor at 25, 50, 100 and 200 nM, including in duplicate at 50 nM, are shown on the left. From the same experiment, two long dissociation phases were collected, as shown on the right. Fits are shown as solid black lines and the results are shown in Table 25.

Figure 46:
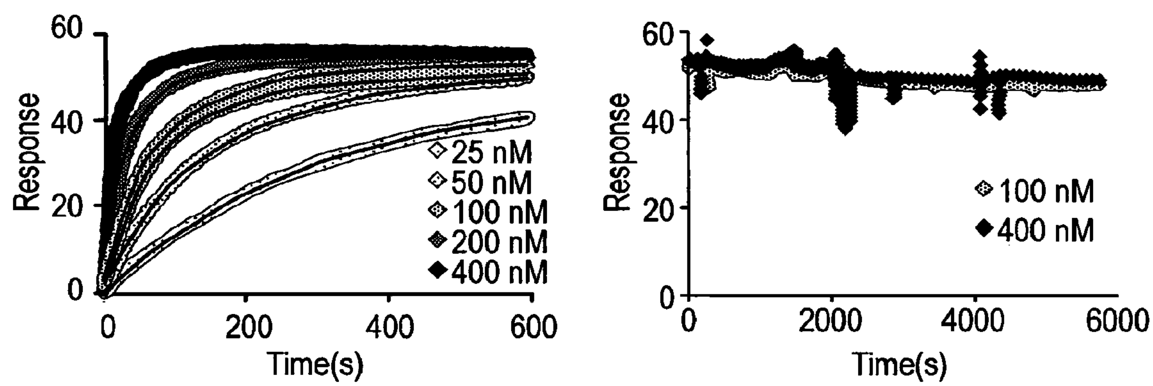

FIG. 46: Cynomolgus monkey TG2 binding to hAB004 immobilised antibody by Biacore. The association phases of cynomolgus monkey TG2 injections over the hAB004-coated biosensor at 25, 50, 100, 200 and 400 nM, including in duplicate at 50 nM, are shown on the left. From the same experiment, two long dissociation phases were collected, as shown on the right. Fits are shown as solid black lines and the results are shown in Table 26.

Figure 47:
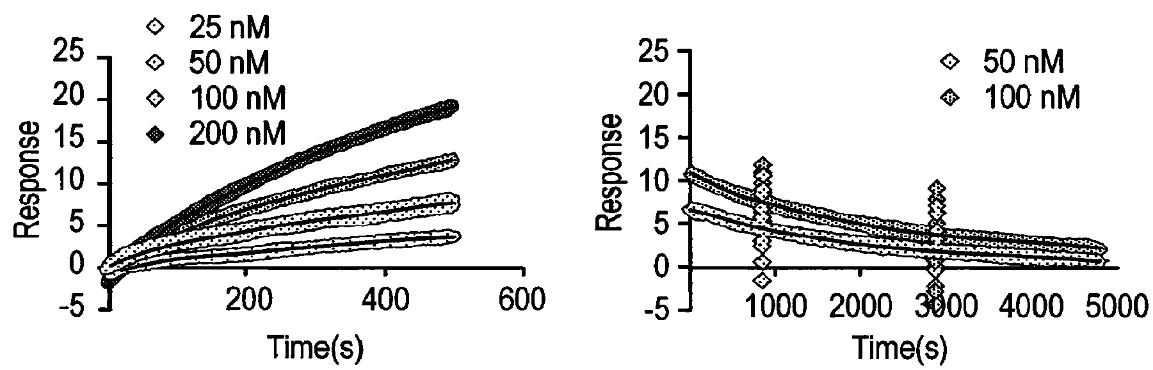

FIG. 47: Human TG2 binding to cDH001 immobilised antibody by Biacore in the absence of calcium. The association phases of human TG2 injections over the cDH001-coated biosensor at 25, 50, 100 and 200 nM, including in duplicate at 50 nM, are shown on the left. From the same experiment, two long dissociation phases were collected, as shown on the right. Fits are shown as solid black lines and the results are shown in Table 25.

EXAMPLE 1: DEVELOPING A TG2 INHIBITORY ANTIBODY SUITABLE FOR THERAPEUTIC USE IN MAN WITH THE IDENTIFICATION OF 3 SPECIFIC INHIBITORY EPITOPES

Transglutaminase type 2 (TG2) catalyses the formation of an ε-(γ-glutamyl)-lysine isopeptide bond between adjacent peptides or proteins including those of the extracellular matrix (ECM). Elevated extracellular TG2 leads to accelerated ECM deposition and reduced clearance that underlies tissue scarring and fibrosis. It also is linked to celiac disease, neurodegenerative disorders and some cancers. While numerous compounds have been developed that inhibit transglutaminases, none of these are specific to TG2, inhibiting all transglutaminases to some extent. While these have allowed proof of concept studies for TG2's role in these pathologies, the lack of isoform specificity has prevented their application in man. To address this, we set out to develop a high affinity TG2 specific antibody that would inhibit only TG2 activity.

A recombinant protein encompassing amino acids 143 to 473 of the human TG2 core was produced in *Escherichia coli*, re-folded and 100 μg injected into 4 mice with boosts at 2, 5, 7, and 10 weeks. Spleens were recovered 4 days after the final boost and splenocytes fused to Sp2/0-Ag-14 myeloma cells. Seventy-five hybridoma supernatants showed specificity to TG2. These hybridoma supernatants were screened for their ability to inhibit TG2 activity in a putrescine incorporation assay containing 100 μg of TG2. Ten TG2 specific supernatants were inhibitory. These were subsequently double cloned. Using phage display to screen a TG2 fragment library, each antibody was mapped to a precise epitope in the TG2 core domain and 3 distinct inhibitory epitopes determined. The amount of antibody to reduce the activity from 100 ng of TG2 by 50% was determined.

The 2 most effective antibodies, AB1 and DC1 bound to amino acids 304 to 327 and had an $IC_{50}$ of $1.1\times10^{-5}$ mg/ml IgG per ng of recombinant TG2. Application of AB1 & DC1 was able to inhibit TG2 successfully in human Hep2G cells and extracellular TG2 in human HK-2 cells when applied to the culture media.

Thus, immunisation of mice with the TG2 core domain surprisingly enabled the generation of monoclonal antibodies that target previously unreported epitopes within the catalytic core. These antibodies are specific, inhibit TG2 activity effectively and are suitable for in vivo application.

Materials and Methods

Transglutaminase 2 Catalytic Core Domain Production

The catalytic core domain of human TG2 (residues Cys143—Met 473 of TG2) was expressed, refolded and purified to permit immunisation in mice. The catalytic core domain (PCR sense primer GCG CGC GCT AGC TGC CCA GCG GAT GCT GTG TAC CTG GAC (SEQ ID NO: 97), anti-sense GCG CGC AAG CTT CAT CCC TGT CTC CTC CTT CTC GGC CAG(SEQ ID NO: 98)) was cloned into the expression vector pET21a(+) and expressed as insoluble inclusion bodies in *E. coli* strain BL21-CodonPlus (DE3)-RIPL (Agilent Technologies). In brief, 50 μl of competent BL21 (DE3) pLysS cells were transformed with 1 μl of the expression plasmid (30 ng/μl) and plated onto LB agar plates containing the selective antibiotics (100 μg/ml ampicillin, 34 μg/ml chloramphenicol) and 1% glucose and incubated overnight at 37° C. A single colony was picked to seed 10 ml of fresh LB medium containing 100 μg/ml ampicillin, 34 μg/ml chloramphenicol and 1% glucose in shaking incubator at 37° C. and at 200 rpm. After overnight growth, cultures were transferred in 100 ml 2×YT media with 1% glucose and grown to an $OD_{600}$ nm of 0.8 and then transferred to 1 L 2×YT medium until the $OD_{600}$ nm reached 0.8 again. After 4 hours induction under 1 mM IPTG to stimulate expression, pelleted and bacteria were lysed by sonication in buffer A (10 mM Tris; 1 mM EDTA; 10 mM DTT; 1 mM PMSF; 0.5 mg/ml lysozyme protease inhibitor tablets (Roche), pH 8.0). Inclusion bodies were harvested by centrifugation at 40,000×g and washed three times in wash buffer B (50 mM Tris; 1 mM EDTA; 10 mM DTT; 2% sodium deoxycholate, pH 8.0) before a final wash in deionised water.

Inclusion bodies were solubilised in 3.5 mls of resolubilisation buffer (40 mM Tris-HCl, 8 M urea, and 10 mM DTT pH12) and refolded over a period of 16 hours in refolding buffer (40 mM Tris HCl; 150 mM NaCl; 20% glycerol; 5 mM cysteine; 0.5 mM cystine pH 8) at 4° C. in the dark.

The resolubilised inclusion bodies were loaded onto a 1 ml Nickel column. Briefly, the column was pre-equilibrated with binding buffer (40 mM Tris; 300 mM NaCl; 10 mM Imidazole) and the inclusion bodies applied. The column was extensively washed (40 mM Tris; 300 mM NaCl; 30 mM imidazole). The recombinant protein was eluted by high concentration imidazole buffer (40 mM Tris; 300 mM NaCl; 300 mM imidazole). Eluted protein containing fractions were pooled and dialysed overnight against an appropriate buffer (40 mM Tris; 300 mM NaCl pH 8). Protein was assessed using the Bradford protein assay HepG2 Cell Culture & Lysates HepG2 cells were kindly supplied by Richard Ross (University of Sheffield). Cells were routinely grown at 37° C. in a 95% humidified atmosphere of 5% $CO_2$ in DMEM/4.5 g per litre glucose supplemented with 10% foetal calf serum (FCS), 100 IU penicillin and 100 μg/ml streptomycin, 2 mM I-glutamine (all GIBCO). Two million cells were seeded on a 10 cm dishes and grown for 48 hours. Cells were lysed in 250 μl of STE buffer (0.32M sucrose, 5 mM Tris, 1 mM EDTA containing protease inhibitors Phenylmethylsulphonyl fluoride (1 mM), benzamidine (5 mM), and leupeptin (10 μg/ml) and sonicated on ice to produce a cell lysate usable in TG2 activity assay.

Human Kidney 2 (HK2) Cells:

HK-2 cells (kidney proximal tubular epithelium) were purchased from the European cell culture collection at passage 3. Cells were routinely grown at 37° C. in a 95% humidified atmosphere of 5% $CO_2$ in keratinocyte serum free medium (KSFM, Gibco 17005-042) with L-glutamine supplemented with recombinant EGF (0.1-0.2 ng/ml) and bovine pituitary extract (20-30 ug/ml). For passage, media was removed and washed once with 1×PBS before trypsinising with 1 ml of 0.25% trypsin/EDTA (T75 flask) for 1 minute at 37° C. Cells were resuspended in 10 mls of KSFM and centrifuged at 400 g for 1 minute. Media was removed and cells plated in KSFM (1:3 to 1:5 split is normal). Cells were used experimentally at passages 5-14. Cells typically grew well to 95% confluence.

Coomassie Staining and Western Blotting

The purity of recombinant proteins was checked by running 5 μg of the recovered protein on a 10% (w/v) polyacrylamide denaturing gel and staining with Coomassie Brilliant Blue R staining solution (Sigma).

Confirmation of TG2 core protein synthesis as well as TG2 and TG2 core reactivity levels following immunisation were all measured by western blotting. Recombinant proteins (10 to 80 ng) were loaded on a 10% (w/v) polyacrylamide denaturing or non-denaturing gel as required and transferred onto PVDF membranes (Transblot SD, Biorad, UK) for one hour at 100 V. Membranes were blocked overnight at 4° C. with 3% (w/v) BSA in TBS/0.1% (v/v) Tween 20. The membranes were then washed and probed with monoclonal mouse anti-transglutaminase antibodies in TBS/Tween containing 1% BSA.

For proof of recombinant TG2 core protein and as a positive control for antibody screening the commercial antibody Cub7402 (neomarkers) was used at a 1:1000 dilution. Binding of primary antibody was detected with the anti-mouse gamma-chain-HRP linked secondary antibody (Sigma, Poole, UK). Bands were visualised using ECL chemiluminescent detection system (Amersham, UK).

Mouse Immunisation and Fusion

Each mouse was immunised with a mixture of 50 μg of antigen (made up to a volume of 50 μl with sterile PBS) and 50 μl of complete Freund's adjuvant. Four (8-12 week old) BALB/C mice were injected. Two boost immunisations were carried out (day 14 and day 35) using the same procedure with the exception that incomplete Freund's adjuvant was used for these injections. At day 45, test bleeds were taken from all animals and assessed for reactivity to TG2 by ELISA.

The two best responders were further boosted by injection of 100 μg of core protein (in PBS) again mixed with incomplete Freuds Adjuvant at 10 weeks, and 4 days later the animals were sacrificed for splenocyte recovery and fusion with Sp2/0-Ag-14 myeloma cells. From this fusion, approximately 1000 wells were screened for reactivity to TG2 protein by ELISA.

Screening for TG2 Specificity

Conditioned medium or purified IgG were tested for reactivity to transglutaminase family members. The ability of each to bind to each transglutaminase (TG1, TG2, TG3, TG5, TG7 and Factor XIIIa; all Zedira) was determined using a plate binding assay. Microtiter plates (Costar, Cambridge, UK) were coated with recombinant TG (Zedira, Darmstadt, Germany) in 50 μl of 0.1 M bicarbonate/carbonate buffer (pH 9.6) overnight at 4° C. Plates were blocked for 2 h at 37° C. with 200 μl PBS containing 3% w/v BSA. Plates were washed three times with PBS containing 0.05% Tween 20 (washing buffer) and 100 μl of diluted conditioned medium (dilution 1:5 to 1:20) or purified anti-TG2 catalytic core mAbs was added. Plates were incubated for a further 1 h at room temperature. The washing step was repeated and anti-mouse gamma chain-horseradish peroxidase (1:5000) in PBS containing 0.05% Tween 20 (v:v) and 1% BSA (w:v) (Sigma, Poole UK) was added for 1 h. After eight washes, binding was revealed with 50 μl of 3,3',5,5'-tetramethylbenzidine substrate. The reaction was stopped by adding 25 μl of 0.1 M $H_2SO_4$ and the absorbance at 450 nm was determined.

Screening for TG2 Inhibition TG activity is measured by the $Ca^{2+}$ dependent incorporation of 3H-putrescine into N',N'-dimethylcasein. Recombinant human TG2 (100 ng) was pre-incubated for twenty minutes at room temperature with the test sample (conditioned medium or purified IgG) before starting the reaction. Twenty-five μl of reaction mix (5 μl of 25 mM $CaCl_2$, 5 μl of 40 mM dithiothreitol, 5 μl $^3$H-putrescine mix, and 10 μl 25 mg/ml of N,N'dimethylcasein (replace 25 mM $CaCl_2$) with 100 mM EDTA for a non-enzymatic control) was added to start the reaction and the samples incubated at 37° C. for up to 1 hour. Aliquots of 10 μl were spotted onto a strip of 3 MM Whatman filter paper and plunged immediately into ice-cold 10% trichloroacetic acid (TCA) in order to precipitate the cross-linked proteins typically at time 0, 10, 30 and 60 minutes into the reaction. After three extensive washes in ice-cold 5% TCA followed by 3 rinses with ice-cold 95% ethanol, the air dried filter was counted in 2 ml of scintillation fluid (Ultima Gold Packard, Perkin Elmer). The rate of reaction was calculated. 1 TG unit is equivalent to the incorporation of 1 nmol of putrescine per hour at 37° C.

The same protocol was used to assess TG inhibition in cell lysates by replacing the 25 μl of recombinant protein with 25 μl of cell lysate.

Hybridoma Cloning & Purification of Antibodies from Conditioned Medium

Monoclonal antibody isolation was undertaken from the cloned inhibitory hybridomas. Initially identified hybridoma wells were doubly cloned by a limiting dilution process (to ensure stability and clonality) according to conventional methods (Loirat M J et al, 1992) with sub-clones tested as described by ELISA and activity screens. Selected antibody producing clones were expanded in 25 and 75 cm$^2$ flasks and fed with serum free medium (Hyclone, Fisher Scientific, Loughborough, UK). As cells were expanded, conditioned medium was collected for IgG purification using affinity chromatography on protein G column (Amersham Life Sciences). The conditioned medium was diluted in an equal volume of 10 mM sodium phosphate, pH 7.25, and applied to the protein G column at a flow rate of 1.0 to 2.0 ml/min. The column was extensively washed with 10 column volumes of the same buffer. Bound antibody was eluted in glycine solution (0.1M; pH 2.7) and neutralised by 0.15% volumes of 1M Tris/HCl pH 9. Samples were dialysed against 1000 volumes of phosphate buffer saline solution for 24 hours with 2 buffer changes.

Phage Display Mapping of Antibody Epitopes

The full length coding sequence of human TG2 was amplified by polymerase chain reaction using the following primers; TG2-FL-1 5' ATGGCCGAGGAGCTGGTCTTAGAGA 3'(SEQ ID NO: 99) and TG2-FL-2 5' GGCGGGGCCAATGATGACATTCCGGA 3' (SEQ ID NO: 100). The approximately 2 kb amplification product was purified using Quiagen PCR cleanup kit (Qiagen) and digested into random fragments using RQ DNAse I (Promega). The RQ DNAse reaction was treated with Klenow fragment of DNA polymerase I and T4 DNA polymerase to generate blunt-ended fragments. These were purified by gel electrophoresis, and fragments in the range of 50-150 bp extracted using Qiagen gel recovery kit (Qiagen, Crawley UK).

A phage display vector was digested with EcoRV, treated with alkaline phosphatase and purified by gel electrophoresis and the Qiagen gel recovery kit. 100 ng of purified vector was ligated to 15 ng of prepared blunt fragments of human TG2 cDNA. The resultant ligation was electroporated into XL1-Blue electrocompetent cells (Agilent Technologies) and the fragment library rescued with VCSM13 helper phage (Agilent). Phage particles were precipitated with 2% glucose and 4% PEG 6000 and resuspended in PBS 0.1% Tween 20 (v:v) 1% BSA (w:v).

Epitope mapping was carried out using the following procedure. ELISA wells were coated overnight at 4° C. with 30 μg of monoclonal antibody in 100 μl of coating buffer. The coated well was washed with PBS/Tween and blocked with 400 μl of 3% BSA in PBS (w:v) for 1 h at room temperature. Approximately $10^{10}$ phage particles (100 μl) were added to the blocked well and incubated at room temperature for 1 h. The well was washed 8 times with 400 μl PBS/0.5% Tween (v:v) and adherent phage eluted with 0.2 M glycine pH 2.2. Eluted phage were used to infect 1 ml of XL1-Blue host and samples plated onto LB agar (60 μg/ml ampicillin, 15 μg/ml tetracycline), the remaining host was added to 100 ml LB media (60 μg/ml ampicillin, 15 μg/ml tetracycline) and grown overnight at 37° C. in a shaking incubator at 200 rpm to generate the enriched library of selected fragments. This enrichment process was repeated 5 times and random colonies from the final round were selected for sequencing.

Determining the Sequence of the Antibody VL Region

Primers

Heavy chain sense primers—A pair of highly degenerate FR1 primers, MH1 and MH2 (Wang et al 2000), were combined with 3 constant region primers to amplify VH genes.

```
MH1
                                  (SEQ ID NO: 101)
5' CGCGCGCTCGAGSARGTNMAGCTGSAGTC 3'

MH2
                                  (SEQ ID NO: 102)
5'CGCGCGCTCGAGSARGTNMAGCTGSAGSAGTC 3'

Mouse-G1
                                  (SEQ ID NO: 103)
5' AGGCGCAGTACTACAATCCCTGGGCACAATTTTCTTGTCCACC 3'

Mouse-G2a
                                  (SEQ ID NO: 104)
5' AGGCGCAGTACTACAGGGCTTGATTGTGGGCCCTCTGGG 3'

Mouse-G2b
                                  (SEQ ID NO: 105)
5' AGGCGCAGTACTACAGGGGTTGATTGTTGAAATGGGCCCG 3'

Kappa primers
VK1
                                  (SEQ ID NO: 106)
5' CGCTGCGAGCTCGATATTGTGATGACBCAGDC 3'

VK2
                                  (SEQ ID NO: 107)
5' CGCTGCGAGCTCGAGRTTKTGATGACCCARAC 3'

VK3
                                  (SEQ ID NO: 108)
5' CGCTGCGAGCTCGAAAATGTGCTCACCCAGTC 3'

VK4
                                  (SEQ ID NO: 109)
5' CGCTGCGAGCTCGAYATTGTGATGACACAGTC 3'
```

-continued

```
VK5
                                  (SEQ ID NO: 110)
5' CGCTGCGAGCTCGACATCCAGATGACACAGAC 3'

VK6
                                  (SEQ ID NO: 111)
5' CGCTGCGAGCTCGAYATTGTGCTSACYCARTC 3'

VK7
                                  (SEQ ID NO: 112)
5' CGCTGCGAGCTCGACATCCAGATGACYCARTC 3'

VK8
                                  (SEQ ID NO: 113)
5' CGCTGCGAGCTCCAAATTGTTCTCACCCAGTC 3'

K-CONST
                                  (SEQ ID NO: 114)
5' GCGCCGTCTAGAATTAACACTCATTCCTGTTGAA 3'
```

Total RNA was extracted from monoclonal hybridoma cells (~105 cells) using Trizol (GIBCO) according to the manufacturer's protocol and quantified by $A_{260nm}$. cDNA was synthesised using ImProm reverse transcriptase (Promega) and random hexamer primers. The reaction mix was as follows; 1 μg total RNA, 0.1 μg oligo $(dN)_6$, 12 μl ImProm buffer, 1 μl 10 mM dNTPs (Promega), 8 μl 25 mM $MgC_2$, 4 μl ImProm reverse transcriptase (Promega), DEPC-treated $H_2O$ up to total reaction volume of 60 μl. The RNA and random primer mix was heated to 70° C. for 10 min and then placed on ice. The remaining reaction components were added and then incubated at 20° C. for 10 min, then at 40° C. for a further 40 min.

Amplification of VH and VK genes was carried out with GoTaq polymerase (Promega). Each 50 μl reaction contained the following; cDNA 2 μl, 20 pmol sense and anti-sense primers, 10 μl GoTaq reaction buffer, 1 μl 10 mM dNTPs, 5 μl 25 mM $MgCl_2$, 2.5 u GoTaq polymerase, $H_2O$ to a final volume of 50 μl. Reactions were cycled 35 times using the following conditions: initial denature 95° C. 2 min; denature 94° C. 1 min, anneal 56° C. 1 min, extension 72° C. 1 min. PCR products were analysed by gel electrophoresis and cloned using the TOPO TA cloning kit (Invitrogen). Random minipreps of heavy and light chain PCR products were selected for sequencing.

Measurement of Extracellular TG Activity

Extracellular TG activity was measured by modified cell ELISA. HK-2 epithelial cells were harvested using 0.1M EDTA or 0.25% trypsin/EDTA and plated at a density of $8\times10^4$ cells/well in serum free medium onto a 96 well plate that had been coated overnight with 100 μl/well of fibronectin (5 μg/ml in 50 mM Tris-HCl pH 7.4) (Sigma, Poole UK). Cells were allowed to attach for 2.5 h at 37° C. in the presence of the 0.1 mM biotin cadaverine [N-(5 amino pentyl biotinamide) trifluoroacetic acid] (Molecular Probes, Eugene Oreg., USA). Plates were washed twice with 3 mM EDTA/PBS and cells removed with 0.1% (w/v) deoxycholate in 5 mM EDTA/PBS. The supernatant was collected and used for protein determination. Plates were washed with 50 mMTris-HCl and incorporated biotin cadaverine revealed using 1:5000 extravidin HRP (Sigma, Poole, UK) for 1 h at room temperature followed by a TMB (3,3',5,5'-tetramethylbenzidine) substrate. The reaction was stopped with 50 μl 2.5 M H2SO4 and the absorbance read at 450 nm.

Measurement of Collagen Levels by Radiolabelling

Cells were seeded at a density of $3.75\times10^6/10\ cm^2$ Petri dish or $1\times10^6$/well of a 6 well plate. ECM collagen was assessed by labelling with 20 ìCi of $^{3,4}H$ proline (1.0 mCi/ml, ICN). Labelling was performed for 72 h under standard cell culture conditions. Following labelling, the media was removed, cells washed with PBS and removed with 2 ml of 0.25 M ammonium hydroxide in 50 mM Tris pH 7.4 at 37° C. for 10 min. The soluble fraction was collected and protein concentration determined using the bicinchoninic acid (BCA) assay. The dishes were washed extensively with increasing volumes of PBS before the ECM was solubilised with 2 ml of 2.5% (w/v) SDS in 50 mM Tris pH 6.8. The dish was scraped to ensure complete removal of the ECM and 200 ìl was measured for radioactivity in a beta scintillation counter. Counts were corrected per mg of solubilised cell protein and expressed as a percentage of the mean control value.

Generation of Recombinant Ratified Quark IgG

For experimental purposes a human-rat chimeric antibody from the sequence of a 'human' single-chain Fv of an antibody against human type-II transglutaminase was generated. The antibody is called QPCDTGII (shortened to QCT), and the sequences of the variable regions are available in WO 2006/100679A2.

A rat γ2a subclass was selected for the heavy chain constant regions, removing the glycosylation site to reduce the chance of an ADCC reaction in the rat test animals. The selected rat constant region for the heavy chain was 013593 (Bruggemann, M. Gene 74: 473-482 (1988); Bruggemann, M., Free, J., Diamond, A., Howard, J., Cobbold, S. and Waldmann, H. Proc. Natl. Acad. Sci USA 83: 6075-6079 (1986)) from the Kabat database (Kabat, E. A., Wu, T. T., Perry, H. M., Gottesman, K. S., and Foeller, C. Sequences of Proteins of Immunological Interest. (NIH National Technical Information Service, 1991)). That for the kappa light chain was 013718 (Sheppard, H. W. and Gutman, G. A. Proc. Natl. Acad. Sci. USA 78: 7064-7068 (1981)) from Kabat.

In brief, heavy chain and kappa chain coding sequences were generated by DNA synthesis (codon usage was adapted to a mammalian codon bias).

The heavy chain gene synthesis product was amplified by PCR using the primers QCT_HindIII and QCT_H_rev. The PCR-product was cut with HindIII and NgoMIV and ligated into MRCT expression vector. Clones of competent DH5a bacteria chemically transformed by the ligation product were PCR-screened using the primers HCMVi and rat_gamma1. Three clones generating a PCR product of the predicted size were sequenced.

The kappa chain gene synthesis product was amplified by PCR using the primers QCT_HindIII and QCT_L_rev. The PCR-product was cut with HindIII and PpuMI and ligated into the expression vector pKN100. Clones of competent DH5a bacteria chemically transformed by the ligation product were PCR-screened using the primers HCMVi and rat_kappa. Three clones generating a PCR product of the predicted size were sequenced.

A double insert expression vector coding for both Heavy and kappa chains was generated and transfected into HEK293T cells. Cell culture supernatant from two large scale HEK293T transfections was pooled and affinity purified on a 1 ml Protein L-agarose column using an ÄKTA Explorer chromatography system, in accordance with the manufacturer's protocols. A single OD 280 nm peak eluted with IgG Elution Buffer, and was dialysed against two changes of PBS. This was assayed both by UV absorption at 280 nm, and by rat $IgG_{2a}$ ELISA. The total yield was approximately 700 µg (by $OD_{280nm}$); 303.5 µg (by ELISA).

Humanisation of AB1 Antibody

Human VH and VK cDNA Databases

The protein sequences of human and mouse immunoglobulins from the International Immunogenetics Database 2009[101] and the Kabat Database Release 5 of Sequences of Proteins of Immunological Interest (last update 17 Nov. 1999)[102] were used to compile a database of human immunoglobulin sequences in a Kabat alignment. Our database contains 10,606 VH and 2,910 VK sequences.

Molecular Model of AB1

A homology model of the mouse antibody AB1 variable regions has been calculated using the Modeller program[103] run in automatic mode. The atomic coordinates of 1 MQK.pdb, 3LIZ.pdb and 1MQK.pdb were the highest identity sequence templates for the Interface, VL and VH respectively as determined by Blast analysis of the Accelrys antibody pdb structures database. These templates were used to generate 20 initial models, the best of which was refined by modeling each CDR loop with its 3 best loop templates.

hAB1 Framework Selection

The sequence analysis program, gibsSR, was used to interrogate the human VH and VK databases with the AB1 VHc, VKc and $VKc_1$ protein sequences using various selection criteria. FW residues within 5A of a CDR residue (Kabat definition) in the homology model of mouse antibody AB1, were identified, and designated as the "5 Å Proximity" residues.

AF06220 was chosen as the FW on which to base the initial humanised AB1 VHc construct. Table 1 shows the alignment and residue identity of AF06220 to murine Ab1. Table 2 shows the 5 Å proximity envelope of the sequences. AF062260 has only 1 somatic mutation away from its germline VH gene Z12347 (Table 3).

AY247656 was chosen as the FW on which to base the initial humanised AB1 VKc construct. The alignment and residue identity to murine AB1 are shown in Table 4; Table shows the 5 Å proximity envelope of the sequences. The sequence shows 5 somatic mutations from its germline VK gene X93620 (Table 6).

AF193851 was chosen as the FW on which to base the initial AB1 $VKc_1$ construct. The alignment and residue identity to murine AB1 are shown in Table 7. Table 8 shows the 5 Å proximity envelope of the sequences. The sequence shows no somatic mutations from its germline VK gene J00248 (Table 9).

Binding ELISA

HEK 293F cells were co-transfected with combinations of different humanised light chain vectors in association with different humanised heavy chain vectors. Recombinant human TG2 was used to measure antibody binding by ELISA. The results indicated that the Heavy Chain version RHA (Table 10), in combination with either Light Chain versions RKE and RKJ (Table 11) (representing the different Light Chain versions humanised) showed optimal binding (FIG. 16).

Heavy Chain version RHA is an un-modified graft of the mouse CDR regions of the AB1 antibody onto the Human donor sequence. However, both Light Chain versions RKE and RKJ, have the same single 5 Å proximity reside back-mutation, F72 (Kabat numbering-shown in green). This backmutation lies outside the Vernier[104], Canonical[105] or Interface[06] residues (see Table 11).

101. Lefranc, M. P. IMGT, the international ImMunoGeneTics Database®. Nucleic Acids Res. 31, 307-310 (2003).

102. Kabat, E. A., Wu, T. T., Perry, H. M., Gottesman, K. S. & Foeller, C. Sequences of Proteins of Immunological Interest. NIH National Technical Information Service, (1991).

103. Eswar, N. et al. Comparative protein structure modeling using Modeller. Curr. Protoc. Bioinformatics. Chapter 5:Unit 5.6., Unit (2006).

104. Foote, J. & Winter, G. (1992). Antibody framework residues affecting the conformation of the hypervariable loops. J Mol. Biol. 224, 487-499.

105. Morea, V., Lesk, A. M. & Tramontano, A. (2000). Antibody modeling: implications for engineering and design. Methods 20, 267-279.

106. Chothia, C., Novotny, J., Bruccoleri, R. & Karplus, M. (1985). Domain association in immunoglobulin molecules. The packing of variable domains. J Mol. Biol. 186, 651-663.

Tables

TABLE 1

```
Kabat Numbers[2]             1        10        20        30          40        50           60
                             -|--------|---------|---------|-----AB----|---------|--ABC-------|------
Vernier[4]                   -.*........................****..................***.....................
Canonical[5]                 -.......................1.11.1....1....................2...22............
Interface[6]                 -..................................I...I.I.....I.I.......................
5Å Proximity                  ****                 * *  ****       ***        ***                   *
AB_VHc (SEQ ID NO: 115)      -EVQLXESGGGLVKPGGSLKLSCAASGFTLSSSAMS--WVRQTPDRRLEWVATISV--GGGKTYYPDSVKGR
AF062260 (SEQ ID NO:         C....L.......Q.....R.........F..Y...--....A.GKG....SA..G--S..S...A......
116

Kabat Numbers[2]              70        80            90       100                    110
                             ---|---------|--ABC-------|---------|ABCDEFGHIJK---------|-
Vernier[4]                   *.*.*.*....*.................**.................*..........
Canonical[5]                 ....2........................1............................
Interface[6]                 ..........................I.I.I................I..........
5Å Proximity                 ***** *    *              ****                   **
AB_VHc (SEQ ID NO: 115)      FTISRDNAKNTLYLQMNSLRSEDTAMYYCAKLI------------SLYWGQGTTLTVSS
AF062260 (SEQ ID NO:         .......S.........A....V......DG------------GV.....LV....
116
```

TABLE 2

| | 5Å Proximity Residues | |
|---|---|---|
| AB_VHc | EVQLCAFTLSWVRWVARFTISRNLYCAKWG | SEQ ID NO: 117 |
| AF062260 | ........F......S.............. | SEQ ID NO: 118 |

TABLE 3

```
             ---------+---------+---------+---------+---------+---------+-----
                      10        20        30        40        50        60
             ---------+---------+---------+---------+---------+---------+-----
Z12347.seq   EVQLLESGGGLVQPGGSLRLSCAASGFTFSSYAMSWVRQAPGKGLEWVSAISGSGGSTYYADSVK
AF062260.seq.................................................................
                                          <--->             <----------------

                          ----+---------+---------+--------
                              70        80        90
                          ----+---------+---------+--------
             Z12347.seq   GRFTISRDNSKNTLYLQMNSLRAEDTAVYYCAK    SEQ ID NO: 119
             AF062260.seq ................................R    SEQ ID NO: 120
                          >
```

TABLE 4

```
Kabat Numbers[2]              1        10        20                30        40        50
                             -|--------|---------|-------ABCDEF--|---------|---------|-------
Vernier[4]                   -.*.*...................................**.........****........
Canonical[5]                 -.1.....................1.......1111..1..............2..22.....
Interface[6]                 -.........................................I.I.....I............
5Å Proximity                  ******                **                  **         ****      **
AB_VKc (SEQ ID NO: 121_      -EIVLTQSPSSMYASLGERVTITCKASQ------DINSYLTWFQQKPGKSPKTLIYRTNRLFDG
AY247656 (SEQ ID NO: 122)    -.........LS..V.D......Q...-------..SN..N.Y......A..L...DASN.ET.
```

TABLE 4-continued

```
Kabat Numbers2            60        70        80        90             100
                          -|---------|---------|---------|-----ABCDEF----|------A-
Vernier4                  .....*.*.**.*..............................*..........
Canonical5                .....2......1.................3....3...................
Interface6                ...........................I..I............II..........
5Å Proximity              *  ***********             **                **
AB_VKc (SEQ ID NO: 121_   VPSRFSGSGSGQDFFLTISSLEYEDMGIYYCLQYDDFP------YTFGGGTKLEI-K
AY247656 (SEQ ID NO: 122).........T..TF.....QP..F.T...Q..NTY.------L..........-.
```

TABLE 5

| | 5Å Proximity Residues |
|---|---|
| AB_VKc | EIVLTQTCWFTLIYGVPFSGSGSGQDFFYCFG<br>SEQ ID NO: 123 |
| AY247656 | .........YL.............T..T....<br>SEQ ID NO: 124 |

TABLE 6

```
              ---------+---------+---------+---------+---------+---------+-----
                      10        20        30        40        50        60
              ---------+---------+---------+---------+---------+---------+-----
X9362C.seq    DIQMTQSPSSLSASVGDRVTITCQASQDISNYLNWYQQKPGKAPKLLIYDASNLETGVPSRFSGS
AY247656.seqE.VL.............................................................
                                   <---------->              <----->
```

```
                          ----+---------+---------+--------
                              70        80        90
                          ----+---------+---------+--------
                          GSGTDFTFTISSLQPEDIATYYCQQYDNLPP      SEQ ID NO: 125
              X9362C.seq  ................FG.......NTY.L      SEQ ID NO: 126
              AY247656.seq                      <-------
```

TABLE 7

```
Katbat Numbers2            1        10        20              30        40        50
                           -|--------|---------|-------ABCDEF--|---------|---------|--------
Vernier4                   -.*.*.................................**.........****.........
Canonical5                 -.1......................1.......1111..1...............2..22......
Interface6                 -......................................I.I.....I..............
5Å Proximity                ******                **                  **        ****       **
AB_VKc (SEQ ID NO: 127)    -DIQMTQSPSSMYASLGERVTITCKASQ------DINSYLTWFQQKPGKSPKTLIYRTNRLFDG
AF193851 (SEQ ID NO: 128)  -.........LS..V.D......R...------G.RN..A........A..S...AASN.QS.

Katbat Numbers2            60        70        80        90             100
                           -|---------|---------|---------|-----ABCDEF----|------A-
Vernier4                   .....*.*.**.*..............................*..........
Canonical5                 .....2......1.................3....3...................
Interface6                 ...........................I..I............II..........
5Å Proximity               *  ***********             **                **
AB_VKc (SEQ ID NO: 127)    VPSRFSGSGSGQDFFLTISSLEYEDMGIYYCLQYDDFP------YTFGGGTKLEI-K
AF193851 (SEQ ID NO: 128)  ..........T..T......QP..FAT...Q.HNTY.------W...Q...V..-.
```

TABLE 8

| 5Å Proximity Residues | | |
|---|---|---|
| AB_VKc | DIQMTQTCWFTLIYGVPFSGSGSGQDFFYCFG | SEQ ID NO: 129 |
| AF193851 | ..........S.............T..T.... | SEQ ID NO: 130 |

TABLE 9

```
               ---------+---------+---------+---------+---------+---------+-----
                        10        20        30        40        50        60
               ---------+---------+---------+---------+---------+---------+-----
J00248.seq     DIQMTQSPSSLSASVGDRVTITCRASQGISNYLAWFQQKPGKAPKSLIYAASSLQSGVPSRFSGS
AF193851.seq   ...........................R......................N............
                                      <         >                <     >

                             ----+---------+---------+------
                                 70        80        90
                             ----+---------+---------+------
               J00248.seq    GSGTDFTLTISSLQPEDFATYYCQQYNSYPP    SEQ ID NO: 131
               AF193851.seq  ........................H.Y..W     SEQ ID NO: 132
                                                    <
```

TABLE 10

```
Kabat Numbers                 1         10        20        30             40        50
                             110
                             -|--------|---------|---------|-----AB----|---------|--ABC-------|--------
Vernier[4]                   -.*.......................****.................***....................*.
Canonical[5]                 -.......................1.11.1....1....................2...22............
Interface[6]                 -.................................I...I.I.....I.I.......................
5Å Proximity                  ****                   * *  ****       ***       ***                    ***
AB_VHc (SEQ ID NO:           -EVQLXESGGGLVKPGGSLKLSCAASGFTLSSSAMS--WVRQTPDRRLEWVATISV--GGGKTYYPDSVKGRFT
133)                         SLYWGOGTTLTVSS
AB_RHA (SEQ ID NO: 134       -EVQLLESGGGLVQPGGSLRLSCAASGFTFSSSAMS--WVRQAPGKGLEWVSTISV--GGGKTYYPDSVKGRFT
                             SLYWGQGRLVTVSS

Kabat Numbers                   60        70        80              90        100

                             -|---------|--ABC-------|---------|ABCDEFGHIJK---------|-
Vernier[4]                   *.*.*....*.................**.................*.........
Canonical[5]                 ..2.......................1............................
Interface[6]                 .........................I.I.I................I.........
5Å Proximity                 *** *    *               ****                ** 
AB_VHc (SEQ ID NO:           ISRDNAKNTLYLQMNSLRSEDTAMYYCAKLI------------
133)
AB_RHA (SEQ ID NO: 134       ISRDNSKNTLYLQMNSLRAEDTAVYYCAKLI------------
```

TABLE 11

```
Kabat Numbers                 1        10         20                30        40        50
                             -|--------|---------|-------ABCDEF--|---------|---------|-------
Vernier[4]                   -.*.*..................................**.........****........
Canonical[5]                 -.1.....................1.......1111..1..............2..22.....
Interface[6]                 -.......................................I.I.....I.............
5A Proximity                  ******                 **                 **         ****       *
AB_VKc (SEQ ID NO: 135)      -EIVLTQSPSSMYASLGERVTITCKASQ------DINSYLTWFQQKPGKSPKTLIYRTNRLFDG
AB_RKE(SEQ ID NO: 136)       -EIVLTQSPSSLSASVGDRVTITCKASQ------DINSYLTWYQQKPGKAPKLLIYRTNRLFDC
AB_RKJ(SEQ ID NO: 137)       -DIQMTQSPSSLSASVGDRVTITCKSAQ------DINSYLTWFQQKPGKAKPSLIYRTNRLFDG
```

TABLE 11-continued

```
Kabat Numbers                  60        70        80        90             100
                              --|---------|---------|---------|-----ABCDEF----|------A-
Vernier4                      ......*.*.**.*................................*..........
Canonical5                    ......2......1..................3....3...................
Interface6                    .............................I..I............II..........
5A Proximity                  **  ***********              **              **
AB_VKc (SEQ ID NO: 135)       VPSRFSGSGSGQDFFLTISSLEYEDMGIYYCLQYDDFP------YTFGGGTKLEI-K
AB_RKE(SEQ ID NO: 136)        VPSRFSGSGSGTDFFFTISSLQPEDFGTYYCLQYDDFP------YTFGGGTKLEI-K
AB_RKJ(SEQ ID NO: 137)        VPSRFSGSGSGTDFFLTISSLQPEDFATYYCLQYDDFP------YTFGQGTKVEI-K
```

Results

Generation of Rh TG2 Core Protein.

To force the generation of antibodies that would be more likely to target epitopes critical for TG2 activity, rather than favoured sites on the TG2 molecule, we immunised mice with the TG2 catalytic core rather than the full-length TG2 molecule. To generate the recombinant TG2 domain, a PCR construct was generated running from bases 329 to 1419 and inserted into the Pet21+(a) vector (FIG. 1A). Insertion and expression of this vector in BL21-CodonPlus (DE3)-RIPL bacteria resulted in the generation of an insoluble protein spanning amino acids 143 to 473 encompassing the entire catalytic core. This protein was solubilised and refolded in 40 mM Tris HCl; 150 mM NaCl; 20% glycerol; 5 mM cysteine; 0.5 mM cystine pH 8. 10 ng of this was run on a non-reducing polyacrylamide gel, western blotted and immunoprobed with CUB7402. A clear band was visible at 37 kDa which is consistent with the predicted size of the TG2 core (FIG. 1B). Larger bands were also immunoreactive to CUB7402 which most likely represent aggregates of the core protein as these were not present when a reducing gel was run (data not shown).

Immunisation and Fusion.

Four mice were immunised with 50 μg of rhTG2 core. At approximately five and nine weeks post immunisation, a serum sample was taken from each mouse and tested for reactivity against rh TG2 by ELISA using a serial dilution of the serum. All mice showed a strong immune reaction to rhTG2 core, even at the highest dilution used (1:51 000) (FIG. 2A). To confirm the antibodies would also recognise the full-length TG2, rhTG2 and rhTG2 core protein were run on a non-denaturing gel, western blotted and immunoprobed with a 1 in 1000 dilution of mouse serum (FIG. 2B). The mouse with the strongest reactivity (mouse C) against both proteins was boosted and splenocytes recovered for fusion using the University of Sheffield's Hybridoma service, Bioserv.

Selection of Positive Hybridoma and Cloning.

Out of 400 hybridoma wells selected by Bioserv as highest positives, supernatants from 109 showed persistent reactivity to TG2, however only 34 did not react with other key TG family members when tested in ELISA (representative examples shown in FIG. 3A). Those that were specific to TG2 had the supernatant screened by $^3$H-putrescine incorporation assay for the ability to inhibit TG2 activity resulting from 100 ng of TG2 (FIG. 4). This initial screen indicated that 10 hybridoma supernatants were able to inhibit TG2 activity (AB1; DC1; BB7; EH6; DH2; DD9; JE12; AG9; AH3; DF4). Nine of the ten were successfully cloned by limited dilution. For the clone DF4, although clones were isolated post-cloning, they did not appear to be inhibitory. Post cloning, IgG was purified from each cloned hybridoma and retested for selective reactivity to TG2 (FIG. 3B).

TG2 Inhibitory Potential.

Each cloned hybridoma had its IgG tested for TG2 inhibitory activity against human, rat and mouse TG2 and the $IC_{50}$ calculated based on the amount of IgG required to inhibit 1 ng of TG2. There was approximately a 12 fold range in $IC_{50}$ values against human TG2 ranging from the most effective AB-1 at $1.1\times10^{-5}$ mg/ml of IgG to the least effective JE12 at 12.3 $1.1\times10^{-5}$ mg/ml of IgG (FIG. 9; Table 1). Interestingly we were only able to determine an $IC_{50}$ for 4 antibodies (DH2, DD9, EH6 and BB7) against rat TG2 with the best, DH2 having a $IC_{50}$ of $2.23\times10^{-4}$ mg/ml of IgG being some 6 fold less active than against human TG2 and comparatively 38 fold less active that the best AB-1 inhibitor against TG2 (FIG. 9; Table 1). None of the inhibitory antibodies were able to inhibit mouse TG2, probably due to immune tolerance.

Mapping the Epitopes of Inhibitory Antibodies

To establish which epitopes in TG2 were immunologically unique to TG2 while inhibitory, as well as establishing if these 10 antibodies were targeting the same or different sites, each antibody was mapped using phage display. A TG2 phage library was constructed and panned against each mAb. The epitope was then determined by consensus sequencing of the binding phages.

AB1, AG1, AH1, BB7, DC1, EH6 and JE12 all appeared to bind in whole or part to a single epitope (FIG. 5) which encompasses amino acids 304 to 326 and appears to sit in front of active site within a substrate binding pocket (FIG. 6). This region we termed the AB-1 site and called antibodies targeting this site Group 1 antibodies.

DF4 uniquely targeted a sequence running from amino acid 351 to 365 (FIG. 5) which runs from front to rear of core encompassing Asp 358 in the catalytic triad (FIG. 6). This we termed Group 2.

DH2 and DD9 bound to a sequence spanning amino acids 450 to 467 (FIG. 5). These Group 3 antibodies bind to a region at the rear of core near the junction with p barrel-1, that we termed the DH2 site. The epitope encompasses a putative calcium binding site (FIG. 6).

Antibody Sequencing

In order to establish the variable light chain sequence for each antibody, RNA from each inhibitory hybridoma was extracted, reverse transcribed and amplified by PCR using a pair of highly degenerate FR1 primers, MH1 and MH2 primers being combined with 3 constant region primers to amplify VH genes.

The resulting VH and VK sequences are shown in FIG. 7 for AB1.

The Ability of AB1 to Inhibit TG2 Activity in a Protein Mixture In Vitro.

The most potent inhibitory antibody against recombinant TG2 is AB1. To be of value therapeutically, it must be able to not only inhibit TG2 activity in a pure solution, but also in a complex protein solution and not associate in anyway with other proteins. To test this, a homogenate of the human hepatocyte cell line HepG2 was prepared. Application of 0.5 μg of AB1 was able to inhibit 70% of the TG2 activity (FIG. 8A). However BB7 produced a significantly better inhibition knocking down 90% of the TG2 activity. Immunoprobing 25 μg of this lysate with AB1 showed no off target association with a single immunoreactive band at a size corresponding to TG2 (FIG. 8B).

The Ability of AB1 and DC1 to Inhibit Extracellular TG2 Activity.

To asses if these antibodies could inhibit TG2 activity in a cell system. AB1 (FIG. 10*a*) and DC1 (FIG. 10*b*) were applied to human kidney 2 (HK-2) tubular epithelial cells in culture and extracellular TG activity assayed using the biotin cadaverine assay. AB1 was able to achieve a 60% inhibition and DC1 a 55% inhibition of activity when applied at 4 ng/ul in the culture media which was comparable to the chemical pan TG inhibitor 1,3-Dimethyl-2-[(2-oxo-propyl)thio]imidazolium chloride applied at 400 uM.

Comparison of Antibody AB1 with Other Known Inhibitory Antibodies

To test the effectiveness of AB1 in comparison to other known TG2 inhibitory antibodies both fab fragments (FIGS. 11,12) and full IgG (FIGS. 13, 14) of an antibody as described by Quark biotechnology in patent application number WO2006/100679 were tested to inhibit TG2 activity in the $^{3}$H Putrescine incorporation assay. The activity from 100 ng of human TG2 could be inhibited by 60 to 80% by 500 ng of AB1. In comparison neither the fab fragment or the full IgG of the Quark antibody could inhibit TG2 significantly in this assay.

Discussion

There is a clear need to validate TG2 as a therapeutic target in man across a range of diseases where experimental studies have suggested its involvement. These include tissue scarring, celiac disease, neurodegenerative diseases and chemo-resistance in some cancers. Limiting this has been the lack of truly TG2 specific compounds that can selectively inhibit TG2 activity in man.

In this study we have for the first time immunised mice with a fragment of TG2 with the aim of being able to isolate a wider range of anti TG2 antibodies against the enzyme's catalytic core in the search of an inhibitory epitope. This elicited a good immune response with antibodies recognising both the rhTG2 core and native TG2 but no other TG.

10 of the antibodies isolated showed inhibitory activity. These were subsequently mapped to 3 TG2 specific, yet inhibitory epitopes. These antibodies have been cloned, sequenced and IgG isolated with $IC_{50}$ values calculated. Three antibodies (AB1, DC1 and BB7) targeting a substrate pocket proved particularly effective inhibitors. Most importantly these antibodies also worked well both in a cell lysate and in cell culture indicating that these antibodies have the potential to function in a protein rich environment which is critical for in vivo application.

We believe a key element in the successful generation of these inhibitory antibodies has been the decision to immunise with just the core protein. To our knowledge none of the commercial TG2 antibodies have inhibitory potential of any significance. Our own attempts to use full length TG2 resulted in a large number of antibodies, few of which were specific to TG2 and none of which were inhibitory. This would appear to be due to a clear immunogenic preference for protein loops within full length TG2 many of which fall on the rear of the catalytic core in similar positions to the most widely used anti TG2 antibody, CUB7402 (aa447 aa478).

It is surprising that our approach has led to the production of much more effective antibodies. Without being bound by any theory we think that by simply raising antibodies to a smaller protein covering just the central core, we not only eliminate some of the favoured immunological epitopes, but we also force core targeting. This alone increases the variety of antibodies available for selection and thus wider coverage of the core. However, immunising with just the core means that much of the folding of the core is lost and thus some of the epitopes that perhaps may be less available within a whole TG2 molecule may be more attractive epitopes with the core in this format. Given that all 10 of the antibodies recognised linear epitopes (i.e. bound to TG2 on a reducing gel), while 80% of the antibodies we previously isolated using full length TG2 as an immunogen were conformation dependent, does suggest this may be a major factor.

There have previously been other studies that have postulated the idea of a TG2 inhibitory antibody for human application. Esposito and colleagues developed recombinant antibodies from patients with celiac disease where it has been postulated that TG2 antibodies may have an inhibitory role [19]. One of these antibodies was developed for commercial application by Quark Biotechnology and a patent application filed (WO2006/100679). This antibody demonstrated some exciting early data in the prevention of kidney fibrosis in the rat UUO model. However, we produced a recombinant version of this antibody and while it reacted with TG2 in ELISA (FIG. 17) and western blot, we achieved little inhibition up to 500 ng of IgG per ng of TG2 for this antibody at which all of the antibodies developed in this study block essentially all TG2 activity. Furthermore WO2006/100679 describes the generation of a mouse version of this human antibody, and as such, long application in recognised rat models of kidney disease would prove difficult.

Of note in the present study is the mapping of the 3 inhibitory epitopes within the TG2 core. The AB1 epitope is by far the most potent to target, which is perhaps surprising given the position of the epitope. Examination of its position within the predicted TG2 active structure [20] suggests it binds in the entry port to the catalytic triad in what may be a substrate pocket. Given the substrates we used in our screening assay are relatively small (putrescine and dimethyl casein), it is perhaps surprising that this site is so effective. However the position of the epitope must be such that the large IgG (150 kDa) is positioned tightly into the catalytic site. From the epitope data one may have predicted that the DD9 site may be more effective as it is associated with a putative calcium binding site [21]. However examination of the literature suggests 5 or more putative $Ca^{2+}$ binding sites [21] and while it clearly has a dramatic effect, is not critical for all TG2 activity.

The DF4 site would be hypothetically the most effective epitope as the antibody binds to 1 of the essential amino acids in the catalytic triad. However it has not been possible to successfully clone out DF4 producing this inhibitory antibody and as such the production of sufficient IgG to adequately perform $IC_{50}$ tests has not been possible. It may in fact be very difficult to clone out antibodies that have too high efficacy given the work from Gunzler et al (1982) *FEBS Lett.* 150(2): 390-6 that suggested that lymphocytes needed TG2 activity to proliferate and thus antibodies with better inhibitory potential may only be possible using recombinant approaches or a continual IgG extraction system.

One of the most frustrating problems in undertaking this work has been the apparent inability of all antibodies developed to efficiently block non-human TG2 activity, which is critical for preclinical testing. All antibodies reacted with rat and mouse TG2 in both western blot and ELISA, in some cases with little difference in intensity. However out of the 9 antibodies we produced IgG for, it was only possible to determine an $IC_{50}$ for 4 in rat and none in mouse. The 4 where an $IC_{50}$ was calculated against rat TG2 showed a fold or lower $IC_{50}$ against rat TG2 than AB1 against human TG2 meaning any in vivo dose would be prohibitively large. Further none would inhibit at all in a rat cell lysate. Given the reactivity in ELISA and western blots, plus there are just 5 mismatches between species for AB1 and 3 for DD9 the significant species specificity for inhibition was surprising and clearly demonstrates the critical importance of affinity for effective inhibition. Thus having identified these inhibitory epitopes for human TG2 it is now critical that analogue antibodies are developed for these sites in rat TG2 if their value is to be established in in vivo pre clinical models of disease.

There are a wide range of TG inhibitors available. Notably the thiomidazole based compounds originally developed by Merke Sharpe Dome [22] the CBZ-glutamyl analogues developed by Griffin and colleagues [23] which we have used very successfully to treat experimental kidney scarring [16] and the dihydroisoxazole type inhibitors developed by Khosla and collegues [24-27] used successfully in various cancer models. There has been hope that continual refinement of these compounds may yield a viable human TG2 inhibitor, but cross TG family reactivity or the potential toxic nature of the compounds seems to have prevented this. More recently Acylideneoxoindoles have been described as a new reversible class of TG2 inhibitors [24], but data regarding their cross reactivity to other TG family members is lacking. At the 2010 Gordon conference on TG2 in human disease Pasternack and collegues from Zedira presented details of a range of compounds that use side chain Michael acceptors as TG2 inhibitors with claims of suitability for in vivo application and TG2 selectivity, however a full publication on these has not materialised to date. At the same meeting early work from Macdonald et al demonstrated some interesting developments in designing a TG2 inhibitor for treatment of Huntington's Chorea, but again a full publication is still awaited. Undoubtedly a small molecule inhibitor of TG2 would be highly desirable should it be achievable. Tissue penetration, the ability to cross the blood brain barrier, production, cost and easy dosing are just some of the benefits. However, an antibody inhibitor as developed here may in some way be preferable.

TG2 clearly is a multifunction enzyme and has been linked to a range of cellular functions including nuclear stabilisation and transport [28, 29], endocytosis [30, 31], GTPase signalling [32-34], Apoptosis [35, 36], cell adhesion [37-39], cytoskeletal integrity [28, 29] and ECM stabilisation [9]. Clearly a small molecule inhibitor may impede on all of these functions as in general they have free access to the extracellular space and cell interior. An antibody cannot enter the cell and as such the intracellular roles of TG2 would not be affected. Importantly most of the pathological roles of TG2 appear to be extracellular such as its role in tissue scarring and fibrosis, celiac disease and cancer. Thus using an antibody would bring an additional degree of selectivity preventing undesired intracellular effects. Therefore an antibody would offer advantages in blocking TG2 in fibrotic and scarring diseases where TG2 crosslinks ECM proteins, in celiac disease where gliadin is deamidated in the extracellular space and in chemo-resistance in cancer where cell adhesion appears to be the protective factor. However, unless a small Fab fragment could be designed that could cross the blood brain barrier a TG2 inhibiting antibody would be little use in treating neurological pathologies.

In conclusion, for the first time we have been able to develop TG2 inhibitory antibodies that selectively target TG2. We have also identified 3 novel inhibitory epitopes within the core domain of TG2. Humanisation of antibody AB1 will open up the possibility for the first time of targeted TG2 therapy in man.

REFERENCES

1. Tissue transglutaminase in normal and abnormal wound healing: review article. Verderio, E. A., T. Johnson, and M. Griffin, Amino Acids, 2004. 26(4): p. 387-404.
2. Transglutaminase-mediated cross-linking is involved in the stabilization of extracellular matrix in human liver fibrosis. Grenard, P., S. Bresson-Hadni, S. El Alaoui, M. Chevallier, D. A. Vuitton, and S. Ricard-Blum, J Hepatol, 2001. 35(3): p. 367-75.
3. Changes in transglutaminase activity in an experimental model of pulmonary fibrosis induced by paraquat. Griffin, M., L. L. Smith, and J. Wynne, Br J Exp Pathol, 1979. 60(6): p. 653-61.
4. Cardiac specific overexpression of transglutaminase II (G(h)) results in a unique hypertrophy phenotype independent of phospholipase C activation. Small, K., J. F. Feng, J. Lorenz, E. T. Donnelly, A. Yu, M. J. Im, G. W. Dorn, 2nd, and S. B. Liggett, J Biol Chem, 1999. 274(30): p. 21291-6.
5. Tissue transglutaminase and the progression of human renal scarring. Johnson, T. S., A. F. El-Koraie, N. J. Skill, N. M. Baddour, A. M. El Nahas, M. Njloma, A. G. Adam, and M. Griffin, J Am Soc Nephrol, 2003.14(8): p. 2052-62.
6. Thrombin upregulates tissue transglutaminase in endothelial cells: a potential role for tissue transglutaminase in stability of atherosclerotic plaque. Auld, G. C., H. Ritchie, L. A. Robbie, and N. A. Booth, Arterioscler Thromb Vasc Biol, 2001.21(10):p. 1689-94.
7. Cross-linking of fibronectin to collagenous proteins. Mosher, D. F., Mol Cell Biochem, 1984. 58(1-2): p. 63-8.
8. Transglutaminases. Lorand, L. and S. M. Conrad, Mol Cell Biochem, 1984. 58(1-2): p. 9-35.
9. Modulation of tissue transglutaminase in tubular epithelial cells alters extracellular matrix levels: a potential mechanism of tissue scarring. Fisher, M., R. A. Jones, L. Huang, J. L. Haylor, M. El Nahas, M. Griffin, and T. S. Johnson, Matrix Biol, 2009. 28(1): p. 20-31.
10. Transglutaminase transcription and antigen translocation in experimental renal scarring. Johnson, T. S., N. J. Skill, A. M. El Nahas, S. D. Oldroyd, G. L. Thomas, J. A. Douthwaite, J. L. Haylor, and M. Griffin, J Am Soc Nephrol, 1999. 10(10): p. 2146-57.
11. Do changes in transglutaminase activity alter latent transforming growth factor beta activation in experimental diabetic nephropathy? Huang, L., J. L. Haylor, M. Fisher, Z. Hau, A. M. El Nahas, M. Griffin, and T. S. Johnson, Nephrol Dial Transplant, 2010.25(12):p. 3897-910.
12. Expression induced by interleukin-6 of tissue-type transglutaminase in human hepatoblastoma HepG2 cells. Suto, N., K. Ikura, and R. Sasaki, J Biol Chem, 1993.268(10):p. 7469-73.
13. TNF-alpha modulates expression of the tissue transglutaminase gene in liver cells. Kuncio, G. S., M. Tsyganskaya, J. Zhu, S. L. Liu, L. Nagy, V. Thomazy, P. J. Davies, and M. A. Zern, Am J Physiol, 1998. 274(2 Pt 1): p. G240-5.

14. Inhibition of transglutaminase activity reduces extracellular matrix accumulation induced by high glucose levels in proximal tubular epithelial cells. Skill, N. J., T. S. Johnson, I. G. Coutts, R. E. Saint, M. Fisher, L. Huang, A. M. El Nahas, R. J. Collighan, and M. Griffin, J Biol Chem, 2004. 279(46): p. 47754-62.

15. Transglutaminase inhibition reduces fibrosis and preserves function in experimental chronic kidney disease. Johnson, T. S., M. Fisher, J. L. Haylor, Z. Hau, N. J. Skill, R. Jones, R. Saint, I. Coutts, M. E. Vickers, A. M. El Nahas, and M. Griffin, J Am Soc Nephrol, 2007.18(12): p. 3078-88.

16. Transglutaminase inhibition ameliorates experimental diabetic nephropathy. Huang, L., J. L. Haylor, Z. Hau, R. A. Jones, M. E. Vickers, B. Wagner, M. Griffin, R. E. Saint, I. G. Coutts, A. M. El Nahas, and T. S. Johnson, Kidney Int, 2009. 76(4): p. 383-94.

17. Tissue transglutaminase contributes to interstitial renal fibrosis by favoring accumulation of fibrillar collagen through TGF-beta activation and cell infiltration. Shweke, N., N. Boulos, C. Jouanneau, S. Vandermeersch, G. Melino, J. C. Dussaule, C. Chatziantoniou, P. Ronco, and J. J. Boffa, Am J Pathol, 2008. 173(3): p. 631-42.

18. GPR56, an atypical G protein-coupled receptor, binds tissue transglutaminase, TG2, and inhibits melanoma tumor growth and metastasis. Xu, L., S. Begum, J. D. Hearn, and R. O. Hynes, Proc Natl Acad Sci USA, 2006. 103(24): p. 9023-8.

19. Anti-tissue transglutaminase antibodies from celiac patients inhibit transglutaminase activity both in vitro and in situ. Esposito, C., F. Paparo, I. Caputo, M. Rossi, M. Maglio, D. Sblattero, T. Not, R. Porta, S. Auricchio, R. Marzari, and R. Troncone, Gut, 2002. 51(2): p. 177-81.

20. Transglutaminase 2 undergoes a large conformational change upon activation. Pinkas, D. M., P. Strop, A. T. Brunger, and C. Khosla, PLoS Biol, 2007. 5(12): p. e327.

21. Functional significance of five noncanonical Ca2+-binding sites of human transglutaminase 2 characterized by site-directed mutagenesis. Kiraly, R., E. Csosz, T. Kurtan, S. Antus, K. Szigeti, Z. Simon-Vecsei, I. R. Korponay-Szabo, Z. Keresztessy, and L. Fesus, Febs J, 2009. 276(23): p. 7083-96.

22. 3,5 substituted 4,5-dihydroisoxazoles as transglutaminase inhibitors. Syntex, U.S. Pat. No. 4,912,120, 1990. March.

23. Griffin M, Coutts I G, and S. R, Novel Compounds and Methods of Using The Same., in International Publication Number WO 2004/113363, 2004: GB patent PCT/GB2004/002569.

24. Acylideneoxoindoles: a new class of reversible inhibitors of human transglutaminase 2. Klock, C., X. Jin, K. Choi, C. Khosla, P. B. Madrid, A. Spencer, B. C. Raimundo, P. Boardman, G. Lanza, and J. H. Griffin, Bioorg Med Chem Lett. 21(9): p. 2692-6.

25. Transglutaminase 2 inhibitors and their therapeutic role in disease states. Siegel, M. and C. Khosla, Pharmacol Ther, 2007.115(2): p. 232-45.

26. Structure-based design of alpha-amido aldehyde containing gluten peptide analogues as modulators of HLA-DQ2 and transglutaminase 2. Siegel, M., J. Xia, and C. Khosla, Bioorg Med Chem, 2007.15(18): p. 6253-61.

27. Novel therapies for celiac disease. Sollid, L. M. and C. Khosla, J Intern Med. 269(6): p. 604-13.

28. Transglutaminase 2: an enigmatic enzyme with diverse functions. Fesus, L. and M. Piacentini, Trends Biochem Sci, 2002. 27(10): p. 534-9.

29. Transglutaminases: crosslinking enzymes with pleiotropic functions. Lorand, L. and R. M. Graham, Nat Rev Mol Cell Biol, 2003. 4(2): p. 140-56.

30. Transglutaminase 2 is needed for the formation of an efficient phagocyte portal in macrophages engulfing apoptotic cells. Toth, B., E. Garabuczi, Z. Sarang, G. Vereb, G. Vamosi, D. Aeschlimann, B. Blasko, B. Becsi, F. Erdodi, A. Lacy-Hulbert, A. Zhang, L. Falasca, R. B. Birge, Z. Balajthy, G. Melino, L. Fesus, and Z. Szondy, J Immunol, 2009.182(4): p. 2084-92.

31. Transglutaminase is essential in receptor-mediated endocytosis of alpha 2-macroglobulin and polypeptide hormones. Davies, P. J., D. R. Davies, A. Levitzki, F. R. Maxfield, P. Milhaud, M. C. Willingham, and I. H. Pastan, Nature, 1980. 283(5743): p. 162-7.

32. GTP binding and signaling by Gh/transglutaminase II involves distinct residues in a unique GTP-binding pocket. Iismaa, S. E., M. J. Wu, N. Nanda, W. B. Church, and R. M. Graham, J Biol Chem, 2000. 275(24): p. 18259-65.

33. The core domain of the tissue transglutaminase Gh hydrolyzes GTP and ATP. Iismaa, S. E., L. Chung, M. J. Wu, D. C. Teller, V. C. Yee, and R. M. Graham, Biochemistry, 1997. 36(39): p. 11655-64.

34. Gh: a GTP-binding protein with transglutaminase activity and receptor signaling function. Nakaoka, H., D. M. Perez, K. J. Baek, T. Das, A. Husain, K. Misono, M. J. Im, and R. M. Graham, Science, 1994. 264(5165): p. 1593-6.

35. Searching for the function of tissue transglutaminase: its possible involvement in the biochemical pathway of programmed cell death. Fesus, L. and V. Thomazy, Adv Exp Med Biol, 1988. 231: p. 119-34.

36. Induction and activation of tissue transglutaminase during programmed cell death. Fesus, L., V. Thomazy, and A. Falus, FEBS Lett, 1987. 224(1): p. 104-8.

37. Fibronectin-tissue transglutaminase matrix rescues RGD-impaired cell adhesion through syndecan-4 and beta1 integrin co-signaling. Telci, D., Z. Wang, X. Li, E. A. Verderio, M. J. Humphries, M. Baccarini, H. Basaga, and M. Griffin, J Biol Chem, 2008. 283(30): p. 20937-47.

38. Regulated expression of tissue transglutaminase in Swiss 3T3 fibroblasts: effects on the processing of fibronectin, cell attachment, and cell death. Verderio, E., B. Nicholas, S. Gross, and M. Griffin, Exp Cell Res, 1998. 239(1): p. 119-38.

39. A novel RGD-independent cel adhesion pathway mediated by fibronectin-bound tissue transglutaminase rescues cells from anoikis. Verderio, E. A., D. Telci, A. Okoye, G. Melino, and M. Griffin, J Biol Chem, 2003. 278(43): p. 42604-14.

EXAMPLE 2: SEQUENCING OF NOVEL TG2 INHIBITORY ANTIBODIES OF THE INVENTION

Antibody Sequencing In order to establish the sequences of the variable regions of each antibody of the invention, a pellet of the hybridoma cells was processed using the Qiagen RNeasy Mini Kit to extract the RNA following the manufacturer's protocols. The extracted RNA was reverse transcribed to produce a cDNA using a 1st Strand cDNA Synthesis Kit (GE Healthcare), using a NotI-$dT_{18}$ primer, in accordance with the manufacturer's protocols. The cDNA preparation was cleaned up using the Qiagen PCR Purification Kit, in accordance with the manufacturer's protocols.

To determine the heavy chain sequence, the mouse cDNA was amplified by PCR using a set of degenerate primers (MHV1-12) with a constant region primer (MHCG1, MHCG2A, MHCG2B, MHCG3, or a mixture of the four) as shown in Table 12. Similarly, to determine the light chain sequence, the mouse cDNA was amplified using a set of degenerate primers (MVK1-11) with a constant region primer MKC as shown in Table 13.

If no amplification products were seen using the initial set of Heavy Chain PCR a 5' RACE PCR (Invitrogen) was carried out, using the NotI-$dT_{18}$ primer to generate cDNA; and the constant region primers (MHCG1, MHCG2A, MHCG2B, MHCG3, or a mixture of the four) and the 5' RACE Anchor Primer, GGCCACGCGTCGACTAGTACGGGIIGGGIIGGGIIG (SEQ ID NO: 138) (where I is the base for deoxyinosine) for the PCR.

The resulting amplification bands were ligated into the pCR2.1®-TOPO® vector using the TOPO-TA Cloning® kit (Invitrogen) using the manufacturer's protocol and sent to GATC Biotech AG for sequencing.

TABLE 12

PCR Primers for Cloning Mouse Heavy Chain Variable Regions

| Name | Sequence | |
|---|---|---|
| MHV1 | ATGAAATGCAGCTGGGGCATCTTCTTC | SEQ ID NO: 139 |
| MHV2 | ATGGGATGGAGCTRTATCATSYTCTT | SEQ ID NO: 140 |
| MHV3 | ATGAAGWTGTGGTTAAACTGGGTTTTT | SEQ ID NO: 141 |
| MHV4 | ATGRACTTTGGGYTCAGCTTGRTTT | SEQ ID NO: 142 |
| MHV5 | ATGGACTCCAGGCTCAATTTAGTTTTC CTT | SEQ ID NO: 143 |
| MHV6 | ATGGCTGTCYTRGSGCTRCTCTTCTGC | SEQ ID NO: 144 |
| MHV7 | ATGGRATGGAGCKGGRTCTTTMTCTT | SEQ ID NO: 145 |
| MHV8 | ATGAGAGTGCTGATTCTTTTGTG | SEQ ID NO: 146 |
| MHV9 | ATGGMTTGGGTGTGGAMCTTGCTATTC CTG | SEQ ID NO: 147 |
| MHV10 | ATGGGCAGACTTACATTCTCATTCCTG | SEQ ID NO: 148 |
| MHV11 | ATGGATTTTGGGCTGATTTTTTTTATTG | SEQ ID NO: 149 |
| MHV12 | ATGATGGTGTTAAGTCTTCTGTACCTG | SEQ ID NO: 150 |
| MHCG1 | CAGTGGATAGACAGATGGGGG | SEQ ID NO: 151 |
| MHCG2A | CAGTGGATAGACCGATGGGGC | SEQ ID NO: 152 |
| MHCG2b | CAGTGGATAGACTGATGGGGG | SEQ ID NO: 153 |
| MHCG3 | CAAGGGATAGACAGATGGGGC | SEQ ID NO: 154 |

Ambiguity codes: R=A or G; Y=C or T; M=A or C; K=G or T; S=G or C; W=A or T.

MHV indicates primers that hybridize to the leader sequences of mouse heavy chain variable region genes, MHCG indicates primers that hybridize to the mouse constant region genes.

TABLE 13

PCR Primers for Cloning Mouse Kappa Light Chain Variable Regions

| Name | Size | Sequence | |
|---|---|---|---|
| MKV1 | 30-mer | ATGAAGTTGVVTGTTAGGCTGTTGGTGCTG | SEQ ID NO: 155 |
| MKV2 | 29-mer | ATGGAGWCAGACACACTCCTGYTATGGGTG | SEQ ID NO: 156 |
| MKV3 | 30-mer | ATGAGTGTGCTCACTCAGGTCCTGGSGTTG | SEQ ID NO: 157 |
| MKV4 | 33-mer | ATGAGGRCCCCTGCTCAGWTTYTTGGMWTCTTG | SEQ ID NO: 158 |
| MKV5 | 30-mer | ATGGATTTWAGGTGCAGATTWTCAGCTTC | SEQ ID NO: 159 |
| MKV6 | 27-mer | ATGAGGTKCKKTGKTSAGSTSCTGRGG | SEQ ID NO: 160 |
| MKV7 | 31-mer | ATGGGCWTCAAGATGGAGTCACAKWYYCWGG | SEQ ID NO: 161 |
| MKV8 | 31-mer | ATGTGGGGAYCTKTTTYCMMTTTTTCAATTG | SEQ ID NO: 162 |
| MKV9 | 25-mer | ATGGTRTCCWCASCTCAGTTCCTTG | SEQ ID NO: 163 |
| MKV10 | 27-mer | ATGTATATATGTTTGTTGTCTATTTCT | SEQ ID NO: 164 |
| MKV11 | 28-mer | ATGGAAGCCCCAGCTCAGCTTCTCTTCC | SEQ ID NO: 165 |
| CL12A | | ATGRAGTYWCAGACCCAGGTCTTYRT | SEQ ID NO: 166 |
| CL12B | | ATGGAGACACATTCTCAGGTCTTTGT | SEQ ID NO: 167 |
| CL13 | | ATGGATTCACAGGCCCAGGTTCTTAT | SEQ ID NO: 168 |
| CL14 | | ATGATGAGTCCTGCCCAGTTCCTGTT | SEQ ID NO: 169 |

TABLE 13-continued

PCR Primers for Cloning Mouse Kappa Light Chain Variable Regions

| Name | Size | Sequence | |
|---|---|---|---|
| CL15 | | ATGAATTTGCCTGTTCATCTCTTGGTGCT | SEQ ID NO: 170 |
| CL16 | | ATGGATTTTCAATTGGTCCTCATCTCCTT | SEQ ID NO: 171 |
| CL17A | | ATGAGGTGCCTARCTSAGTTCCTGRG | SEQ ID NO: 172 |
| CL17B | | ATGAAGTACTCTGCTCAGTTTCTAGG | SEQ ID NO: 173 |
| CL17C | | ATGAGGCATTCTCTTCAATTCTTGGG | SEQ ID NO: 174 |
| MKC | 20-mer | ACTGGATGGTGGGAAGATGG | SEQ ID NO: 175 |

Ambiguity codes: R=A or G; Y=C or T; M=A or C; K=G or T; S=G or C; W=A or T.

MKV indicates primers that hybridise to leader sequences of the mouse kappa light chain variable region genes, MKC indicates the primer that hybridises to the mouse kappa constant region gene.

Sequence Data

Antibody AB1 was sequenced in addition to Antibodies BB7, DC1, JE12, EH6, AG9, AH3, DD9, DH2, DD6 and IA12. The sequences are provided in FIGS. 18 to 28.

EXAMPLE 3: CONSTRUCTION AND CHARACTERISATION OF CHIMERIC AND HUMANISED NOVEL ANTI-TG2 ANTIBODIES OF THE INVENTION

To further characterise the antibodies of the invention and to enable ranking and prioritisation of antibodies for humanisation, a panel of chimeric TG2 antibodies were constructed (murine variable regions and human IgG1 and human kappa). The methodology used to produce the chimeric antibodies is set out below.

Methods

Human VH and VK cDNA Databases

The protein sequences of human and mouse immunoglobulins from the International Immunogenetics Database 20091 and the Kabat Database Release 5 of Sequences of Proteins of Immunological Interest (last update 17 Nov. 1999)[2] were used to compile a database of human immunoglobulin sequences in a Kabat alignment. Our database contains 10,606 VH and 2,910 VK sequences.

Molecular Model of AB1

As a representative of the Group 1 antibodies (i.e. antibodies that bind the epitope spanning amino acids 304 to 326 of human TG2), a homology model of the mouse antibody AB1 variable regions has been calculated using the Modeller program[3] run in automatic mode. The atomic coordinates of 1 MQK.pdb, 3LIZ.pdb and 1MQK.pdb were the highest identity sequence templates for the Interface, VL and VH respectively as determined by Blast analysis of the Accelrys antibody pdb structures database. These templates were used to generate 20 initial models, the best of which was refined by modeling each CDR loop with its 3 best loop templates.

hAB1 Framework Selection

The sequence analysis program, gibsSR, was used to interrogate the human VH and VK databases with the AB1 VHc, VKc and $VKc_1$, the BB7 VHc and VKc and the DC1 VHc and VKc protein sequences using various selection criteria. FW residues within 5A of a CDR residue (Kabat definition) in the homology model of mouse antibody AB1, were identified, and designated as the "5 Å Proximity" residues.

AF06220 was chosen as the FW on which to base the initial humanised heavy chain versions. Table 14 shows the alignment and residue identity of AF06220 to murine antibodies. Table 15 shows the 5 Å proximity envelope of the sequences. AF062260 has only 1 somatic mutation away from its germline VH gene Z12347 (Table 16).

AY247656 was chosen as the FW on which to base the initial AB1 humanised kappa light chain. The alignment and residue identity to murine AB1 antibody kappa light chain are shown in Table 17; Table 18 shows the 5 Å proximity envelope of the sequences. The sequence shows 5 somatic mutations from its germline VK gene X93620 (Table 19). AF193851 was chosen as the FW on which to base the other humanised kappa light chain constructs. The alignment and residue identity to the murine antibodies are shown in Table 20. Table 21 shows the 5 Å proximity envelope of the sequences. The sequence shows no somatic mutations from its germline VK gene J00248 (Table 22).

Generation of Expression Vectors

Construction of chimeric expression vectors entails adding a suitable leader sequence to VH and VL, preceded by a Hind III restriction site and a Kozak sequence. The Kozak sequence ensures efficient translation of the variable region sequence. It defines the correct AUG codon from which a ribosome can commence translation, and the most critical base is the adenine at position-3, upstream of the AUG start.

For the heavy chain, the construction of the chimeric expression vectors entails introducing a 5' fragment of the human γ1 constant region, up to a natural ApaI restriction site, contiguous with the 3' end of the J region of the variable region. The CH is encoded in the expression vector downstream of the inserted VH sequence but lacks the V-C intron.

For the light chain, the natural splice donor site and a BamHI site is added downstream of the V region. The splice donor sequence facilitates splicing out the kappa V:C intron which is necessary for in-frame attachment of the VL to the constant region.

The DNA sequences of the variable regions were optimized and synthesized by GeneArt®. The leader sequence has been selected as one that gives good expression of antibody in cultured mammalian cells.

Heavy Chain variable region constructs were excised from the cloning vector using HindIII+ApaI digestion, purified and ligated into the similarly-cut and phosphatase-treated MRCT heavy chain expression vector, and were used to transform TOP10 bacteria.

Kappa chain variable region constructs were excised using HindIII+BamHI digestion, purified, ligated into the similarly-cut and phosphatase treated MRCT kappa light chain expression vector, and were used to transform TOP10 bacteria.

Antibody Expression

A double insert expression vector coding for both Heavy and kappa chains was generated and transfected into HEK293T cells. Cell culture supernatant was purified by affinity chromatography on Protein G-agarose in accordance with the manufacturer's protocols.

Binding ELISA

HEK 293F cells were co-transfected with combinations of different humanised light chain vectors in association with different humanised heavy chain vectors. Recombinant human TG2 was used to measure antibody binding by ELISA. The results indicated that the Heavy Chain version RHA (Table 23), in combination with either Light Chain versions RKE and RKJ (Table 24) (representing the different Light Chain versions humanised) showed optimal binding (FIG. 34), and was therefore selected for further characterization. A similar approach was used to identify optimal pairs of humanized BB7 heavy and light chains, and humanised DC1 heavy and light chains.

Heavy Chain version RHA is an un-modified graft of the mouse CDR regions of the AB1 antibody onto the Human donor sequence. However, both Light Chain versions RKE and RKJ, have the same single 5 Å proximity reside back-mutation, F72 (Table 24). This back mutation lies outside the Vernier[4], Canonical[5] or Interface[6] residues.

REFERENCES

1. Lefranc, M. P. IMGT, the international ImMunoGeneTics Database®. Nucleic Acids Res. 31, 307-310 (2003).

2. Kabat, E. A., Wu, T. T., Perry, H. M., Gottesman, K. S. & Foeller, C. Sequences of Proteins of Immunological Interest. NIH National Technical Information Service, (1991).

3. Eswar, N. et al. Comparative protein structure modeling using Modeller. Curr. Protoc. Bioinformatics. Chapter 5:Unit 5.6., Unit (2006).

4. Foote, J. & Winter, G. (1992). Antibody framework residues affecting the conformation of the hypervariable loops. J Mol. Biol. 224, 487-499.

5. Morea, V., Lesk, A. M. & Tramontano, A. (2000). Antibody modeling: implications for engineering and design. Methods 20, 267-279.

6. Chothia, C., Novotny, J., Bruccoleri, R. & Karplus, M. (1985). Domain association in immunoglobulin molecules. The packing of variable domains. J Mol. Biol. 186, 651-663.

The following table A summarises the chimeric and humanised antibodies produced with a cross reference to the identifiers used in the figures.

| Murine Antibody | Chimeric Antibody | Humanised Antibody |
|---|---|---|
| AB1 | cAB001 | hAB004 (hAB001AE) |
| | cAB003 | hAB005 (hAB001AJ) |
| BB7 | cBB001 | hBB001AA |
| | | hBB001BB |
| DC1 | cDC001 | hDC001AA |
| | | hDC001BB |
| DD6 | cDD6001 | |
| DD9 | cDD9001 | |
| DH2 | cDH001 | |

Tables

TABLE 14

```
Kabat Numbers[2]                        1        10        20        30          40        50
                                        -|--------|---------|---------|-----AB----|---------|--ABC-------
Vernier[4]                              -.*........................****..................***.............
Canonical[5]                            -.......................1.11.1....1....................2...22....
Interface[6]                            -..................................I...I.I.....I.I...............
5Å Proximity                             ****                 * *  ****       ***        ***
CDR                                                                    <----->              <------------
AB_VHc (mAB001VH)(SEQ ID NO: 176_       -EVQLVESGGGLVKPGGSLKLSCAASGFILSSSAMS--WVRQTPDARLEWVATISV--GGGKTYY
BB7_VHc (mBB7001VH)(SEQ ID NO: 177      -AVQLVESGGGLVKPGGSLKLSCAASGIIFSSSAMS--WVRQTPEKRLEWVATISS--GGRSTYY
DC1_VHc (mDC001VH)(SEQ ID NO: 178       -EVQLVESGGGLVKPGGSLKLSCAASGFILSTHAMS--WVRQTPEKRLEWVATISS--GGRSTYY
AF062260 SEQ ID NO: 179                 C....L.......Q.....R.........F..Y...--....A.GKG....SA..G--S..S...
with reference to AB_VHc
SEQ ID NO: 180 with
reference to BB7_VHc
SEQ ID NO: 181 with
reference to DC1_VHc

Kabat Numbers[2]                        60        70        80           90        100                 110
                                        |---------|---------|--ABC-------|---------|ABCDEFGHIJK---------|-
Vernier[4]                              .......*.*.*.*....*.................**.................*..........
Canonical[5]                            ...........2.........................1............................
Interface[6]                            ..................................I.I.I................I..........
5Å Proximity                                  ****** *    *               ****                 **
CDR                                     ----->                                <--------------->
AB_VHc (mAB001VH)(SEQ ID NO: 176_       PDSVKGRFTISRDNAKNTLYLQMNSLASEDIAMYYCAKLI------------SLYWGQGTTLTVSS
BB7_VHc (mBB7001VH)(SEQ ID NO: 177      PDSVKGRFTVSRDSAKNTLYLQMDSLASEDTAIYYCAKLI------------SPYWGQGTTLTVSS
DC1_VHc (mDC001VH) SEQ ID NO: 178       PDSVKGRFTISRDNVKNTLYLQLSSLASEDIAVYFCARLI------------STYWGQGTTLTVSS
AF062260 SEQ ID NO: 179                 A............S...........A...V.....DG-----------GV......LV....
with reference to AB_VHc
SEQ ID NO: 180 with
reference to BB7_VHc
SEQ ID NO: 181 with
reference to DC1_VHc
```

Table 14 showing the alignment and residue identity of AF062260 to the murine antibodies. Residue identities are shown by a dot (.) character. Residue differences are shown where applicable. Gaps (–) are used to maintain Kabat numbering, and to show residue insertion or deletion where applicable.

TABLE 15

| | 5 Å Proximity Residues | |
|---|---|---|
| AB_VHc (mAB001VH) | EVQLCAFTLSWVRWVARFTISRNLYCAKWGS | EQ ID NO: 182 |
| BB7_VHc (mBB7001VH) | AVQLCAIIFSWVRWVARFTVSRSLYCAKWGS | EQ ID NO: 183 |
| DC1_VHc (mDC001VH | EVQLCAFTLSWVRWVARFTISRNLFCARWGS | EQ ID NO: 184 |
| AF062260 | ........F......S.............. | SEQ ID NO: 185 with reference to AB_VHc SEQ ID NO: 186 with reference to BB7_VHc SEQ ID NO: 187 with reference to DC1_VHc |

Table 15 showing the antibody heavy chain framework residues that lie within a 5 Å envelope of the CDR's. Residue identities are shown by a dot (.) character. Residue differences are shown where applicable.

TABLE 16

```
             ---------+---------+---------+---------+---------+---------+-----
                     10        20        30        40        50        60
             ---------+---------+---------+---------+---------+---------+-----
Z12347.seq   EVQLLESGGGLVQPGGSLRLSCAASGFTFSSYAMSWVRQAPGKGLEWVSAISGSGGSTYYADSVK
AF062260.seq.................................................................
                                         <--->                <----------------

                          ----+---------+---------+--------
                              70        80        90
                          ----+---------+---------+--------
             Z12347.seq   GRFTISRONSKNTLYLQMNSLRAEDTAVYYCAK    SEQ ID NO: 119
             AF062260.seq ................................R    SEO ID NO: 120
                          >
```

Table 16 showing AF062260 has 1 somatic mutation away from the germline VH gene Z12347. Residue identities are shown by a dot (.) character. Residue differences are shown where applicable.

TABLE 17

```
Kabat Numbers[2]              1        10        20               30        40        50
                             -|--------|---------|-------ABCDEF--|---------|---------|-----
Vernier[4]                   -.*.*...................................**.........****......
Canonical[5]                 -.1.....................1.......1111..1..............2..22...
Interface[6]                 -.......................................I.I.....I...........
5Å Proximity                  ******                  **                 **         ****
CDR                                                     <---------------->            <-----
AB_VKc (mABOOlVK)            -EIVLTQSPSSMYASLGERVTITCKASQ------DINSYLTWFQQKPGKSPKTLIYRTNRLF
(SEQ ID NO: 188)
AY247656 (SEQ ID NO: 189)    -..........LS..V.D......Q...------..SN..N.Y......A..L...DASN.E

Kabat Numbers[2]                60        70        80        90             100
                             ----|---------|---------|---------|-----ABCDEF----|------A-
Vernier[4]                   ........*.*.**.*...............................*..........
Canonical[5]                 ........2......1.................3....3...................
Interface[6]                 ..............................I..I...........II..........
5Å Proximity                  ***   ***********              **                **
CDR                          >                                <------------->
AB_VKc (mABOOlVK)            DGVPSRFSGSGSGQDFFLTISSLEYEDMGIYYCLQYDDFP------YTFGGGTKLEI-K
(SEQ ID NO: 188)
AY247656 (SEQ ID NO: 189)    T............T..TF.....QP..F.T...Q..NTY.------L...........-.
```

Table 17 showing the alignment and residue identity of AY247656 to the murine AB1 antibody. Residue identities are shown by a dot (.) character. Residue differences are shown where applicable. Gaps (–) are used to maintain Kabat numbering, and to show residue insertion or deletion where applicable.

TABLE 18

| | 5Å Proximity Residues |
|---|---|
| AB_VKc (mAB001VK) | EIVLTQTCWFTLIYGVPFSGSGSGQDFFYCFG<br>SEQ ID NO: 190 |
| AY247656 | .........YL............T..T....<br>SEQ ID NO: 191 |

Table 18 showing the AB1 antibody kappa light chain framework residues that lie within a 5 Å envelope of the CDR's. Residue identities are shown by a dot (.) character. Residue differences are shown where applicable.

TABLE 19

| | |
|---|---|
| | ---------+---------+---------+---------+---------+---------+----- |
| | 10 20 30 40 50 60 |
| | ---------+---------+---------+---------+---------+---------+----- |
| X93620.seq | DIQMTQSPSSLSASVGDRVTITCQASQDISNYLNWYQQKPGKAPKLLIYDASNLETGVPSRFSGS |
| AY247656.seq | E.VL............................................................. |
| | <----------> <-----> |

| | | |
|---|---|---|
| | ----+---------+---------+------ | |
| | 70 80 90 | |
| | ----+---------+---------+------ | |
| X93620.seq | GSGTOFTFTISSLQPEDIATYYCQQYDNLPP | SEQ ID NO: 125 |
| AY247656.seq | .................FG.......NTY.L | SEQ ID NO: 126 |
| | <------- | |

Table 19 showing AY247656 has 5 somatic mutation away from the germline VK gene X93620. Residue identities are shown by a dot (.) character. Residue differences are shown where applicable.

TABLE 20

<table>
<tr><td>Kabat Numbers[2]</td><td>1 10 20 30 40 50<br>-|--------|---------|-------ABCDEF--|---------|---------|-----</td></tr>
<tr><td>Vernier[4]</td><td>-.*.*....................................**.........****......</td></tr>
<tr><td>Canonical[5]</td><td>-.1.....................1.......1111..1..............2..22...</td></tr>
<tr><td>Interface[6]</td><td>-.......................................I.I.....I...........</td></tr>
<tr><td>5Å Proximity</td><td>****** ** ** ****</td></tr>
<tr><td>CDR</td><td><----------------> <-----</td></tr>
<tr><td>AB_VKcl (mAB002VK) (SEQ ID NO: 192)</td><td>-DIQMTQSPSSMYASLGERVTITCKASQ------DINSYLTWFQQKPGKSPKTLIYRTTRLF</td></tr>
<tr><td>AB1_VKc2 (mAB003VK) (SEQ ID NO: 193</td><td>-DIQKTQSPSSMYASLGERVTITCKASQ------DINSYLTWFQQKPGKSPKTLIYRTTRLF</td></tr>
<tr><td>BB7_VKc (mBBOO1VK) (SEQ ID NO: 194)</td><td>-AIKMIQSPSSMYASLGERVIIICKASQ------DINSYLTWFQQKPGKSPKTLIYLITRLM</td></tr>
<tr><td>DCl_VKc (mDC001VK) (SEQ ID NO: 195)</td><td>-DITMTQSPSSIYASLGERVTITCKASQ------DINSYLTWFQQKPGKSPKILIYLVNRLV</td></tr>
<tr><td>AF193851 SEQ ID NO: 196 with reference to AB_VKcl<br>SEQ ID NO: 197 with reference to ABl_VKc2<br>SEQ ID NO: 198 with reference to BB7_VKc<br>SEQ ID NO: 199 with reference to DCl_VKc</td><td>-...M......LS..V.F......T...------G.RN..A........A..S...AASN.Q</td></tr>
<tr><td>Kabat Numbers[2]</td><td>60 70 80 90 100<br>----|---------|---------|---------|-----ABCDEF----|------A-</td></tr>
<tr><td>Vernier[4]</td><td>........*.*.**.*..............................*..........</td></tr>
<tr><td>Canonical[5]</td><td>........2......1.................3....3...................</td></tr>
<tr><td>Interface[6]</td><td>..............................I..I...........II..........</td></tr>
<tr><td>5Å Proximity</td><td>*** *********** ** **</td></tr>
<tr><td>CDR</td><td>> <-------------></td></tr>
<tr><td>AB_VKcl (mAB002VK) (SEQ ID NO: 192)</td><td>DGVPSRFSGSGSGQDFFLTISSLEYEDMGIYYCLQYDDFP------YTFGGGTKLEI-K</td></tr>
<tr><td>AB1_VKc2 (mAB003VK) (SEQ ID NO: 193</td><td>DGVPSRFSGSGSGQDFFLTISSLEYEDMGIYYCLQYDDFP------YTFGGGTKLEI-K</td></tr>
<tr><td>BB7_VKc (mBBOO1VK) (SEQ ID NO: 194)</td><td>DGVPSRFSGSGSGQEFLLTISGLEHEDMGIYYCLQYVDFP------YTFGGGTKLEI-K</td></tr>
<tr><td>DCl_VKc (mDC001VK) (SEQ ID NO: 195)</td><td>DGVPSRFSGSGSGQDYALTISSLEYEDMGIYYCLQYDDFP------YTFGGGTKLEI-K</td></tr>
</table>

TABLE 20-continued

| | |
|---|---|
| AF193851 SEQ ID NO: 196 with reference to AB_VKc1 SEQ ID NO: 197 with reference to AB1_VKc2 SEQ ID NO: 198 with reference to BB7_VKc SEQ ID NO: 199 with reference to DC1_VKc | S............T..T......QP..FAT...Q.HNTY.------W...Q...V..-. |

Table 20 showing the alignment and residue identity of AF193851 to the murine antibodies. Residue identities are shown by a dot (.) character. Residue differences are shown where applicable. Gaps (–) are used to maintain Kabat numbering, and to show residue insertion or deletion where applicable.

TABLE 21

| | 5 Å Proximity Residues | |
|---|---|---|
| AB_VKc1 (mAB002VK) | DIQMTQTCWFTLIYGVPFSGSGSGQDFFYCFG | |
| AB1_VKc2 (mAB003VK) | DIQKTQTCWFTLIYGVPFSGSGSGQDFFYCFG | SEQ ID NO: 200 |
| BB7_VKc (mBB001VK) | AIKMTQTCWFTLIYGVPFSGSGSGQEFLY-CFG | SEQ ID NO: 201 |
| DC1_VKc (mDC001VK) | DITMTQTCWFIL-IYGVPFSGSGSGQDYAYCFG | SEQ ID NO: 202 |
| AF193851 | ...M......S.............T..T.... | SEQ ID NO: 203 with reference to AB_VKc1 SEQ ID NO: 204 with reference to AB1_VKc2 SEQ ID NO: 205 with reference to BB7_VKc SEQ ID NO: 206 with reference to DC1_VKc |

Table 21 showing the antibody kappa light chain framework residues that lie within a 5 Å envelope of the CDR's. Residue identities are shown by a dot (.) character. Residue differences are shown where applicable.

TABLE 22

```
             ---------+---------+---------+---------+---------+---------+-----
                      10        20        30        40        50        60
             ---------+---------+---------+---------+---------+---------+-----
J00248.seq   DIQMTQSPSSLSASVGDRVTITCRASQGISNYLAWFQQKPGKAPKSLIYAASSLQSGVPSRFSGS
AF193851.seq .............................R......................N............
                                     <---------->              <----->

                           ----+---------+---------+------
                               70        80        90
                           ----+---------+---------+------
             J00248.seq    GSGTOFTLTISSLQPEDFATYYCQQYNSYPP    SEQ ID NO: 131
             AF193851.seq  ........................H.T..W     SEQ ID NO: 132
                                                   <-------
```

Table 22 showing AF193851 has no somatic mutation away from the germline VK gene J00248. Residue identities are shown by a dot (.) character. Residue differences are shown where applicable.

TABLE 23

```
Kabat Numbers                          1        10        20        30          40        50
                                      -|--------|---------|---------|-----AB----|---------|--ABC------
Vernier[4]                            -.*........................****..................***............
Canonical[5]                          -.......................1.11.1....1....................2...22...
Interface[6]                          -..................................I...I.I.....I.I..............
5Å Proximity                           ****                 * *  ****       ***        ***
CDR                                                                  <----->              <-----------
AB_RHA (hAB001HA) (SEQ ID NO: 134)    -EVQLLESGGGLVQPGGSLRLSCAASGFTFSSSAMS--WVRQAPGKGLEWVSTISV--GGGKTY
BB7_RHA (hBB001HA)(SEQ ID NO: 64)     -EVQLLESGGGLVQPGGSLRLSCAASGFTFSSSAMS--WVRQAPGKGLEWVSTISS--GGRSTY
BB7_RHB (hBB001HB)(SEQ ID NO: 55)     -EVQLLESGGGLVQPGGSLRLSCAASGIIFSSSAMS--WVRQAPGKGLEWVATISS--RGGRST
DC1_RHA (hDC001HA)(SEQ ID NO: 74)     -EVQLLESGGGLVQPGGSLRLSCAASGFTFSTHAMS--WVRQAPGKGLEWVSTISS--GGRSTY
DC1_RHB (hDC001HB)(SEQ ID NO: 75)     -EVQLLESGGGLVQPGGSLRLSCAASGFTLSTHAMS--WVRQAPGKGLEWVATISS--GGRSTY
```

```
Kabat Numbers                         60        70        80           90        100                 110
                                      -|---------|---------|--ABC-------|---------|ABCDEFGHIJK---------|-
Vernier[4]                            ........*.*.*.*....*.................**.................*..........
Canonical[5]                          ............2.........................1............................
Interface[6]                          ...................................I.I.I................I..........
5Å Proximity                                    ****** *    *               ****                 **
CDR                                   --------->                                <--------------->
AB_RHA (hAB001HA) (SEQ ID NO: 134)    YPDSVKGRFTISRDNSKSTLYLQMNSLRAEDTAVYYCAKLI------------SLYWGQGTLVTVSS
BB7_RHA (hBB001HA)(SEQ ID NO: 64)     YPDSVKGRFTISRDNSKSTLYLQMNSLRAEDTAVYYCAKLI------------SPYWGQGTLVTVSS
BB7_RHB (hBB001HB)(SEQ ID NO: 55)     YYPDSVKGFTVSRDSSKSTLYLQMNSLRAEDTAVYYCAKLI------------SPYWGQGTLVTVSS
DC1_RHA (hDC001HA)(SEQ ID NO: 74)     YPDSVKGRFTISRDNSKSTLYLQMNSLRAEDTAVYYCAKLI------------STYWGQGTLVTVSS
DC1_RHB (hDC001HB)(SEQ ID NO: 75)     YPDSVKGRFTISRDNSKSTLYLQMNSLRAEDTAVYFCARLI------------STYWGQGTLVTVSS
```

Table 23 showing the sequence alignments of the final humanised versions of AB1, BB7 and DC1 heavy chains. Gaps (–) are used to maintain Kabat numbering, and to show residue insertion or deletion where applicable.

TABLE 24

```
Kabat Numbers                          1        10        20              30        40        50
                                      -|--------|---------|-------ABCDEF--|---------|---------|-----
Vernier[4]                            -.*.*....................................**.........****......
Canonical[5]                          -.1......................1.......1111..1..............2..22...
Interface[6]                          -.........................................I.I.....I...........
5Å Proximity                           ******              **                  **         ****
CDR                                                          <---------------->               <-----
AB_RKE (hABOO1KE) (SEQ ID NO: 136)    -EIVLTQSPSSLSASVGDRVTITCKASQ------DINSYLIWYQQKPGKAPKLLIYRTNRLF
AB_RKJ (hAB001KJ) (SEQ ID NO: 137)    -DIQMTQSPSSLSASVGDRVTITCKASQ------DINSYLTWFQQKPGKAPKSLIYRTNRLF
BB7_RKA (hBB001KA) (SEQ ID NO: 62     -DIQMTQSPSSLSASVGDRVTITCKASQ------DINSYLTWFQQKPGKAPKSLIYLTNRLM
BB7_RKB (hBB001KB) (SEQ ID NO: 63)    -DIKMTQSPSSLSASVGDRVTITCKASQ------DINSYLTWFQQKPGKAPKTLIYLTNRLM
DC1_RKA (hDC001KA)(SEQ ID NO: 72)     -DIQMTQSPSSLSASVGDRVTITCKASQ------DINSYLTWFQQKPGKAPKSLIYLVNRLV
DC1_RKB (hDC001KB) (SEQ ID NO: 73)    -DITMTQSPSSLSASVGDRVTITCKASQ------DINSYLTWFQQKPGKAPKILIYLVNRLV
```

```
Kabat Numbers                            60        70        80        90             100
                                      ----|---------|---------|---------|-----ABCDEF----|------A-
Vernier[4]                            ........*.*.**.*................................*..........
Canonical[5]                          ........2......1..................3....3...................
Interface[6]                          ...............................I..I............II..........
5Å Proximity                           ***  ***********              **               **
CDR                                   >                                <------------->
AB_RKE (hABOO1KE) (SEQ ID NO: 136)    DGVPSRFSGSGSGTDFFFTISSLQPEDFGIVYCLQYDDFP------YTFGGGTKLEI-K
AB_RKJ (hAB001KJ) (SEQ ID NO: 137)    DGVPSRFSGSGSGTDFFLTISSLQPEDFATYYCLQYDDFP------YTFGQGTKVEI-K
BB7_RKA (hBB001KA) (SEQ ID NO: 62     DGVPSRFSGSGSGTDFFLTISSLQPEDFATYYCLQYVDFP------YTFGQGTKVEI-K
BB7_RKB (hBB001KB) (SEQ ID NO: 63)    DGVPSRFSGSGSGQEFLLTISSLQPEDFATYYCLQYVDFP------YTFGQGTKVEI-K
DC1_RKA (hDC001KA)(SEQ ID NO: 72)     DGVPSRFSGSGSGTDFFLTISSLQPEDFATYYCLQYDDEP------YTFGQGTKVEI-K
DC1_RKB (hDC001KB) (SEQ ID NO: 73)    DGVPSRFSGSGSGQDYALTISSLQPEDFATYYCLQYDDEP------YTFGQGTKVEI-K
```

Table 24 showing the sequence alignments of the final humanised versions of AB1, BB7 and DC1 kappa light chains. Gaps (–) are used to maintain Kabat numbering, and to show residue insertion or deletion where applicable.

TABLE 24A

Table 24a summarises the sequence information presented in Tables 23 and 24, in particular showing the sequence of the CDRs, and the CDRs with flanking regions, in the heavy- and light-chains of the AB, BB-7 and DC-1 antibodies.

| | |
|---|---|
| Heavy chain - CDR1 | |
| AB | CAASGFTFSSSAMSWVR (SEQ ID NO: 207) or |
| | FTFSSSAMSWVR (SEQ ID NO: 42) or |
| | SSAMS (SEQ ID NO: 10). |
| BB7 RHB | CAASGFTFSSSAMSWVR (SEQ ID NO: 207) or |
| | FTFSSSAMSWVR (SEQ ID NO: 42) or |
| | SSAMS (SEQ ID NO: 10). |
| BB7 RHA | CAASGIIFSSSAMSWVR (SEQ ID NO: 208) or |
| | IIFSSSAMSWVR (SEQ ID NO: 209) or |
| | SSAMS (SEQ ID NO: 10). |
| DC1 RHA | CAASGFTFSTHAMSWVR (SEQ ID NO: 201) or |
| | FTFSTHAMSWVR (SEQ ID NO: 211) or |
| | THAMS (SEQ ID NO: 212). |
| DC1 RHB | CAASGFTLSTHAMSWVR (SEQ ID NO: 213) or |
| | FTLSTHAMSWVR (SEQ ID NO: 214) or |
| | THAMS (SEQ ID NO: 212). |
| Heavy chain - CDR2 | |
| AB | WVSTISVGGGKTYYPDSVKGRFTISRDNSKNTL (SEQ ID NO: 215) or |
| | WVSTISVGGGKTYYPDSVKGRFTISRDN (SEQ ID NO: 216) or |
| | WVSTISVGGGKTYYPDSVKGRFTISR (SEQ ID NO: 44) or |
| | TISVGGGKTYYPDSVKG (SEQ ID NO: 11). |
| BB7 RHB | WVSTISSGGRSTYYPDSVKGRFTISRDNSKNTL (SEQ ID NO: 217) or |
| | WVSTISSGGRSTYYPDSVKGRFTISRDN (SEQ ID NO: 218) or |
| | WVSTISSGGRSTYYPDSVKGRFTISR (SEQ ID NO: 219) or |
| | TISSGGRSTYYPDSVKG (SEQ ID NO: 15). |
| BB7 RHA | WVATISSGGRSTYYPDSVKGRFTVSRDSSKNTL (SEQ ID NO: 220) or |
| | WVATISSGGRSTYYPDSVKGRFTVSRDS (SEQ ID NO: 221) or |
| | WVATISSGGRSTYYPDSVKGRFTVSR (SEQ ID NO: 222) or |
| | TISSGGRSTYYPDSVKG (SEQ ID NO: 15). |
| DC1 RHA | WVSTISSGGRSTYYPDSVKGRFTISRDNSKNTL (SEQ ID NO: 215) or |
| | WVSTISSGGRSTYYPDSVKGRFTISRDN (SEQ ID NO: 218) or |
| | WVSTISSGGRSTYYPDSVKGRFTISR (SEQ ID NO: 219) or |
| | TISSGGRSTYYPDSVKG (SEQ ID NO: 15). |
| DC1 RHB | WVATISSGGRSTYYPDSVKGRFTISRDNSKNTL (SEQ ID NO: 223) or |
| | WVATISSGGRSTYYPDSVKGRFTISRDN (SEQ ID NO: 224) or |
| | WVATISSGGRSTYYPDSVKGRFTISR (SEQ ID NO: 225) or |
| | TISSGGRSTYYPDSVKG (SEQ ID NO: 15). |
| Heavy chain - CDR3 | |
| AB | YCAKLISLYWG (SEQ ID NO: 32) or |
| | LISLY (SEQ ID NO: 12). |
| BB7 RHB | YCAKLISPYWG (SEQ ID NO: 226) or |
| | LISPY (SEQ ID NO: 16). |
| BB7 RHA | YCAKLISPYWG (SEQ ID NO: 226) or |
| | LISPY (SEQ ID NO: 16). |
| DC1 RHA | YCAKLISTYWG (SEQ ID NO: 227) or |
| | LISTY (SEQ ID NO: 19). |
| DC1 RHB | FCARLISTYWG (SEQ ID NO: 228) or |
| | LISTY (SEQ ID NO: 19). |
| Light chain - CDR1 | |
| AB RKE | TCKASQDINSYLTWY (SEQ ID NO: 37) or |
| | KASQDINSYLT (SEQ ID NO: 7). |
| AB RKJ | TCKASQDINSYLTWF (SEQ ID NO: 24) or |
| | KASQDINSYLT (SEQ ID NO: 7). |
| BB7 RKB | TCKASQDINSYLTWF (SEQ ID NO: 24) or |
| | KASQDINSYLT (SEQ ID NO: 7). |
| BB7 RKA | TCKASQDINSYLTWF (SEQ ID NO: 24) or |
| | KASQDINSYLT (SEQ ID NO: 7). |
| DC1 RKA | TCKASQDINSYLTWF (SEQ ID NO: 24) or |
| | KASQDINSYLT (SEQ ID NO: 7). |
| DC1 RKB | TCKASQDINSYLTWF (SEQ ID NO: 24) or |
| | KASQDINSYLT (SEQ ID NO: 7). |

TABLE 24A-continued

Table 24a summarises the sequence information presented in Tables 23 and 24, in particular showing the sequence of the CDRs, and the CDRs with flanking regions, in the heavy- and light-chains of the AB, BB-7 and DC-1 antibodies.

| | |
|---|---|
| **Light chain - CDR2** | |
| AB RKE | LLIYRTNRLFDGVPSRFSGSGSGTDFF (SEQ ID NO: 229) or LLIYRTNRLFDGVP (SEQ ID NO: 38) or RTNRLFD (SEQ ID NO: 8) |
| AB RKJ | SLIYRTNRLFDGVPSRFSGSGSGTDFF (SEQ ID NO: 230) or SLIYRTNRLFDGVP (SEQ ID NO: 39) or RTNRLFD (SEQ ID NO: 8) |
| BB7 RKB | SLIYLTNRLMDGVPSRFSGSGSGTDFF (SEQ ID NO: 231) or SLIYLTNRLMDGVP (SEQ ID NO: 232) or LTNRLMD (SEQ ID NO: 13) |
| BB7 RKA | TLIYLTNRLMDGVPSRFSGSGSGQEFL (SEQ ID NO: 233) or TLIYLTNRLMDGVP (SEQ ID NO: 234) or LTNRLMD (SEQ ID NO: 13) |
| DC1 RKA | SLIYLVNRLVDGVPSRFSGSGSGTDFF (SEQ ID NO: 235) or SLIYLVNRLVDGVP (SEQ ID NO: 236) or LVNRLVD (SEQ ID NO: 17) |
| DC1 RKB | ILIYLVNRLVDGVPSRFSGSGSGQDYA (SEQ ID NO: 237) or ILIYLVNRLVDGVP (SEQ ID NO: 238) or LVNRLVD (SEQ ID NO: 17) |
| **Light chain - CDR3** | |
| AB RKE | YCLQYDDFPYTFG (SEQ ID NO: 27) or LQYDDFPYT (SEQ ID NO: 9). |
| AB RKJ | YCLQYDDFPYTFG (SEQ ID NO: 27) or LQYDDFPYT (SEQ ID NO: 9). |
| BB7 RKB | YCLQYVDFPYTFG (SEQ ID NO: 239) or LQYVDFPYT (SEQ ID NO: 14). |
| BB7 RKA | YCLQYVDFPYTFG (SEQ ID NO: 239) or LQYVDFPYT (SEQ ID NO: 14). |
| DC1 RKA | YCLQYDDFPYTFG (SEQ ID NO: 27) or LQYDDFPYT (SEQ ID NO: 9). |
| DC1 RKB | YCLQYDDFPYTFG (SEQ ID NO: 27) or LQYDDFPYT (SEQ ID NO: 9). |

Characterization of Chimeric and Humanised Antibodies

Chimeric and humanised Abs were assayed for binding to human and cynomolgus monkey TG2 and for enzymatic inhibition of these enzymes according to the methodology described below.

Methods

ELISA Assay for TG2 Binding

Antibody binding to human and cynomolgus monkey TG2 was determined in an ELISA assay. Clear polystyrene "Maxisorp" 96-well plates (Nunc) were coated with 50 ng purified human or cynomogulus monkey TG2 in 50 μl 0.05 M carbonate-bicarbonate buffer pH 9.6 at 4° C. overnight. Control wells were coated with 50 μl 100 μg/ml bovine serum albumin (BSA). Plates were washed 3× with 300 μl phosphate-buffered saline pH7.4 (PBS) containing 0.1% Tween 20 (PBST) and blocked with 300 μl 3% w/v Marvel skimmed milk in PBS for 1 hour at room temperature. After 3× wash with PBST, 50 μl protein-A purified chimeric or humanised anti-TG2 antibodies or human IgG1 kappa isotope control antibody or CUB7402 (Abcam) were serially diluted 4-fold from a top concentration of 50 nM in PBS, and added to the plate in duplicate. After 1 hour at room temperature, the plates were washed 3× in PBST and incubated with 50 μl peroxidase-conjugated goat anti-human IgG (Fc) (Serotec) diluted 1/5,000 in 3% w/v Marvel skimmed milk in PBS or for wells containing CUB7402 peroxidase-conjugated 1/5,000 goat anti-mouse IgG (Fc) (Sigma) for 1 hour at room temperature. After 3× washes with PBST, the plates were developed with 50 μl TMB substrate (Sigma) for 5 min at room temperature before stopping the reaction with 25 μl 0.5M H2SO4 and reading absorbance at 450 nM in a microtiter plate reader (BioTek EL808). Dose response curves were analysed and EC50 values and other statistical parameters determined using a 4-parameter logistical fit of the data (GraphPad Prism).

Fluorescence-Based Transglutaminase Assay of TG2 Inhibition by Antibodies of the Invention.

Transglutaminase activities of purified human (Zedira) or cynomogolus monkey TG2 enzymes (Trenzyme) were measured by incorporation of dansylated lysine KxD (Zedira) into N,N-dimethylated casein (DMC, Sigma). Human or cynomogolus monkey TG2 were diluted in transamidation buffer (25 mM HEPES pH 7.4 containing 250 mM NaCl, 2 mM $MgCl_2$, 5 mM $CaCl_2$, 0.2 mM DTT and 0.05% v/v Pluronic F-127) to 1 nM and 10 nM respectively and mixed with various concentrations of protein-A purified murine, chimeric or humanised TG2 antibodies for 180 min at room temperature in 384-well black microtiter plates (Corning). Reactions were initiated by addition of DMC and KxD to a final concentration of 10 uM and 20 uM respectively and a final reaction volume of 30 ul, and allowed to proceed at RT for 180 min and the increase in fluorescence (RFU) (excitation at 280 nm, emission 550 nm) monitored using a Tecan Safire$^2$ plate reader. Data were normalised to percentage activity where % activity=(RFU test antibody−RFU low controls)/RFU high controls−RFU low controls)×100, where low controls contained all components except enzyme and high controls contained all components except antibody.

Antibody dose response curves were plotted using GraphPad prism software and fitted using a 4-parameter logistical model to return IC50 and other statistical parameters. The results are illustrated in FIGS. 29 to 33.

Results and Discussion of Enzyme Inhibition and ELISA Binding Experiments by Humanized and Murine Anti-TG2 Antibodies The ability of chimeric and humanized TG2 antibodies to inhibit transamidation by human TG2 was determined by dose-dependent inhibition of TG2-dependent incorporation of dansylated lysine into N,N-dimethylated casein (exemplified in FIGS. 29 and 31). Both chimeric and humanized antibodies from group 1 (e.g. cAB003, cBB001, cDC001, hBB001AA, hAB001BB, hAB005 and hAB004) show potent inhibition of TG2 activity in the low nanomolar range, consistent with ELISA data that shows binding to immobilized human TG2 in the same range (FIGS. 35 and 37). In contrast, the commercial antibody CUB7402 failed to inhibit human or cynomogulus monkey TG2 enzymatic activities (FIGS. 29F and 30B), despite comparable binding to group 1 antibodies in the ELISA assays (FIGS. 35A, 36A, 37A and 38A) consistent with recognition by CUB7402 of an epitope that does not interfere with the transamidation function of the enzyme. Therefore group 1 antibodies can be distinguished by their ability to inhibit enzyme function from other antibodies such as CUB7402, which bind but have no effect on enzymatic activity. Similarly, murine and chimeric antibodies representative of group 3 (e.g. mDD9001, mDH001, cDD9001 and cDH001) consistently inhibited human TG2 transamidation, but with lower potency than group 1 antibodies (FIGS. 29 and 33). Inhibition of human TG2 by exemplified parent murine monoclonal antibodies from group 1 and group 3 (FIG. 33) show comparable potencies to their chimeric and humanized versions, indicating that the functional potency of the murine antibodies has been retained in the humanized versions. Similarly the human TG2 ELISA binding data for the exemplified humanized antibodies hBB001AA, hBB001BB and hAB004 (FIG. 37) show comparable EC50 values with those obtained for the chimeric versions cBB001 and cAB003, indicating that binding affinity has also been preserved in the humanized versions. Chimeric and humanized antibodies also demonstrate potent inhibition of cynomogulus monkey TG2 (FIGS. 30 and 32) and comparable ELISA EC50's (FIGS. 36 and 38) across the species, consistent with the conservation of the cognate epitope in cynomogulus monkey TG2, which has overall 99% sequence identity. In contrast CUB7402 shows comparable binding to TG2 of both species as the group 1 antibodies, but inhibits neither enzyme activity (FIGS. 35-38 and 29-30).

Cell Based Assays

Binding of antibodies of the invention to extracellular TG2 from HK-2 epithelial cells was assayed using the following protocol.

Measurement of Extracellular TG Activity

Extracellular TG activity was measured by modified cell ELISA. HK-2 epithelial cells were harvested using Accutase and plated at a density of $2\times10^4$ cells/well in serum free medium onto a 96 well plate that had been coated overnight with 100 μl/well of fibronectin (5 μg/ml in 50 mM Tris-HCl pH 7.4) (Sigma, Poole UK). Cells were allowed to attach for O/N at 37° C. Media was replaced with DMEM (Life Technologies) and compounds, antibodies or controls were added and allowed to bind at 37° C. 0.1 mM biotin cadaverine [N-(5 amino pentyl biotinamide) trifluoroacetic acid] (Zedira) was added to wells and the plate returned to 37° C. for 2 hours. Plates were washed twice with 3 mM EDTA/PBS and cells removed with 0.1% (w/v) deoxycholate in 5 mM EDTA/PBS. The supernatant was collected and used for protein determination. Plates were washed with PBS/Tween and incorporated biotin cadaverine revealed using 1:5000 extravidin HRP (Sigma, Poole, UK) for 1 h at room temperature followed by K Blue substrate (SkyBio). The reaction was stopped with Red Stop (SkyBio) and the absorbance read at 4 650 nm. Each antibody was tested on at least three separate occasions.

Results are provided in FIGS. 39 and 40 and show an exemplar curve and table of IC50 values obtained for the antibodies tested. FIG. 39 displays the results with Humanised AB1 and FIG. 40 displays the results with Humanised BB7.

hAB005 inhibited the extracellular TG2 of the HK2 cells with an IC50 of 71.85 nM and a maximal inhibition of about 30% control activity. hBB001AA inhibited the activity with an IC50 of 19.8 nM and a maximal inhibition of 40% control activity. hBB001BB had a better IC50 of 4.9 nM but a maximal inhibition of about 55% control.

Scratch Assays

Scratch wound assays were also performed to assess binding activity of humanised and or chimeric anti-TG2 antibodies of the invention.

TG2 has been shown to have an important role in lung fibrosis and TG2 knockout mice show reduced scarring and fibrosis in the bleomycin model. (Keith C. Olsen, Ramil E. Sapinoro, R. M. Kottmann, Ajit A. Kulkarni, Siiri E. lismaa, Gail V. W. Johnson, Thomas H. Thatcher, Richard P. Phipps, and Patricia J. Sime. (2011) Transglutaminase 2 and Its Role in Pulmonary Fibrosis. Am. J of Respiratory & Critical Care Med. 184 0699-707) Migration of cells from TG2 knockout mice on wounding was reduced compared to wild type. Scratch wound assay were performed to assess the effect of humanised and/or chimeric anti-TG2 antibodies of the invention on the rate of wound closure in a layer of normal lung fibroblasts (WI-38 cells).

Scratch Assay Protocol:

WI-38 cells (normal human lung fibroblasts ATCC cat#CCL-75) were plated in a 96 well Image Lock plate (Essen cat#4379) at $2\times10^4$/well in αMEM media (Life Technologies cat#32561) with 10% FBS and grown O/N to >97% confluence. Cells were washed 2× with αMEM media without serum and a scratch wound was generated using an Essen Wound Maker and the manufacturers protocol. The media was removed and replaced with 95 μl/well serum free media. Controls and test antibodies were added to the wells. The plate was placed in an Essen Incucyte and the closure of the wound was analysed using the scratch wound protocol.

Cytochalasin D was used as an assay control at 0.1 μM. R281, a small molecule non-specific transglutaminase inhibitor, was tested at 100 μM. Z DON, a peptide non reversible transglutaminase inhibitor was tested at 10 μM and 100 μM. The commercially available TG2 antibody Cub7402 (ABcam cat#ab2386) was tested at 5 μg/ml. Antibodies of the invention were tested on at least three occasions at various concentrations as indicated. In all experiments controls were Cytochalasin D at 0.1 uM and ZDON at two concentrations to show a dose dependant effect.

Exemplar results of the scratch assays are shown in FIGS. 41 to 44. As can be seen in FIG. 41, Cytochalasin D, R281 and ZDON all inhibited wound closure (ZDON was shown to inhibit in a dose dependant manner) but the antibody Cub7402 did not inhibit wound closure. Humanised BB7, Humanised AB1 and Chimeric DC1 all inhibited wound closure.

Affinities of Chimeric and Humanised Anti TG2 Abs

The binding affinities (Kds and off rates) for a panel of chimeric and humanised Abs of the invention against human TG2 and cyano TG2 were assessed using Biacore techniques. The protocols and results are described below and shown in FIGS. 45 to 47.

Biacore Methods

Recombinant human TG2 was obtained from Zedira GmbH (cat. no.: T002). Recombinant cynomolgus monkey TG2 was obtained from Trenzyme. Surface plasmon resonance (SPR) was measured on a Biacore T200 instrument (GE Healthcare). CM5 chips (GE Healthcare cat. no.: BR-1006-68) were coated with monoclonal mouse anti-human IgG1 (Fc) (MAH) antibody (GE Healthcare cat. no.: BR-1008-39) by amine-coupling as described in the manufacturers instructions. HBS-EP+ buffer (0.01 M HEPES, 0.15 M NaCl, 3 mM EDTA, 0.05% v/v Surfactant P20) and HBS-P+ buffer (0.01 M HEPES, 0.15 M NaCl, 0.05% Surfactant P20) were purchased from GE Healthcare as 10× stocks (cat. nos.: BR-1006-69 and BR-1006-71). Calcium Chloride solution was obtained from Sigma Aldrich (cat. no.:21115).

The method employed to determine the affinity of the anti-TG2 antibodies involved the capture of the chimeric or humanised antibodies on a MAH coated CM5 chip, followed by the injection of a series of TG2 samples in running buffer. The running buffer was 1× HBS-P+ containing 1 mM $CaCl_2$, or 1×HBS-EP+ for calcium-free experiments. Antibody capture was carried out for a contact time of 120 seconds at a flow rate of 10 μl/min resulting in the capture of approximately 40-80 RU. TG2 was injected over the immobilised antibody at concentrations ranging from 25 nM to 400 nM with a contact time up to 600 seconds at a flow rate of 30 μl/min. Dissociation of TG2 was typically measured for up to 5400 seconds (1.5 hours). Regeneration of the chip was then performed using 3 M $MgC_2$, for a contact time of 60 seconds at a flow rate of 30 μl/ml, followed by a 300s stabilisation period before the next sample. For each of human and cynomolgus monkey TG2, at least 5 injections at a variety of concentrations were performed in at least two separate experiments.

Kinetic data were exported from the Biacore T200 Evaluation Software and analysed using GraphPad Prism, where the association phases and dissociation phases were analysed separately using a one phase association model and one-phase exponential decay model respectively. Association rates ($k_{on}$) were calculated for each curve individually, and dissociation rates ($k_{off}$) values from the long dissociation phase data collected. Where $k_{off}$ values were calculated to be $<1\times10^{-5}$ $s^{-1}$, values were set at $1\times10^{-5}$ for analysis, as rates slower than this could not be estimated accurately. Values for $k_{on}$ and $k_{off}$ are presented in the tables below as the mean of the individual calculated values for each antibody for each TG2 species from multiple concentrations+/−1 standard deviation. KD values are calculated as mean $k_{off}$/mean $k_{on}$.

Results of Biacore Experiments

TABLE 25

| Antibody | | Human TG2 | | | | |
|---|---|---|---|---|---|---|
| | | $k_{off}$ ($s^{-1}$) | st. dev | $k_{on}$ ($M^{-1}s^{-1}$) | st. dev | $K_D$ (M) |
| cAB003 | $+Ca^{2+}$ | $<10^{-5}$ | — | $1.7 \times 10^5$ | $3.2 \times 10^4$ | $<6 \times 10^{-11}$ |
| | $-Ca^{2+}$ | $<10^{-5}$ | — | $8.6 \times 10^4$ | $2.1 \times 10^4$ | $<1 \times 10^{-10}$ |
| cBB001 | $+Ca^{2+}$ | $<10^{-5}$ | — | $2.1 \times 10^5$ | $6.9 \times 10^4$ | $<5 \times 10^{-11}$ |
| | $-Ca^{2+}$ | $<10^{-5}$ | — | $1.5 \times 10^5$ | $1.8 \times 10^4$ | $<7 \times 10^{-11}$ |
| hAB004 (hAB001AE) | | $2.4 \times 10^{-5}$ | $1.0 \times 10^{-5}$ | $2.0 \times 10^5$ | $1.4 \times 10^5$ | $1.2 \times 10^{-10}$ |
| hAB005 (hAB001AJ) | | $<10^{-5}$ | — | $1.9 \times 10^5$ | $6.8 \times 10^4$ | $<5 \times 10^{-11}$ |
| hBB001AA | | $<10^{-5}$ | — | $2.7 \times 10^5$ | $1.1 \times 10^5$ | $<4 \times 10^{-11}$ |
| hBB001BB | | $<10^{-5}$ | — | $2.4 \times 10^5$ | $1.2 \times 10^5$ | $<4 \times 10^{-11}$ |
| cDC001 | | $<10^{-5}$ | — | $3.2 \times 10^5$ | $5.7 \times 10^4$ | $<3 \times 10^{-11}$ |
| cDH001 | $+Ca^{2+}$ | $1.8 \times 10^{-5}$ | $4.9 \times 10^{-6}$ | $2.8 \times 10^4$ | $1.3 \times 10^4$ | $6.4 \times 10^{-10}$ |
| | $-Ca^{2+}$ | $4.9 \times 10^{-4}$ | $1.6 \times 10^{-5}$ | $2.1 \times 10^4$ | $1.2 \times 10^4$ | $2.3 \times 10^{-8}$ |
| cDD9001 | $+Ca^{2+}$ | $1.3 \times 10^{-5}$ | $1.8 \times 10^{-6}$ | $3.0 \times 10^4$ | $2.3 \times 10^4$ | $4.3 \times 10^{-10}$ |
| | $-Ca^{2+}$ | $7.1 \times 10^{-5}$ | $1.6 \times 10^{-5}$ | $2.3 \times 10^4$ | $7.6 \times 10^3$ | $3.1 \times 10^{-9}$ |

Table 25 shows the kinetic data obtained against human TG2. Where $k_{off}$ rates were calculated to be less than $10^{-5}$ $s^{-1}$, values were set to $10^{-5}$ $s^{-1}$ for analysis, as rates slower than this could not be accurately determined.

TABLE 26

| Antibody | | Cynomolgus TG2 | | | | |
|---|---|---|---|---|---|---|
| | | $k_{off}$ ($s^{-1}$) | st. dev | $k_{on}$ ($M^{-1}s^{-1}$) | st. dev | $K_D$ (M) |
| cAB003 | $+Ca^{2+}$ | $1.2 \times 10^{-5}$ | $8.1 \times 10^{-6}$ | $2.4 \times 10^5$ | $1.1 \times 10^5$ | $5.0 \times 10^{-11}$ |
| | $-Ca^{2+}$ | $1.3 \times 10^{-5}$ | $1.5 \times 10^{-6}$ | $1.4 \times 10^5$ | $1.9 \times 10^4$ | $9.3 \times 10^{-11}$ |
| cBB001 | $+Ca^{2+}$ | $<10^{-5}$ | — | $2.9 \times 10^5$ | $9.0 \times 10^4$ | $<3 \times 10^{-11}$ |
| | $-Ca^{2+}$ | $<10^{-5}$ | — | $1.9 \times 10^5$ | $2.1 \times 10^4$ | $<5 \times 10^{-11}$ |
| hAB004 (hAB001AE) | | $1.8 \times 10^{-5}$ | $2.3 \times 10^{-6}$ | $1.6 \times 10^5$ | $7.3 \times 10^4$ | $1.1 \times 10^{-11}$ |
| hAB005 (hAB001AJ) | | $3.4 \times 10^{-5}$ | $4.6 \times 10^{-6}$ | $1.4 \times 10^5$ | $4.1 \times 10^4$ | $2.4 \times 10^{-10}$ |
| hBB001AA | | $<10^{-5}$ | — | $3.0 \times 10^5$ | $1.4 \times 10^5$ | $<3 \times 10^{-11}$ |
| hBB001BB | | $3.7 \times 10^{-5}$ | $3.4 \times 10^{-6}$ | $2.7 \times 10^5$ | $1.3 \times 10^5$ | $1.4 \times 10^{-10}$ |
| cDC001 | | $<10^{-5}$ | — | $4.2 \times 10^5$ | $3.3 \times 10^5$ | $2.4 \times 10^{-11}$ |
| cDH001 | $+Ca^{2+}$ | $<10^{-5}$ | — | $1.5 \times 10^4$ | $9.5 \times 10^3$ | $<7 \times 10^{-10}$ |
| | $-Ca^{2+}$ | $6.3 \times 10^{-5}$ | $1.2 \times 10^{-5}$ | $2.6 \times 10^4$ | $1.0 \times 10^4$ | $2.4 \times 10^{-9}$ |
| cDD9001 | $+Ca^{2+}$ | $1.6 \times 10^{-5}$ | $1.4 \times 10^{-5}$ | $3.1 \times 10^4$ | $1.6 \times 10^4$ | $5.2 \times 10^{-10}$ |
| | $-Ca^{2+}$ | $4.1 \times 10^{-5}$ | $1.6 \times 10^{-5}$ | $4.6 \times 10^4$ | $1.3 \times 10^4$ | $8.9 \times 10^{-10}$ |

Table 26 shows the kinetic data obtained against cynomolgus TG2. Where $k_{off}$ rates were calculated to be less than $10^{-5}$ $s^{-1}$, values were set to $10^{-5}$ $s^{-1}$ for analysis, as rates slower than this could not be accurately determined.

Figure 45:
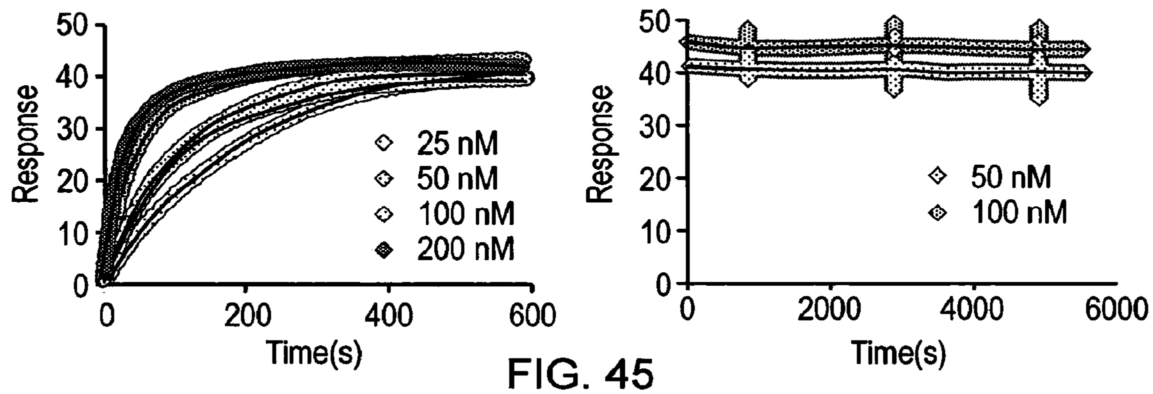

FIGS. 45 to 47 provide example Biacore data sets. As can be seen, the humanised and chimeric antibodies cAB003, cBB001, hAB004, hAB005, hBB001AA, hBB001BB, cDC001 for TG2 have excellent affinity for human and cynomolgus TG2, with KD values of 120 μM or better. The chimeric antibodies cDH001 and cDD9001 exhibit slower association rates to human and cynomolgus TG2 and weaker overall affinity. Examination of a selection of antibodies in the absence of calcium shows that there is little or no effect, except in the case of cDH001 and cDD9001, where binding is weaker due to faster dissociation rates ($k_{off}$).

The invention claimed is:

1. A method of inhibiting human transglutaminase type 2 (TG2)-mediated cross-linking of lysine and glutamine with Nε(γ-glutamyl)lysine isopeptide bonds, the method comprising contacting human TG2 with an antibody that comprises the amino acid sequences set forth in SEQ ID NO: 7 (LCDR1), SEQ ID NO: 17 (LCDR2), SEQ ID NO: 9 (LCDR3), SEQ ID NO: 18 (HCDR1), SEQ ID NO: 15 (HCDR2) and SEQ ID NO: 19 (HCDR3).

2. The method of claim 1, wherein the antibody selectively binds to amino acids 304 to 326 of human TG2 (SEQ ID NO: 2).

3. The method of claim 1, wherein the antibody comprises at least one light chain variable region comprising the amino acid sequence DITMTQSPSSLSASVGDRVTITCKASQDINSYLTWFQQKPGKAPKILIYLVNRLVDGVPSRFSGSGSGQDYALTISSLQPEDFATYYCLQYDDFPYTFGQGTKVEIK (SEQ ID NO: 73); and/or at least one heavy chain variable region comprising the amino acid sequence EVQLLESGGGLVQPGGSLRLSCAASGFTLSTHAMSWVRQAPGKGLEWVATISSGGRSTYYPDSVKGRFTISRDNSKNTLYLQMNSLRAEDTAVYFCARLISTYWGQGTLVTVSS (SEQ ID NO: 75), or an amino acid sequence having at least 90% identity with the amino acid sequence set forth in SEQ ID NO: 73 or the amino acid sequence set forth in SEQ ID NO: 75.

4. The method of claim 1, wherein the antibody has:

a light chain variable region comprising the sequence DITMTQSPSSLSASVGDRVTITCKASQDINSYLTWFQQKPGKAPKILIYLVNRLVDGVPSRFSGSGSGQDYALTISSLQPEDFATYYCLQYDDFPYTFGQGTKVEIK (SEQ ID NO: 73), and a heavy chain variable region comprising the sequence EVQLLESGGGLVQPGGSLRLSCAASGFTLSTHAMSWVRQAPGKGLEWVATISSGGRSTYYPDSVKGRFTISRDNSKNTLYLQMNSLRAEDTAVYFCARLISTYWGQGTLVTVSS (SEQ ID NO: 75).

5. The method of claim 1, wherein the antibody comprises or consists of an intact antibody.

6. The method of claim 1, wherein the antibody is an antigen-binding fragment selected from the group consisting of: a Fv, a single chain Fv (scFv) or a disulfide-bonded Fv; a Fab; and a Fab-like, a Fab' or a $F(ab)_2$.

7. The method according to claim 1, wherein the antibody thereof does not inhibit TG1, TG3, TG13 and/or TG7 activity.

8. The method of claim 1, wherein the antibody is an IgG1, IgG2, IgG3 or IgG4.

9. The method of claim 1, that is an in vivo method.

10. A method of treating fibrosis in an individual comprising administering an antibody or antigen-binding fragment thereof that comprises the amino acid sequences set forth in SEQ ID NO: 7 (LCDR1), SEQ ID NO: 17 (LCDR2), SEQ ID NO: 9 (LCDR3), SEQ ID NO: 18 (HCDR1), SEQ ID NO: 15 (HCDR2) and SEQ ID NO: 19 (HCDR3).

11. A method of inhibiting human transglutaminase type 2 (TG2)-mediated cross-linking of lysine and glutamine with Nε(γ-glutamyl)lysine isopeptide bonds in an individual, the method comprising administering to an individual in need thereof an antibody or antigen-binding fragment thereof that comprises the amino acid sequences set forth in SEQ ID NO: 7 (LCDR1), SEQ ID NO: 17 (LCDR2), SEQ ID NO: 9 (LCDR3), SEQ ID NO: 18 (HCDR1), SEQ ID NO: 15 (HCDR2) and SEQ ID NO: 19 (HCDR3).

* * * * *

SEQUENCE LISTING

```
<160> NUMBER OF SEQ ID NOS: 296

<210> SEQ ID NO 1
<211> LENGTH: 2064
<212> TYPE: DNA
<213> ORGANISM: Homo sapiens
<220> FEATURE:
<221> NAME/KEY: source
<222> LOCATION: (1)..(2064)
<223> OTHER INFORMATION: Human TG2 nucleotide sequence

<400> SEQUENCE: 1

atggccgagg agctggtctt agagaggtgt gatctggagc tggagaccaa tggccgagac      60

caccacacgg ccgacctgtg ccgggagaag ctggtggtgc gacggggcca gcccttctgg     120

ctgaccctgc actttgaggg ccgcaactac gaggccagtg tagacagtct caccttcagt     180

gtcgtgaccg gcccagcccc tagccaggag gccgggacca aggcccgttt tccactaaga     240

gatgctgtgg aggagggtga ctggacagcc accgtggtgg accagcaaga ctgcaccctc     300

tcgctgcagc tcaccacccc ggccaacgcc cccatcggcc tgtatcgcct cagcctggag     360

gcctccactg gctaccaggg atccagcttt gtgctgggcc acttcatttt gctcttcaac     420

gcctggtgcc cagcggatgc tgtgtacctg gactcggaag aggagcggca ggagtatgtc     480

ctcacccagc agggctttat ctaccagggc tcggccaagt tcatcaagaa cataccttgg     540

aattttgggc agtttgaaga tgggatccta gacatctgcc tgatccttct agatgtcaac     600

cccaagttcc tgaagaacgc cggccgtgac tgctcccgcc gcagcagccc cgtctacgtg     660

ggccgggtgg tgagtggcat ggtcaactgc aacgatgacc agggtgtgct gctgggacgc     720

tgggacaaca actacgggga cggcgtcagc cccatgtcct ggatcggcag cgtggacatc     780

ctgcggcgct ggaagaacca cggctgccag cgcgtcaagt atggccagtg ctgggtcttc     840

gccgccgtgg cctgcacagt gctgaggtgc ctgggcatcc ctacccgcgt cgtgaccaac     900

tacaactcgg cccatgacca gaacagcaac cttctcatcg agtacttccg caatgagttt     960

ggggagatcc agggtgacaa gagcgagatg atctggaact tccactgctg ggtggagtcg    1020

tggatgacca ggccggacct gcagccgggg tacgagggct ggcaggccct ggacccaacg    1080

ccccaggaga agagcgaagg gacgtactgc tgtggcccag ttccagttcg tgccatcaag    1140

gagggcgacc tgagcaccaa gtacgatgcg ccctttgtct ttgcggaggt caatgccgac    1200

gtggtagact ggatccagca ggacgatggg tctgtgcaca aatccatcaa ccgttccctg    1260

atcgttgggc tgaagatcag cactaagagc gtgggccgag acgagcggga ggatatcacc    1320

cacacctaca aatacccaga ggggtcctca gaggagaggg aggccttcac aagggcgaac    1380

cacctgaaca aactggccga gaaggaggag acagggatgg ccatgcggat ccgtgtgggc    1440

cagagcatga acatgggcag tgactttgac gtctttgccc acatcaccaa caacaccgct    1500

gaggagtacg tctgccgcct cctgctctgt gcccgcaccg tcagctacaa tgggatcttg    1560

gggcccgagt gtggcaccaa gtacctgctc aacctcaacc tggagccttt ctctgagaag    1620
```

```
agcgttcctc tttgcatcct ctatgagaaa taccgtgact gccttacgga gtccaacctc   1680

atcaaggtgc gggccctcct cgtggagcca gttatcaaca gctacctgct ggctgagagg   1740

gacctctacc tggagaatcc agaaatcaag atccggatcc ttggggagcc caagcagaaa   1800

cgcaagctgg tggctgaggt gtccctgcag aacccgctcc ctgtggccct ggaaggctgc   1860

accttcactg tggagggggc cggcctgact gaggagcaga agacggtgga gatcccagac   1920

cccgtggagg caggggagga agttaaggtg agaatggacc tgctgccgct ccacatgggc   1980

ctccacaagc tggtggtgaa cttcgagagc gacaagctga aggctgtgaa gggcttccgg   2040

aatgtcatca ttggccccgc ctaa                                          2064
```

```
<210> SEQ ID NO 2
<211> LENGTH: 687
<212> TYPE: PRT
<213> ORGANISM: Homo sapiens
<220> FEATURE:
<221> NAME/KEY: MISC_FEATURE
<223> OTHER INFORMATION: Human TG2 Amino Acid sequence

<400> SEQUENCE: 2

Met Ala Glu Glu Leu Val Leu Glu Arg Cys Asp Leu Glu Leu Glu Thr
1               5                   10                  15

Asn Gly Arg Asp His His Thr Ala Asp Leu Cys Arg Glu Lys Leu Val
            20                  25                  30

Val Arg Arg Gly Gln Pro Phe Trp Leu Thr Leu His Phe Glu Gly Arg
        35                  40                  45

Asn Tyr Glu Ala Ser Val Asp Ser Leu Thr Phe Ser Val Val Thr Gly
    50                  55                  60

Pro Ala Pro Ser Gln Glu Ala Gly Thr Lys Ala Arg Phe Pro Leu Arg
65                  70                  75                  80

Asp Ala Val Glu Glu Gly Asp Trp Thr Ala Thr Val Val Asp Gln Gln
                85                  90                  95

Asp Cys Thr Leu Ser Leu Gln Leu Thr Thr Pro Ala Asn Ala Pro Ile
            100                 105                 110

Gly Leu Tyr Arg Leu Ser Leu Glu Ala Ser Thr Gly Tyr Gln Gly Ser
        115                 120                 125

Ser Phe Val Leu Gly His Phe Ile Leu Leu Phe Asn Ala Trp Cys Pro
    130                 135                 140

Ala Asp Ala Val Tyr Leu Asp Ser Glu Glu Glu Arg Gln Glu Tyr Val
145                 150                 155                 160

Leu Thr Gln Gln Gly Phe Ile Tyr Gln Gly Ser Ala Lys Phe Ile Lys
                165                 170                 175

Asn Ile Pro Trp Asn Phe Gly Gln Phe Glu Asp Gly Ile Leu Asp Ile
            180                 185                 190

Cys Leu Ile Leu Leu Asp Val Asn Pro Lys Phe Leu Lys Asn Ala Gly
        195                 200                 205

Arg Asp Cys Ser Arg Arg Ser Ser Pro Val Tyr Val Gly Arg Val Val
    210                 215                 220

Ser Gly Met Val Asn Cys Asn Asp Asp Gln Gly Val Leu Leu Gly Arg
225                 230                 235                 240

Trp Asp Asn Asn Tyr Gly Asp Gly Val Ser Pro Met Ser Trp Ile Gly
                245                 250                 255

Ser Val Asp Ile Leu Arg Arg Trp Lys Asn His Gly Cys Gln Arg Val
            260                 265                 270

Lys Tyr Gly Gln Cys Trp Val Phe Ala Ala Val Ala Cys Thr Val Leu
```

```
        275                 280                 285

Arg Cys Leu Gly Ile Pro Thr Arg Val Val Thr Asn Tyr Asn Ser Ala
    290                 295                 300

His Asp Gln Asn Ser Asn Leu Leu Ile Glu Tyr Phe Arg Asn Glu Phe
305                 310                 315                 320

Gly Glu Ile Gln Gly Asp Lys Ser Glu Met Ile Trp Asn Phe His Cys
                325                 330                 335

Trp Val Glu Ser Trp Met Thr Arg Pro Asp Leu Gln Pro Gly Tyr Glu
            340                 345                 350

Gly Trp Gln Ala Leu Asp Pro Thr Pro Gln Glu Lys Ser Glu Gly Thr
        355                 360                 365

Tyr Cys Cys Gly Pro Val Pro Val Arg Ala Ile Lys Glu Gly Asp Leu
    370                 375                 380

Ser Thr Lys Tyr Asp Ala Pro Phe Val Phe Ala Glu Val Asn Ala Asp
385                 390                 395                 400

Val Val Asp Trp Ile Gln Gln Asp Asp Gly Ser Val His Lys Ser Ile
                405                 410                 415

Asn Arg Ser Leu Ile Val Gly Leu Lys Ile Ser Thr Lys Ser Val Gly
            420                 425                 430

Arg Asp Glu Arg Glu Asp Ile Thr His Thr Tyr Lys Tyr Pro Glu Gly
        435                 440                 445

Ser Ser Glu Glu Arg Glu Ala Phe Thr Arg Ala Asn His Leu Asn Lys
    450                 455                 460

Leu Ala Glu Lys Glu Glu Thr Gly Met Ala Met Arg Ile Arg Val Gly
465                 470                 475                 480

Gln Ser Met Asn Met Gly Ser Asp Phe Asp Val Phe Ala His Ile Thr
                485                 490                 495

Asn Asn Thr Ala Glu Glu Tyr Val Cys Arg Leu Leu Leu Cys Ala Arg
            500                 505                 510

Thr Val Ser Tyr Asn Gly Ile Leu Gly Pro Glu Cys Gly Thr Lys Tyr
        515                 520                 525

Leu Leu Asn Leu Asn Leu Glu Pro Phe Ser Glu Lys Ser Val Pro Leu
    530                 535                 540

Cys Ile Leu Tyr Glu Lys Tyr Arg Asp Cys Leu Thr Glu Ser Asn Leu
545                 550                 555                 560

Ile Lys Val Arg Ala Leu Leu Val Glu Pro Val Ile Asn Ser Tyr Leu
                565                 570                 575

Leu Ala Glu Arg Asp Leu Tyr Leu Glu Asn Pro Glu Ile Lys Ile Arg
            580                 585                 590

Ile Leu Gly Glu Pro Lys Gln Lys Arg Lys Leu Val Ala Glu Val Ser
        595                 600                 605

Leu Gln Asn Pro Leu Pro Val Ala Leu Glu Gly Cys Thr Phe Thr Val
    610                 615                 620

Glu Gly Ala Gly Leu Thr Glu Glu Gln Lys Thr Val Glu Ile Pro Asp
625                 630                 635                 640

Pro Val Glu Ala Gly Glu Glu Val Lys Val Arg Met Asp Leu Leu Pro
                645                 650                 655

Leu His Met Gly Leu His Lys Leu Val Val Asn Phe Glu Ser Asp Lys
            660                 665                 670

Leu Lys Ala Val Lys Gly Phe Arg Asn Val Ile Ile Gly Pro Ala
        675                 680                 685
```

<210> SEQ ID NO 3

```
<211> LENGTH: 2062
<212> TYPE: DNA
<213> ORGANISM: Rattus
<220> FEATURE:
<221> NAME/KEY: source
<222> LOCATION: (1)..(2062)
<223> OTHER INFORMATION: Rat TG2 Nucleotide sequence

<400> SEQUENCE: 3

atggccgagg agctgaacct ggagaggtgc gatttggaga tacaggccaa tggccgtgat     60

caccacacgg ccgacctgtg ccaagagaaa ctggtgctgc ggcgaggcca gcgcttccgg    120

ctgacactgt acttcgaggg ccgtggctat gaggccagcg tggacagact tacatttggt    180

gccgtgaccg gcccagatcc cagtgaagag gcagggacca aggcccgctt ctcactgtct    240

gacgatgtgg aggagggatc ctggtcagcc tctgtgctgg accaacagga caatgtcctc    300

tcgctgcagc tctgcacccc agccaatgct cctgttggcc agtaccgcct cagcctggag    360

acttctactg gctaccaagg ctccagcttc atgctgggtc acttcatcct gctcttcaat    420

gcctggtgcc cagcggatga cgtgtaccta gattcagagg cggagcgccg ggaatacgtc    480

ctcacacagc agggcttcat ctaccagggc tctgtcaagt tcatcaagag tgtgccttgg    540

aactttgggc agtttgagga tgggatcctg gatgcctgcc tgatgctttt ggatgtgaac    600

cccaagttcc tgaaggaccg tagccgggac tgctcacgac gcagcagtcc catctatgtg    660

ggccgcgtgg tgagcggcat ggtcaactgc aatgatgacc agggtgtgct tctgggtcgc    720

tgggacaaca attatgggga cggtatcagt cccatggcct ggattggcag cgtggacatt    780

ctgcggcgct ggaaggaaca cggctgtcag caagtgaagt atggccagtg ctgggtgttt    840

gcggcggtag cctgcacagt gctgcggtgc cttggcatcc ctaccagagt ggtgaccaac    900

tacaactccg cccacgacca gaacagcaac ctgctcatcg agtacttccg aaacgagtac    960

ggggagctgg agagcaacaa gagcgagatg atctggaatt tccactgctg ggtggagtcc   1020

tggatgacca ggccagacct acagccaggc tatgaggggt ggcaggccat tgaccccaca   1080

ccgcaggaga agagcgaagg aacatactgt tgtggcccag tctcagtgcg ggccatcaag   1140

gagggtgacc tgagcaccaa gtatgatgcg tccttcgtgt ttgccgaggt caacgctgat   1200

gtggtggact ggatccggca gtcagatggg tctgtgctca aatccatcaa caattccctg   1260

gtcgtggggc agaagatcag cactaagagc gtgggccgtg atgaccggga ggacatcacc   1320

tatacctaca agtacccaga ggggtcccca gaggagaggg aagtcttcac cagagccaac   1380

cacctgaaca aactggcaga gaaagaggag acaggggtgg ccatgcggat ccgagtgggg   1440

gatggtatga gcttgggcaa tgactttgac gtgtttgccc acatcggcaa cgacacctcg   1500

gagagccgtg agtgccgcct cctgctctgt gcccgcactg tcagctacaa cggcgtgctg   1560

gggcccgagt gtggcactga ggacatcaac ctgaccctgg atccctactc tgagaacagc   1620

atccccctc gcatcctcta cgagaagtac agcggttgcc tgaccgagtc aaacctcatc   1680

aaggtgcggg gtctcctcgt cgagccagcc gctaacagct acctgctggc tgagagagat   1740

ctctacctgg agaatcctga aatcaagatc cggatcctgg gggagcccaa gcagaaccgc   1800

aaactggtgg ctgaggtgtc cctgaagaac ccactttctg attccctgta tgactgtgtc   1860

ttcactgtgg agggggctgg cctgaccaag gaacagaagt ctgtggaggt ctcagaccct   1920

gtgccagcag gagatgcggt caaggtgcgg gttgacctgt tcccgactga tattggcctc   1980

cacaagttgg tggtgaactt ccagtgtgac aagctgaagt cggtcaaggg ttaccggaat   2040

atcatcatcg gcccggccta ag                                             2062
```

<210> SEQ ID NO 4
<211> LENGTH: 686
<212> TYPE: PRT
<213> ORGANISM: Rattus
<220> FEATURE:
<221> NAME/KEY: MISC_FEATURE
<223> OTHER INFORMATION: Rat TG2 Amino Acid sequence

<400> SEQUENCE: 4

```
Met Ala Glu Glu Leu Asn Leu Glu Arg Cys Asp Leu Glu Ile Gln Ala
1               5                   10                  15

Asn Gly Arg Asp His His Thr Ala Asp Leu Cys Gln Glu Lys Leu Val
            20                  25                  30

Leu Arg Arg Gly Gln Arg Phe Arg Leu Thr Leu Tyr Phe Glu Gly Arg
        35                  40                  45

Gly Tyr Glu Ala Ser Val Asp Arg Leu Thr Phe Gly Ala Val Thr Gly
    50                  55                  60

Pro Asp Pro Ser Glu Glu Ala Gly Thr Lys Ala Arg Phe Ser Leu Ser
65                  70                  75                  80

Asp Asp Val Glu Glu Gly Ser Trp Ser Ala Ser Val Leu Asp Gln Gln
                85                  90                  95

Asp Asn Val Leu Ser Leu Gln Leu Cys Thr Pro Ala Asn Ala Pro Val
            100                 105                 110

Gly Gln Tyr Arg Leu Ser Leu Glu Thr Ser Thr Gly Tyr Gln Gly Ser
        115                 120                 125

Ser Phe Met Leu Gly His Phe Ile Leu Leu Phe Asn Ala Trp Cys Pro
    130                 135                 140

Ala Asp Asp Val Tyr Leu Asp Ser Glu Ala Glu Arg Arg Glu Tyr Val
145                 150                 155                 160

Leu Thr Gln Gln Gly Phe Ile Tyr Gln Gly Ser Val Lys Phe Ile Lys
                165                 170                 175

Ser Val Pro Trp Asn Phe Gly Gln Phe Glu Asp Gly Ile Leu Asp Ala
            180                 185                 190

Cys Leu Met Leu Leu Asp Val Asn Pro Lys Phe Leu Lys Asp Arg Ser
        195                 200                 205

Arg Asp Cys Ser Arg Arg Ser Ser Pro Ile Tyr Val Gly Arg Val Val
    210                 215                 220

Ser Gly Met Val Asn Cys Asn Asp Asp Gln Gly Val Leu Leu Gly Arg
225                 230                 235                 240

Trp Asp Asn Asn Tyr Gly Asp Gly Ile Ser Pro Met Ala Trp Ile Gly
                245                 250                 255

Ser Val Asp Ile Leu Arg Arg Trp Lys Glu His Gly Cys Gln Gln Val
            260                 265                 270

Lys Tyr Gly Gln Cys Trp Val Phe Ala Ala Val Ala Cys Thr Val Leu
        275                 280                 285

Arg Cys Leu Gly Ile Pro Thr Arg Val Val Thr Asn Tyr Asn Ser Ala
    290                 295                 300

His Asp Gln Asn Ser Asn Leu Leu Ile Glu Tyr Phe Arg Asn Glu Tyr
305                 310                 315                 320

Gly Glu Leu Glu Ser Asn Lys Ser Glu Met Ile Trp Asn Phe His Cys
                325                 330                 335

Trp Val Glu Ser Trp Met Thr Arg Pro Asp Leu Gln Pro Gly Tyr Glu
            340                 345                 350

Gly Trp Gln Ala Ile Asp Pro Thr Pro Gln Glu Lys Ser Glu Gly Thr
```

```
        355                 360                 365

Tyr Cys Cys Gly Pro Val Ser Val Arg Ala Ile Lys Glu Gly Asp Leu
    370                 375                 380

Ser Thr Lys Tyr Asp Ala Ser Phe Val Phe Ala Glu Val Asn Ala Asp
385                 390                 395                 400

Val Val Asp Trp Ile Arg Gln Ser Asp Gly Ser Val Leu Lys Ser Ile
                405                 410                 415

Asn Asn Ser Leu Val Val Gly Gln Lys Ile Ser Thr Lys Ser Val Gly
            420                 425                 430

Arg Asp Asp Arg Glu Asp Ile Thr Tyr Thr Tyr Lys Tyr Pro Glu Gly
        435                 440                 445

Ser Pro Glu Glu Arg Glu Val Phe Thr Arg Ala Asn His Leu Asn Lys
    450                 455                 460

Leu Ala Glu Lys Glu Glu Thr Gly Val Ala Met Arg Ile Arg Val Gly
465                 470                 475                 480

Asp Gly Met Ser Leu Gly Asn Asp Phe Asp Val Phe Ala His Ile Gly
                485                 490                 495

Asn Asp Thr Ser Glu Ser Arg Glu Cys Arg Leu Leu Leu Cys Ala Arg
            500                 505                 510

Thr Val Ser Tyr Asn Gly Val Leu Gly Pro Glu Cys Gly Thr Glu Asp
        515                 520                 525

Ile Asn Leu Thr Leu Asp Pro Tyr Ser Glu Asn Ser Ile Pro Leu Arg
    530                 535                 540

Ile Leu Tyr Glu Lys Tyr Ser Gly Cys Leu Thr Glu Ser Asn Leu Ile
545                 550                 555                 560

Lys Val Arg Gly Leu Leu Val Glu Pro Ala Ala Asn Ser Tyr Leu Leu
                565                 570                 575

Ala Glu Arg Asp Leu Tyr Leu Glu Asn Pro Glu Ile Lys Ile Arg Ile
            580                 585                 590

Leu Gly Glu Pro Lys Gln Asn Arg Lys Leu Val Ala Glu Val Ser Leu
        595                 600                 605

Lys Asn Pro Leu Ser Asp Ser Leu Tyr Asp Cys Val Phe Thr Val Glu
    610                 615                 620

Gly Ala Gly Leu Thr Lys Glu Gln Lys Ser Val Glu Val Ser Asp Pro
625                 630                 635                 640

Val Pro Ala Gly Asp Ala Val Lys Val Arg Val Asp Leu Phe Pro Thr
                645                 650                 655

Asp Ile Gly Leu His Lys Leu Val Val Asn Phe Gln Cys Asp Lys Leu
            660                 665                 670

Lys Ser Val Lys Gly Tyr Arg Asn Ile Ile Ile Gly Pro Ala
        675                 680                 685
```

<210> SEQ ID NO 5
<211> LENGTH: 2061
<212> TYPE: DNA
<213> ORGANISM: Mus musculus
<220> FEATURE:
<221> NAME/KEY: source
<222> LOCATION: (1)..(2061)
<223> OTHER INFORMATION: Mouse TG2 Nucleotide sequence

<400> SEQUENCE: 5

```
atggcagagg agctgctcct ggagaggtgt gatttggaga ttcaggccaa tggccgtgac      60

caccacacgg ccgacctatg ccaagagaaa ctggtgctgc gtcgtggtca gcgcttccgg     120

ctgactctgt acttcgaggg ccgtggctac gaggccagcg tggacagcct cacgttcggt     180
```

```
gctgtgaccg gcccagatcc cagtgaagag gcagggacca aggcccgctt ctcactgtct    240
gacaatgtgg aggagggatc ttggtcagcc tcagtgctgg accaacagga caatgtcctc    300
tcgctacagc tctgcacccc agccaatgct cctattggcc tgtaccgtct cagcctagag    360
gcttctactg gctaccaggg ctccagcttt gtgctgggcc acttcatcct gctctacaat    420
gcctggtgcc cagccgatga tgtgtaccta gactcagagg aggagcgacg ggaatatgtc    480
cttacgcaac agggcttcat ctaccaaggc tctgtcaagt tcatcaagag tgtgccttgg    540
aactttgggc agttcgagga tggaatcctg gatacctgcc tgatgctctt ggatatgaac    600
cccaagttcc tgaagaaccg tagtcgggac tgctcacgcc gcagcagtcc catctatgtg    660
ggccgcgtgg tgagcgccat ggtcaactgc aatgatgacc agggtgtgct tctgggccgc    720
tgggacaaca actatgggga tggtatcagt cccatggcct ggattggcag tgtggacatt    780
ctgcggcgct ggaaggaaca cggctgtcag caagtgaagt acgggcagtg ctgggtgttt    840
gcagcggtgg cctgcacagt gctgcggtgc ctcggcatcc ctaccagagt ggtgaccaac    900
tacaactccg cccacgacca gaacagcaac ctgctcatcg agtacttccg aaatgagttc    960
ggggagctgg agagcaacaa gagcgagatg atctggaact tccactgctg ggtggagtcc   1020
tggatgacca ggccagacct acagccgggc tatgaggggt ggcaggccat tgaccccaca   1080
ccacaggaga agagcgaagg gacatactgt tgtggcccag tctcagtgcg agccatcaag   1140
gagggagacc tgagtaccaa gtatgatgca cccttcgtgt ttgccgaggt caacgctgat   1200
gtggtggact ggatccggca ggaagatggg tctgtgctca aatccatcaa ccgttccttg   1260
gtcgtggggc agaagatcag cactaagagt gtgggccgtg atgaccggga ggacatcacc   1320
catacctaca agtacccaga ggggtcaccc gaggagaggg aagtcttcac caaggccaac   1380
cacctgaaca aactggcaga gaaagaggag acaggggtgg ccatgcgcat ccgagtgggg   1440
gacagtatga gcatgggcaa cgacttcgac gtgtttgccc acatcggcaa cgacacctcg   1500
gagactcgag agtgtcgtct cctgctctgt gcccgcactg tcagctacaa cggggtgctg   1560
gggcccgagt gtggcactga ggacatcaac ctgaccctgg atccctactc tgagaacagc   1620
atcccacttc gaatcctcta cgagaagtac agcgggtgcc tgacagagtc aaacctcatc   1680
aaggtgcggg gccttctcat cgaaccagct gccaacagct acctgctggc tgagagagat   1740
ctctacctgg agaatcccga aatcaagatc cgggtcctgg gagaacccaa gcaaaaccgc   1800
aaactggtgg ctgaggtgtc cctgaagaac ccactttccg atcccctgta tgactgcatc   1860
ttcactgtgg agggggctgg cctgaccaag gagcagaagt ctgtggaagt ctcagacccg   1920
gtgccagcgg gcgatttggt caaggcacgg gtcgacctgt tcccgactga tattggcctc   1980
cacaagctgg tggtgaactt ccagtgtgac aagctgaagt cggtgaaggg ttaccggaat   2040
gttatcatcg gcccggccta a                                             2061
```

<210> SEQ ID NO 6
<211> LENGTH: 686
<212> TYPE: PRT
<213> ORGANISM: Mus musculus
<220> FEATURE:
<221> NAME/KEY: MISC_FEATURE
<223> OTHER INFORMATION: Mouse TG2 Amino Acid sequence

<400> SEQUENCE: 6

```
Met Ala Glu Glu Leu Leu Leu Glu Arg Cys Asp Leu Glu Ile Gln Ala
1               5                   10                  15
```

```
Asn Gly Arg Asp His His Thr Ala Asp Leu Cys Gln Glu Lys Leu Val
            20                  25                  30

Leu Arg Arg Gly Gln Arg Phe Arg Leu Thr Leu Tyr Phe Glu Gly Arg
        35                  40                  45

Gly Tyr Glu Ala Ser Val Asp Ser Leu Thr Phe Gly Ala Val Thr Gly
    50                  55                  60

Pro Asp Pro Ser Glu Glu Ala Gly Thr Lys Ala Arg Phe Ser Leu Ser
65                  70                  75                  80

Asp Asn Val Glu Glu Gly Ser Trp Ser Ala Ser Val Leu Asp Gln Gln
                85                  90                  95

Asp Asn Val Leu Ser Leu Gln Leu Cys Thr Pro Ala Asn Ala Pro Ile
            100                 105                 110

Gly Leu Tyr Arg Leu Ser Leu Glu Ala Ser Thr Gly Tyr Gln Gly Ser
        115                 120                 125

Ser Phe Val Leu Gly His Phe Ile Leu Leu Tyr Asn Ala Trp Cys Pro
    130                 135                 140

Ala Asp Asp Val Tyr Leu Asp Ser Glu Glu Glu Arg Arg Glu Tyr Val
145                 150                 155                 160

Leu Thr Gln Gln Gly Phe Ile Tyr Gln Gly Ser Val Lys Phe Ile Lys
                165                 170                 175

Ser Val Pro Trp Asn Phe Gly Gln Phe Glu Asp Gly Ile Leu Asp Thr
            180                 185                 190

Cys Leu Met Leu Leu Asp Met Asn Pro Lys Phe Leu Lys Asn Arg Ser
        195                 200                 205

Arg Asp Cys Ser Arg Arg Ser Ser Pro Ile Tyr Val Gly Arg Val Val
    210                 215                 220

Ser Ala Met Val Asn Cys Asn Asp Asp Gln Gly Val Leu Leu Gly Arg
225                 230                 235                 240

Trp Asp Asn Asn Tyr Gly Asp Gly Ile Ser Pro Met Ala Trp Ile Gly
                245                 250                 255

Ser Val Asp Ile Leu Arg Arg Trp Lys Glu His Gly Cys Gln Gln Val
            260                 265                 270

Lys Tyr Gly Gln Cys Trp Val Phe Ala Ala Val Ala Cys Thr Val Leu
        275                 280                 285

Arg Cys Leu Gly Ile Pro Thr Arg Val Val Thr Asn Tyr Asn Ser Ala
    290                 295                 300

His Asp Gln Asn Ser Asn Leu Leu Ile Glu Tyr Phe Arg Asn Glu Phe
305                 310                 315                 320

Gly Glu Leu Glu Ser Asn Lys Ser Glu Met Ile Trp Asn Phe His Cys
                325                 330                 335

Trp Val Glu Ser Trp Met Thr Arg Pro Asp Leu Gln Pro Gly Tyr Glu
            340                 345                 350

Gly Trp Gln Ala Ile Asp Pro Thr Pro Gln Glu Lys Ser Glu Gly Thr
        355                 360                 365

Tyr Cys Cys Gly Pro Val Ser Val Arg Ala Ile Lys Glu Gly Asp Leu
    370                 375                 380

Ser Thr Lys Tyr Asp Ala Pro Phe Val Phe Ala Glu Val Asn Ala Asp
385                 390                 395                 400

Val Val Asp Trp Ile Arg Gln Glu Asp Gly Ser Val Leu Lys Ser Ile
                405                 410                 415

Asn Arg Ser Leu Val Val Gly Gln Lys Ile Ser Thr Lys Ser Val Gly
            420                 425                 430

Arg Asp Asp Arg Glu Asp Ile Thr His Thr Tyr Lys Tyr Pro Glu Gly
```

-continued

```
        435                 440                 445

Ser Pro Glu Glu Arg Glu Val Phe Thr Lys Ala Asn His Leu Asn Lys
    450                 455                 460

Leu Ala Glu Lys Glu Glu Thr Gly Val Ala Met Arg Ile Arg Val Gly
465                 470                 475                 480

Asp Ser Met Ser Met Gly Asn Asp Phe Asp Val Phe Ala His Ile Gly
                485                 490                 495

Asn Asp Thr Ser Glu Thr Arg Glu Cys Arg Leu Leu Leu Cys Ala Arg
            500                 505                 510

Thr Val Ser Tyr Asn Gly Val Leu Gly Pro Glu Cys Gly Thr Glu Asp
        515                 520                 525

Ile Asn Leu Thr Leu Asp Pro Tyr Ser Glu Asn Ser Ile Pro Leu Arg
    530                 535                 540

Ile Leu Tyr Glu Lys Tyr Ser Gly Cys Leu Thr Glu Ser Asn Leu Ile
545                 550                 555                 560

Lys Val Arg Gly Leu Leu Ile Glu Pro Ala Ala Asn Ser Tyr Leu Leu
                565                 570                 575

Ala Glu Arg Asp Leu Tyr Leu Glu Asn Pro Glu Ile Lys Ile Arg Val
            580                 585                 590

Leu Gly Glu Pro Lys Gln Asn Arg Lys Leu Val Ala Glu Val Ser Leu
        595                 600                 605

Lys Asn Pro Leu Ser Asp Pro Leu Tyr Asp Cys Ile Phe Thr Val Glu
    610                 615                 620

Gly Ala Gly Leu Thr Lys Glu Gln Lys Ser Val Glu Val Ser Asp Pro
625                 630                 635                 640

Val Pro Ala Gly Asp Leu Val Lys Ala Arg Val Asp Leu Phe Pro Thr
                645                 650                 655

Asp Ile Gly Leu His Lys Leu Val Val Asn Phe Gln Cys Asp Lys Leu
            660                 665                 670

Lys Ser Val Lys Gly Tyr Arg Asn Val Ile Ile Gly Pro Ala
        675                 680                 685
```

```
<210> SEQ ID NO 7
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AB-1, BB-7 and DC-1 CDR

<400> SEQUENCE: 7

Lys Ala Ser Gln Asp Ile Asn Ser Tyr Leu Thr
1               5                   10


<210> SEQ ID NO 8
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AB-1 CDR

<400> SEQUENCE: 8

Arg Thr Asn Arg Leu Phe Asp
1               5
```

<210> SEQ ID NO 9
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AB-1 and DC-1 CDR

<400> SEQUENCE: 9

Leu Gln Tyr Asp Asp Phe Pro Tyr Thr
1 5

<210> SEQ ID NO 10
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AB-1 and BB-7 CDR

<400> SEQUENCE: 10

Ser Ser Ala Met Ser
1 5

<210> SEQ ID NO 11
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AB-1 CDR

<400> SEQUENCE: 11

Thr Ile Ser Val Gly Gly Gly Lys Thr Tyr Tyr Pro Asp Ser Val Lys
1 5 10 15

Gly

<210> SEQ ID NO 12
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AB-1 CDR

<400> SEQUENCE: 12

Leu Ile Ser Leu Tyr
1 5

<210> SEQ ID NO 13
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: BB-7 CDR - 1

<400> SEQUENCE: 13

```
Leu Thr Asn Arg Leu Met Asp
1               5


<210> SEQ ID NO 14
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: BB-7 CDR - 1

<400> SEQUENCE: 14

Leu Gln Tyr Val Asp Phe Pro Tyr Thr
1               5


<210> SEQ ID NO 15
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: BB-7 CDR

<400> SEQUENCE: 15

Thr Ile Ser Ser Gly Gly Arg Ser Thr Tyr Tyr Pro Asp Ser Val Lys
1               5                   10                  15

Gly


<210> SEQ ID NO 16
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: BB-7 CDR

<400> SEQUENCE: 16

Leu Ile Ser Pro Tyr
1               5


<210> SEQ ID NO 17
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: DC-1 CDR

<400> SEQUENCE: 17

Leu Val Asn Arg Leu Val Asp
1               5


<210> SEQ ID NO 18
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: DC-1 CDR
```

<400> SEQUENCE: 18

Thr His Ala Met Ser
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: DC-1 CDR

<400> SEQUENCE: 19

Leu Ile Ser Thr Tyr
1               5

<210> SEQ ID NO 20
<211> LENGTH: 331
<212> TYPE: PRT
<213> ORGANISM: Homo sapiens
<220> FEATURE:
<221> NAME/KEY: MISC_FEATURE
<223> OTHER INFORMATION: Amino acids 143 to 473 of human TG2

<400> SEQUENCE: 20

```
Cys Pro Ala Asp Ala Val Tyr Leu Asp Ser Glu Glu Glu Arg Gln Glu
1               5                   10                  15

Tyr Val Leu Thr Gln Gln Gly Phe Ile Tyr Gln Gly Ser Ala Lys Phe
            20                  25                  30

Ile Lys Asn Ile Pro Trp Asn Phe Gly Gln Phe Glu Asp Gly Ile Leu
        35                  40                  45

Asp Ile Cys Leu Ile Leu Leu Asp Val Asn Pro Lys Phe Leu Lys Asn
    50                  55                  60

Ala Gly Arg Asp Cys Ser Arg Arg Ser Ser Pro Val Tyr Val Gly Arg
65                  70                  75                  80

Val Val Ser Gly Met Val Asn Cys Asn Asp Asp Gln Gly Val Leu Leu
                85                  90                  95

Gly Arg Trp Asp Asn Asn Tyr Gly Asp Gly Val Ser Pro Met Ser Trp
            100                 105                 110

Ile Gly Ser Val Asp Ile Leu Arg Arg Trp Lys Asn His Gly Cys Gln
        115                 120                 125

Arg Val Lys Tyr Gly Gln Cys Trp Val Phe Ala Ala Val Ala Cys Thr
    130                 135                 140

Val Leu Arg Cys Leu Gly Ile Pro Thr Arg Val Val Thr Asn Tyr Asn
145                 150                 155                 160

Ser Ala His Asp Gln Asn Ser Asn Leu Leu Ile Glu Tyr Phe Arg Asn
                165                 170                 175

Glu Phe Gly Glu Ile Gln Gly Asp Lys Ser Glu Met Ile Trp Asn Phe
            180                 185                 190

His Cys Trp Val Glu Ser Trp Met Thr Arg Pro Asp Leu Gln Pro Gly
        195                 200                 205

Tyr Glu Gly Trp Gln Ala Leu Asp Pro Thr Pro Gln Glu Lys Ser Glu
    210                 215                 220

Gly Thr Tyr Cys Cys Gly Pro Val Pro Val Arg Ala Ile Lys Glu Gly
225                 230                 235                 240

Asp Leu Ser Thr Lys Tyr Asp Ala Pro Phe Val Phe Ala Glu Val Asn
```

```
                245                 250                 255

Ala Asp Val Val Asp Trp Ile Gln Gln Asp Asp Gly Ser Val His Lys
            260                 265                 270

Ser Ile Asn Arg Ser Leu Ile Val Gly Leu Lys Ile Ser Thr Lys Ser
        275                 280                 285

Val Gly Arg Asp Glu Arg Glu Asp Ile Thr His Thr Tyr Lys Tyr Pro
    290                 295                 300

Glu Gly Ser Ser Glu Glu Arg Glu Ala Phe Thr Arg Ala Asn His Leu
305                 310                 315                 320

Asn Lys Leu Ala Glu Lys Glu Glu Thr Gly Met
                325                 330


<210> SEQ ID NO 21
<211> LENGTH: 23
<212> TYPE: PRT
<213> ORGANISM: Homo sapiens
<220> FEATURE:
<221> NAME/KEY: MISC_FEATURE
<223> OTHER INFORMATION: Amino acids 304 to 326 of human TG2

<400> SEQUENCE: 21

Ala His Asp Gln Asn Ser Asn Leu Leu Ile Glu Tyr Phe Arg Asn Glu
1               5                   10                  15

Phe Gly Glu Ile Gln Gly Asp
            20


<210> SEQ ID NO 22
<211> LENGTH: 15
<212> TYPE: PRT
<213> ORGANISM: Homo sapiens
<220> FEATURE:
<221> NAME/KEY: MISC_FEATURE
<223> OTHER INFORMATION: Amino acids 351 to 365 of human TG2

<400> SEQUENCE: 22

Tyr Glu Gly Trp Gln Ala Leu Asp Pro Thr Pro Gln Glu Lys Ser
1               5                   10                  15


<210> SEQ ID NO 23
<211> LENGTH: 18
<212> TYPE: PRT
<213> ORGANISM: Homo sapiens
<220> FEATURE:
<221> NAME/KEY: MISC_FEATURE
<223> OTHER INFORMATION: Amino acids 450 to 467 of human TG2

<400> SEQUENCE: 23

Ser Glu Glu Arg Glu Ala Phe Thr Arg Ala Asn His Leu Asn Lys Leu
1               5                   10                  15

Ala Glu


<210> SEQ ID NO 24
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Antibody or antigen-binding fragment

<400> SEQUENCE: 24

Thr Cys Lys Ala Ser Gln Asp Ile Asn Ser Tyr Leu Thr Trp Phe
1               5                   10                  15
```

<210> SEQ ID NO 25
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Antibody or antigen-binding fragment

<400> SEQUENCE: 25

```
Thr Leu Ile Tyr Arg Thr Asn Arg Leu Phe Asp Gly Val Pro
1               5                   10
```

<210> SEQ ID NO 26
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Antibody or antigen-binding fragment
<220> FEATURE:
<221> NAME/KEY: VARIANT
<222> LOCATION: (15)..(16)
<223> OTHER INFORMATION: Xaa can be any amino acid

<400> SEQUENCE: 26

```
Thr Leu Ile Tyr Arg Thr Asn Arg Leu Phe Asp Gly Val Pro Xaa Xaa
1               5                   10                  15

Phe Ser Gly Ser Gly Ser Gly Gln Asp Phe Phe
            20                  25
```

<210> SEQ ID NO 27
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Antibody or antigen-binding fragment

<400> SEQUENCE: 27

```
Tyr Cys Leu Gln Tyr Asp Asp Phe Pro Tyr Thr Phe Gly
1               5                   10
```

<210> SEQ ID NO 28
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Antibody or antigen-binding fragment

<400> SEQUENCE: 28

```
Phe Thr Leu Ser Ser Ser Ala Met Ser Trp Val Arg
1               5                   10
```

<210> SEQ ID NO 29
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Antibody or antigen-binding fragment
<220> FEATURE:
<221> NAME/KEY: VARIANT
<222> LOCATION: (2)..(2)
<223> OTHER INFORMATION: Xaa can be any amino acid
<220> FEATURE:
<221> NAME/KEY: VARIANT
<222> LOCATION: (4)..(5)
<223> OTHER INFORMATION: Xaa can be any amino acid

<400> SEQUENCE: 29

Cys Xaa Ala Xaa Xaa Phe Thr Leu Ser Ser Ser Ala Met Ser Trp Val
1               5                   10                  15

Arg

<210> SEQ ID NO 30
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Antibody or antigen-binding fragment

<400> SEQUENCE: 30

Trp Val Ala Thr Ile Ser Val Gly Gly Gly Lys Thr Tyr Tyr Pro Asp
1               5                   10                  15

Ser Val Lys Gly Arg Phe Thr Ile Ser Arg
            20                  25

<210> SEQ ID NO 31
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Antibody or antigen-binding fragment
<220> FEATURE:
<221> NAME/KEY: VARIANT
<222> LOCATION: (27)..(27)
<223> OTHER INFORMATION: Xaa can be any amino acid
<220> FEATURE:
<221> NAME/KEY: VARIANT
<222> LOCATION: (29)..(32)
<223> OTHER INFORMATION: Xaa can be any amino acid

<400> SEQUENCE: 31

Trp Val Ala Thr Ile Ser Val Gly Gly Gly Lys Thr Tyr Tyr Pro Asp
1               5                   10                  15

Ser Val Lys Gly Arg Phe Thr Ile Ser Arg Xaa Asn Xaa Xaa Xaa Xaa
            20                  25                  30

Leu

<210> SEQ ID NO 32
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Antibody or antigen-binding fragment

<400> SEQUENCE: 32

```
Tyr Cys Ala Lys Leu Ile Ser Leu Tyr Trp Gly
1               5                   10


<210> SEQ ID NO 33
<211> LENGTH: 74
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Antibody amino acid sequence
<220> FEATURE:
<221> NAME/KEY: VARIANT
<222> LOCATION: (12)..(26)
<223> OTHER INFORMATION: Xaa can be any amino acid
<220> FEATURE:
<221> NAME/KEY: VARIANT
<222> LOCATION: (34)..(65)
<223> OTHER INFORMATION: Xaa can be any amino acid

<400> SEQUENCE: 33

Lys Ala Ser Gln Asp Ile Asn Ser Tyr Leu Thr Xaa Xaa Xaa Xaa Xaa
1               5                   10                  15

Xaa Xaa Xaa Xaa Xaa Xaa Xaa Xaa Xaa Xaa Arg Thr Asn Arg Leu Phe
            20                  25                  30

Asp Xaa Xaa Xaa Xaa Xaa Xaa Xaa Xaa Xaa Xaa Xaa Xaa Xaa Xaa Xaa
        35                  40                  45

Phe Xaa Xaa Xaa Xaa Xaa Xaa Xaa Xaa Xaa Xaa Xaa Xaa Xaa Xaa Xaa
    50                  55                  60

Xaa Leu Gln Tyr Asp Asp Phe Pro Tyr Thr
65                  70


<210> SEQ ID NO 34
<211> LENGTH: 49
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Antibody amino acid sequence
<220> FEATURE:
<221> NAME/KEY: VARIANT
<222> LOCATION: (12)..(48)
<223> OTHER INFORMATION: Xaa can be any amino acid

<400> SEQUENCE: 34

Lys Ala Ser Gln Asp Ile Asn Ser Tyr Leu Thr Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Phe


<210> SEQ ID NO 35
<211> LENGTH: 23
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Antibody amino acid sequence
<220> FEATURE:
```

```
<221> NAME/KEY: VARIANT
<222> LOCATION: (8)..(22)
<223> OTHER INFORMATION: Xaa can be any amino acid.

<400> SEQUENCE: 35

Arg Thr Asn Arg Leu Phe Asp Xaa Xaa Xaa Xaa Xaa Xaa Xaa Xaa Xaa
1               5                   10                  15

Xaa Xaa Xaa Xaa Xaa Xaa Phe
            20


<210> SEQ ID NO 36
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Antibody amino acid sequence
<220> FEATURE:
<221> NAME/KEY: VARIANT
<222> LOCATION: (2)..(17)
<223> OTHER INFORMATION: Xaa can be any amino acid

<400> SEQUENCE: 36

Phe Xaa Xaa Xaa Xaa Xaa Xaa Xaa Xaa Xaa Xaa Xaa Xaa Xaa Xaa Xaa
1               5                   10                  15

Xaa Leu Gln Tyr Asp Asp Phe Pro Tyr Thr
            20                  25


<210> SEQ ID NO 37
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Antibody or antigen-binding fragment

<400> SEQUENCE: 37

Thr Cys Lys Ala Ser Gln Asp Ile Asn Ser Tyr Leu Thr Trp Tyr
1               5                   10                  15


<210> SEQ ID NO 38
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Antibody or antigen-binding fragment

<400> SEQUENCE: 38

Leu Leu Ile Tyr Arg Thr Asn Arg Leu Phe Asp Gly Val Pro
1               5                   10


<210> SEQ ID NO 39
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Antibody or antigen-binding fragment

<400> SEQUENCE: 39
```

```
Ser Leu Ile Tyr Arg Thr Asn Arg Leu Phe Asp Gly Val Pro
1               5                   10


<210> SEQ ID NO 40
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Antibody or antigen-binding fragment
<220> FEATURE:
<221> NAME/KEY: VARIANT
<222> LOCATION: (15)..(16)
<223> OTHER INFORMATION: Xaa can be any amino acid

<400> SEQUENCE: 40

Leu Leu Ile Tyr Arg Thr Asn Arg Leu Phe Asp Gly Val Pro Xaa Xaa
1               5                   10                  15

Phe Ser Gly Ser Gly Ser Gly Gln Asp Phe Phe
            20                  25


<210> SEQ ID NO 41
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Antibody or antigen-binding fragment
<220> FEATURE:
<221> NAME/KEY: VARIANT
<222> LOCATION: (15)..(16)
<223> OTHER INFORMATION: Xaa can be any amino acid.

<400> SEQUENCE: 41

Ser Leu Ile Tyr Arg Thr Asn Arg Leu Phe Asp Gly Val Pro Xaa Xaa
1               5                   10                  15

Phe Ser Gly Ser Gly Ser Gly Gln Asp Phe Phe
            20                  25


<210> SEQ ID NO 42
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Antibody or antigen-binding fragment

<400> SEQUENCE: 42

Phe Thr Phe Ser Ser Ser Ala Met Ser Trp Val Arg
1               5                   10


<210> SEQ ID NO 43
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Antibody or antigen-binding fragment
<220> FEATURE:
<221> NAME/KEY: VARIANT
<222> LOCATION: (2)..(2)
```

```
<223> OTHER INFORMATION: Xaa can be any amino acid
<220> FEATURE:
<221> NAME/KEY: VARIANT
<222> LOCATION: (4)..(5)
<223> OTHER INFORMATION: Xaa can be any amino acid

<400> SEQUENCE: 43

Cys Xaa Ala Xaa Xaa Phe Thr Phe Ser Ser Ser Ala Met Ser Trp Val
1               5                   10                  15

Arg


<210> SEQ ID NO 44
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Antibody or antigen-binding fragment

<400> SEQUENCE: 44

Trp Val Ser Thr Ile Ser Val Gly Gly Gly Lys Thr Tyr Tyr Pro Asp
1               5                   10                  15

Ser Val Lys Gly Arg Phe Thr Ile Ser Arg
            20                  25


<210> SEQ ID NO 45
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Antibody or antigen-binding fragment
<220> FEATURE:
<221> NAME/KEY: VARIANT
<222> LOCATION: (27)..(27)
<223> OTHER INFORMATION: Xaa can be any amino acid
<220> FEATURE:
<221> NAME/KEY: VARIANT
<222> LOCATION: (29)..(32)
<223> OTHER INFORMATION: Xaa can be any amino acid

<400> SEQUENCE: 45

Trp Val Ser Thr Ile Ser Val Gly Gly Gly Lys Thr Tyr Tyr Pro Asp
1               5                   10                  15

Ser Val Lys Gly Arg Phe Thr Ile Ser Arg Xaa Asn Xaa Xaa Xaa Xaa
            20                  25                  30

Leu


<210> SEQ ID NO 46
<211> LENGTH: 107
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AB-1 light chain variable region

<400> SEQUENCE: 46

Asp Ile Gln Met Thr Gln Thr Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30
```

```
Leu Thr Trp Phe Gln Gln Lys Pro Gly Lys Ser Pro Lys Thr Leu Ile
        35                  40                  45

Tyr Arg Thr Asn Arg Leu Phe Asp Gly Val Pro Ser Arg Phe Ser Gly
    50                  55                  60

Ser Gly Ser Gly Gln Asp Phe Phe Leu Thr Ile Ser Ser Leu Glu Tyr
65                  70                  75                  80

Glu Asp Met Gly Ile Tyr Tyr Cys Leu Gln Tyr Asp Asp Phe Pro Tyr
                85                  90                  95

Thr Phe Gly Gly Gly Thr Lys Leu Glu Ile Lys
            100                 105


<210> SEQ ID NO 47
<211> LENGTH: 107
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AB-1 light chain variable region

<400> SEQUENCE: 47

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Thr Trp Phe Gln Gln Lys Pro Gly Lys Ser Pro Lys Thr Leu Ile
        35                  40                  45

Tyr Arg Thr Asn Arg Leu Phe Asp Gly Val Pro Ser Arg Phe Ser Gly
    50                  55                  60

Ser Gly Ser Gly Gln Asp Phe Phe Leu Thr Ile Ser Ser Leu Glu Tyr
65                  70                  75                  80

Glu Asp Met Gly Ile Tyr Tyr Cys Leu Gln Tyr Asp Asp Phe Pro Tyr
                85                  90                  95

Thr Phe Gly Gly Gly Thr Lys Leu Glu Ile Lys
            100                 105


<210> SEQ ID NO 48
<211> LENGTH: 107
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AB-1_VK

<400> SEQUENCE: 48

Glu Ile Val Leu Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Thr Trp Phe Gln Gln Lys Pro Gly Lys Ser Pro Lys Thr Leu Ile
        35                  40                  45

Tyr Arg Thr Asn Arg Leu Phe Asp Gly Val Pro Ser Arg Phe Ser Gly
    50                  55                  60

Ser Gly Ser Gly Gln Asp Phe Phe Leu Thr Ile Ser Ser Leu Glu Tyr
65                  70                  75                  80

Glu Asp Met Gly Ile Tyr Tyr Cys Leu Gln Tyr Asp Asp Phe Pro Tyr
```

```
                85                  90                  95

Thr Phe Gly Gly Gly Thr Lys Leu Glu Ile Lys
            100                 105


<210> SEQ ID NO 49
<211> LENGTH: 107
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AB-1_VK1

<400> SEQUENCE: 49

Asp Ile Gln Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Thr Trp Phe Gln Gln Lys Pro Gly Lys Ser Pro Lys Thr Leu Ile
        35                  40                  45

Tyr Arg Thr Asn Arg Leu Phe Asp Gly Val Pro Ser Arg Phe Ser Gly
    50                  55                  60

Ser Gly Ser Gly Gln Asp Phe Phe Leu Thr Ile Ser Ser Leu Glu Tyr
65                  70                  75                  80

Glu Asp Met Gly Ile Tyr Tyr Cys Leu Gln Tyr Asp Asp Phe Pro Tyr
                85                  90                  95

Thr Phe Gly Gly Gly Thr Lys Leu Glu Ile Lys
            100                 105


<210> SEQ ID NO 50
<211> LENGTH: 107
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: hAB-1_RKE

<400> SEQUENCE: 50

Glu Ile Val Leu Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Thr Trp Tyr Gln Gln Lys Pro Gly Lys Ala Pro Lys Leu Leu Ile
        35                  40                  45

Tyr Arg Thr Asn Arg Leu Phe Asp Gly Val Pro Ser Arg Phe Ser Gly
    50                  55                  60

Ser Gly Ser Gly Thr Asp Phe Phe Phe Thr Ile Ser Ser Leu Gln Pro
65                  70                  75                  80

Glu Asp Phe Gly Thr Tyr Tyr Cys Leu Gln Tyr Asp Asp Phe Pro Tyr
                85                  90                  95

Thr Phe Gly Gly Gly Thr Lys Leu Glu Ile Lys
            100                 105


<210> SEQ ID NO 51
<211> LENGTH: 107
<212> TYPE: PRT
<213> ORGANISM: Artificial Sequence
<220> FEATURE:
```

<223> OTHER INFORMATION: Synthetic peptide
<220> FEATURE:
<221> NAME/KEY: MISC_FEATURE
<223> OTHER INFORMATION: hAB-1_RKJ

<400> SEQUENCE: 51

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Thr Trp Phe Gln Gln Lys Pro Gly Lys Ala Pro Lys Ser Leu Ile
        35                  40                  45

Tyr Arg Thr Asn Arg Leu Phe Asp Gly Val Pro Ser Arg Phe Ser Gly
    50                  55                  60

Ser Gly Ser Gly Thr Asp Phe Phe Leu Thr Ile Ser Ser Leu Gln Pro
65                  70                  75                  80

Glu Asp Phe Ala Thr Tyr Tyr Cys Leu Gln Tyr Asp Asp Phe Pro Tyr
                85                  90                  95

Thr Phe Gly Gln Gly Thr Lys Val Glu Ile Lys
            100                 105
```

<210> SEQ ID NO 52
<211> LENGTH: 114
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AB-1 heavy chain variable region

<400> SEQUENCE: 52

```
Glu Val Gln Leu Glu Glu Ser Gly Gly Gly Leu Val Lys Pro Gly Gly
1               5                   10                  15

Ser Leu Lys Leu Ser Cys Ala Ala Ser Gly Phe Thr Leu Ser Ser Ser
            20                  25                  30

Ala Met Ser Trp Val Arg Gln Thr Pro Asp Arg Arg Leu Glu Trp Val
        35                  40                  45

Ala Thr Ile Ser Val Gly Gly Gly Lys Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ser Glu Asp Thr Ala Met Tyr Tyr Cys
                85                  90                  95

Ala Lys Leu Ile Ser Leu Tyr Trp Gly Gln Gly Thr Thr Leu Thr Val
            100                 105                 110

Ser Ser
```

<210> SEQ ID NO 53
<211> LENGTH: 114
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AB-1 heavy chain variable region

<400> SEQUENCE: 53

```
Glu Val Gln Leu Val Glu Ser Gly Gly Gly Leu Val Lys Pro Gly Gly
1               5                   10                  15
```

Ser Leu Lys Leu Ser Cys Ala Ala Ser Gly Phe Thr Leu Ser Ser Ser
20 25 30

Ala Met Ser Trp Val Arg Gln Thr Pro Asp Arg Arg Leu Glu Trp Val
35 40 45

Ala Thr Ile Ser Val Gly Gly Gly Lys Thr Tyr Tyr Pro Asp Ser Val
50 55 60

Lys Gly Arg Phe Thr Ile Ser Arg Asp Asn Ala Lys Asn Thr Leu Tyr
65 70 75 80

Leu Gln Met Asn Ser Leu Arg Ser Glu Asp Thr Ala Met Tyr Tyr Cys
85 90 95

Ala Lys Leu Ile Ser Leu Tyr Trp Gly Gln Gly Thr Thr Leu Thr Val
100 105 110

Ser Ser

<210> SEQ ID NO 54
<211> LENGTH: 114
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AB-1_VH

<400> SEQUENCE: 54

Glu Val Gln Leu Gln Glu Ser Gly Gly Gly Leu Val Lys Pro Gly Gly
1 5 10 15

Ser Leu Lys Leu Ser Cys Ala Ala Ser Gly Phe Thr Leu Ser Ser Ser
20 25 30

Ala Met Ser Trp Val Arg Gln Thr Pro Asp Arg Arg Leu Glu Trp Val
35 40 45

Ala Thr Ile Ser Val Gly Gly Gly Lys Thr Tyr Tyr Pro Asp Ser Val
50 55 60

Lys Gly Arg Phe Thr Ile Ser Arg Asp Asn Ala Lys Asn Thr Leu Tyr
65 70 75 80

Leu Gln Met Asn Ser Leu Arg Ser Glu Asp Thr Ala Met Tyr Tyr Cys
85 90 95

Ala Lys Leu Ile Ser Leu Tyr Trp Gly Gln Gly Thr Thr Leu Thr Val
100 105 110

Ser Ser

<210> SEQ ID NO 55
<211> LENGTH: 114
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: hAB-1_RHA

<400> SEQUENCE: 55

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Ser
20 25 30

Ala Met Ser Trp Val Arg Gln Ala Pro Gly Lys Gly Leu Glu Trp Val
35 40 45

```
Ser Thr Ile Ser Val Gly Gly Gly Lys Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Ile Ser Leu Tyr Trp Gly Gln Gly Thr Leu Val Thr Val
            100                 105                 110

Ser Ser


<210> SEQ ID NO 56
<211> LENGTH: 74
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Antibody amino acid sequence
<220> FEATURE:
<221> NAME/KEY: VARIANT
<222> LOCATION: (12)..(26)
<223> OTHER INFORMATION: Xaa can be any amino acid
<220> FEATURE:
<221> NAME/KEY: VARIANT
<222> LOCATION: (34)..(65)
<223> OTHER INFORMATION: Xaa can be any amino acid

<400> SEQUENCE: 56

Lys Ala Ser Gln Asp Ile Asn Ser Tyr Leu Thr Xaa Xaa Xaa Xaa Xaa
1               5                   10                  15

Xaa Xaa Xaa Xaa Xaa Xaa Xaa Xaa Xaa Xaa Leu Thr Asn Arg Leu Met
            20                  25                  30

Asp Xaa Xaa Xaa Xaa Xaa Xaa Xaa Xaa Xaa Xaa Xaa Xaa Xaa Xaa Phe
        35                  40                  45

Xaa Xaa Xaa Xaa Xaa Xaa Xaa Xaa Xaa Xaa Xaa Xaa Xaa Xaa Xaa Xaa
    50                  55                  60

Xaa Leu Gln Tyr Val Asp Phe Pro Tyr Thr
65                  70


<210> SEQ ID NO 57
<211> LENGTH: 48
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Antibody amino acid sequence
<220> FEATURE:
<221> NAME/KEY: VARIANT
<222> LOCATION: (12)..(47)
<223> OTHER INFORMATION: Xaa can be any amino acid

<400> SEQUENCE: 57

Lys Ala Ser Gln Asp Ile Asn Ser Tyr Leu Thr Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Phe
        35                  40                  45


<210> SEQ ID NO 58
<211> LENGTH: 22
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Antibody amino acid sequence
<220> FEATURE:
<221> NAME/KEY: VARIANT
<222> LOCATION: (8)..(21)
<223> OTHER INFORMATION: Xaa can be any amino acid.

<400> SEQUENCE: 58

Leu Thr Asn Arg Leu Met Asp Xaa Xaa Xaa Xaa Xaa Xaa Xaa Xaa Xaa
1               5                   10                  15

Xaa Xaa Xaa Xaa Xaa Phe
            20


<210> SEQ ID NO 59
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Antibody amino acid sequence
<220> FEATURE:
<221> NAME/KEY: VARIANT
<222> LOCATION: (2)..(18)
<223> OTHER INFORMATION: Xaa can be any amino acid

<400> SEQUENCE: 59

Phe Xaa Xaa Xaa Xaa Xaa Xaa Xaa Xaa Xaa Xaa Xaa Xaa Xaa Xaa Xaa
1               5                   10                  15

Xaa Xaa Leu Gln Tyr Val Asp Phe Pro Tyr Thr
            20                  25


<210> SEQ ID NO 60
<211> LENGTH: 107
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: BB-7 light chain variable region

<400> SEQUENCE: 60

Ala Ile Lys Met Thr Gln Ser Pro Ser Ser Met Tyr Ala Ser Leu Gly
1               5                   10                  15

Glu Arg Val Ile Ile Thr Cys Lys Ala Ser Gln Asp Ile Asn Ser Tyr
            20                  25                  30

Leu Thr Trp Phe Gln Gln Lys Pro Gly Lys Ser Pro Lys Thr Leu Ile
        35                  40                  45

Tyr Leu Thr Asn Arg Leu Met Asp Gly Val Pro Ser Arg Phe Ser Gly
    50                  55                  60

Ser Gly Ser Gly Gln Glu Phe Leu Leu Thr Ile Ser Gly Leu Glu His
65                  70                  75                  80

Glu Asp Met Gly Ile Tyr Tyr Cys Leu Gln Tyr Val Asp Phe Pro Tyr
                85                  90                  95

Thr Phe Gly Gly Gly Thr Lys Leu Glu Ile Lys
            100                 105


<210> SEQ ID NO 61
```

```
<211> LENGTH: 114
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: BB-7 heavy chain variable region

<400> SEQUENCE: 61

Ala Val Gln Leu Val Glu Ser Gly Gly Gly Leu Val Lys Pro Gly Gly
1               5                   10                  15

Ser Leu Lys Leu Ser Cys Ala Ala Ser Gly Ile Ile Phe Ser Ser Ser
            20                  25                  30

Ala Met Ser Trp Val Arg Gln Thr Pro Glu Lys Arg Leu Glu Trp Val
        35                  40                  45

Ala Thr Ile Ser Ser Gly Gly Arg Ser Thr Tyr Tyr Pro Asp Ser Val
    50                  55                  60

Lys Gly Arg Phe Thr Val Ser Arg Asp Ser Ala Lys Asn Thr Leu Tyr
65                  70                  75                  80

Leu Gln Met Asp Ser Leu Arg Ser Glu Asp Thr Ala Ile Tyr Tyr Cys
                85                  90                  95

Ala Lys Leu Ile Ser Pro Tyr Trp Gly Gln Gly Thr Thr Leu Thr Val
            100                 105                 110

Ser Ser


<210> SEQ ID NO 62
<211> LENGTH: 107
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: BB-7 light chain variable region (humanised)

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Thr Trp Phe Gln Gln Lys Pro Gly Lys Ala Pro Lys Ser Leu Ile
        35                  40                  45

Tyr Leu Thr Asn Arg Leu Met Asp Gly Val Pro Ser Arg Phe Ser Gly
    50                  55                  60

Ser Gly Ser Gly Thr Asp Phe Phe Leu Thr Ile Ser Ser Leu Gln Pro
65                  70                  75                  80

Glu Asp Phe Ala Thr Tyr Tyr Cys Leu Gln Tyr Val Asp Phe Pro Tyr
                85                  90                  95

Thr Phe Gly Gln Gly Thr Lys Val Glu Ile Lys
            100                 105


<210> SEQ ID NO 63
<211> LENGTH: 107
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: BB-7 light chain variable region (humanised)
```

<400> SEQUENCE: 63

```
Asp Ile Lys Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Thr Trp Phe Gln Gln Lys Pro Gly Lys Ala Pro Lys Thr Leu Ile
        35                  40                  45

Tyr Leu Thr Asn Arg Leu Met Asp Gly Val Pro Ser Arg Phe Ser Gly
    50                  55                  60

Ser Gly Ser Gly Gln Glu Phe Leu Leu Thr Ile Ser Ser Leu Gln Pro
65                  70                  75                  80

Glu Asp Phe Ala Thr Tyr Tyr Cys Leu Gln Tyr Val Asp Phe Pro Tyr
                85                  90                  95

Thr Phe Gly Gln Gly Thr Lys Val Glu Ile Lys
            100                 105
```

<210> SEQ ID NO 64
<211> LENGTH: 114
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: BB-7 heavy chain variable region (humanised)

<400> SEQUENCE: 64

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Ala Met Ser Trp Val Arg Gln Ala Pro Gly Lys Gly Leu Glu Trp Val
        35                  40                  45

Ser Thr Ile Ser Ser Gly Gly Arg Ser Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Ile Ser Pro Tyr Trp Gly Gln Gly Thr Leu Val Thr Val
            100                 105                 110

Ser Ser
```

<210> SEQ ID NO 65
<211> LENGTH: 114
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: BB-7 heavy chain variable region (humanised)

<400> SEQUENCE: 65

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Ile Ile Phe Ser Ser Ser
            20                  25                  30

Ala Met Ser Trp Val Arg Gln Ala Pro Gly Lys Gly Leu Glu Trp Val
```

```
        35                  40                  45

Ala Thr Ile Ser Ser Gly Gly Arg Ser Thr Tyr Tyr Pro Asp Ser Val
    50                  55                  60

Lys Gly Arg Phe Thr Val Ser Arg Asp Ser Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Ile Ser Pro Tyr Trp Gly Gln Gly Thr Leu Val Thr Val
            100                 105                 110

Ser Ser


<210> SEQ ID NO 66
<211> LENGTH: 74
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Antibody amino acid sequence
<220> FEATURE:
<221> NAME/KEY: VARIANT
<222> LOCATION: (12)..(26)
<223> OTHER INFORMATION: Xaa can be any amino acid
<220> FEATURE:
<221> NAME/KEY: VARIANT
<222> LOCATION: (34)..(65)
<223> OTHER INFORMATION: Xaa can be any amino acid

<400> SEQUENCE: 66

Lys Ala Ser Gln Asp Ile Asn Ser Tyr Leu Thr Xaa Xaa Xaa Xaa Xaa
1               5                   10                  15

Xaa Xaa Xaa Xaa Xaa Xaa Xaa Xaa Xaa Xaa Leu Val Asn Arg Leu Val
            20                  25                  30

Asp Xaa Xaa Xaa Xaa Xaa Xaa Xaa Xaa Xaa Xaa Xaa Xaa Xaa Xaa Xaa
        35                  40                  45

Ala Xaa Xaa Xaa Xaa Xaa Xaa Xaa Xaa Xaa Xaa Xaa Xaa Xaa Xaa Xaa
    50                  55                  60

Xaa Leu Gln Tyr Asp Asp Phe Pro Tyr Thr
65                  70


<210> SEQ ID NO 67
<211> LENGTH: 49
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Antibody amino acid sequence
<220> FEATURE:
<221> NAME/KEY: VARIANT
<222> LOCATION: (12)..(48)
<223> OTHER INFORMATION: Xaa can be any amino acid

<400> SEQUENCE: 67

Lys Ala Ser Gln Asp Ile Asn Ser Tyr Leu Thr Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Ala
```

<210> SEQ ID NO 68
<211> LENGTH: 23
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Antibody amino acid sequence
<220> FEATURE:
<221> NAME/KEY: VARIANT
<222> LOCATION: (8)..(22)
<223> OTHER INFORMATION: Xaa can be any amino acid.

<400> SEQUENCE: 68

```
Leu Val Asn Arg Leu Val Asp Xaa Xaa Xaa Xaa Xaa Xaa Xaa Xaa Xaa
1               5                   10                  15

Xaa Xaa Xaa Xaa Xaa Xaa Ala
            20
```

<210> SEQ ID NO 69
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Antibody amino acid sequence
<220> FEATURE:
<221> NAME/KEY: VARIANT
<222> LOCATION: (2)..(17)
<223> OTHER INFORMATION: Xaa can be any amino acid

<400> SEQUENCE: 69

```
Ala Xaa Xaa Xaa Xaa Xaa Xaa Xaa Xaa Xaa Xaa Xaa Xaa Xaa Xaa Xaa
1               5                   10                  15

Xaa Leu Gln Tyr Asp Asp Phe Pro Tyr Thr
            20                  25
```

<210> SEQ ID NO 70
<211> LENGTH: 107
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: DC-1 light chain variable region

<400> SEQUENCE: 70

```
Asp Ile Thr Met Thr Gln Ser Pro Ser Ser Ile Tyr Ala Ser Leu Gly
1               5                   10                  15

Glu Arg Val Thr Ile Thr Cys Lys Ala Ser Gln Asp Ile Asn Ser Tyr
            20                  25                  30

Leu Thr Trp Phe Gln Gln Lys Pro Gly Lys Ser Pro Lys Ile Leu Ile
        35                  40                  45

Tyr Leu Val Asn Arg Leu Val Asp Gly Val Pro Ser Arg Phe Ser Gly
    50                  55                  60

Ser Gly Ser Gly Gln Asp Tyr Ala Leu Thr Ile Ser Ser Leu Glu Tyr
65                  70                  75                  80

Glu Asp Met Gly Ile Tyr Tyr Cys Leu Gln Tyr Asp Asp Phe Pro Tyr
                85                  90                  95

Thr Phe Gly Gly Gly Thr Lys Leu Glu Ile Lys
```

```
            100                 105


<210> SEQ ID NO 71
<211> LENGTH: 114
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: DC-1 heavy chain variable region

<400> SEQUENCE: 71

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Leu Ser Thr His
            20                  25                  30

Ala Met Ser Trp Val Arg Gln Thr Pro Glu Lys Arg Leu Glu Trp Val
        35                  40                  45

Ala Thr Ile Ser Ser Gly Gly Arg Ser Thr Tyr Tyr Pro Asp Ser Val
    50                  55                  60

Lys Gly Arg Phe Thr Ile Ser Arg Asp Asn Val Lys Asn Thr Leu Tyr
65                  70                  75                  80

Leu Gln Leu Ser Ser Leu Arg Ser Glu Asp Thr Ala Val Tyr Phe Cys
                85                  90                  95

Ala Arg Leu Ile Ser Thr Tyr Trp Gly Gln Gly Thr Thr Leu Thr Val
            100                 105                 110

Ser Ser


<210> SEQ ID NO 72
<211> LENGTH: 107
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: DC-1 light chain variable region (humanised)

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Thr Trp Phe Gln Gln Lys Pro Gly Lys Ala Pro Lys Ser Leu Ile
        35                  40                  45

Tyr Leu Val Asn Arg Leu Val Asp Gly Val Pro Ser Arg Phe Ser Gly
    50                  55                  60

Ser Gly Ser Gly Thr Asp Phe Phe Leu Thr Ile Ser Ser Leu Gln Pro
65                  70                  75                  80

Glu Asp Phe Ala Thr Tyr Tyr Cys Leu Gln Tyr Asp Asp Phe Pro Tyr
                85                  90                  95

Thr Phe Gly Gln Gly Thr Lys Val Glu Ile Lys
            100                 105


<210> SEQ ID NO 73
<211> LENGTH: 107
<212> TYPE: PRT
<213> ORGANISM: Artificial Sequence
<220> FEATURE:
<223> OTHER INFORMATION: Synthetic peptide
```

<220> FEATURE:
<221> NAME/KEY: MISC_FEATURE
<223> OTHER INFORMATION: DC-1 light chain variable region (humanised)

<400> SEQUENCE: 73

```
Asp Ile Thr Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Thr Trp Phe Gln Gln Lys Pro Gly Lys Ala Pro Lys Ile Leu Ile
        35                  40                  45

Tyr Leu Val Asn Arg Leu Val Asp Gly Val Pro Ser Arg Phe Ser Gly
    50                  55                  60

Ser Gly Ser Gly Gln Asp Tyr Ala Leu Thr Ile Ser Ser Leu Gln Pro
65                  70                  75                  80

Glu Asp Phe Ala Thr Tyr Tyr Cys Leu Gln Tyr Asp Asp Phe Pro Tyr
                85                  90                  95

Thr Phe Gly Gln Gly Thr Lys Val Glu Ile Lys
            100                 105
```

<210> SEQ ID NO 74
<211> LENGTH: 114
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: DC-1 heavy chain variable region (humanised)

<400> SEQUENCE: 74

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr His
            20                  25                  30

Ala Met Ser Trp Val Arg Gln Ala Pro Gly Lys Gly Leu Glu Trp Val
        35                  40                  45

Ser Thr Ile Ser Ser Gly Gly Arg Ser Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Ile Ser Thr Tyr Trp Gly Gln Gly Thr Leu Val Thr Val
            100                 105                 110

Ser Ser
```

<210> SEQ ID NO 75
<211> LENGTH: 114
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: DC-1 heavy chain variable region (humanised)

<400> SEQUENCE: 75

```
Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Leu Ser Thr His
            20                  25                  30

Ala Met Ser Trp Val Arg Gln Ala Pro Gly Lys Gly Leu Glu Trp Val
        35                  40                  45

Ala Thr Ile Ser Ser Gly Gly Arg Ser Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Leu Ile Ser Thr Tyr Trp Gly Gln Gly Thr Leu Val Thr Val
            100                 105                 110

Ser Ser


<210> SEQ ID NO 76
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Antibody or antigen-binding fragment
<220> FEATURE:
<221> NAME/KEY: VARIANT
<222> LOCATION: (1)..(2)
<223> OTHER INFORMATION: Xaa can be any amino acid
<220> FEATURE:
<221> NAME/KEY: VARIANT
<222> LOCATION: (6)..(6)
<223> OTHER INFORMATION: Xaa can be any amino acid

<400> SEQUENCE: 76

Xaa Xaa Asn Arg Leu Xaa Asp
1               5


<210> SEQ ID NO 77
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Antibody or antigen-binding fragment
<220> FEATURE:
<221> NAME/KEY: VARIANT
<222> LOCATION: (4)..(4)
<223> OTHER INFORMATION: Xaa can be any amino acid.

<400> SEQUENCE: 77

Leu Gln Tyr Xaa Asp Phe Pro Tyr Thr
1               5


<210> SEQ ID NO 78
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Antibody or antigen-binding fragment
<220> FEATURE:
<221> NAME/KEY: VARIANT
<222> LOCATION: (1)..(2)
<223> OTHER INFORMATION: Xaa can be any amino acid
```

<400> SEQUENCE: 78

Xaa Xaa Ala Met Ser
1 5

<210> SEQ ID NO 79
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Antibody or antigen-binding fragment
<220> FEATURE:
<221> NAME/KEY: VARIANT
<222> LOCATION: (4)..(4)
<223> OTHER INFORMATION: Xaa can be any amino acid
<220> FEATURE:
<221> NAME/KEY: VARIANT
<222> LOCATION: (7)..(8)
<223> OTHER INFORMATION: Xaa can be any amino acid

<400> SEQUENCE: 79

Thr Ile Ser Xaa Gly Gly Xaa Xaa Thr Tyr Tyr Pro Asp Ser Val Lys
1 5 10 15

Gly

<210> SEQ ID NO 80
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Antibody or antigen-binding fragment
<220> FEATURE:
<221> NAME/KEY: VARIANT
<222> LOCATION: (4)..(4)
<223> OTHER INFORMATION: Xaa can be any amino acid

<400> SEQUENCE: 80

Leu Ile Ser Xaa Tyr
1 5

<210> SEQ ID NO 81
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Antibody or antigen-binding fragment
<220> FEATURE:
<221> NAME/KEY: VARIANT
<222> LOCATION: (1)..(1)
<223> OTHER INFORMATION: May also be Gln or Arg
<220> FEATURE:
<221> NAME/KEY: VARIANT
<222> LOCATION: (5)..(5)
<223> OTHER INFORMATION: May also be Gly
<220> FEATURE:
<221> NAME/KEY: VARIANT
<222> LOCATION: (7)..(7)
<223> OTHER INFORMATION: May also be Ser or Arg
<220> FEATURE:
<221> NAME/KEY: VARIANT
<222> LOCATION: (8)..(8)
<223> OTHER INFORMATION: May also be Asn
<220> FEATURE:
<221> NAME/KEY: VARIANT
<222> LOCATION: (11)..(11)
<223> OTHER INFORMATION: May also be Asn or Ala

<400> SEQUENCE: 81

Lys Ala Ser Gln Asp Ile Asn Ser Tyr Leu Thr
1 5 10

<210> SEQ ID NO 82
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Antibody or antigen-binding fragment
<220> FEATURE:
<221> NAME/KEY: VARIANT
<222> LOCATION: (1)..(1)
<223> OTHER INFORMATION: May also be Leu or Val or Asp or Ala
<220> FEATURE:
<221> NAME/KEY: VARIANT
<222> LOCATION: (2)..(2)
<223> OTHER INFORMATION: May also be Val or Ala
<220> FEATURE:
<221> NAME/KEY: VARIANT
<222> LOCATION: (3)..(3)
<223> OTHER INFORMATION: May also be Ser
<220> FEATURE:
<221> NAME/KEY: VARIANT
<222> LOCATION: (4)..(4)
<223> OTHER INFORMATION: May also be Asn
<220> FEATURE:
<221> NAME/KEY: VARIANT
<222> LOCATION: (6)..(6)
<223> OTHER INFORMATION: May also be Met or, Val, or Glu or Gln
<220> FEATURE:
<221> NAME/KEY: VARIANT
<222> LOCATION: (7)..(7)
<223> OTHER INFORMATION: May also be Thr or Ser

<400> SEQUENCE: 82

Arg Thr Asn Arg Leu Phe Asp
1 5

<210> SEQ ID NO 83
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Antibody or antigen-binding fragment
<220> FEATURE:
<221> NAME/KEY: VARIANT
<222> LOCATION: (1)..(1)
<223> OTHER INFORMATION: May also be Gln
<220> FEATURE:
<221> NAME/KEY: VARIANT
<222> LOCATION: (3)..(3)
<223> OTHER INFORMATION: May also be His.
<220> FEATURE:
<221> NAME/KEY: VARIANT
<222> LOCATION: (4)..(4)
<223> OTHER INFORMATION: May also be Val or Asn.
<220> FEATURE:
<221> NAME/KEY: VARIANT
<222> LOCATION: (5)..(5)
<223> OTHER INFORMATION: May also be Thr.
<220> FEATURE:
<221> NAME/KEY: VARIANT
<222> LOCATION: (6)..(6)
<223> OTHER INFORMATION: May also be Tyr.
<220> FEATURE:

<221> NAME/KEY: VARIANT
<222> LOCATION: (8)..(8)
<223> OTHER INFORMATION: May also be Leu or Trp.

<400> SEQUENCE: 83

Leu Gln Tyr Asp Asp Phe Pro Tyr Thr
1 5

<210> SEQ ID NO 84
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Antibody or antigen-binding fragment
<220> FEATURE:
<221> NAME/KEY: VARIANT
<222> LOCATION: (1)..(1)
<223> OTHER INFORMATION: May also be Thr
<220> FEATURE:
<221> NAME/KEY: VARIANT
<222> LOCATION: (2)..(2)
<223> OTHER INFORMATION: May also be His or Tyr

<400> SEQUENCE: 84

Ser Ser Ala Met Ser
1 5

<210> SEQ ID NO 85
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Antibody or antigen-binding fragment
<220> FEATURE:
<221> NAME/KEY: VARIANT
<222> LOCATION: (1)..(1)
<223> OTHER INFORMATION: May also be Ala
<220> FEATURE:
<221> NAME/KEY: VARIANT
<222> LOCATION: (4)..(4)
<223> OTHER INFORMATION: May also be Ser or Gly
<220> FEATURE:
<221> NAME/KEY: VARIANT
<222> LOCATION: (5)..(5)
<223> OTHER INFORMATION: May also be Ser
<220> FEATURE:
<221> NAME/KEY: VARIANT
<222> LOCATION: (7)..(7)
<223> OTHER INFORMATION: May also be Arg
<220> FEATURE:
<221> NAME/KEY: VARIANT
<222> LOCATION: (8)..(8)
<223> OTHER INFORMATION: May also be Ser
<220> FEATURE:
<221> NAME/KEY: VARIANT
<222> LOCATION: (12)..(12)
<223> OTHER INFORMATION: May also be Ala

<400> SEQUENCE: 85

Thr Ile Ser Val Gly Gly Gly Lys Thr Tyr Tyr Pro Asp Ser Val Lys
1 5 10 15

Gly

<210> SEQ ID NO 86
<211> LENGTH: 5
<212> TYPE: PRT

<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Antibody or antigen-binding fragment
<220> FEATURE:
<221> NAME/KEY: VARIANT
<222> LOCATION: (1)..(1)
<223> OTHER INFORMATION: May also be Asp
<220> FEATURE:
<221> NAME/KEY: VARIANT
<222> LOCATION: (2)..(2)
<223> OTHER INFORMATION: May also be Gly
<220> FEATURE:
<221> NAME/KEY: VARIANT
<222> LOCATION: (3)..(3)
<223> OTHER INFORMATION: May also be Gly
<220> FEATURE:
<221> NAME/KEY: VARIANT
<222> LOCATION: (4)..(4)
<223> OTHER INFORMATION: May also be Pro or Thr or Val

<400> SEQUENCE: 86

```
Leu Ile Ser Leu Tyr
1               5
```

<210> SEQ ID NO 87
<211> LENGTH: 106
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: DD-9 light chain variable region

<400> SEQUENCE: 87

```
Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Asp Tyr Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Gly Ala Glu
65                  70                  75                  80

Asp Ala Ala Thr Tyr Tyr Cys Gln Gln Trp Asn Ser Ser Pro Leu Thr
                85                  90                  95

Phe Gly Ala Gly Thr Lys Leu Glu Leu Lys
            100                 105
```

<210> SEQ ID NO 88
<211> LENGTH: 119
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: DD-9 heavy chain variable region

<400> SEQUENCE: 88

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
```

```
            20                  25                  30

Gly Met Gly Val Ser Trp Ile Arg Gln Ser Ser Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Ile Thr Ile Ser Lys Asp Ser Ser Ser Asn Gln Val
65                  70                  75                  80

Phe Leu Lys Ile Thr Ser Val Asp Thr Ala Asp Thr Ala Thr Tyr Tyr
                85                  90                  95

Cys Ala Arg Ser Trp Thr Thr Ala Pro Phe Ala Phe Trp Gly Gln Gly
            100                 105                 110

Thr Leu Val Thr Val Ser Ala
        115


<210> SEQ ID NO 89
<211> LENGTH: 106
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: DH-2 light chain variable region

<400> SEQUENCE: 89

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Phe Tyr Cys Gln Gln Trp Ser Ser Ser Pro Leu Thr
                85                  90                  95

Phe Gly Ala Gly Thr Lys Leu Glu Leu Lys
            100                 105


<210> SEQ ID NO 90
<211> LENGTH: 119
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: DH-2 heavy chain variable region

<400> SEQUENCE: 90

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Asp Lys Arg Tyr Asn Pro Ser
    50                  55                  60
```

```
Leu Lys Ser Arg Leu Thr Ile Ser Lys Asp Thr Ser Ser Asn Gln Val
65                  70                  75                  80

Phe Leu Lys Ile Thr Ser Val Asp Thr Ala Asp Thr Ala Thr Tyr Tyr
                85                  90                  95

Cys Ala Arg Ser Gly Thr Thr Ala Pro Phe Ala Tyr Trp Gly Gln Gly
            100                 105                 110

Thr Leu Val Thr Val Ser Ala
        115


<210> SEQ ID NO 91
<211> LENGTH: 321
<212> TYPE: DNA
<213> ORGANISM: Artificial Sequence
<220> FEATURE:
<223> OTHER INFORMATION: Isolated polynucleotide

<400> SEQUENCE: 91

gacatccaga tgacacagac tccatcttcc atgtatgcat ctctaggaga gagagtcact     60

atcacttgca aggcgagtca ggacattaat agctatttaa cctggttcca gcagaaacca    120

gggaaatctc ctaagaccct gatctatcgt acaaatagat tgtttgatgg ggtcccatcc    180

aggttcagtg gcagtggatc tgggcaagat ttttttctca ccatcagcag cctggaatat    240

gaagatatgg gaatttatta ttgtctacag tatgatgact ttccgtacac gttcggaggg    300

gggaccaaac tggaaataaa a                                              321


<210> SEQ ID NO 92
<211> LENGTH: 342
<212> TYPE: DNA
<213> ORGANISM: Artificial Sequence
<220> FEATURE:
<223> OTHER INFORMATION: Isolated polynucleotide

<400> SEQUENCE: 92

gaagtacagc tggaggagtc aggggggggc ttagtgaagc ctggagggtc cctgaaactc     60

tcctgtgcag cctctggatt cactctcagt tcctctgcca tgtcttgggt tcgccagact    120

ccggacagga ggctggagtg ggtcgcaacc attagtgttg gtggtggtaa aacctactat    180

ccagacagtg tgaagggtcg cttcaccatc tccagagaca atgccaagaa caccctctat    240

ctgcaaatga acagtctgag gtctgaggac acggccatgt attactgtgc aaaactaatc    300

agtctctact ggggccaagg caccactctc acagtctcct ca                       342


<210> SEQ ID NO 93
<211> LENGTH: 321
<212> TYPE: DNA
<213> ORGANISM: Artificial Sequence
<220> FEATURE:
<223> OTHER INFORMATION: Isolated polynucleotide

<400> SEQUENCE: 93

gccatcaaga tgacccagtc tccatcttcc atgtatgcat ctctaggaga gagagtcatc     60

atcacttgca aggcgagtca ggacataaat agttatttaa cctggttcca acagaaacca    120

ggaaagtctc ctaagaccct gatctatctt acaaatagat tgatggatgg ggtcccatca    180

aggttcagtg gcagtggatc tgggcaagaa tttttactca ccatcagcgg cctggaacat    240

gaagatatgg gcatttatta ttgtctccag tatgttgact ttccgtacac gttcggaggg    300

gggaccaagc tggaaataaa a                                              321
```

<210> SEQ ID NO 94
<211> LENGTH: 342
<212> TYPE: DNA
<213> ORGANISM: Artificial Sequence
<220> FEATURE:
<223> OTHER INFORMATION: Isolated polynucleotide

<400> SEQUENCE: 94
gcagtgcaac tggtagagtc tgggggaggc ttggtgaagc ctggagggtc cctgaaactc 60
tcctgtgcag cctctggaat cattttcagt tcctctgcca tgtcttgggt tcgccagact 120
ccggaaaaga gactggagtg ggtcgcaact attagtagtg gtggtcgttc cacctactat 180
ccagacagtg tgaagggtcg attcaccgtc tccagagaca gtgccaagaa caccctatac 240
ctgcaaatgg acagtctgag gtctgaggac acggccattt attactgtgc aaaactaatc 300
agtccctact ggggccaagg caccactctc acagtctcct ca 342

<210> SEQ ID NO 95
<211> LENGTH: 321
<212> TYPE: DNA
<213> ORGANISM: Artificial Sequence
<220> FEATURE:
<223> OTHER INFORMATION: Isolated polynucleotide

<400> SEQUENCE: 95
gacatcacga tgacccagtc tccatcttcc atatatgcat ctctgggaga gagagtcact 60
atcacttgca aggcgagtca ggacattaat agctatttaa cctggttcca gcagaaacca 120
gggaaatctc ctaagatcct gatctatctt gtaaatagat tggtagatgg ggtcccatca 180
aggttcagtg gcagtggatc tggcaagat tatgctctca ccatcagcag tctggaatat 240
gaagatatgg gaatttatta ttgtctacaa tatgatgact ttccgtacac gttcggaggg 300
gggaccaagc tggaaataaa a 321

<210> SEQ ID NO 96
<211> LENGTH: 342
<212> TYPE: DNA
<213> ORGANISM: Artificial Sequence
<220> FEATURE:
<223> OTHER INFORMATION: Isolated polynucleotide

<400> SEQUENCE: 96
gaagtgcagt tggtggagtc tgggggaggc ttagtgaagc ctggagggtc cctgaaactc 60
tcctgtgcag cctctggatt cactctcagt acccatgcca tgtcttgggt tcgccagact 120
ccggagaaga ggctggagtg ggtcgcaacc attagtagtg gtggtcgttc cacctactat 180
ccagacagtg tgaagggtcg attcactatc tccagagaca atgtcaagaa caccctatat 240
ctgcaactga gcagtctgag gtctgaggac acggccgtgt atttctgtgc aagactaatc 300
agtacctact ggggccaagg caccactctc acagtctcct ca 342

<210> SEQ ID NO 97
<211> LENGTH: 39
<212> TYPE: DNA
<213> ORGANISM: Artificial Sequence
<220> FEATURE:
<223> OTHER INFORMATION: Isolated polynucleotide

<400> SEQUENCE: 97
gcgcgcgcta gctgcccagc ggatgctgtg tacctggac 39

<210> SEQ ID NO 98

<211> LENGTH: 39
<212> TYPE: DNA
<213> ORGANISM: Artificial Sequence
<220> FEATURE:
<223> OTHER INFORMATION: Isolated polynucleotide

<400> SEQUENCE: 98
gcgcgcaagc ttcatccctg tctcctcctt ctcggccag 39

<210> SEQ ID NO 99
<211> LENGTH: 25
<212> TYPE: DNA
<213> ORGANISM: Artificial Sequence
<220> FEATURE:
<223> OTHER INFORMATION: Isolated polynucleotide

<400> SEQUENCE: 99
atggccgagg agctggtctt agaga 25

<210> SEQ ID NO 100
<211> LENGTH: 26
<212> TYPE: DNA
<213> ORGANISM: Artificial Sequence
<220> FEATURE:
<223> OTHER INFORMATION: Isolated polynucleotide

<400> SEQUENCE: 100
ggcggggcca atgatgacat tccgga 26

<210> SEQ ID NO 101
<211> LENGTH: 29
<212> TYPE: DNA
<213> ORGANISM: Artificial Sequence
<220> FEATURE:
<223> OTHER INFORMATION: Isolated polynucleotide
<220> FEATURE:
<221> NAME/KEY: misc_feature
<222> LOCATION: (18)..(18)
<223> OTHER INFORMATION: n can be any nucleotide

<400> SEQUENCE: 101
cgcgcgctcg agsargtnma gctgsagtc 29

<210> SEQ ID NO 102
<211> LENGTH: 32
<212> TYPE: DNA
<213> ORGANISM: Artificial Sequence
<220> FEATURE:
<223> OTHER INFORMATION: Isolated polynucleotide
<220> FEATURE:
<221> NAME/KEY: misc_feature
<222> LOCATION: (18)..(18)
<223> OTHER INFORMATION: n can be any nucleotide

<400> SEQUENCE: 102
cgcgcgctcg agsargtnma gctgsagsag tc 32

<210> SEQ ID NO 103
<211> LENGTH: 43
<212> TYPE: DNA
<213> ORGANISM: Artificial Sequence
<220> FEATURE:
<223> OTHER INFORMATION: Mouse-G1 primer

<400> SEQUENCE: 103
aggcgcagta ctacaatccc tgggcacaat ttcttgtcc acc 43

<210> SEQ ID NO 104
<211> LENGTH: 39
<212> TYPE: DNA
<213> ORGANISM: Artificial Sequence
<220> FEATURE:
<223> OTHER INFORMATION: Mouse-G2a primer

<400> SEQUENCE: 104
aggcgcagta ctacagggct tgattgtggg ccctctggg 39

<210> SEQ ID NO 105
<211> LENGTH: 40
<212> TYPE: DNA
<213> ORGANISM: Artificial Sequence
<220> FEATURE:
<223> OTHER INFORMATION: Mouse-G2b primer

<400> SEQUENCE: 105
aggcgcagta ctacaggggt tgattgttga aatgggcccg 40

<210> SEQ ID NO 106
<211> LENGTH: 32
<212> TYPE: DNA
<213> ORGANISM: Artificial Sequence
<220> FEATURE:
<223> OTHER INFORMATION: VK1 primer

<400> SEQUENCE: 106
cgctgcgagc tcgatattgt gatgacbcag dc 32

<210> SEQ ID NO 107
<211> LENGTH: 32
<212> TYPE: DNA
<213> ORGANISM: Artificial Sequence
<220> FEATURE:
<223> OTHER INFORMATION: VK2 primer

<400> SEQUENCE: 107
cgctgcgagc tcgagrttkt gatgacccar ac 32

<210> SEQ ID NO 108
<211> LENGTH: 32
<212> TYPE: DNA
<213> ORGANISM: Artificial Sequence
<220> FEATURE:
<223> OTHER INFORMATION: VK3 primer

<400> SEQUENCE: 108
cgctgcgagc tcgaaaatgt gctcacccag tc 32

<210> SEQ ID NO 109
<211> LENGTH: 32
<212> TYPE: DNA
<213> ORGANISM: Artificial Sequence
<220> FEATURE:
<223> OTHER INFORMATION: VK4 primer

<400> SEQUENCE: 109
cgctgcgagc tcgayattgt gatgacacag tc 32

<210> SEQ ID NO 110
<211> LENGTH: 32
<212> TYPE: DNA
<213> ORGANISM: Artificial Sequence
<220> FEATURE:
<223> OTHER INFORMATION: VK5 primer

<400> SEQUENCE: 110
cgctgcgagc tcgacatcca gatgacacag ac 32

<210> SEQ ID NO 111
<211> LENGTH: 32
<212> TYPE: DNA
<213> ORGANISM: Artificial Sequence
<220> FEATURE:
<223> OTHER INFORMATION: VK6 primer

<400> SEQUENCE: 111
cgctgcgagc tcgayattgt gctsacycar tc 32

<210> SEQ ID NO 112
<211> LENGTH: 32
<212> TYPE: DNA
<213> ORGANISM: Artificial Sequence
<220> FEATURE:
<223> OTHER INFORMATION: VK7 primer

<400> SEQUENCE: 112
cgctgcgagc tcgacatcca gatgacycar tc 32

<210> SEQ ID NO 113
<211> LENGTH: 32
<212> TYPE: DNA
<213> ORGANISM: Artificial Sequence
<220> FEATURE:
<223> OTHER INFORMATION: VK8 primer

<400> SEQUENCE: 113
cgctgcgagc tccaaattgt tctcacccag tc 32

<210> SEQ ID NO 114
<211> LENGTH: 34
<212> TYPE: DNA
<213> ORGANISM: Artificial Sequence
<220> FEATURE:
<223> OTHER INFORMATION: K-CONST primer

<400> SEQUENCE: 114
gcgccgtcta gaattaacac tcattcctgt tgaa 34

<210> SEQ ID NO 115
<211> LENGTH: 114
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AB_VHc
<220> FEATURE:
<221> NAME/KEY: VARIANT
<222> LOCATION: (5)..(5)
<223> OTHER INFORMATION: Xaa can be any amino acid

<400> SEQUENCE: 115

Glu Val Gln Leu Xaa Glu Ser Gly Gly Gly Leu Val Lys Pro Gly Gly
1 5 10 15

Ser Leu Lys Leu Ser Cys Ala Ala Ser Gly Phe Thr Leu Ser Ser Ser
20 25 30

Ala Met Ser Trp Val Arg Gln Thr Pro Asp Arg Arg Leu Glu Trp Val
35 40 45

Ala Thr Ile Ser Val Gly Gly Gly Lys Thr Tyr Tyr Pro Asp Ser Val

```
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ser Glu Asp Thr Ala Met Tyr Tyr Cys
                85                  90                  95

Ala Lys Leu Ile Ser Leu Tyr Trp Gly Gln Gly Thr Thr Leu Thr Val
            100                 105                 110

Ser Ser


<210> SEQ ID NO 116
<211> LENGTH: 115
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AF062260

<400> SEQUENCE: 116

Cys Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Ser Ser
            20                  25                  30

Tyr Ala Met Ser Trp Val Arg Gln Ala Pro Gly Lys Gly Leu Glu Trp
        35                  40                  45

Val Ser Ala Ile Ser Gly Ser Gly Gly Ser Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Asp Gly Gly Val Tyr Trp Gly Gln Gly Thr Leu Val Thr
            100                 105                 110

Val Ser Ser
        115


<210> SEQ ID NO 117
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AB_VHc 5 Angstrom Proximity Residues

<400> SEQUENCE: 117

Glu Val Gln Leu Cys Ala Phe Thr Leu Ser Trp Val Arg Trp Val Ala
1               5                   10                  15

Arg Phe Thr Ile Ser Arg Asn Leu Tyr Cys Ala Lys Trp Gly
            20                  25                  30


<210> SEQ ID NO 118
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AF062260 5 Angstrom Proximity Residues
```

<400> SEQUENCE: 118

```
Glu Val Gln Leu Cys Ala Phe Thr Phe Ser Trp Val Arg Trp Val Ser
1               5                   10                  15

Arg Phe Thr Ile Ser Arg Asn Leu Tyr Cys Ala Lys Trp Gly
            20                  25                  30
```

<210> SEQ ID NO 119
<211> LENGTH: 98
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Z12347.seq

<400> SEQUENCE: 119

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys
```

<210> SEQ ID NO 120
<211> LENGTH: 98
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AF062260.seq

<400> SEQUENCE: 120

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg
```

<210> SEQ ID NO 121
<211> LENGTH: 107
<212> TYPE: PRT

```
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AB_VKc

<400> SEQUENCE: 121

Glu Ile Val Leu Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Thr Trp Phe Gln Gln Lys Pro Gly Lys Ser Pro Lys Thr Leu Ile
        35                  40                  45

Tyr Arg Thr Asn Arg Leu Phe Asp Gly Val Pro Ser Arg Phe Ser Gly
    50                  55                  60

Ser Gly Ser Gly Gln Asp Phe Phe Leu Thr Ile Ser Ser Leu Glu Tyr
65                  70                  75                  80

Glu Asp Met Gly Ile Tyr Tyr Cys Leu Gln Tyr Asp Asp Phe Pro Tyr
                85                  90                  95

Thr Phe Gly Gly Gly Thr Lys Leu Glu Ile Lys
            100                 105


<210> SEQ ID NO 122
<211> LENGTH: 107
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AY247656

<400> SEQUENCE: 122

Glu Ile Val Leu Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Gly Thr Tyr Tyr Cys Gln Gln Tyr Asn Thr Tyr Pro Leu
                85                  90                  95

Thr Phe Gly Gly Gly Thr Lys Leu Glu Ile Lys
            100                 105


<210> SEQ ID NO 123
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AB_VKc 5 Angstrom Proximity Residues

<400> SEQUENCE: 123

Glu Ile Val Leu Thr Gln Thr Cys Trp Phe Thr Leu Ile Tyr Gly Val
1               5                   10                  15
```

```
Pro Phe Ser Gly Ser Gly Ser Gly Gln Asp Phe Phe Tyr Cys Phe Gly
            20                  25                  30


<210> SEQ ID NO 124
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AY247656 5 Angstrom Proximity Residues

<400> SEQUENCE: 124

Glu Ile Val Leu Thr Gln Thr Cys Trp Tyr Leu Leu Ile Tyr Gly Val
1               5                   10                  15

Pro Phe Ser Gly Ser Gly Ser Gly Thr Asp Phe Thr Tyr Cys Phe Gly
            20                  25                  30


<210> SEQ ID NO 125
<211> LENGTH: 96
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: X93620.seq

<400> SEQUENCE: 125

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Pro
                85                  90                  95


<210> SEQ ID NO 126
<211> LENGTH: 96
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AY247656.seq

<400> SEQUENCE: 126

Glu Ile Val Leu Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60
```

```
Ser Gly Ser Gly Thr Asp Phe Thr Phe Thr Ile Ser Ser Leu Gln Pro
65                  70                  75                  80

Glu Asp Phe Gly Thr Tyr Tyr Cys Gln Gln Tyr Asn Thr Tyr Pro Leu
                85                  90                  95


<210> SEQ ID NO 127
<211> LENGTH: 107
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AB_VKc

<400> SEQUENCE: 127

Asp Ile Gln Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Thr Trp Phe Gln Gln Lys Pro Gly Lys Ser Pro Lys Thr Leu Ile
        35                  40                  45

Tyr Arg Thr Asn Arg Leu Phe Asp Gly Val Pro Ser Arg Phe Ser Gly
    50                  55                  60

Ser Gly Ser Gly Gln Asp Phe Phe Leu Thr Ile Ser Ser Leu Glu Tyr
65                  70                  75                  80

Glu Asp Met Gly Ile Tyr Tyr Cys Leu Gln Tyr Asp Asp Phe Pro Tyr
                85                  90                  95

Thr Phe Gly Gly Gly Thr Lys Leu Glu Ile Lys
            100                 105


<210> SEQ ID NO 128
<211> LENGTH: 107
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AF193851

<400> SEQUENCE: 128

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Phe Gln Gln Lys Pro Gly Lys Ala Pro Lys Ser Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Thr Tyr Pro Trp
                85                  90                  95

Thr Phe Gly Gln Gly Thr Lys Val Glu Ile Lys
            100                 105


<210> SEQ ID NO 129
<211> LENGTH: 32
<212> TYPE: PRT
<213> ORGANISM: Artificial Sequence
```

<220> FEATURE:
<223> OTHER INFORMATION: Synthetic peptide
<220> FEATURE:
<221> NAME/KEY: MISC_FEATURE
<223> OTHER INFORMATION: AB_VKc 5 Angstrom Proximity Residues

<400> SEQUENCE: 129

Asp Ile Gln Met Thr Gln Thr Cys Trp Phe Thr Leu Ile Tyr Gly Val
1               5                   10                  15

Pro Phe Ser Gly Ser Gly Ser Gly Gln Asp Phe Phe Tyr Cys Phe Gly
            20                  25                  30

<210> SEQ ID NO 130
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AF193851 5 Angstrom Proximity Residues

<400> SEQUENCE: 130

Asp Ile Gln Met Thr Gln Thr Cys Trp Phe Ser Leu Ile Tyr Gly Val
1               5                   10                  15

Pro Phe Ser Gly Ser Gly Ser Gly Thr Asp Phe Thr Tyr Cys Phe Gly
            20                  25                  30

<210> SEQ ID NO 131
<211> LENGTH: 96
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: J00248.seq

<400> SEQUENCE: 131

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

<210> SEQ ID NO 132
<211> LENGTH: 96
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AF193851.seq

<400> SEQUENCE: 132

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Gln Gly Ile Arg Asn Tyr
            20                  25                  30

Leu Ala Trp Phe Gln Gln Lys Pro Gly Lys Ala Pro Lys Ser Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Thr Tyr Pro Trp
                85                  90                  95


<210> SEQ ID NO 133
<211> LENGTH: 114
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AB_VHc
<220> FEATURE:
<221> NAME/KEY: VARIANT
<222> LOCATION: (5)..(5)
<223> OTHER INFORMATION: Xaa can be any amino acid

<400> SEQUENCE: 133

Glu Val Gln Leu Xaa Glu Ser Gly Gly Gly Leu Val Lys Pro Gly Gly
1               5                   10                  15

Ser Leu Lys Leu Ser Cys Ala Ala Ser Gly Phe Thr Leu Ser Ser Ser
            20                  25                  30

Ala Met Ser Trp Val Arg Gln Thr Pro Asp Arg Arg Leu Glu Trp Val
        35                  40                  45

Ala Thr Ile Ser Val Gly Gly Gly Lys Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ser Glu Asp Thr Ala Met Tyr Tyr Cys
                85                  90                  95

Ala Lys Leu Ile Ser Leu Tyr Trp Gly Gln Gly Thr Thr Leu Thr Val
            100                 105                 110

Ser Ser


<210> SEQ ID NO 134
<211> LENGTH: 114
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AB_RHA

<400> SEQUENCE: 134

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Ala Met Ser Trp Val Arg Gln Ala Pro Gly Lys Gly Leu Glu Trp Val
        35                  40                  45

Ser Thr Ile Ser Val Gly Gly Gly Lys Thr Tyr Tyr Pro Asp Ser Val
```

```
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Ile Ser Leu Tyr Trp Gly Gln Gly Thr Leu Val Thr Val
            100                 105                 110

Ser Ser


<210> SEQ ID NO 135
<211> LENGTH: 107
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AB_VKc

<400> SEQUENCE: 135

Glu Ile Val Leu Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Thr Trp Phe Gln Gln Lys Pro Gly Lys Ser Pro Lys Thr Leu Ile
        35                  40                  45

Tyr Arg Thr Asn Arg Leu Phe Asp Gly Val Pro Ser Arg Phe Ser Gly
    50                  55                  60

Ser Gly Ser Gly Gln Asp Phe Phe Leu Thr Ile Ser Ser Leu Glu Tyr
65                  70                  75                  80

Glu Asp Met Gly Ile Tyr Tyr Cys Leu Gln Tyr Asp Asp Phe Pro Tyr
                85                  90                  95

Thr Phe Gly Gly Gly Thr Lys Leu Glu Ile Lys
            100                 105


<210> SEQ ID NO 136
<211> LENGTH: 107
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AB_RKE

<400> SEQUENCE: 136

Glu Ile Val Leu Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Thr Trp Tyr Gln Gln Lys Pro Gly Lys Ala Pro Lys Leu Leu Ile
        35                  40                  45

Tyr Arg Thr Asn Arg Leu Phe Asp Gly Val Pro Ser Arg Phe Ser Gly
    50                  55                  60

Ser Gly Ser Gly Thr Asp Phe Phe Phe Thr Ile Ser Ser Leu Gln Pro
65                  70                  75                  80

Glu Asp Phe Gly Thr Tyr Tyr Cys Leu Gln Tyr Asp Asp Phe Pro Tyr
                85                  90                  95

Thr Phe Gly Gly Gly Thr Lys Leu Glu Ile Lys
```

100 105

<210> SEQ ID NO 137
<211> LENGTH: 107
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AB_RKJ

<400> SEQUENCE: 137

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Thr Trp Phe Gln Gln Lys Pro Gly Lys Ala Pro Lys Ser Leu Ile
        35                  40                  45

Tyr Arg Thr Asn Arg Leu Phe Asp Gly Val Pro Ser Arg Phe Ser Gly
    50                  55                  60

Ser Gly Ser Gly Thr Asp Phe Phe Leu Thr Ile Ser Ser Leu Gln Pro
65                  70                  75                  80

Glu Asp Phe Ala Thr Tyr Tyr Cys Leu Gln Tyr Asp Asp Phe Pro Tyr
                85                  90                  95

Thr Phe Gly Gln Gly Thr Lys Val Glu Ile Lys
            100                 105
```

<210> SEQ ID NO 138
<211> LENGTH: 36
<212> TYPE: DNA
<213> ORGANISM: Artificial Sequence
<220> FEATURE:
<223> OTHER INFORMATION: RACE Anchor Primer
<220> FEATURE:
<221> NAME/KEY: misc_feature
<222> LOCATION: (24)..(25)
<223> OTHER INFORMATION: n is deoxyinosine
<220> FEATURE:
<221> NAME/KEY: misc_feature
<222> LOCATION: (29)..(30)
<223> OTHER INFORMATION: n is deoxyinosine
<220> FEATURE:
<221> NAME/KEY: misc_feature
<222> LOCATION: (34)..(35)
<223> OTHER INFORMATION: n is deoxyinosine

<400> SEQUENCE: 138
ggccacgcgt cgactagtac gggnngggnn gggnng 36

<210> SEQ ID NO 139
<211> LENGTH: 27
<212> TYPE: DNA
<213> ORGANISM: Artificial Sequence
<220> FEATURE:
<223> OTHER INFORMATION: MHV1 primer

<400> SEQUENCE: 139
atgaaatgca gctggggcat cttcttc 27

<210> SEQ ID NO 140
<211> LENGTH: 26
<212> TYPE: DNA
<213> ORGANISM: Artificial Sequence
<220> FEATURE:
<223> OTHER INFORMATION: MHV2 primer

<400> SEQUENCE: 140
atgggatgga gctrtatcat sytctt 26

<210> SEQ ID NO 141
<211> LENGTH: 27
<212> TYPE: DNA
<213> ORGANISM: Artificial Sequence
<220> FEATURE:
<223> OTHER INFORMATION: MHV3 primer

<400> SEQUENCE: 141
atgaagwtgt ggttaaactg ggttttt 27

<210> SEQ ID NO 142
<211> LENGTH: 25
<212> TYPE: DNA
<213> ORGANISM: Artificial Sequence
<220> FEATURE:
<223> OTHER INFORMATION: MHV4 primer

<400> SEQUENCE: 142
atgractttg ggytcagctt grttt 25

<210> SEQ ID NO 143
<211> LENGTH: 30
<212> TYPE: DNA
<213> ORGANISM: Artificial Sequence
<220> FEATURE:
<223> OTHER INFORMATION: MHV5 primer

<400> SEQUENCE: 143
atggactcca ggctcaattt agttttcctt 30

<210> SEQ ID NO 144
<211> LENGTH: 27
<212> TYPE: DNA
<213> ORGANISM: Artificial Sequence
<220> FEATURE:
<223> OTHER INFORMATION: MHV6 primer

<400> SEQUENCE: 144
atggctgtcy trgsgctrct cttctgc 27

<210> SEQ ID NO 145
<211> LENGTH: 26
<212> TYPE: DNA
<213> ORGANISM: Artificial Sequence
<220> FEATURE:
<223> OTHER INFORMATION: MHV7 primer

<400> SEQUENCE: 145
atggratgga gckggrtctt tmtctt 26

<210> SEQ ID NO 146
<211> LENGTH: 23
<212> TYPE: DNA
<213> ORGANISM: Artificial Sequence
<220> FEATURE:
<223> OTHER INFORMATION: MHV8 primer

<400> SEQUENCE: 146
atgagagtgc tgattctttt gtg 23

<210> SEQ ID NO 147

<211> LENGTH: 30
<212> TYPE: DNA
<213> ORGANISM: Artificial Sequence
<220> FEATURE:
<223> OTHER INFORMATION: MHV9 primer

<400> SEQUENCE: 147
atggmttggg tgtggamctt gctattcctg 30

<210> SEQ ID NO 148
<211> LENGTH: 27
<212> TYPE: DNA
<213> ORGANISM: Artificial Sequence
<220> FEATURE:
<223> OTHER INFORMATION: MHV10 primer

<400> SEQUENCE: 148
atgggcagac ttacattctc attcctg 27

<210> SEQ ID NO 149
<211> LENGTH: 28
<212> TYPE: DNA
<213> ORGANISM: Artificial Sequence
<220> FEATURE:
<223> OTHER INFORMATION: MHV11 primer

<400> SEQUENCE: 149
atggattttg ggctgatttt ttttattg 28

<210> SEQ ID NO 150
<211> LENGTH: 27
<212> TYPE: DNA
<213> ORGANISM: Artificial Sequence
<220> FEATURE:
<223> OTHER INFORMATION: MHV12 primer

<400> SEQUENCE: 150
atgatggtgt taagtcttct gtacctg 27

<210> SEQ ID NO 151
<211> LENGTH: 21
<212> TYPE: DNA
<213> ORGANISM: Artificial Sequence
<220> FEATURE:
<223> OTHER INFORMATION: MHCG1 primer

<400> SEQUENCE: 151
cagtggatag acagatgggg g 21

<210> SEQ ID NO 152
<211> LENGTH: 21
<212> TYPE: DNA
<213> ORGANISM: Artificial Sequence
<220> FEATURE:
<223> OTHER INFORMATION: MHCG2A primer

<400> SEQUENCE: 152
cagtggatag accgatgggg c 21

<210> SEQ ID NO 153
<211> LENGTH: 21
<212> TYPE: DNA
<213> ORGANISM: Artificial Sequence
<220> FEATURE:
<223> OTHER INFORMATION: MHCG2b primer

<400> SEQUENCE: 153
cagtggatag actgatgggg g 21

<210> SEQ ID NO 154
<211> LENGTH: 21
<212> TYPE: DNA
<213> ORGANISM: Artificial Sequence
<220> FEATURE:
<223> OTHER INFORMATION: MHCG3 primer

<400> SEQUENCE: 154
caagggatag acagatgggg c 21

<210> SEQ ID NO 155
<211> LENGTH: 30
<212> TYPE: DNA
<213> ORGANISM: Artificial Sequence
<220> FEATURE:
<223> OTHER INFORMATION: MKV1 30-mer

<400> SEQUENCE: 155
atgaagttgv vtgttaggct gttggtgctg 30

<210> SEQ ID NO 156
<211> LENGTH: 30
<212> TYPE: DNA
<213> ORGANISM: Artificial Sequence
<220> FEATURE:
<223> OTHER INFORMATION: MKV2 29-mer

<400> SEQUENCE: 156
atggagwcag acacactcct gytatgggtg 30

<210> SEQ ID NO 157
<211> LENGTH: 30
<212> TYPE: DNA
<213> ORGANISM: Artificial Sequence
<220> FEATURE:
<223> OTHER INFORMATION: MKV3 30-mer

<400> SEQUENCE: 157
atgagtgtgc tcactcaggt cctggsgttg 30

<210> SEQ ID NO 158
<211> LENGTH: 33
<212> TYPE: DNA
<213> ORGANISM: Artificial Sequence
<220> FEATURE:
<223> OTHER INFORMATION: MKV4 33-mer

<400> SEQUENCE: 158
atgaggrccc ctgctcagwt tyttggmwtc ttg 33

<210> SEQ ID NO 159
<211> LENGTH: 29
<212> TYPE: DNA
<213> ORGANISM: Artificial Sequence
<220> FEATURE:
<223> OTHER INFORMATION: MKV5 30-mer

<400> SEQUENCE: 159
atggatttwa ggtgcagatt wtcagcttc 29

<210> SEQ ID NO 160
<211> LENGTH: 27
<212> TYPE: DNA

```
<213> ORGANISM: Artificial Sequence
<220> FEATURE:
<223> OTHER INFORMATION: MKV6 27-mer

<400> SEQUENCE: 160

atgaggtkck ktgktsagst sctgrgg                                      27


<210> SEQ ID NO 161
<211> LENGTH: 31
<212> TYPE: DNA
<213> ORGANISM: Artificial Sequence
<220> FEATURE:
<223> OTHER INFORMATION: MKV7 31-mer

<400> SEQUENCE: 161

atgggcwtca agatggagtc acakwyycwg g                                 31


<210> SEQ ID NO 162
<211> LENGTH: 31
<212> TYPE: DNA
<213> ORGANISM: Artificial Sequence
<220> FEATURE:
<223> OTHER INFORMATION: MKV8 31-mer

<400> SEQUENCE: 162

atgtggggay ctktttycmm tttttcaatt g                                 31


<210> SEQ ID NO 163
<211> LENGTH: 25
<212> TYPE: DNA
<213> ORGANISM: Artificial Sequence
<220> FEATURE:
<223> OTHER INFORMATION: MKV9 25-mer

<400> SEQUENCE: 163

atggtrtccw casctcagtt ccttg                                        25


<210> SEQ ID NO 164
<211> LENGTH: 27
<212> TYPE: DNA
<213> ORGANISM: Artificial Sequence
<220> FEATURE:
<223> OTHER INFORMATION: MKV10 27-mer

<400> SEQUENCE: 164

atgtatatat gtttgttgtc tatttct                                      27


<210> SEQ ID NO 165
<211> LENGTH: 28
<212> TYPE: DNA
<213> ORGANISM: Artificial Sequence
<220> FEATURE:
<223> OTHER INFORMATION: MKV11 28-mer

<400> SEQUENCE: 165

atggaagccc cagctcagct tctcttcc                                     28


<210> SEQ ID NO 166
<211> LENGTH: 26
<212> TYPE: DNA
<213> ORGANISM: Artificial Sequence
<220> FEATURE:
<223> OTHER INFORMATION: CL12A primer

<400> SEQUENCE: 166

atgragtywc agacccaggt cttyrt                                       26
```

<210> SEQ ID NO 167
<211> LENGTH: 26
<212> TYPE: DNA
<213> ORGANISM: Artificial Sequence
<220> FEATURE:
<223> OTHER INFORMATION: CL12B primer

<400> SEQUENCE: 167
atggagacac attctcaggt ctttgt 26

<210> SEQ ID NO 168
<211> LENGTH: 26
<212> TYPE: DNA
<213> ORGANISM: Artificial Sequence
<220> FEATURE:
<223> OTHER INFORMATION: CL13 primer

<400> SEQUENCE: 168
atggattcac aggcccaggt tcttat 26

<210> SEQ ID NO 169
<211> LENGTH: 26
<212> TYPE: DNA
<213> ORGANISM: Artificial Sequence
<220> FEATURE:
<223> OTHER INFORMATION: CL14 primer

<400> SEQUENCE: 169
atgatgagtc ctgcccagtt cctgtt 26

<210> SEQ ID NO 170
<211> LENGTH: 29
<212> TYPE: DNA
<213> ORGANISM: Artificial Sequence
<220> FEATURE:
<223> OTHER INFORMATION: CL15 primer

<400> SEQUENCE: 170
atgaatttgc ctgttcatct cttggtgct 29

<210> SEQ ID NO 171
<211> LENGTH: 29
<212> TYPE: DNA
<213> ORGANISM: Artificial Sequence
<220> FEATURE:
<223> OTHER INFORMATION: CL16 primer

<400> SEQUENCE: 171
atggattttc aattggtcct catctcctt 29

<210> SEQ ID NO 172
<211> LENGTH: 26
<212> TYPE: DNA
<213> ORGANISM: Artificial Sequence
<220> FEATURE:
<223> OTHER INFORMATION: CL17A primer

<400> SEQUENCE: 172
atgaggtgcc tarctsagtt cctgrg 26

<210> SEQ ID NO 173
<211> LENGTH: 26
<212> TYPE: DNA
<213> ORGANISM: Artificial Sequence
<220> FEATURE:

<223> OTHER INFORMATION: CL17B primer

<400> SEQUENCE: 173
atgaagtact ctgctcagtt tctagg 26

<210> SEQ ID NO 174
<211> LENGTH: 26
<212> TYPE: DNA
<213> ORGANISM: Artificial Sequence
<220> FEATURE:
<223> OTHER INFORMATION: CL17C primer

<400> SEQUENCE: 174
atgaggcatt ctcttcaatt cttggg 26

<210> SEQ ID NO 175
<211> LENGTH: 20
<212> TYPE: DNA
<213> ORGANISM: Artificial Sequence
<220> FEATURE:
<223> OTHER INFORMATION: MKC 20-mer

<400> SEQUENCE: 175
actggatggt gggaagatgg 20

<210> SEQ ID NO 176
<211> LENGTH: 114
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AB_VHc (mAB001VH)

<400> SEQUENCE: 176

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Leu Ser Ser Ser
            20                  25                  30

Ala Met Ser Trp Val Arg Gln Thr Pro Asp Arg Arg Leu Glu Trp Val
        35                  40                  45

Ala Thr Ile Ser Val Gly Gly Gly Lys Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ser Glu Asp Thr Ala Met Tyr Tyr Cys
                85                  90                  95

Ala Lys Leu Ile Ser Leu Tyr Trp Gly Gln Gly Thr Thr Leu Thr Val
            100                 105                 110

Ser Ser
```

<210> SEQ ID NO 177
<211> LENGTH: 114
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: BB7_VHc (mBB7001VH)

<400> SEQUENCE: 177

```
Ala Val Gln Leu Val Glu Ser Gly Gly Gly Leu Val Lys Pro Gly Gly
1               5                   10                  15

Ser Leu Lys Leu Ser Cys Ala Ala Ser Gly Ile Ile Phe Ser Ser Ser
            20                  25                  30

Ala Met Ser Trp Val Arg Gln Thr Pro Glu Lys Arg Leu Glu Trp Val
        35                  40                  45

Ala Thr Ile Ser Ser Gly Gly Arg Ser Thr Tyr Tyr Pro Asp Ser Val
    50                  55                  60

Lys Gly Arg Phe Thr Val Ser Arg Asp Ser Ala Lys Asn Thr Leu Tyr
65                  70                  75                  80

Leu Gln Met Asp Ser Leu Arg Ser Glu Asp Thr Ala Ile Tyr Tyr Cys
                85                  90                  95

Ala Lys Leu Ile Ser Pro Tyr Trp Gly Gln Gly Thr Thr Leu Thr Val
            100                 105                 110

Ser Ser


<210> SEQ ID NO 178
<211> LENGTH: 114
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: DC1_VHc (mDC001VH)

<400> SEQUENCE: 178

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Leu Ser Thr His
            20                  25                  30

Ala Met Ser Trp Val Arg Gln Thr Pro Glu Lys Arg Leu Glu Trp Val
        35                  40                  45

Ala Thr Ile Ser Ser Gly Gly Arg Ser Thr Tyr Tyr Pro Asp Ser Val
    50                  55                  60

Lys Gly Arg Phe Thr Ile Ser Arg Asp Asn Val Lys Asn Thr Leu Tyr
65                  70                  75                  80

Leu Gln Leu Ser Ser Leu Arg Ser Glu Asp Thr Ala Val Tyr Phe Cys
                85                  90                  95

Ala Arg Leu Ile Ser Thr Tyr Trp Gly Gln Gly Thr Thr Leu Thr Val
            100                 105                 110

Ser Ser


<210> SEQ ID NO 179
<211> LENGTH: 115
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AF062260

<400> SEQUENCE: 179

Cys Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Ser Ser
            20                  25                  30

Tyr Ala Met Ser Trp Val Arg Gln Ala Pro Gly Lys Gly Leu Glu Trp
```

```
        35                  40                  45

Val Ser Ala Ile Ser Gly Ser Gly Gly Ser Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Asp Gly Gly Val Tyr Trp Gly Gln Gly Thr Leu Val Thr
            100                 105                 110

Val Ser Ser
        115


<210> SEQ ID NO 180
<211> LENGTH: 115
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AF062260

<400> SEQUENCE: 180

Cys Ala Val Gln Leu Leu Glu Ser Gly Gly Gly Leu Val Gln Pro Gly
1               5                   10                  15

Gly Ser Leu Arg Leu Ser Cys Ala Ala Ser Gly Ile Ile Phe Ser Ser
            20                  25                  30

Tyr Ala Met Ser Trp Val Arg Gln Ala Pro Gly Lys Gly Leu Glu Trp
        35                  40                  45

Val Ser Ala Ile Ser Gly Ser Gly Arg Ser Thr Tyr Tyr Ala Asp Ser
    50                  55                  60

Val Lys Gly Arg Phe Thr Val Ser Arg Asp Ser Ser Lys Asn Thr Leu
65                  70                  75                  80

Tyr Leu Gln Met Asp Ser Leu Arg Ala Glu Asp Thr Ala Val Tyr Tyr
                85                  90                  95

Cys Ala Lys Asp Gly Gly Val Tyr Trp Gly Gln Gly Thr Leu Val Thr
            100                 105                 110

Val Ser Ser
        115


<210> SEQ ID NO 181
<211> LENGTH: 115
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AF062260

<400> SEQUENCE: 181

Cys Glu Val Gln Leu Leu Glu Ser Gly Gly Gly Leu Val Gln Pro Gly
1               5                   10                  15

Gly Ser Leu Arg Leu Ser Cys Ala Ala Ser Gly Phe Thr Phe Ser Thr
            20                  25                  30

Tyr Ala Met Ser Trp Val Arg Gln Ala Pro Gly Lys Gly Leu Glu Trp
        35                  40                  45

Val Ser Ala Ile Ser Gly Ser Gly Arg Ser Thr Tyr Tyr Ala Asp Ser
    50                  55                  60
```

```
Val Lys Gly Arg Phe Thr Ile Ser Arg Asp Asn Ser Lys Asn Thr Leu
65                  70                  75                  80

Tyr Leu Gln Leu Ser Ser Leu Arg Ala Glu Asp Thr Ala Val Tyr Phe
                85                  90                  95

Cys Ala Arg Asp Gly Gly Val Tyr Trp Gly Gln Gly Thr Leu Val Thr
            100                 105                 110

Val Ser Ser
        115


<210> SEQ ID NO 182
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AB_VHc (mAB001VH) 5 Angstrom Proximity Residues

<400> SEQUENCE: 182

Glu Val Gln Leu Cys Ala Phe Thr Leu Ser Trp Val Arg Trp Val Ala
1               5                   10                  15

Arg Phe Thr Ile Ser Arg Asn Leu Tyr Cys Ala Lys Trp Gly
            20                  25                  30


<210> SEQ ID NO 183
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: BB7_VHc (mBB7001VH) 5 Angstrom Proximity
      Residues

<400> SEQUENCE: 183

Ala Val Gln Leu Cys Ala Ile Ile Phe Ser Trp Val Arg Trp Val Ala
1               5                   10                  15

Arg Phe Thr Val Ser Arg Ser Leu Tyr Cys Ala Lys Trp Gly
            20                  25                  30


<210> SEQ ID NO 184
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: DC1_VHc (mDC001VH) 5 Angstrom Proximity
      Residues

<400> SEQUENCE: 184

Glu Val Gln Leu Cys Ala Phe Thr Leu Ser Trp Val Arg Trp Val Ala
1               5                   10                  15

Arg Phe Thr Ile Ser Arg Asn Leu Phe Cys Ala Arg Trp Gly
            20                  25                  30


<210> SEQ ID NO 185
<211> LENGTH: 30
<212> TYPE: PRT
<213> ORGANISM: Artificial Sequence
<220> FEATURE:
<223> OTHER INFORMATION: Synthetic peptide
<220> FEATURE:
```

<221> NAME/KEY: MISC_FEATURE
<223> OTHER INFORMATION: AF062260 5 Angstrom Proximity Residues

<400> SEQUENCE: 185

Glu Val Gln Leu Cys Ala Phe Thr Phe Ser Trp Val Arg Trp Val Ser
1               5                   10                  15

Arg Phe Thr Ile Ser Arg Asn Leu Tyr Cys Ala Lys Trp Gly
            20                  25                  30

<210> SEQ ID NO 186
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AF062260 5 Angstrom Proximity Residues

<400> SEQUENCE: 186

Ala Val Gln Leu Cys Ala Ile Ile Phe Ser Trp Val Arg Trp Val Ser
1               5                   10                  15

Arg Phe Thr Val Ser Arg Ser Leu Tyr Cys Ala Lys Trp Gly
            20                  25                  30

<210> SEQ ID NO 187
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AF062260 5 Angstrom Proximity Residues

<400> SEQUENCE: 187

Glu Val Gln Leu Cys Ala Phe Thr Phe Ser Trp Val Arg Trp Val Ser
1               5                   10                  15

Arg Phe Thr Ile Ser Arg Asn Leu Phe Cys Ala Arg Trp Gly
            20                  25                  30

<210> SEQ ID NO 188
<211> LENGTH: 107
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AB_VKc (mAB001VK)

<400> SEQUENCE: 188

Glu Ile Val Leu Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Thr Trp Phe Gln Gln Lys Pro Gly Lys Ser Pro Lys Thr Leu Ile
        35                  40                  45

Tyr Arg Thr Asn Arg Leu Phe Asp Gly Val Pro Ser Arg Phe Ser Gly
    50                  55                  60

Ser Gly Ser Gly Gln Asp Phe Phe Leu Thr Ile Ser Ser Leu Glu Tyr
65                  70                  75                  80

Glu Asp Met Gly Ile Tyr Tyr Cys Leu Gln Tyr Asp Asp Phe Pro Tyr
                85                  90                  95

```
Thr Phe Gly Gly Gly Thr Lys Leu Glu Ile Lys
            100                 105


<210> SEQ ID NO 189
<211> LENGTH: 107
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AY247656

<400> SEQUENCE: 189

Glu Ile Val Leu Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Gly Thr Tyr Tyr Cys Gln Gln Tyr Asn Thr Tyr Pro Leu
                85                  90                  95

Thr Phe Gly Gly Gly Thr Lys Leu Glu Ile Lys
            100                 105


<210> SEQ ID NO 190
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AB_VKc (mAB001VK)

<400> SEQUENCE: 190

Glu Ile Val Leu Thr Gln Thr Cys Trp Phe Thr Leu Ile Tyr Gly Val
1               5                   10                  15

Pro Phe Ser Gly Ser Gly Ser Gly Gln Asp Phe Phe Tyr Cys Phe Gly
            20                  25                  30


<210> SEQ ID NO 191
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AY247656 5 Angstrom Proximity Residues

<400> SEQUENCE: 191

Glu Ile Val Leu Thr Gln Thr Cys Trp Tyr Leu Leu Ile Tyr Gly Val
1               5                   10                  15

Pro Phe Ser Gly Ser Gly Ser Gly Thr Asp Phe Thr Tyr Cys Phe Gly
            20                  25                  30


<210> SEQ ID NO 192
<211> LENGTH: 107
```

<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AB_VKc1 (mAB002VK)

<400> SEQUENCE: 192

```
Asp Ile Gln Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Thr Trp Phe Gln Gln Lys Pro Gly Lys Ser Pro Lys Thr Leu Ile
        35                  40                  45

Tyr Arg Thr Asn Arg Leu Phe Asp Gly Val Pro Ser Arg Phe Ser Gly
    50                  55                  60

Ser Gly Ser Gly Gln Asp Phe Phe Leu Thr Ile Ser Ser Leu Glu Tyr
65                  70                  75                  80

Glu Asp Met Gly Ile Tyr Tyr Cys Leu Gln Tyr Asp Asp Phe Pro Tyr
                85                  90                  95

Thr Phe Gly Gly Gly Thr Lys Leu Glu Ile Lys
            100                 105
```

<210> SEQ ID NO 193
<211> LENGTH: 107
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AB1_VKc2 (mAB003VK)

<400> SEQUENCE: 193

```
Asp Ile Gln Lys Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Thr Trp Phe Gln Gln Lys Pro Gly Lys Ser Pro Lys Thr Leu Ile
        35                  40                  45

Tyr Arg Thr Asn Arg Leu Phe Asp Gly Val Pro Ser Arg Phe Ser Gly
    50                  55                  60

Ser Gly Ser Gly Gln Asp Phe Phe Leu Thr Ile Ser Ser Leu Glu Tyr
65                  70                  75                  80

Glu Asp Met Gly Ile Tyr Tyr Cys Leu Gln Tyr Asp Asp Phe Pro Tyr
                85                  90                  95

Thr Phe Gly Gly Gly Thr Lys Leu Glu Ile Lys
            100                 105
```

<210> SEQ ID NO 194
<211> LENGTH: 107
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: BB7_VKc (mBB001VK)

<400> SEQUENCE: 194

```
Ala Ile Lys Met Thr Gln Ser Pro Ser Ser Met Tyr Ala Ser Leu Gly
```

```
1               5                   10                  15

Glu Arg Val Ile Ile Thr Cys Lys Ala Ser Gln Asp Ile Asn Ser Tyr
            20                  25                  30

Leu Thr Trp Phe Gln Gln Lys Pro Gly Lys Ser Pro Lys Thr Leu Ile
        35                  40                  45

Tyr Leu Thr Asn Arg Leu Met Asp Gly Val Pro Ser Arg Phe Ser Gly
    50                  55                  60

Ser Gly Ser Gly Gln Glu Phe Leu Leu Thr Ile Ser Gly Leu Glu His
65                  70                  75                  80

Glu Asp Met Gly Ile Tyr Tyr Cys Leu Gln Tyr Val Asp Phe Pro Tyr
                85                  90                  95

Thr Phe Gly Gly Gly Thr Lys Leu Glu Ile Lys
            100                 105


<210> SEQ ID NO 195
<211> LENGTH: 107
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: DC1_VKc (mDC001VK)

<400> SEQUENCE: 195

Asp Ile Thr Met Thr Gln Ser Pro Ser Ser Ile Tyr Ala Ser Leu Gly
1               5                   10                  15

Glu Arg Val Thr Ile Thr Cys Lys Ala Ser Gln Asp Ile Asn Ser Tyr
            20                  25                  30

Leu Thr Trp Phe Gln Gln Lys Pro Gly Lys Ser Pro Lys Ile Leu Ile
        35                  40                  45

Tyr Leu Val Asn Arg Leu Val Asp Gly Val Pro Ser Arg Phe Ser Gly
    50                  55                  60

Ser Gly Ser Gly Gln Asp Tyr Ala Leu Thr Ile Ser Ser Leu Glu Tyr
65                  70                  75                  80

Glu Asp Met Gly Ile Tyr Tyr Cys Leu Gln Tyr Asp Asp Phe Pro Tyr
                85                  90                  95

Thr Phe Gly Gly Gly Thr Lys Leu Glu Ile Lys
            100                 105


<210> SEQ ID NO 196
<211> LENGTH: 107
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AF193851

<400> SEQUENCE: 196

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Phe Gln Gln Lys Pro Gly Lys Ala Pro Lys Ser Leu Ile
        35                  40                  45

Tyr Ala Ala Ser Asn Leu Gln Ser Gly Val Pro Ser Arg Phe Ser Gly
    50                  55                  60
```

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Thr Tyr Pro Trp
                85                  90                  95

Thr Phe Gly Gln Gly Thr Lys Val Glu Ile Lys
            100                 105


<210> SEQ ID NO 197
<211> LENGTH: 107
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AF193851

<400> SEQUENCE: 197

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Phe Gln Gln Lys Pro Gly Lys Ala Pro Lys Ser Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Thr Tyr Pro Trp
                85                  90                  95

Thr Phe Gly Gln Gly Thr Lys Val Glu Ile Lys
            100                 105


<210> SEQ ID NO 198
<211> LENGTH: 107
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AF193851

<400> SEQUENCE: 198

Ala Ile Lys Met Thr Gln Ser Pro Ser Ser Leu Ser Ala Ser Val Gly
1               5                   10                  15

Asp Arg Val Ile Ile Thr Cys Arg Ala Ser Gln Gly Ile Arg Asn Tyr
            20                  25                  30

Leu Ala Trp Phe Gln Gln Lys Pro Gly Lys Ala Pro Lys Ser Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Glu Phe Thr Leu Thr Ile Ser Gly Leu Gln Pro
65                  70                  75                  80

Glu Asp Phe Ala Thr Tyr Tyr Cys Gln Gln His Asn Thr Tyr Pro Trp
                85                  90                  95

Thr Phe Gly Gln Gly Thr Lys Val Glu Ile Lys
            100                 105


<210> SEQ ID NO 199
```

```
<211> LENGTH: 107
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AF193851

<400> SEQUENCE: 199

Asp Ile Thr Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Phe Gln Gln Lys Pro Gly Lys Ala Pro Lys Ser Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln His Asn Thr Tyr Pro Trp
                85                  90                  95

Thr Phe Gly Gln Gly Thr Lys Val Glu Ile Lys
            100                 105


<210> SEQ ID NO 200
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AB1_VKc2 (mAB003VK) 5 Angstrom Proximity
      Residues

<400> SEQUENCE: 200

Asp Ile Gln Lys Thr Gln Thr Cys Trp Phe Thr Leu Ile Tyr Gly Val
1               5                   10                  15

Pro Phe Ser Gly Ser Gly Ser Gly Gln Asp Phe Phe Tyr Cys Phe Gly
            20                  25                  30


<210> SEQ ID NO 201
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: BB7_VKc (mBB001VK) 5 Angstrom Proximity
      Residues

<400> SEQUENCE: 201

Ala Ile Lys Met Thr Gln Thr Cys Trp Phe Thr Leu Ile Tyr Gly Val
1               5                   10                  15

Pro Phe Ser Gly Ser Gly Ser Gly Gln Glu Phe Leu Tyr Cys Phe Gly
            20                  25                  30


<210> SEQ ID NO 202
<211> LENGTH: 32
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MISC_FEATURE
<223> OTHER INFORMATION: DC1_VKc (mDC001VK)

<400> SEQUENCE: 202

Asp Ile Thr Met Thr Gln Thr Cys Trp Phe Ile Leu Ile Tyr Gly Val
1               5                   10                  15

Pro Phe Ser Gly Ser Gly Ser Gly Gln Asp Tyr Ala Tyr Cys Phe Gly
            20                  25                  30


<210> SEQ ID NO 203
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AF193851

<400> SEQUENCE: 203

Asp Ile Gln Met Thr Gln Thr Cys Trp Phe Ser Leu Ile Tyr Gly Val
1               5                   10                  15

Pro Phe Ser Gly Ser Gly Ser Gly Thr Asp Phe Thr Tyr Cys Phe Gly
            20                  25                  30


<210> SEQ ID NO 204
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AF193851

<400> SEQUENCE: 204

Asp Ile Gln Met Thr Gln Thr Cys Trp Phe Ser Leu Ile Tyr Gly Val
1               5                   10                  15

Pro Phe Ser Gly Ser Gly Ser Gly Thr Asp Phe Thr Tyr Cys Phe Gly
            20                  25                  30


<210> SEQ ID NO 205
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AF193851

<400> SEQUENCE: 205

Ala Ile Lys Met Thr Gln Thr Cys Trp Phe Ser Leu Ile Tyr Gly Val
1               5                   10                  15

Pro Phe Ser Gly Ser Gly Ser Gly Thr Glu Phe Thr Tyr Cys Phe Gly
            20                  25                  30


<210> SEQ ID NO 206
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AF193851
```

<400> SEQUENCE: 206

```
Asp Ile Thr Met Thr Gln Thr Cys Trp Phe Ser Leu Ile Tyr Gly Val
1               5                   10                  15

Pro Phe Ser Gly Ser Gly Ser Gly Thr Asp Tyr Thr Tyr Cys Phe Gly
            20                  25                  30
```

<210> SEQ ID NO 207
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AB Heavy Chain CDR1

<400> SEQUENCE: 207

```
Cys Ala Ala Ser Gly Phe Thr Phe Ser Ser Ser Ala Met Ser Trp Val
1               5                   10                  15

Arg
```

<210> SEQ ID NO 208
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: BB7 RHA Heavy Chain CDR 1

<400> SEQUENCE: 208

```
Cys Ala Ala Ser Gly Ile Ile Phe Ser Ser Ser Ala Met Ser Trp Val
1               5                   10                  15

Arg
```

<210> SEQ ID NO 209
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: BB7 RHA Heavy Chain CDR 1

<400> SEQUENCE: 209

```
Ile Ile Phe Ser Ser Ser Ala Met Ser Trp Val Arg
1               5                   10
```

<210> SEQ ID NO 210
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: DC1 RHA Heavy Chain CDR1

<400> SEQUENCE: 210

```
Cys Ala Ala Ser Gly Phe Thr Phe Ser Thr His Ala Met Ser Trp Val
1               5                   10                  15

Arg
```

<210> SEQ ID NO 211
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: DC1 RHA Heavy Chain CDR1

<400> SEQUENCE: 211

Phe Thr Phe Ser Thr His Ala Met Ser Trp Val Arg
1 5 10

<210> SEQ ID NO 212
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: DC1 RHA/DC1 RHB Heavy Chain CDR1

<400> SEQUENCE: 212

Thr His Ala Met Ser
1 5

<210> SEQ ID NO 213
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: DC1 RHB Heavy Chain CDR1

<400> SEQUENCE: 213

Cys Ala Ala Ser Gly Phe Thr Leu Ser Thr His Ala Met Ser Trp Val
1 5 10 15

Arg

<210> SEQ ID NO 214
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: DC1 RHB Heavy Chain CDR1

<400> SEQUENCE: 214

Phe Thr Leu Ser Thr His Ala Met Ser Trp Val Arg
1 5 10

<210> SEQ ID NO 215
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AB Heavy Chain CDR2

<400> SEQUENCE: 215

Trp Val Ser Thr Ile Ser Val Gly Gly Gly Lys Thr Tyr Tyr Pro Asp
1 5 10 15

Ser Val Lys Gly Arg Phe Thr Ile Ser Arg Asp Asn Ser Lys Asn Thr
20 25 30

Leu

<210> SEQ ID NO 216
<211> LENGTH: 28
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AB Heavy Chain CDR2

<400> SEQUENCE: 216

Trp Val Ser Thr Ile Ser Val Gly Gly Gly Lys Thr Tyr Tyr Pro Asp
1 5 10 15

Ser Val Lys Gly Arg Phe Thr Ile Ser Arg Asp Asn
20 25

<210> SEQ ID NO 217
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: BB7 RHB Heavy Chain CDR2

<400> SEQUENCE: 217

Trp Val Ser Thr Ile Ser Ser Gly Gly Arg Ser Thr Tyr Tyr Pro Asp
1 5 10 15

Ser Val Lys Gly Arg Phe Thr Ile Ser Arg Asp Asn Ser Lys Asn Thr
20 25 30

Leu

<210> SEQ ID NO 218
<211> LENGTH: 28
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: BB7 RHB Heavy Chain CDR2

<400> SEQUENCE: 218

Trp Val Ser Thr Ile Ser Ser Gly Gly Arg Ser Thr Tyr Tyr Pro Asp
1 5 10 15

Ser Val Lys Gly Arg Phe Thr Ile Ser Arg Asp Asn
20 25

<210> SEQ ID NO 219
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: BB7 RHB/DC1 RHA Heavy Chain CDR2

<400> SEQUENCE: 219

Trp Val Ser Thr Ile Ser Ser Gly Gly Arg Ser Thr Tyr Tyr Pro Asp
1 5 10 15

Ser Val Lys Gly Arg Phe Thr Ile Ser Arg
20 25

<210> SEQ ID NO 220
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: BB7 RHA Heavy Chain CDR2

<400> SEQUENCE: 220

Trp Val Ala Thr Ile Ser Ser Gly Gly Arg Ser Thr Tyr Tyr Pro Asp
1 5 10 15

Ser Val Lys Gly Arg Phe Thr Val Ser Arg Asp Ser Ser Lys Asn Thr
20 25 30

Leu

<210> SEQ ID NO 221
<211> LENGTH: 28
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: BB7 RHA Heavy Chain CDR2

<400> SEQUENCE: 221

Trp Val Ala Thr Ile Ser Ser Gly Gly Arg Ser Thr Tyr Tyr Pro Asp
1 5 10 15

Ser Val Lys Gly Arg Phe Thr Val Ser Arg Asp Ser
20 25

<210> SEQ ID NO 222
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: BB7 RHA Heavy Chain CDR2

<400> SEQUENCE: 222

Trp Val Ala Thr Ile Ser Ser Gly Gly Arg Ser Thr Tyr Tyr Pro Asp
1 5 10 15

Ser Val Lys Gly Arg Phe Thr Val Ser Arg
20 25

<210> SEQ ID NO 223
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: DC1 RHB Heavy Chain CDR2

<400> SEQUENCE: 223

Trp Val Ala Thr Ile Ser Ser Gly Gly Arg Ser Thr Tyr Tyr Pro Asp
1 5 10 15

Ser Val Lys Gly Arg Phe Thr Ile Ser Arg Asp Asn Ser Lys Asn Thr
20 25 30

Leu

<210> SEQ ID NO 224
<211> LENGTH: 28
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: DC1 RHB Heavy Chain CDR2

<400> SEQUENCE: 224

Trp Val Ala Thr Ile Ser Ser Gly Gly Arg Ser Thr Tyr Tyr Pro Asp
1 5 10 15

Ser Val Lys Gly Arg Phe Thr Ile Ser Arg Asp Asn
20 25

<210> SEQ ID NO 225
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: DC1 RHB Heavy Chain CDR2

<400> SEQUENCE: 225

Trp Val Ala Thr Ile Ser Ser Gly Gly Arg Ser Thr Tyr Tyr Pro Asp
1 5 10 15

Ser Val Lys Gly Arg Phe Thr Ile Ser Arg
20 25

<210> SEQ ID NO 226
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: BB7 RHB/BB7 RHA Heavy Chain CDR3

<400> SEQUENCE: 226

Tyr Cys Ala Lys Leu Ile Ser Pro Tyr Trp Gly
1 5 10

<210> SEQ ID NO 227
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: DC1 RHA Heavy Chain CDR3

<400> SEQUENCE: 227

Tyr Cys Ala Lys Leu Ile Ser Thr Tyr Trp Gly
1 5 10

<210> SEQ ID NO 228
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: DC1 RHB Heavy Chain CDR3

<400> SEQUENCE: 228

```
Phe Cys Ala Arg Leu Ile Ser Thr Tyr Trp Gly
1               5                   10
```

<210> SEQ ID NO 229
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AB RKE Light Chain CDR2

<400> SEQUENCE: 229

```
Leu Leu Ile Tyr Arg Thr Asn Arg Leu Phe Asp Gly Val Pro Ser Arg
1               5                   10                  15

Phe Ser Gly Ser Gly Ser Gly Thr Asp Phe Phe
            20                  25
```

<210> SEQ ID NO 230
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AB RJK Light Chain CDR2

<400> SEQUENCE: 230

```
Ser Leu Ile Tyr Arg Thr Asn Arg Leu Phe Asp Gly Val Pro Ser Arg
1               5                   10                  15

Phe Ser Gly Ser Gly Ser Gly Thr Asp Phe Phe
            20                  25
```

<210> SEQ ID NO 231
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: BB7 RKB Light Chain CDR2

<400> SEQUENCE: 231

```
Ser Leu Ile Tyr Leu Thr Asn Arg Leu Met Asp Gly Val Pro Ser Arg
1               5                   10                  15

Phe Ser Gly Ser Gly Ser Gly Thr Asp Phe Phe
            20                  25
```

<210> SEQ ID NO 232
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: BB7 RKB Light Chain CDR2

<400> SEQUENCE: 232

Ser Leu Ile Tyr Leu Thr Asn Arg Leu Met Asp Gly Val Pro
1 5 10

<210> SEQ ID NO 233
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: BB7 RKA Light Chain CDR2

<400> SEQUENCE: 233

Thr Leu Ile Tyr Leu Thr Asn Arg Leu Met Asp Gly Val Pro Ser Arg
1 5 10 15

Phe Ser Gly Ser Gly Ser Gly Gln Glu Phe Leu
20 25

<210> SEQ ID NO 234
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: BB7 RKA Light Chain CDR2

<400> SEQUENCE: 234

Thr Leu Ile Tyr Leu Thr Asn Arg Leu Met Asp Gly Val Pro
1 5 10

<210> SEQ ID NO 235
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: DC1 RKA Light Chain CDR2

<400> SEQUENCE: 235

Ser Leu Ile Tyr Leu Val Asn Arg Leu Val Asp Gly Val Pro Ser Arg
1 5 10 15

Phe Ser Gly Ser Gly Ser Gly Thr Asp Phe Phe
20 25

<210> SEQ ID NO 236
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: DC1 RKA Light Chain CDR2

<400> SEQUENCE: 236

Ser Leu Ile Tyr Leu Val Asn Arg Leu Val Asp Gly Val Pro
1 5 10

<210> SEQ ID NO 237
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: DC1 RKB Light Chain CDR2

<400> SEQUENCE: 237

```
Ile Leu Ile Tyr Leu Val Asn Arg Leu Val Asp Gly Val Pro Ser Arg
1               5                   10                  15

Phe Ser Gly Ser Gly Ser Gly Gln Asp Tyr Ala
            20                  25
```

<210> SEQ ID NO 238
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: DC1 RKB Light Chain CDR2

<400> SEQUENCE: 238

```
Ile Leu Ile Tyr Leu Val Asn Arg Leu Val Asp Gly Val Pro
1               5                   10
```

<210> SEQ ID NO 239
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: BB7 RKB Light Chain CDR3

<400> SEQUENCE: 239

```
Tyr Cys Leu Gln Tyr Val Asp Phe Pro Tyr Thr Phe Gly
1               5                   10
```

<210> SEQ ID NO 240
<211> LENGTH: 31
<212> TYPE: PRT
<213> ORGANISM: Mus musculus
<220> FEATURE:
<221> NAME/KEY: MISC_FEATURE
<223> OTHER INFORMATION: Mouse substrate binding pocket

<400> SEQUENCE: 240

```
Tyr Asn Ser Ala His Asp Gln Asn Ser Asn Leu Leu Ile Glu Tyr Phe
1               5                   10                  15

Arg Asn Glu Phe Gly Glu Leu Glu Ser Asn Lys Ser Glu Met Ile
            20                  25                  30
```

<210> SEQ ID NO 241
<211> LENGTH: 31
<212> TYPE: PRT
<213> ORGANISM: Rattus
<220> FEATURE:
<221> NAME/KEY: MISC_FEATURE
<223> OTHER INFORMATION: Rat substrate binding pocket

<400> SEQUENCE: 241

```
Tyr Asn Ser Ala His Asp Gln Asn Ser Asn Leu Leu Ile Glu Tyr Phe
1               5                   10                  15

Arg Asn Glu Tyr Gly Glu Leu Glu Ser Asn Lys Ser Glu Met Ile
            20                  25                  30


<210> SEQ ID NO 242
<211> LENGTH: 31
<212> TYPE: PRT
<213> ORGANISM: Homo sapiens
<220> FEATURE:
<221> NAME/KEY: MISC_FEATURE
<223> OTHER INFORMATION: Human substrate binding pocket

<400> SEQUENCE: 242

Tyr Asn Ser Ala His Asp Gln Asn Ser Asn Leu Leu Ile Glu Tyr Phe
1               5                   10                  15

Arg Asn Glu Phe Gly Glu Ile Gln Gly Asp Lys Ser Glu Met Ile
            20                  25                  30


<210> SEQ ID NO 243
<211> LENGTH: 48
<212> TYPE: PRT
<213> ORGANISM: Mus musculus
<220> FEATURE:
<221> NAME/KEY: MISC_FEATURE
<223> OTHER INFORMATION: Mouse rear of core behind active site

<400> SEQUENCE: 243

Ser Glu Met Ile Trp Asn Phe His Cys Trp Val Glu Ser Trp Met Thr
1               5                   10                  15

Arg Pro Asp Leu Gln Pro Gly Tyr Glu Gly Trp Gln Ala Ile Asp Pro
            20                  25                  30

Thr Pro Gln Glu Lys Ser Glu Gly Thr Tyr Cys Cys Gly Pro Val Ser
        35                  40                  45


<210> SEQ ID NO 244
<211> LENGTH: 48
<212> TYPE: PRT
<213> ORGANISM: Rattus
<220> FEATURE:
<221> NAME/KEY: MISC_FEATURE
<223> OTHER INFORMATION: Rat rear of core behind active site

<400> SEQUENCE: 244

Ser Glu Met Ile Trp Asn Phe His Cys Trp Val Glu Ser Trp Met Thr
1               5                   10                  15

Arg Pro Asp Leu Gln Pro Gly Tyr Glu Gly Trp Gln Ala Ile Asp Pro
            20                  25                  30

Thr Pro Gln Glu Lys Ser Glu Gly Thr Tyr Cys Cys Gly Pro Val Ser
        35                  40                  45


<210> SEQ ID NO 245
<211> LENGTH: 48
<212> TYPE: PRT
<213> ORGANISM: Homo sapiens
<220> FEATURE:
<221> NAME/KEY: MISC_FEATURE
<223> OTHER INFORMATION: Human rear of core behind active site

<400> SEQUENCE: 245

Ser Glu Met Ile Trp Asn Phe His Cys Trp Val Glu Ser Trp Met Thr
1               5                   10                  15

Arg Pro Asp Leu Gln Pro Gly Tyr Glu Gly Trp Gln Ala Leu Asp Pro
            20                  25                  30
```

```
Thr Pro Gln Glu Lys Ser Glu Gly Thr Tyr Cys Cys Gly Pro Val Pro
        35                  40                  45


<210> SEQ ID NO 246
<211> LENGTH: 39
<212> TYPE: PRT
<213> ORGANISM: Mus musculus
<220> FEATURE:
<221> NAME/KEY: MISC_FEATURE
<223> OTHER INFORMATION: Mouse rear of core junction with beta barrel-1

<400> SEQUENCE: 246

Thr Tyr Lys Tyr Pro Glu Gly Ser Pro Glu Glu Arg Glu Val Phe Thr
1               5                   10                  15

Lys Ala Asn His Leu Asn Lys Leu Ala Glu Lys Glu Glu Thr Gly Val
            20                  25                  30

Ala Met Arg Ile Arg Val Gly
        35


<210> SEQ ID NO 247
<211> LENGTH: 39
<212> TYPE: PRT
<213> ORGANISM: Rattus
<220> FEATURE:
<221> NAME/KEY: MISC_FEATURE
<223> OTHER INFORMATION: Rat rear of core junction with beta barrel-1

<400> SEQUENCE: 247

Thr Tyr Lys Tyr Pro Glu Gly Ser Pro Glu Glu Arg Glu Val Phe Thr
1               5                   10                  15

Arg Ala Asn His Leu Asn Lys Leu Ala Glu Lys Glu Glu Thr Gly Val
            20                  25                  30

Ala Met Arg Ile Arg Val Gly
        35


<210> SEQ ID NO 248
<211> LENGTH: 39
<212> TYPE: PRT
<213> ORGANISM: Homo sapiens
<220> FEATURE:
<221> NAME/KEY: MISC_FEATURE
<223> OTHER INFORMATION: Human rear of core junction with beta barrel-1

<400> SEQUENCE: 248

Thr Tyr Lys Tyr Pro Glu Gly Ser Ser Glu Glu Arg Glu Ala Phe Thr
1               5                   10                  15

Arg Ala Asn His Leu Asn Lys Leu Ala Glu Lys Glu Glu Thr Gly Met
            20                  25                  30

Ala Met Arg Ile Arg Val Gly
        35


<210> SEQ ID NO 249
<211> LENGTH: 342
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: AB VH1

<400> SEQUENCE: 249

gaagtacagc tggaggagtc aggggggggc ttagtgaagc ctggagggtc cctgaaactc     60
```

```
tcctgtgcag cctctggatt cactctcagt tcctctgcca tgtcttgggt tcgccagact    120

ccggacagga ggctggagtg ggtcgcaacc attagtgttg gtggtggtaa aacccactat    180

ccagacagtg tgaagggtcg cttcaccatc tccagagaca atgccaagaa caccctctat    240

ctgcaaatga acagtctgag gtctgaggac acggccatgt attactgtgc aaaactaatc    300

agtctctact ggggccaagg caccactctc acagtctcct ca                       342


<210> SEQ ID NO 250
<211> LENGTH: 114
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AB VH1

<400> SEQUENCE: 250

Glu Val Gln Leu Glu Glu Ser Gly Gly Gly Leu Val Lys Pro Gly Gly
1               5                   10                  15

Ser Leu Lys Leu Ser Cys Ala Ala Ser Gly Phe Thr Leu Ser Ser Ser
            20                  25                  30

Ala Met Ser Trp Val Arg Gln Thr Pro Asp Arg Arg Leu Glu Trp Val
        35                  40                  45

Ala Thr Ile Ser Val Gly Gly Gly Lys Thr His Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ser Glu Asp Thr Ala Met Tyr Tyr Cys
                85                  90                  95

Ala Lys Leu Ile Ser Leu Tyr Trp Gly Gln Gly Thr Thr Leu Thr Val
            100                 105                 110

Ser Ser


<210> SEQ ID NO 251
<211> LENGTH: 321
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: AB1 VK

<400> SEQUENCE: 251

gacatccaga tgacacagac tccatcttcc atgtatgcat ctctaggaga gagagtcact     60

atcacttgca aggcgagtca ggacattaat agctatttaa cctggttcca gcagaaacca    120

gggaaatctc ctaagaccct gatctatcgt acaaatagat tgtttgatgg ggtcccatcc    180

aggttcagtg gcagtggatc tgggcaagat ttttttctca ccatcagcag cctggaatat    240

gaagatatgg gaatttatta ttgtctacag tatgatgact ttccgtacac gttcggaggg    300

gggaccaaac tggaaataaa a                                              321


<210> SEQ ID NO 252
<211> LENGTH: 107
<212> TYPE: PRT
<213> ORGANISM: Artificial Sequence
<220> FEATURE:
<223> OTHER INFORMATION: Synthetic peptide
<220> FEATURE:
```

<221> NAME/KEY: MISC_FEATURE
<223> OTHER INFORMATION: AB1 VK

<400> SEQUENCE: 252

Asp Ile Gln Met Thr Gln Thr Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Thr Trp Phe Gln Gln Lys Pro Gly Lys Ser Pro Lys Thr Leu Ile
        35                  40                  45

Tyr Arg Thr Asn Arg Leu Phe Asp Gly Val Pro Ser Arg Phe Ser Gly
    50                  55                  60

Ser Gly Ser Gly Gln Asp Phe Phe Leu Thr Ile Ser Ser Leu Glu Tyr
65                  70                  75                  80

Glu Asp Met Gly Ile Tyr Tyr Cys Leu Gln Tyr Asp Asp Phe Pro Tyr
                85                  90                  95

Thr Phe Gly Gly Gly Thr Lys Leu Glu Ile Lys
            100                 105

<210> SEQ ID NO 253
<211> LENGTH: 342
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: AB1 VH

<400> SEQUENCE: 253
gaagtgcagc tggtggagtc tgggggggc ttagtgaagc ctggagggtc cctgaaactc      60
tcctgtgcag cctctggatt cactctcagt tcctctgcca tgtcttgggt tcgccagact     120
ccggacagga ggctggagtg ggtcgcaacc attagtgttg gtggtggtaa aacctactat     180
ccagacagtg tgaagggtcg cttcaccatc tccagagaca atgccaagaa caccctctat     240
ctgcaaatga acagtctgag gtctgaggac acggccatgt attactgtgc aaaactaatc     300
agtctctact ggggccaagg caccactctc acagtctcct ca                        342

<210> SEQ ID NO 254
<211> LENGTH: 114
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AB1 VH

<400> SEQUENCE: 254

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Leu Ser Ser Ser
            20                  25                  30

Ala Met Ser Trp Val Arg Gln Thr Pro Asp Arg Arg Leu Glu Trp Val
        35                  40                  45

Ala Thr Ile Ser Val Gly Gly Gly Lys Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

```
Leu Gln Met Asn Ser Leu Arg Ser Glu Asp Thr Ala Met Tyr Tyr Cys
                85                  90                  95

Ala Lys Leu Ile Ser Leu Tyr Trp Gly Gln Gly Thr Thr Leu Thr Val
            100                 105                 110

Ser Ser


<210> SEQ ID NO 255
<211> LENGTH: 321
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: AB1 VK

<400> SEQUENCE: 255

gacatcaaga tgacccagtc tccatcttcc atgtatgcat ctctaggaga gagagtcact     60

atcacttgca aggcgagtca ggacattaat agctatttaa cctggttcca gcagaaacca    120

gggaaatctc ctaagaccct gatctatcgt acaaatagat tgtttgatgg ggtcccatcc    180

aggttcagtg gcagtggatc tgggcaagat ttttttctca ccatcagcag cctggaatat    240

gaagatatgg gaatttatta ttgtctacag tatgatgact ttccgtacac gttcggaggg    300

gggaccaaac tggaaataaa a                                              321


<210> SEQ ID NO 256
<211> LENGTH: 107
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AB1 VK

<400> SEQUENCE: 256

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Thr Trp Phe Gln Gln Lys Pro Gly Lys Ser Pro Lys Thr Leu Ile
        35                  40                  45

Tyr Arg Thr Asn Arg Leu Phe Asp Gly Val Pro Ser Arg Phe Ser Gly
    50                  55                  60

Ser Gly Ser Gly Gln Asp Phe Phe Leu Thr Ile Ser Ser Leu Glu Tyr
65                  70                  75                  80

Glu Asp Met Gly Ile Tyr Tyr Cys Leu Gln Tyr Asp Asp Phe Pro Tyr
                85                  90                  95

Thr Phe Gly Gly Gly Thr Lys Leu Glu Ile Lys
            100                 105


<210> SEQ ID NO 257
<211> LENGTH: 342
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: BB7 VH

<400> SEQUENCE: 257
```

gcagtgcaac tggtagagtc tgggggaggc ttggtgaagc ctggagggtc cctgaaactc 60
tcctgtgcag cctctggaat cattttcagt tcctctgcca tgtcttgggt tcgccagact 120
ccggaaaaga gactggagtg ggtcgcaact attagtagtg gtggtcgttc cacctactat 180
ccagacagtg tgaagggtcg attcaccgtc tccagagaca gtgccaagaa caccctatac 240
ctgcaaatgg acagtctgag gtctgaggac acggccattt attactgtgc aaaactaatc 300
agtccctact ggggccaagg caccactctc acagtctcct ca 342

<210> SEQ ID NO 258
<211> LENGTH: 114
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: BB7 VH

<400> SEQUENCE: 258

Ala Val Gln Leu Val Glu Ser Gly Gly Gly Leu Val Lys Pro Gly Gly
1               5                   10                  15

Ser Leu Lys Leu Ser Cys Ala Ala Ser Gly Ile Ile Phe Ser Ser Ser
            20                  25                  30

Ala Met Ser Trp Val Arg Gln Thr Pro Glu Lys Arg Leu Glu Trp Val
        35                  40                  45

Ala Thr Ile Ser Ser Gly Gly Arg Ser Thr Tyr Tyr Pro Asp Ser Val
    50                  55                  60

Lys Gly Arg Phe Thr Val Ser Arg Asp Ser Ala Lys Asn Thr Leu Tyr
65                  70                  75                  80

Leu Gln Met Asp Ser Leu Arg Ser Glu Asp Thr Ala Ile Tyr Tyr Cys
                85                  90                  95

Ala Lys Leu Ile Ser Pro Tyr Trp Gly Gln Gly Thr Thr Leu Thr Val
            100                 105                 110

Ser Ser

<210> SEQ ID NO 259
<211> LENGTH: 321
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: BB7 VK

<400> SEQUENCE: 259
gccatcaaga tgacccagtc tccatcttcc atgtatgcat ctctaggaga gagagtcatc 60
atcacttgca aggcgagtca ggacataaat agttatttaa cctggttcca acagaaacca 120
ggaaagtctc ctaagaccct gatctatctt acaaatagat tgatggatgg ggtcccatca 180
aggttcagtg gcagtggatc tgggcaagaa tttttactca ccatcagcgg cctggaacat 240
gaagatatgg gcatttatta ttgtctccag tatgttgact ttccgtacac gttcggaggg 300
gggaccaagc tggaaataaa a 321

<210> SEQ ID NO 260
<211> LENGTH: 107
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: BB7 VK

<400> SEQUENCE: 260

```
Ala Ile Lys Met Thr Gln Ser Pro Ser Ser Met Tyr Ala Ser Leu Gly
1               5                   10                  15

Glu Arg Val Ile Ile Thr Cys Lys Ala Ser Gln Asp Ile Asn Ser Tyr
            20                  25                  30

Leu Thr Trp Phe Gln Gln Lys Pro Gly Lys Ser Pro Lys Thr Leu Ile
        35                  40                  45

Tyr Leu Thr Asn Arg Leu Met Asp Gly Val Pro Ser Arg Phe Ser Gly
    50                  55                  60

Ser Gly Ser Gly Gln Glu Phe Leu Leu Thr Ile Ser Gly Leu Glu His
65                  70                  75                  80

Glu Asp Met Gly Ile Tyr Tyr Cys Leu Gln Tyr Val Asp Phe Pro Tyr
                85                  90                  95

Thr Phe Gly Gly Gly Thr Lys Leu Glu Ile Lys
            100                 105
```

<210> SEQ ID NO 261
<211> LENGTH: 342
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: DC1 VH

<400> SEQUENCE: 261

```
gaagtgcagt tggtggagtc tgggggaggc ttagtgaagc ctggagggtc cctgaaactc     60

tcctgtgcag cctctggatt cactctcagt acccatgcca tgtcttgggt tcgccagact    120

ccggagaaga ggctggagtg ggtcgcaacc attagtagtg gtggtcgttc cacctactat    180

ccagacagtg tgaagggtcg attcactatc tccagagaca atgtcaagaa caccctatat    240

ctgcaactga gcagtctgag gtctgaggac acggccgtgt atttctgtgc aagactaatc    300

agtacctact ggggccaagg caccactctc acagtctcct ca                       342
```

<210> SEQ ID NO 262
<211> LENGTH: 114
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: DC1 VH

<400> SEQUENCE: 262

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Leu Ser Thr His
            20                  25                  30

Ala Met Ser Trp Val Arg Gln Thr Pro Glu Lys Arg Leu Glu Trp Val
        35                  40                  45

Ala Thr Ile Ser Ser Gly Gly Arg Ser Thr Tyr Tyr Pro Asp Ser Val
    50                  55                  60
```

```
Lys Gly Arg Phe Thr Ile Ser Arg Asp Asn Val Lys Asn Thr Leu Tyr
65                  70                  75                  80

Leu Gln Leu Ser Ser Leu Arg Ser Glu Asp Thr Ala Val Tyr Phe Cys
                85                  90                  95

Ala Arg Leu Ile Ser Thr Tyr Trp Gly Gln Gly Thr Thr Leu Thr Val
            100                 105                 110

Ser Ser


<210> SEQ ID NO 263
<211> LENGTH: 321
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: DC1 VK

<400> SEQUENCE: 263

gacatcacga tgacccagtc tccatcttcc atatatgcat ctctgggaga gagagtcact      60

atcacttgca aggcgagtca ggacattaat agctatttaa cctggttcca gcagaaacca     120

gggaaatctc ctaagatcct gatctatctt gtaaatagat tggtagatgg ggtcccatca     180

aggttcagtg gcagtggatc tgggcaagat tatgctctca ccatcagcag tctggaatat     240

gaagatatgg gaatttatta ttgtctacaa tatgatgact ttccgtacac gttcggaggg     300

gggaccaagc tggaaataaa a                                               321


<210> SEQ ID NO 264
<211> LENGTH: 107
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: DC1 VK

<400> SEQUENCE: 264

Asp Ile Thr Met Thr Gln Ser Pro Ser Ser Ile Tyr Ala Ser Leu Gly
1               5                   10                  15

Glu Arg Val Thr Ile Thr Cys Lys Ala Ser Gln Asp Ile Asn Ser Tyr
            20                  25                  30

Leu Thr Trp Phe Gln Gln Lys Pro Gly Lys Ser Pro Lys Ile Leu Ile
        35                  40                  45

Tyr Leu Val Asn Arg Leu Val Asp Gly Val Pro Ser Arg Phe Ser Gly
    50                  55                  60

Ser Gly Ser Gly Gln Asp Tyr Ala Leu Thr Ile Ser Ser Leu Glu Tyr
65                  70                  75                  80

Glu Asp Met Gly Ile Tyr Tyr Cys Leu Gln Tyr Asp Asp Phe Pro Tyr
                85                  90                  95

Thr Phe Gly Gly Gly Thr Lys Leu Glu Ile Lys
            100                 105


<210> SEQ ID NO 265
<211> LENGTH: 342
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
```

<223> OTHER INFORMATION: JE12 VH

<400> SEQUENCE: 265

```
gaggtccagc tgcagcagtc tggacctgag ctggtaaagc ctggggcttc agtgaagatg     60
tcctgcaagg cttctggata cagattcact agctatgtta tgcactgggt gaaacagaag    120
tctgggcagg gccttgagtg gattggatat attaatcctt acaatgatgg tgctaagtac    180
aatgagaagt tcaaaggcaa ggccacactg acttcagaca aatcctccag cacagcctac    240
atggagctca gcagcctgac ctctgaggac tctgcggtct attactgtgc aagactatct    300
agtgactatt ggggccaagg caccactctc acagtctcct ca                       342
```

<210> SEQ ID NO 266
<211> LENGTH: 114
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: JE12 VH

<400> SEQUENCE: 266

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Arg Phe Thr Ser Tyr
            20                  25                  30

Val Met His Trp Val Lys Gln Lys Ser Gly Gln Gly Leu Glu Trp Ile
        35                  40                  45

Gly Tyr Ile Asn Pro Tyr Asn Asp Gly Ala Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Leu Ser Ser Asp Tyr Trp Gly Gln Gly Thr Thr Leu Thr Val
            100                 105                 110

Ser Ser
```

<210> SEQ ID NO 267
<211> LENGTH: 336
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: JE12 VK

<400> SEQUENCE: 267

```
gatgttttga tgacccaaaa tccactctcc ctgcctgtca gtcttggaga tcaagcctcc     60
atctcttgca gatctagtca gagcattgaa catattaatg gaaacaccta tttagaatgg    120
tacctgcaga aaccaggcca gtctccaaag ttcctgatct acaaagtttc caaccgattt    180
tctggggtcc cagacaggtt cagtggcagt ggatcaggga cagatttcac actcaggatc    240
agcagagtgg aggctgaaga tctgggaatt tattactgct ttcaaggttc acatgttccg    300
ttcacgttcg gaggggggac caagctggaa ataaaa                              336
```

<210> SEQ ID NO 268

<211> LENGTH: 112
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: JE12 VK

<400> SEQUENCE: 268

```
Asp Val Leu Met Thr Gln Asn Pro Leu Ser Leu Pro Val Ser Leu Gly
1               5                   10                  15

Asp Gln Ala Ser Ile Ser Cys Arg Ser Ser Gln Ser Ile Glu His Ile
            20                  25                  30

Asn Gly Asn Thr Tyr Leu Glu Trp Tyr Leu Gln Lys Pro Gly Gln Ser
        35                  40                  45

Pro Lys Phe Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Ile Tyr Tyr Cys Phe Gln Gly
                85                  90                  95

Ser His Val Pro Phe Thr Phe Gly Gly Gly Thr Lys Leu Glu Ile Lys
            100                 105                 110
```

<210> SEQ ID NO 269
<211> LENGTH: 342
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: EH6 VH

<400> SEQUENCE: 269

```
gaggtccagc tgcagcagtc tggacctgag ctggtaaagc ctggggcttc agtgaagatg     60

tcctgcaagg cttctggata cacattcact agttatgtta tgcactgggt gaagcagaag    120

cctgggcagg gccttgagtg gattggattt attaatcctt acaatgatgg tactaagtac    180

aatgagaagt tcaaaggcaa ggccacactg acctcagaca aagcctccac cacagcctac    240

atggagctca gcagcctgac ctctgaggac tctgcggtct attactgtgc aagattctcc    300

tctgggtact ggggccaagg caccactctc acagtctcct ca                       342
```

<210> SEQ ID NO 270
<211> LENGTH: 114
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: EH6 VH

<400> SEQUENCE: 270

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45
```

```
Gly Phe Ile Asn Pro Tyr Asn Asp Gly Thr Lys Tyr Asn Glu Lys Phe
    50                  55                  60

Lys Gly Lys Ala Thr Leu Thr Ser Asp Lys Ala Ser Thr Thr Ala Tyr
65                  70                  75                  80

Met Glu Leu Ser Ser Leu Thr Ser Glu Asp Ser Ala Val Tyr Tyr Cys
                85                  90                  95

Ala Arg Phe Ser Ser Gly Tyr Trp Gly Gln Gly Thr Thr Leu Thr Val
            100                 105                 110

Ser Ser


<210> SEQ ID NO 271
<211> LENGTH: 336
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: EH6 VK

<400> SEQUENCE: 271

gatgttttga tgacccaaac tccactctcc ctgcctgtca gtcttggaga tcaagcctcc      60

atctcttgca gatctagtca gagtattgta catagtaatg gaaacaccta tttagaatgg     120

tacctgcaga aaccaggcca gtctccaaag ctcctgatct acaaagtttc caatcgattt     180

tctggggtcc cagacaggtt cagtggcagt ggatcaggga cagatttcac actcaagatc     240

agcagagtgg gggctgagga tctgggagtt tattactgcc ttcaagtttc acatgttcct     300

ttcacgttcg gctcggggac aaagttggaa ataaaa                               336


<210> SEQ ID NO 272
<211> LENGTH: 112
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: EH6 VK

<400> SEQUENCE: 272

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Gly Ala Glu Asp Leu Gly Val Tyr Tyr Cys Leu Gln Val
                85                  90                  95

Ser His Val Pro Phe Thr Phe Gly Ser Gly Thr Lys Leu Glu Ile Lys
            100                 105                 110


<210> SEQ ID NO 273
<211> LENGTH: 342
<212> TYPE: DNA
<213> ORGANISM: Artificial Sequence
<220> FEATURE:
```

<223> OTHER INFORMATION: Synthetic polynucleotide
<220> FEATURE:
<221> NAME/KEY: misc_feature
<223> OTHER INFORMATION: AG9 VH

<400> SEQUENCE: 273
gaggtccagc tgcagcagtc tggacctgag ttggtaaagc ctggggcttc agtgaagatg 60
tcctgcaggg cttctggata cacattcact acctatgtta ttcactgggt gaagcagaag 120
cctgggcagg gccttgagtg gattggatat attaatcctt acaatgatgg tgctaggtac 180
aatgagaagt tcaaaggcaa ggccacactg acttcagaca aatcctccac cacagcctac 240
atggaactca gcagcctgac ctctgaggac tctgcggtct attactgtgc aagactttct 300
agtgactact ggggccaagg caccactctc acagtctcct ca 342

<210> SEQ ID NO 274
<211> LENGTH: 114
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AG9 VH

<400> SEQUENCE: 274

Glu Val Gln Leu Gln Gln Ser Gly Pro Glu Leu Val Lys Pro Gly Ala
1 5 10 15

Ser Val Lys Met Ser Cys Arg Ala Ser Gly Tyr Thr Phe Thr Thr Tyr
20 25 30

Val Ile His Trp Val Lys Gln Lys Pro Gly Gln Gly Leu Glu Trp Ile
35 40 45

Gly Tyr Ile Asn Pro Tyr Asn Asp Gly Ala Arg Tyr Asn Glu Lys Phe
50 55 60

Lys Gly Lys Ala Thr Leu Thr Ser Asp Lys Ser Ser Thr Thr Ala Tyr
65 70 75 80

Met Glu Leu Ser Ser Leu Thr Ser Glu Asp Ser Ala Val Tyr Tyr Cys
85 90 95

Ala Arg Leu Ser Ser Asp Tyr Trp Gly Gln Gly Thr Thr Leu Thr Val
100 105 110

Ser Ser

<210> SEQ ID NO 275
<211> LENGTH: 336
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: AG9 VK

<400> SEQUENCE: 275
gatgttttga tgacccaaaa tccactctcc ctgcctgtca gtcttggcga tcaggcctcc 60
atctcttgca gatctagtcg gagcattgaa catagtaatg gaaacaccta tttggaatgg 120
tacctgcaga aaccaggcca gtctccaaag ttcctgatct acaaagtttc caaccgattt 180
tctggggtcc cagacaggtt cagtggcagt ggatcaggga cagatttcac actcaggatc 240
agcagtgtgg aggctgagga tctgggagtt tattactgct ttcaaggttc acatgttccg 300
ttcacgttcg gaggggggac caagctggaa ataaaa 336

<210> SEQ ID NO 276
<211> LENGTH: 112
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AG9 VK

<400> SEQUENCE: 276

```
Asp Val Leu Met Thr Gln Asn Pro Leu Ser Leu Pro Val Ser Leu Gly
1               5                   10                  15

Asp Gln Ala Ser Ile Ser Cys Arg Ser Ser Arg Ser Ile Glu His Ser
            20                  25                  30

Asn Gly Asn Thr Tyr Leu Glu Trp Tyr Leu Gln Lys Pro Gly Gln Ser
        35                  40                  45

Pro Lys Phe Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Ser Val Glu Ala Glu Asp Leu Gly Val Tyr Tyr Cys Phe Gln Gly
                85                  90                  95

Ser His Val Pro Phe Thr Phe Gly Gly Gly Thr Lys Leu Glu Ile Lys
            100                 105                 110
```

<210> SEQ ID NO 277
<211> LENGTH: 342
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: AH3 VH

<400> SEQUENCE: 277

```
gaggtccagc tgcagcagtc tggacctgag ctggtaaagc ctggggcttc agtgaagatg     60

tcctgcaggg cttctggata cacattcact acctatgtta ttcactgggt gaagcagaag    120

cctgggcagg gccttgagtg gattggatat attaatcctt acaatgatgg tgctaggtac    180

aatgagaagt tcaaaggcaa ggccacactg acttcagaca aatcctccac cacagcctac    240

atggaactca gcagcctgac ctctgaggac tctgcggtct attactgtgc aagactatct    300

agtgactact ggggccaagg caccactctc acagtctcct ca                       342
```

<210> SEQ ID NO 278
<211> LENGTH: 114
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AH3 VH

<400> SEQUENCE: 278

```
Glu Val Gln Leu Gln Gln Ser Gly Pro Glu Leu Val Lys Pro Gly Ala
1               5                   10                  15

Ser Val Lys Met Ser Cys Arg Ala Ser Gly Tyr Thr Phe Thr Thr Tyr
            20                  25                  30
```

```
Val Ile His Trp Val Lys Gln Lys Pro Gly Gln Gly Leu Glu Trp Ile
        35                  40                  45

Gly Tyr Ile Asn Pro Tyr Asn Asp Gly Ala Arg Tyr Asn Glu Lys Phe
    50                  55                  60

Lys Gly Lys Ala Thr Leu Thr Ser Asp Lys Ser Ser Thr Thr Ala Tyr
65                  70                  75                  80

Met Glu Leu Ser Ser Leu Thr Ser Glu Asp Ser Ala Val Tyr Tyr Cys
                85                  90                  95

Ala Arg Leu Ser Ser Asp Tyr Trp Gly Gln Gly Thr Thr Leu Thr Val
            100                 105                 110

Ser Ser


<210> SEQ ID NO 279
<211> LENGTH: 336
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: AH3 VK

<400> SEQUENCE: 279

gatgttttga tgacccaaaa tccactctcc ctgcctgtca gtcttggaga tcaggcctcc      60

atctcttgca gatctagtcg gagcattgaa catagtaatg gaaacaccta tttggaatgg     120

tacctgcaga aaccaggcca gtctccaaag ttcctgatct acaaagtttc caaccgattt     180

tctggggtcc cagacaggtt cagtggcagt ggatcaggga cagatttcac actcaggatc     240

agcagtgtgg aggctgagga tctgggagtt tattactgct ttcaaggttc acatgttccg     300

ttcacgttcg gagggggggac caagctggaa ataaaa                             336


<210> SEQ ID NO 280
<211> LENGTH: 112
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: AH3 VK

<400> SEQUENCE: 280

Asp Val Leu Met Thr Gln Asn Pro Leu Ser Leu Pro Val Ser Leu Gly
1               5                   10                  15

Asp Gln Ala Ser Ile Ser Cys Arg Ser Ser Arg Ser Ile Glu His Ser
            20                  25                  30

Asn Gly Asn Thr Tyr Leu Glu Trp Tyr Leu Gln Lys Pro Gly Gln Ser
        35                  40                  45

Pro Lys Phe Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Ser Val Glu Ala Glu Asp Leu Gly Val Tyr Tyr Cys Phe Gln Gly
                85                  90                  95

Ser His Val Pro Phe Thr Phe Gly Gly Gly Thr Lys Leu Glu Ile Lys
            100                 105                 110


<210> SEQ ID NO 281
<211> LENGTH: 357
```

<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: DD9 VH

<400> SEQUENCE: 281
caggttactc tgaaagagtc tggccctggg atattgcagc cctcccagac cctcagtctg 60
acttgttctt tttctgggtt ttcactgagc acttcgggta tgggtgtgag ttggattcgt 120
cagtcctcag gaaagggtct ggagtggctg gcacacattt actgggatga tgacaagcgc 180
tataacccat ccctgaagag ccggatcaca atctccaagg attcctcaag caaccaggta 240
ttcctcaaga tcaccagtgt ggacactgca gatactgcca catattactg tgctcgaagt 300
tggactacgg ccccgtttgc tttctggggc caagggactc tggtcactgt ctctgca 357

<210> SEQ ID NO 282
<211> LENGTH: 119
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: DD9 VH

<400> SEQUENCE: 282

Gln Val Thr Leu Lys Glu Ser Gly Pro Gly Ile Leu Gln Pro Ser Gln
1 5 10 15

Thr Leu Ser Leu Thr Cys Ser Phe Ser Gly Phe Ser Leu Ser Thr Ser
20 25 30

Gly Met Gly Val Ser Trp Ile Arg Gln Ser Ser Gly Lys Gly Leu Glu
35 40 45

Trp Leu Ala His Ile Tyr Trp Asp Asp Asp Lys Arg Tyr Asn Pro Ser
50 55 60

Leu Lys Ser Arg Ile Thr Ile Ser Lys Asp Ser Ser Ser Asn Gln Val
65 70 75 80

Phe Leu Lys Ile Thr Ser Val Asp Thr Ala Asp Thr Ala Thr Tyr Tyr
85 90 95

Cys Ala Arg Ser Trp Thr Thr Ala Pro Phe Ala Phe Trp Gly Gln Gly
100 105 110

Thr Leu Val Thr Val Ser Ala
115

<210> SEQ ID NO 283
<211> LENGTH: 318
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: DD9 VK

<400> SEQUENCE: 283
caaattgttc tcacccagtc tccagcaatc atgtctgcat ctccagggga gaaggtcacc 60
atgacctgca gtgccagctc aagtgtagat tacatgtact ggtaccagca gaagccagga 120
tcctccccca gactcctgat ttatgacaca tccaacctgg cttctggagt ccctgttcgc 180
ttcagtggca gtgggtctgg gacctcttac tctctcacaa tcagccgaat gggggctgaa 240

```
gatgctgcca cttattactg ccaacagtgg aatagttccc cgctcacgtt cggtgctggg    300

accaagctgg agctgaaa                                                  318


<210> SEQ ID NO 284
<211> LENGTH: 106
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: DD9 VK

<400> SEQUENCE: 284

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Asp Tyr Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Gly Ala Glu
65                  70                  75                  80

Asp Ala Ala Thr Tyr Tyr Cys Gln Gln Trp Asn Ser Ser Pro Leu Thr
                85                  90                  95

Phe Gly Ala Gly Thr Lys Leu Glu Leu Lys
            100                 105


<210> SEQ ID NO 285
<211> LENGTH: 357
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: DH2 VH

<400> SEQUENCE: 285

caggttactc tgaaagagtc tggccctggg atattgcagc cctcccagac cctcagtctg     60

acttgttctt tctctgggtt ttcactgagc acttctggta tgggtgtgag ctggattcgt    120

cagccttcag gaaagggtct ggagtggctg gcacacattt actgggatga tgacaagcgc    180

tataacccat ccctgaagag ccggctcaca atctccaagg atacctccag caaccaggta    240

ttcctcaaga tcaccagtgt ggacactgca gatactgcca catactactg tgctcgaagt    300

gggactacgg ccccgtttgc ttactggggc caagggactc tggtcactgt ctctgca       357


<210> SEQ ID NO 286
<211> LENGTH: 119
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: DH2 VH

<400> SEQUENCE: 286

Gln Val Thr Leu Lys Glu Ser Gly Pro Gly Ile Leu Gln Pro Ser Gln
1               5                   10                  15
```

```
Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Ser Asn Gln Val
65                  70                  75                  80

Phe Leu Lys Ile Thr Ser Val Asp Thr Ala Asp Thr Ala Thr Tyr Tyr
                85                  90                  95

Cys Ala Arg Ser Gly Thr Thr Ala Pro Phe Ala Tyr Trp Gly Gln Gly
            100                 105                 110

Thr Leu Val Thr Val Ser Ala
        115


<210> SEQ ID NO 287
<211> LENGTH: 318
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: DH2 VK

<400> SEQUENCE: 287

caaattgttc tcactcagtc tccagcaatc atgtctgcat ctccagggga gaaggtcacc     60

atgacctgca gtgccagctc aagtgtaagt tacatgtact ggtaccagca gaagccagga    120

tcctccccca gactcctgat ttatgacaca tccaacctgg cttctggagt ccctgttcgc    180

ttcagtggca gtgggtctgg gacctcttac tctctcacaa tcagccgaat ggaggctgaa    240

gatgctgcca ctttttactg ccagcagtgg agtagttccc cgctcacgtt cggtgctggg    300

accaagctgg agctgaaa                                                  318


<210> SEQ ID NO 288
<211> LENGTH: 106
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: DH2 VK

<400> SEQUENCE: 288

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Phe Tyr Cys Gln Gln Trp Ser Ser Ser Pro Leu Thr
                85                  90                  95

Phe Gly Ala Gly Thr Lys Leu Glu Leu Lys
```

100                 105

<210> SEQ ID NO 289
<211> LENGTH: 339
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: DD6 VH

<400> SEQUENCE: 289
gaggtccagc tgcaacagtc tgggcctgaa ctggtgaagc ctggggcttc agtgaagatg     60
tcctgcaagg cttctggata cagattcact gactacaaca tgcactgggt gaagcagaac    120
cttggaaaga gccttgagtg gattggatat attaacccta aaaatggtgt tatttactac    180
aaccagaagt tcaagggcaa ggccacattg acagtgaaca ggtcctccaa cacagcctac    240
atggagatcc gcagcctgac atcggaagat tctgcagtct attactgtgc aacagctctg    300
acttactggg gacaagggac tctggtcact gtctctgca                            339

<210> SEQ ID NO 290
<211> LENGTH: 113
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: DD6 VH

<400> SEQUENCE: 290

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Arg Phe Thr Asp Tyr
            20                  25                  30

Asn Met His Trp Val Lys Gln Asn Leu Gly Lys Ser Leu Glu Trp Ile
        35                  40                  45

Gly Tyr Ile Asn Pro Lys Asn Gly Val Ile Tyr Tyr Asn Gln Lys Phe
    50                  55                  60

Lys Gly Lys Ala Thr Leu Thr Val Asn Arg Ser Ser Asn Thr Ala Tyr
65                  70                  75                  80

Met Glu Ile Arg Ser Leu Thr Ser Glu Asp Ser Ala Val Tyr Tyr Cys
                85                  90                  95

Ala Thr Ala Leu Thr Tyr Trp Gly Gln Gly Thr Leu Val Thr Val Ser
            100                 105                 110

Ala

<210> SEQ ID NO 291
<211> LENGTH: 330
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: DD6 VL

<400> SEQUENCE: 291
caggctgttg tgactcagga atctgcactc accacatcac ctggtgaaac agtcacactc     60
acttgtcgct caagtactgg ggctgttgca gctaataact atgccaactg gatccaagaa    120

```
aaaccagatc atttattcac tggtctgata gctggtacca acaagcgagc tccaggtgtt    180

cctgccagat tctcaggctc cctgatagga gacaaggctg ccctcaccat cacaggggca    240

cagactgagg atgaggcaat atatttctgt gctctatggt acagcaacta ttgggtgttc    300

ggtggaggaa ccaaagtgac tgtcctaggc                                     330


<210> SEQ ID NO 292
<211> LENGTH: 110
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: DD6 VL

<400> SEQUENCE: 292

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Ala Ala Asn
            20                  25                  30

Asn Tyr Ala Asn Trp Ile Gln Glu Lys Pro Asp His Leu Phe Thr Gly
        35                  40                  45

Leu Ile Ala Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Tyr Trp Val Phe Gly Gly Gly Thr Lys Val Thr Val Leu Gly
            100                 105                 110


<210> SEQ ID NO 293
<211> LENGTH: 342
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: IA12 VH

<400> SEQUENCE: 293

cagatccagt tggtacagtc tggacctgag ctgaagaagc ctggagagac agtcaagatc     60

tcctgcaagg cttctgggta taccttcaca acctatggaa tgacctgggt gaaacaggct    120

ccaggaaagg gtttaaagtg gatgggctgg ataaacacct cctctggagt gccaacatat    180

gctgatgact tcaagggacg gtttgccttc tctttggaaa cctctgccag cactgcctat    240

ttgcagatca acaacctcaa aagtgaggac acggctacat atttctgtgc aagaccggaa    300

gttgcttact ggggccaagg gactctggtc actgtctctg ca                       342


<210> SEQ ID NO 294
<211> LENGTH: 114
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: IA12 VH
```

<400> SEQUENCE: 294

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Thr Tyr
            20                  25                  30

Gly Met Thr Trp Val Lys Gln Ala Pro Gly Lys Gly Leu Lys Trp Met
        35                  40                  45

Gly Trp Ile Asn Thr Ser Ser Gly Val Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Ser Glu Asp Thr Ala Thr Tyr Phe Cys
                85                  90                  95

Ala Arg Pro Glu Val Ala Tyr Trp Gly Gln Gly Thr Leu Val Thr Val
            100                 105                 110

Ser Ala
```

<210> SEQ ID NO 295
<211> LENGTH: 336
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: IA12 VK

<400> SEQUENCE: 295

```
gatgttgtga tgacccagac tccactcact ttgtcggtta cctttggaca accagcctct     60

atctcttgca agtcaagtca gagcctctta tatgataatg gaaagactta tttgcattgg    120

ttatttcaga ggccaggcca gtctccaagg cgcctaatct atctggtgtc taaactggac    180

tctggagtcc ctgacaggtt cactggcagt ggatcaggaa cagattttac actgaaaatc    240

agcagagtgg aggctgagga tttgggagtt tattactgcg tgcaaggtac acattttccg    300

tacacgttcg gaggggggac caaactggaa ataaaa                               336
```

<210> SEQ ID NO 296
<211> LENGTH: 112
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: IA12 VK

<400> SEQUENCE: 296

```
Asp Val Val Met Thr Gln Thr Pro Leu Thr Leu Ser Val Thr Phe Gly
1               5                   10                  15

Gln Pro Ala Ser Ile Ser Cys Lys Ser Ser Gln Ser Leu Leu Tyr Asp
            20                  25                  30

Asn Gly Lys Thr Tyr Leu His Trp Leu Phe Gln Arg Pro Gly Gln Ser
        35                  40                  45

Pro Arg Arg Leu Ile Tyr Leu Val Ser Lys Leu Asp Ser Gly Val Pro
    50                  55                  60
```

-continued

```
Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Val Gln Gly
                85                  90                  95

Thr His Phe Pro Tyr Thr Phe Gly Gly Gly Thr Lys Leu Glu Ile Lys
            100                 105                 110
```